US009334506B2

(12) United States Patent
Carrington et al.

(10) Patent No.: US 9,334,506 B2
(45) Date of Patent: May 10, 2016

(54) METHOD TO TRIGGER RNA INTERFERENCE

(71) Applicant: State of Oregon acting by and through the State Board of Higher Education on behalf of Oregon State University, Corvallis, OR (US)

(72) Inventors: James C. Carrington, St. Louis, MO (US); Edwards Allen, O'Fallon, MO (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

(21) Appl. No.: 14/261,640

(22) Filed: Apr. 25, 2014

(65) Prior Publication Data
US 2014/0234967 A1    Aug. 21, 2014

Related U.S. Application Data

(60) Division of application No. 13/827,450, filed on Mar. 14, 2013, now Pat. No. 9,018,002, which is a continuation of application No. 13/216,942, filed on Aug. 24, 2011, now Pat. No. 8,476,422, which is a continuation of application No. 11/334,776, filed on Jan. 6, 2006, now Pat. No. 8,030,473.

(60) Provisional application No. 60/642,126, filed on Jan. 7, 2005.

(51) Int. Cl.
| C12N 15/82 | (2006.01) |
| C12N 15/11 | (2006.01) |
| C12N 15/113 | (2010.01) |

(52) U.S. Cl.
CPC .......... *C12N 15/8279* (2013.01); *C12N 15/111* (2013.01); *C12N 15/113* (2013.01); *C12N 15/8218* (2013.01); *C12N 15/8245* (2013.01); *C12N 15/8246* (2013.01); *C12N 15/8247* (2013.01); *C12N 15/8251* (2013.01); *C12N 15/8261* (2013.01); *C12N 15/8271* (2013.01); *C12N 15/8274* (2013.01); *C12N 2310/14* (2013.01); *C12N 2320/11* (2013.01)

(58) Field of Classification Search
None
See application file for complete search history.

(56) References Cited

U.S. PATENT DOCUMENTS

| 6,459,019 | B1 | 10/2002 | Falco et al. | |
| 6,753,139 | B1 | 6/2004 | Baulcombe et al. | |
| 7,847,156 | B2 * | 12/2010 | Inze et al. | 800/290 |
| 2003/0135888 | A1 | 7/2003 | Zhu et al. | |
| 2003/0221211 | A1 | 11/2003 | Rottmann et al. | |
| 2004/0009476 | A9 | 1/2004 | Harper et al. | |
| 2004/0053411 | A1 * | 3/2004 | Cullen et al. | 435/455 |
| 2004/0053876 | A1 | 3/2004 | Turner et al. | |
| 2004/0086884 | A1 | 5/2004 | Beach et al. | |
| 2004/0261149 | A1 | 12/2004 | Fauquet et al. | |
| 2006/0200878 | A1 | 9/2006 | Lutfiyya et al. | |
| 2007/0130653 | A1 | 6/2007 | Baulcombe et al. | |
| 2011/0035839 | A1 | 2/2011 | Lutfiyya et al. | |

FOREIGN PATENT DOCUMENTS

WO    WO 2007/039454    4/2007

OTHER PUBLICATIONS

Chen et al., "22-nucleotide RNAs trigger secondary siRNA biogenesis in plants," *Proc Natl Acad Sci U S A*, 107(34):15269-74, 2010; doi: 10.1073/pnas.1001738107, Epub 2010.

Cuperus et al., "Unique functionality of 22-nt miRNAs in triggering RDR6- dependent siRNA biogenesis from target transcripts in *Arabidopsis,*" *Nat Struct Mol Biol.*, 17(8):997-1003, 2010; doi: 10.1038/nsmb.1866, Epub 2010.

Fei et al., "Phased, Secondary, Small Interfering RNAs in Post-transcriptional Regulatory Networks," *The Plant Cell*, 25:2400-2415, 2013.

Manavella et al., "Plant secondary siRNA production determined by microRNA-duplex structure," *Proc Natl Acad Sci U S A*, 109(7):2461-2466, 2012.

Wang et al., "Function and Evolution of a MicroRNA That Regulates a $Ca^{2+}$-ATPase and Triggers the Formation of Phased Small Interfering RNAs in Tomato Reproductive Growth," *The Plant Cell*, 23:3185-3203, 2011.

Xia et al., "MicroRNA Superfamilies Descended from miR390 and Their Roles in Secondary Small Interfering RNA Biogenesis in Eudicots," *The Plant Cell*, 25:1555-1572, 2013.

(Continued)

*Primary Examiner* — Brent Page
(74) *Attorney, Agent, or Firm* — Klarquist Sparkman, LLP

(57) ABSTRACT

A method to generate siRNAs in vivo is described, as are constructs and compositions useful in the method. The method does not depend on the use of DNA or synthetic constructs that contain inverted duplications or dual promoters so as to form perfect or largely double-stranded RNA. Rather, the method depends on constructs that yield single-stranded RNA transcripts, and exploits endogenous or in vivo-produced miRNAs or siRNAs to initiate production of siRNAs. The miRNAs or siRNAs guide cleavage of the transcript and set the register for production of siRNAs (usually 21 nucleotides in length) encoded adjacent to the initiation cleavage site within the construct. The method results in specific formation of siRNAs of predictable size and register (phase) relative to the initiation cleavage site. The method can be used to produce specific siRNAs in vivo for inactivation or suppression of one or more target genes or other entities, such as pathogens.

12 Claims, 22 Drawing Sheets

(56) References Cited

OTHER PUBLICATIONS

Allen et al., "Conserved trans-acting siRNAs regulate ARF genes," Abstract for talk given on Jan. 12, 2005, at Keystone Symposium "Diverse Roles of RNA in Gene Regulation.".
Allen et al., "Evolution of microRNA genes by inverted duplication of target gene sequences in *Arabidopsis thaliana*," *Nature Genetics*, 36:1282-1290 (2004).
Allen et al., "microRNA-Directed Phasing during Trans-Acting siRNA Biogenesis in Plants," *Cell*, 121:207-221 (2005).
Allen et al., "miRNA-directed phasing during trans-acting siRNA biogenesis in plants," Poster displayed on Jan. 9, 2005, at Keystone Symposium "Diverse Roles of RNA in Gene Regulation."
Ambros et al., "A uniform system for microRNA annotation," *RNA*, 9:277-279 (2003).
Ambros, "The functions of animal microRNAs," *Nature*, 431:350-355 (2004).
Baulcombe, "RNA silencing in plants," *Nature*, 431:356-363 (2004).
Benfey, "MicroRNA is here to stay," *Nature*, 425:244-245 (2003).
Carrington et al., "Role of MicroRNAs in Plant and Animal Development," *Science*, 301:336-338 (2003).
Carrington, "Small RNAs and Arabidopsis. A Fast Forward Look," *Plant Physiology*, 138:565-566 (2005).
Chan et al., "RNA Silencing Genes Control de Novo DNA Methylation," *Science*, 303:1336 (2004).
Chapman et al., "Viral RNA silencing suppressors inhibit the microRNA pathway at an intermediate step," *Genes & Development*, 18:1179-1186 (2004).
Dugas et al., "MicroRNA regulation of gene expression in plants," *Current Opinion in Plant Biology*, 7:512-520 (2004).
Grey et al., "Identification and Characterization of Human Cytomegalovirus-Encoded MicroRNAs," *J. of Virology*, 79:12095-12099 (2005).
Gustafson et al., "ASRP: the *Arabidopsis* Small RNA Project Database," *Nucleic Acids Research*, 33:D637-D640 (2005).
Gutierrez-Nava et al., "Artificial trans-acting siRNAs confer consistent and effective gene silencing," *Plant Physiology*, 10.1104/108.118307 (2008).
Jones-Rhoades et al., "Computational Identification of Plant MicroRNAs and Their Targets, Including a Stress-Induced miRNA," *Molecular Cell*, 14:787-799 (2004).
Kato et al., "Expression of siRNA from a Single Transcript That Includes Multiple Ribozymes in Mammalian Cells," *Oligonucleotides*, 13:335-343 (2003).
Khvorova et al., "Functional siRNAs and miRNAs Exhibit Strand Bias," *Cell*, 115:209-216, 2003.
Lippman et al., "Role of transposable elements in heterochromatin and epigenetic control," *Nature*, 430:471-476 (2004).
Llave et al., "Cleavage of Scarecrow-like mRNA Targets Directed by a Class of *Arabidopsis* miRNA," *Science*, 297:2053-2056 (2002).
Mallory et al., "MicroRNAs: something important between the genes," *Current Opinion in Plant Biology*, 7:120-125 (2004).
Montgomery et al., "Specificity of ARGONAUTE7-miR390 Interaction and Dual Functionality in TAS3 Trans-Acting siRNA Formation," *Cell*, 122:128-141 (2008).
Montgomery et al., "AGO1-miR173 complex initiates phased siRNA formation in plants," *PNAS*, 105(51):20055-20062, 2008.
Palatnik et al., "Control of Leaf Morphogenesis by microRNAs," *Nature*, 425:257-263 & Supplementary Material S1-S24 (2003).
Parizotto et al., "In vivo investigation of the transcription, processing, endonucleolytic activity, and functional relevance of the spatial distribution of a plant miRNA," *Genes & Development*, 18: 2237-2242 (2004).
Park et al., "Carpel Factory, a Dicer Homolog, and HEN1, a Novel Protein, Act in microRNA Metabolism in *Arabidopsis thaliana*," *Current Biology*, 12:1484-1495 (2002).
Peragine et al., "SGS3 and SGS2/SDE1/RDR6 are required for juvenile development and the production of trans-acting siRNAs in *Arabidopsis*," *Genes & Development*, 18:2368-2379 (2004).
Rajagopalan et al., "A diverse and evolutionarily fluid set of microRNAs in *Arabidopsis thaliana*," *Genes & Development*, 20:3407-3425, 2006.
Rand et al., "Biochemical identification of Argonaute 2 as the sole protein required for RNA-induced silencing complex activity," *PNAS*, 101(40):14385-14389, 2004.
Rhoades et al., "Prediction of Plant MicroRNA Targets," *Cell*, 110:513-520 (2002).
Schwartz et al., "Asymmetry in the Assembly of the RNAi Enzyme Complex," *Cell*, 115:199-208, 2003.
Schmid et al., "Combinatorial RNAi: a method for evaluating the functions of gene families in *Drosophila*," *TRENDS in Neurosciences*, 25:71-74 (2002).
Song et al., "The crystal structure of the Argonaute2 PAZ domain reveals an RNA binding motif in RNAi effector complexes," *Nature Structure Biology*, 10(12):1026-1032, 2003.
Song et al., "Crystal Structure of Argonaute and Its Implications for RISC Sliver Activity," *Science*, 305:1434-1437, 2004.
Vaucheret et al., "The action of ARGONAUTE1 in the miRNA pathway and its regulation by the miRNA pathway are crucial for plant development," *Genes & Development*, 18:1187-1197 (2004).
Vazquez et al., "Endogenous trans-Acting siRNAs Regulate the Accumulation of Arabidopsis mRNAs," *Molecular Cell*, 16:69-79 (2004).
Vazquez Frank et al., "Endogenous trans-acting siRNAs regulate the accumulation of Arabidopsis mRNAs"—Supplemental Data—*Mol. Cell* 16(1):S1-S2, 2004.
Xie et al., "Dicer-Like 4 functions in trans-acting small interfering RNA biogenesis and vegetative phase change in *Arabidopsis thaliana*," *PNAS*, 102:12984-12989 (2005).
Xie et al., "Expression of Arabidopsis MIRNA Genes," *Plant Physiology*, 138:2145-2154 (2005).
Xie et al., "Genetic and Functional Diversification of Small RNA Pathways in Plants," *PLoS Biology*, 2:0642-0652 (2004).
Xie et al., "Negative Feedback Regulation of Dicer-Like1 in *Arabidopsis* by microRNA-Guided mRNA Degradation," *Current Biology*, 13:784-789 (2003).
Zilberman et al., "Role of *Arabidopsis* ARGONAUTE4 in RNA-Directed DNA Methylation Triggered by Inverted Repeats," *Current Biology*, 14:1214-1220 (2004).
EMBL Database Accession No. CD534180, Jan. 1, 2004; 2 pages.
EMBL Database Accession No. CD534192, Jan. 1, 2004; 2 pages.
Supplementary European Search Report for European Patent Application No. 06 71 7682; Mar. 26, 2013 (6 pages).

* cited by examiner

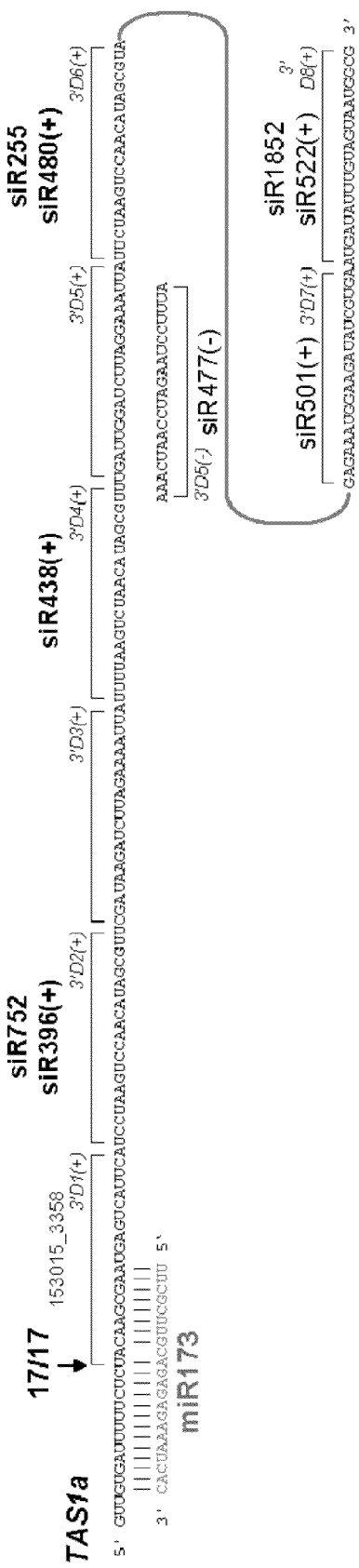
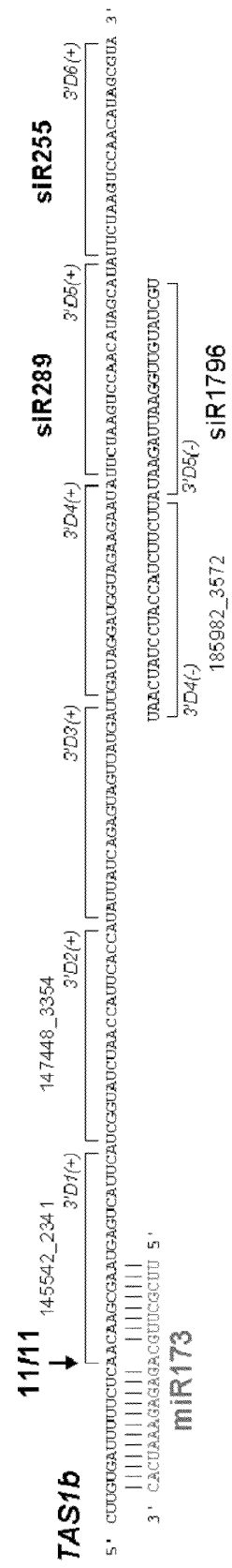
Fig. 5A
Fig. 5B miR390b miR391 miR403 miR447a

Fig. 10B

```
MIR156a  aaacgggttcctaatcttTATATATAccttccatcatcaaaagaccattcAttgttcact
MIR156a  ataaagaaaggtaagactctttgaaatagagagagataaggttttctcttAtcttcttct
MIR156c  tcttctcctctcctcttattaatctaatcctcctccccgaatatttctctGcctttagtt
MIR156c  ctcttctccttcggtTATAAATAttctctccggttttgcttgtttaacctAaaagcctca
MIR156e  tctatcccatttggcTATAAAAAgccccgacaggtctcagtttcttcccAcatccaaag
MIR156f  tctctccattttggcTATAAAAAgccacaacagggtctccatttcttcccGcagccaatg
MIR157c  tttctcaacttactccTATATATAacacattactctctattttcctttGtcacttcat
MIR157d  tggtctcaaatctttccTATATATAcacaccactttccattacaccatttActcttcacc
MIR159a  tgttcctttttttcttttcttttattcttctatcacgaatatctaaaccAcTATAATTA
MIR159a  acgaatatctaaaccacTATAATTAcgactctctatctatcattcttccAaaacatgac
MIR159b  ggctacagattttttgtctttaaaaagccattcaagtttcaatggtttttcActtttgttc
MIR319a  gttctaaatttgaagctTATAAAAAcccatcactacttttgcatacttgtAtccgcagtg
MIR319b  tacctttgtttttgcTATAAAAAgccataactccttcattttctttagacAtctcttctt
MIR160a  tcttgtctacaTATACATATATTTATAtacacacatgtatctctctcatcAcacccttaa
MIR160a  atcccaccccttaattgtttTATATAAAccatttctcctcctctctccatcAccttcaatc
MIR160b  tttatcattttttctcctcTATATATAtgtgccaccattcctcttatactcAtaactctcc
MIR160c  tcttctctcttttcccttTATATATTtgtaccacatattcctcttcaaccAaaactcttc
MIR161a  ctttctcttcttccttcaTATTTATAacaaccttctctcacttatctctAactcatcct
MIR162a  tgttatgagacttttagatacattttagtTATAAATAtgaatcaaatacaTtttagttct
MIR162a  tttagatacattttagtTATAAATAtgaatcaaatacattttagttctagAagaaaaaac
MIR162a  accagatctataaagtttgtTATTAAAAgatagagagagaggagggatgtAgtaggccaa
MIR163a  catcaaaggaaaattagTATAAATAagcatagaggcgtccatggattatcAcagttctca
MIR164a  ctagcaacctagcactTATATATGtagagtttgtgaaatttagggcagacAagccccac
MIR164a  atgcaatctttgggccTATATATAcaaaccttttccataaccaaagttctcAtactacaaa
MIR164b  atagatatttccgtttgcTATAAATGagaaagcacttacaacatacatacAttctctctt
MIR165a  tgtttctgttgtgtctTATTAAAAgcccatcctcgtctccgccactcatcAttccctcat
MIR166a  tctccactactcaatttcttcataaaaccccccttttatttctctcattCtctcttcca
MIR166a  aatttcttcataaaaccccccttttatttctctcattctctcttccatcAtcaccactc
MIR166b  tcttgagttttttctcttcttaaaaacctcttcttcacttatccttctcAtcattctct
MIR166c  tggtcatttgtgcctcTATATATAcaagacataggtttatttgtctcacAcataccttt
MIR166d  ttgctcctctctccctatgTATAAATAttcgctcacacatagacctatttAgcttcttct
MIR167a  tctcctccttatcccttcTATATAAAcactcgtctcttcttcacttgatGaacagaaaa
MIR167b  caaatcctctctcatctctttcTATAAGTAtctatagcgcctcttaaaccAcaaagcatc
MIR169a  tatctctgacccatcttcTATATAAAcccagagcgggtaagtcctctagtAttcataagc
MIR169c  aactggtagaaagatcTATAAGTAcgatacaccttatacttcaagagagcAagacaatgc
MIR169h  ttcgtacggtcatgcctatataacacacatagtagtcttgtgggatactcAtcaacaacc
MIR169l  ttccttctctcaaggggtTATAAATAaaacgagagcacatgaatgtaaggcAtgagacata
MIR169n  cgagtctcgagggtTATAAAAAgagagcacatgcatgtatggaataaggcAaaaacatat
MIR170a  tgagagtagcagagtTATTAAATgcttcgcagaattgcagttgcacattcActcccttct
MIR171a  taattcttcctcaaaatcttttctctttttttggtTATATATAtttgaatTttgatttat
MIR171b  cttcttcaaccatcttcgTATTTATAtcttcttcttcactatgcatactcAtaaactttg
MIR171c  tcttcatcaccctcttcgTATTTATAtctccttcactctgcaaacccaagAaaaaacatt
MIR172a  ccaaataaatcaacaTATATATTattacacagtcacatctcttactgtgcATATATATTt
MIR172a  acatctcttactgtgcaTATATATTagacaaacacatctctctctctctAtctctctca
MIR172a  gttttactattttagcagTATATATTaagaagttcagatgttattcgatcAtctgttttt
MIR172b  aagtcattgcgtgtctcTATAAATAccacacttcaccttcttcttcacttGcacctctca
MIR172b  tttttctcgtttttttcttcttctccaagaaaatagagatcgaaaagAttagatcta
MIR172c  tttaatttgttaatTATATATAttttatgcacatcattgggagaaaacaccAaataggctc
MIR172c  tctttatcgcttcaTATATATAaaagtctacatctatctctttctaggtcActagctaga
MIR172e  aaaaggttttacggtttgtgTATAAAAGacttgcaatcttgagatatgtcAtattgagaa
MIR172e  atatgtcatattgagaactctttagcctttggcttctgttcctgacacttAtatagtgaa
MIR172e  tttcatatgagtgTATATATTcatgtcctatctctctcaattgcttctcAccaaaatca
MIR394a  tgttagatctgaggtcTATTAAAAtccgaatcctttcaatctcttctcttAttccatcac
MIR394a  agggttttaagccaagcttatatagcccgtcataaagagaactcatctgcCtctctctca
MIR394a  ctctcaataccAATAAATAtcaccaccgtccttctctcctatcactattcAatctatcgc
MIR395c  gactctttgcaataataTATAAATAggcatgcagtgttagtgttgtttgtAtcatgacag
MIR395e  acaatgcttccaattgTATATATAaaacgccagtccctccattcttttccAaaccctaac
MIR396a  ctcttcccttgtccccTATAAAATActtttctatcgaccatcttccttctcAcaacttcaa
MIR397b  aagacacgaccaaatgtctTATAAATGatatttgtgtttatctccatgctAatagaaatg
MIR398c  tcatttgttgtgttgtgTATATATAgtagctctcagcagatttgaaggatAtcgaaactc
MIR399b  cacacacgcatatataTATAAATAcagacacaagccttcatatggatcttAtagagatga
MIR399c  ccactttTATTAAAActcaTATATATAcactgagccattagtccatgaatAaccaaccag
MIR399d  aaacactttcatcaacTATATATAcatactttgctagtccaacttccaatAactcaaaat
```

35S:GUS     35S:TAS1cPDSd3d4

35S:TAS1cPDSd3d4     35S:TAS1cPDSd3d4

SEQUENCE LISTING

```
<160> NUMBER OF SEQ ID NOS: 614

<210> SEQ ID NO 1
<211> LENGTH: 20
<212> TYPE: RNA
<213> ORGANISM: artificial sequence
<220> FEATURE:
<223> OTHER INFORMATION: synthetic nucleotide

<400> SEQUENCE: 1
gugcucucuc ucuucuguca                                           20

<210> SEQ ID NO 2
<211> LENGTH: 20
<212> TYPE: RNA
<213> ORGANISM: artificial sequence
<220> FEATURE:
<223> OTHER INFORMATION: synthetic nucleotide

<400> SEQUENCE: 2
```

```
cugcucucuc ucuucuguca                                        20

<210> SEQ ID NO 3
<211> LENGTH: 20
<212> TYPE: RNA
<213> ORGANISM: artificial sequence
<220> FEATURE:
<223> OTHER INFORMATION: synthetic nucleotide

<400> SEQUENCE: 3
uugcuuacuc ucuucuguca                                        20

<210> SEQ ID NO 4
<211> LENGTH: 20
<212> TYPE: RNA
<213> ORGANISM: artificial sequence
<220> FEATURE:
<223> OTHER INFORMATION: synthetic nucleotide

<400> SEQUENCE: 4
ccgcucucuc ucuucuguca                                        20

<210> SEQ ID NO 5
<211> LENGTH: 21
<212> TYPE: RNA
<213> ORGANISM: artificial sequence
<220> FEATURE:
<223> OTHER INFORMATION: synthetic nucleotide

<400> SEQUENCE: 5
uggagcuccc uucauuccaa u                                      21

<210> SEQ ID NO 6
<211> LENGTH: 21
<212> TYPE: RNA
<213> ORGANISM: artificial sequence
<220> FEATURE:
<223> OTHER INFORMATION: synthetic nucleotide

<400> SEQUENCE: 6
ucgaguuccc uucauuccaa u                                      21

<210> SEQ ID NO 7
<211> LENGTH: 21
<212> TYPE: RNA
<213> ORGANISM: artificial sequence
<220> FEATURE:
<223> OTHER INFORMATION: synthetic nucleotide

<400> SEQUENCE: 7
augagcucuc uucaaaccaa a                                      21

<210> SEQ ID NO 8
<211> LENGTH: 21
<212> TYPE: RNA
<213> ORGANISM: artificial sequence
<220> FEATURE:
<223> OTHER INFORMATION: synthetic nucleotide

<400> SEQUENCE: 8
uggagcuccc uucauuccaa g                                      21

<210> SEQ ID NO 9
<211> LENGTH: 21
<212> TYPE: RNA
<213> ORGANISM: artificial sequence
```

```
<220> FEATURE:
<223> OTHER INFORMATION: synthetic nucleotide

<400> SEQUENCE: 9
uagagcuucc uucaaaccaa a                                               21

<210> SEQ ID NO 10
<211> LENGTH: 21
<212> TYPE: RNA
<213> ORGANISM: artificial sequence
<220> FEATURE:
<223> OTHER INFORMATION: synthetic nucleotide

<400> SEQUENCE: 10
uggagcucca uucgauccaa a                                               21

<210> SEQ ID NO 11
<211> LENGTH: 21
<212> TYPE: RNA
<213> ORGANISM: artificial sequence
<220> FEATURE:
<223> OTHER INFORMATION: synthetic nucleotide

<400> SEQUENCE: 11
agcagcuccc uucaaaccaa a                                               21

<210> SEQ ID NO 12
<211> LENGTH: 21
<212> TYPE: RNA
<213> ORGANISM: artificial sequence
<220> FEATURE:
<223> OTHER INFORMATION: synthetic nucleotide

<400> SEQUENCE: 12
cagagcuccc uucacuccaa u                                               21

<210> SEQ ID NO 13
<211> LENGTH: 21
<212> TYPE: RNA
<213> ORGANISM: artificial sequence
<220> FEATURE:
<223> OTHER INFORMATION: synthetic nucleotide

<400> SEQUENCE: 13
uggagcuccc uucacuccaa u                                               21

<210> SEQ ID NO 14
<211> LENGTH: 21
<212> TYPE: RNA
<213> ORGANISM: artificial sequence
<220> FEATURE:
<223> OTHER INFORMATION: synthetic nucleotide

<400> SEQUENCE: 14
uggagcuccc uucacuccaa g                                               21

<210> SEQ ID NO 15
<211> LENGTH: 21
<212> TYPE: RNA
<213> ORGANISM: artificial sequence
<220> FEATURE:
<223> OTHER INFORMATION: synthetic nucleotide

<400> SEQUENCE: 15
uggagcuccc uuuaauccaa u                                               21
```

```
<210> SEQ ID NO 16
<211> LENGTH: 21
<212> TYPE: RNA
<213> ORGANISM: artificial sequence
<220> FEATURE:
<223> OTHER INFORMATION: synthetic nucleotide

<400> SEQUENCE: 16
uggcaugcag ggagccaggc a                                              21

<210> SEQ ID NO 17
<211> LENGTH: 21
<212> TYPE: RNA
<213> ORGANISM: artificial sequence
<220> FEATURE:
<223> OTHER INFORMATION: synthetic nucleotide

<400> SEQUENCE: 17
aggaauacag ggagccaggc a                                              21

<210> SEQ ID NO 18
<211> LENGTH: 21
<212> TYPE: RNA
<213> ORGANISM: artificial sequence
<220> FEATURE:
<223> OTHER INFORMATION: synthetic nucleotide

<400> SEQUENCE: 18
ggguuuacag ggagccaggc a                                              21

<210> SEQ ID NO 19
<211> LENGTH: 21
<212> TYPE: RNA
<213> ORGANISM: artificial sequence
<220> FEATURE:
<223> OTHER INFORMATION: synthetic nucleotide

<400> SEQUENCE: 19
aggcauacag ggagccaggc a                                              21

<210> SEQ ID NO 20
<211> LENGTH: 21
<212> TYPE: RNA
<213> ORGANISM: artificial sequence
<220> FEATURE:
<223> OTHER INFORMATION: synthetic nucleotide

<400> SEQUENCE: 20
aagcauacag ggagccaggc a                                              21

<210> SEQ ID NO 21
<211> LENGTH: 21
<212> TYPE: RNA
<213> ORGANISM: artificial sequence
<220> FEATURE:
<223> OTHER INFORMATION: synthetic nucleotide

<400> SEQUENCE: 21
accugaugua aucacuuuca a                                              21

<210> SEQ ID NO 22
<211> LENGTH: 21
<212> TYPE: RNA
<213> ORGANISM: artificial sequence
<220> FEATURE:
<223> OTHER INFORMATION: synthetic nucleotide
```

```
<400> SEQUENCE: 22
cccggaugua aucacuuuca g                                               21

<210> SEQ ID NO 23
<211> LENGTH: 21
<212> TYPE: RNA
<213> ORGANISM: artificial sequence
<220> FEATURE:
<223> OTHER INFORMATION: synthetic nucleotide

<400> SEQUENCE: 23
uuguuacuuu caaugcauug a                                               21

<210> SEQ ID NO 24
<211> LENGTH: 21
<212> TYPE: RNA
<213> ORGANISM: artificial sequence
<220> FEATURE:
<223> OTHER INFORMATION: synthetic nucleotide

<400> SEQUENCE: 24
cccugaugua uuuacuuuca a                                               21

<210> SEQ ID NO 25
<211> LENGTH: 21
<212> TYPE: RNA
<213> ORGANISM: artificial sequence
<220> FEATURE:
<223> OTHER INFORMATION: synthetic nucleotide

<400> SEQUENCE: 25
uagucacguu caaugcauug a                                               21

<210> SEQ ID NO 26
<211> LENGTH: 21
<212> TYPE: RNA
<213> ORGANISM: artificial sequence
<220> FEATURE:
<223> OTHER INFORMATION: synthetic nucleotide

<400> SEQUENCE: 26
cccugaugua uucacuuuca g                                               21

<210> SEQ ID NO 27
<211> LENGTH: 21
<212> TYPE: RNA
<213> ORGANISM: artificial sequence
<220> FEATURE:
<223> OTHER INFORMATION: synthetic nucleotide

<400> SEQUENCE: 27
cccugauguu guuacuuuca g                                               21

<210> SEQ ID NO 28
<211> LENGTH: 21
<212> TYPE: RNA
<213> ORGANISM: artificial sequence
<220> FEATURE:
<223> OTHER INFORMATION: synthetic nucleotide

<400> SEQUENCE: 28
uagucacuuu cagcgcauug a                                               21

<210> SEQ ID NO 29
```

```
<211> LENGTH: 21
<212> TYPE: RNA
<213> ORGANISM: artificial sequence
<220> FEATURE:
<223> OTHER INFORMATION: synthetic nucleotide

<400> SEQUENCE: 29
uccaaaugua gucacuuuca g                                              21

<210> SEQ ID NO 30
<211> LENGTH: 21
<212> TYPE: RNA
<213> ORGANISM: artificial sequence
<220> FEATURE:
<223> OTHER INFORMATION: synthetic nucleotide

<400> SEQUENCE: 30
uccaaaugua gucacuuuca a                                              21

<210> SEQ ID NO 31
<211> LENGTH: 21
<212> TYPE: RNA
<213> ORGANISM: artificial sequence
<220> FEATURE:
<223> OTHER INFORMATION: synthetic nucleotide

<400> SEQUENCE: 31
uccaaaugua gucacuuuca g                                              21

<210> SEQ ID NO 32
<211> LENGTH: 21
<212> TYPE: RNA
<213> ORGANISM: artificial sequence
<220> FEATURE:
<223> OTHER INFORMATION: synthetic nucleotide

<400> SEQUENCE: 32
uccaaaugua gucacuuuca a                                              21

<210> SEQ ID NO 33
<211> LENGTH: 21
<212> TYPE: RNA
<213> ORGANISM: artificial sequence
<220> FEATURE:
<223> OTHER INFORMATION: synthetic nucleotide

<400> SEQUENCE: 33
uuguaacuuu cagugcauug a                                              21

<210> SEQ ID NO 34
<211> LENGTH: 21
<212> TYPE: RNA
<213> ORGANISM: artificial sequence
<220> FEATURE:
<223> OTHER INFORMATION: synthetic nucleotide

<400> SEQUENCE: 34
uagucacguu caaugcauug a                                              21

<210> SEQ ID NO 35
<211> LENGTH: 21
<212> TYPE: RNA
<213> ORGANISM: artificial sequence
<220> FEATURE:
<223> OTHER INFORMATION: synthetic nucleotide

<400> SEQUENCE: 35
```

-continued uuguuacuuu cagugcauug a                                          21

<210> SEQ ID NO 36
<211> LENGTH: 21
<212> TYPE: RNA
<213> ORGANISM: artificial sequence
<220> FEATURE:
<223> OTHER INFORMATION: synthetic nucleotide

<400> SEQUENCE: 36
cccugauguu gucacuuuca c                                          21

<210> SEQ ID NO 37
<211> LENGTH: 21
<212> TYPE: RNA
<213> ORGANISM: artificial sequence
<220> FEATURE:
<223> OTHER INFORMATION: synthetic nucleotide

<400> SEQUENCE: 37
uuguuacuua caaugcauug a                                          21

<210> SEQ ID NO 38
<211> LENGTH: 21
<212> TYPE: RNA
<213> ORGANISM: artificial sequence
<220> FEATURE:
<223> OTHER INFORMATION: synthetic nucleotide

<400> SEQUENCE: 38
uagucuuuuu caacgcauug a                                          21

<210> SEQ ID NO 39
<211> LENGTH: 22
<212> TYPE: RNA
<213> ORGANISM: artificial sequence
<220> FEATURE:
<223> OTHER INFORMATION: synthetic nucleotide

<400> SEQUENCE: 39
cuggaugcag agguauuauc ga                                         22

<210> SEQ ID NO 40
<211> LENGTH: 22
<212> TYPE: RNA
<213> ORGANISM: artificial sequence
<220> FEATURE:
<223> OTHER INFORMATION: synthetic nucleotide

<400> SEQUENCE: 40
cuggaugcag aggucuuauc ga                                         22

<210> SEQ ID NO 41
<211> LENGTH: 22
<212> TYPE: RNA
<213> ORGANISM: artificial sequence
<220> FEATURE:
<223> OTHER INFORMATION: synthetic nucleotide

<400> SEQUENCE: 41
cuggaugcag agguuuuauc ga                                         22

<210> SEQ ID NO 42
<211> LENGTH: 23
<212> TYPE: RNA

```
<213> ORGANISM: artificial sequence
<220> FEATURE:
<223> OTHER INFORMATION: synthetic nucleotide

<400> SEQUENCE: 42
aucgaguucc aaguccucuu caa                                              23

<210> SEQ ID NO 43
<211> LENGTH: 23
<212> TYPE: RNA
<213> ORGANISM: artificial sequence
<220> FEATURE:
<223> OTHER INFORMATION: synthetic nucleotide

<400> SEQUENCE: 43
aucgaguucc agguccucuu caa                                              23

<210> SEQ ID NO 44
<211> LENGTH: 23
<212> TYPE: RNA
<213> ORGANISM: artificial sequence
<220> FEATURE:
<223> OTHER INFORMATION: synthetic nucleotide

<400> SEQUENCE: 44
aucgaguucc aaguuucuu caa                                               23

<210> SEQ ID NO 45
<211> LENGTH: 21
<212> TYPE: RNA
<213> ORGANISM: artificial sequence
<220> FEATURE:
<223> OTHER INFORMATION: synthetic nucleotide

<400> SEQUENCE: 45
agcacguacc cugcuucucc a                                                21

<210> SEQ ID NO 46
<211> LENGTH: 21
<212> TYPE: RNA
<213> ORGANISM: artificial sequence
<220> FEATURE:
<223> OTHER INFORMATION: synthetic nucleotide

<400> SEQUENCE: 46
uuuacgugcc cugcuucucc a                                                21

<210> SEQ ID NO 47
<211> LENGTH: 21
<212> TYPE: RNA
<213> ORGANISM: artificial sequence
<220> FEATURE:
<223> OTHER INFORMATION: synthetic nucleotide

<400> SEQUENCE: 47
agcacguguc cuguuucucc a                                                21

<210> SEQ ID NO 48
<211> LENGTH: 21
<212> TYPE: RNA
<213> ORGANISM: artificial sequence
<220> FEATURE:
<223> OTHER INFORMATION: synthetic nucleotide

<400> SEQUENCE: 48
ucuacgugcc cugcuucucc a                                                21
```

<210> SEQ ID NO 49
<211> LENGTH: 21
<212> TYPE: RNA
<213> ORGANISM: artificial sequence
<220> FEATURE:
<223> OTHER INFORMATION: synthetic nucleotide

<400> SEQUENCE: 49
cucacgugac cugcuucucc g                                              21

<210> SEQ ID NO 50
<211> LENGTH: 21
<212> TYPE: RNA
<213> ORGANISM: artificial sequence
<220> FEATURE:
<223> OTHER INFORMATION: synthetic nucleotide

<400> SEQUENCE: 50
cgcacgugac cugcuucucc a                                              21

<210> SEQ ID NO 51
<211> LENGTH: 21
<212> TYPE: RNA
<213> ORGANISM: artificial sequence
<220> FEATURE:
<223> OTHER INFORMATION: synthetic nucleotide

<400> SEQUENCE: 51
cuuacguguc cugcuucucc a                                              21

<210> SEQ ID NO 52
<211> LENGTH: 21
<212> TYPE: RNA
<213> ORGANISM: artificial sequence
<220> FEATURE:
<223> OTHER INFORMATION: synthetic nucleotide

<400> SEQUENCE: 52
cuuacgugcc cugcuucucc a                                              21

<210> SEQ ID NO 53
<211> LENGTH: 21
<212> TYPE: RNA
<213> ORGANISM: artificial sequence
<220> FEATURE:
<223> OTHER INFORMATION: synthetic nucleotide

<400> SEQUENCE: 53
gccacgugca cugcuucucc a                                              21

<210> SEQ ID NO 54
<211> LENGTH: 21
<212> TYPE: RNA
<213> ORGANISM: artificial sequence
<220> FEATURE:
<223> OTHER INFORMATION: synthetic nucleotide

<400> SEQUENCE: 54
uugggaugaa gccugguccg g                                              21

<210> SEQ ID NO 55
<211> LENGTH: 21
<212> TYPE: RNA
<213> ORGANISM: artificial sequence
<220> FEATURE:

<223> OTHER INFORMATION: synthetic nucleotide

<400> SEQUENCE: 55
cugggaugaa gccugguccg g                                              21

<210> SEQ ID NO 56
<211> LENGTH: 21
<212> TYPE: RNA
<213> ORGANISM: artificial sequence
<220> FEATURE:
<223> OTHER INFORMATION: synthetic nucleotide

<400> SEQUENCE: 56
cuggaaugaa gccugguccg g                                              21

<210> SEQ ID NO 57
<211> LENGTH: 21
<212> TYPE: RNA
<213> ORGANISM: artificial sequence
<220> FEATURE:
<223> OTHER INFORMATION: synthetic nucleotide

<400> SEQUENCE: 57
ccgggaugaa gccugguccg g                                              21

<210> SEQ ID NO 58
<211> LENGTH: 21
<212> TYPE: RNA
<213> ORGANISM: artificial sequence
<220> FEATURE:
<223> OTHER INFORMATION: synthetic nucleotide

<400> SEQUENCE: 58
gagaucaggc uggcagcuug u                                              21

<210> SEQ ID NO 59
<211> LENGTH: 21
<212> TYPE: RNA
<213> ORGANISM: artificial sequence
<220> FEATURE:
<223> OTHER INFORMATION: synthetic nucleotide

<400> SEQUENCE: 59
uagaucaggc uggcagcuug u                                              21

<210> SEQ ID NO 60
<211> LENGTH: 21
<212> TYPE: RNA
<213> ORGANISM: artificial sequence
<220> FEATURE:
<223> OTHER INFORMATION: synthetic nucleotide

<400> SEQUENCE: 60
aagaucaggc uggcagcuug u                                              21

<210> SEQ ID NO 61
<211> LENGTH: 21
<212> TYPE: RNA
<213> ORGANISM: artificial sequence
<220> FEATURE:
<223> OTHER INFORMATION: synthetic nucleotide

<400> SEQUENCE: 61
uucccgagcu gcaucaagcu a                                              21

```
<210> SEQ ID NO 62
<211> LENGTH: 21
<212> TYPE: RNA
<213> ORGANISM: artificial sequence
<220> FEATURE:
<223> OTHER INFORMATION: synthetic nucleotide

<400> SEQUENCE: 62
aagggaaguc auccuuggcu g                                              21

<210> SEQ ID NO 63
<211> LENGTH: 21
<212> TYPE: RNA
<213> ORGANISM: artificial sequence
<220> FEATURE:
<223> OTHER INFORMATION: synthetic nucleotide

<400> SEQUENCE: 63
acgggaaguc auccuuggcu a                                              21

<210> SEQ ID NO 64
<211> LENGTH: 21
<212> TYPE: RNA
<213> ORGANISM: artificial sequence
<220> FEATURE:
<223> OTHER INFORMATION: synthetic nucleotide

<400> SEQUENCE: 64 agggggaaguc auccuuggcu a                                             21

<210> SEQ ID NO 65
<211> LENGTH: 21
<212> TYPE: RNA
<213> ORGANISM: artificial sequence
<220> FEATURE:
<223> OTHER INFORMATION: synthetic nucleotide

<400> SEQUENCE: 65
aggcaaauca ucuuuggcuc a                                              21

<210> SEQ ID NO 66
<211> LENGTH: 21
<212> TYPE: RNA
<213> ORGANISM: artificial sequence
<220> FEATURE:
<223> OTHER INFORMATION: synthetic nucleotide

<400> SEQUENCE: 66
gcggcaauuc auucuuggcu u                                              21

<210> SEQ ID NO 67
<211> LENGTH: 21
<212> TYPE: RNA
<213> ORGANISM: artificial sequence
<220> FEATURE:
<223> OTHER INFORMATION: synthetic nucleotide

<400> SEQUENCE: 67
ccggcaaauc auucuuggcu u                                              21

<210> SEQ ID NO 68
<211> LENGTH: 21
<212> TYPE: RNA
<213> ORGANISM: artificial sequence
<220> FEATURE:
<223> OTHER INFORMATION: synthetic nucleotide
```

```
<400> SEQUENCE: 68
aagggaaguc auccuuggcu a                                              21

<210> SEQ ID NO 69
<211> LENGTH: 21
<212> TYPE: RNA
<213> ORGANISM: artificial sequence
<220> FEATURE:
<223> OTHER INFORMATION: synthetic nucleotide

<400> SEQUENCE: 69
guggcaacuc auccuuggcu c                                              21

<210> SEQ ID NO 70
<211> LENGTH: 21
<212> TYPE: RNA
<213> ORGANISM: artificial sequence
<220> FEATURE:
<223> OTHER INFORMATION: synthetic nucleotide

<400> SEQUENCE: 70
ugggcaauuc auccuuggcu u                                              21

<210> SEQ ID NO 71
<211> LENGTH: 21
<212> TYPE: RNA
<213> ORGANISM: artificial sequence
<220> FEATURE:
<223> OTHER INFORMATION: synthetic nucleotide

<400> SEQUENCE: 71
auggcaaauc auccuuggcu u                                              21

<210> SEQ ID NO 72
<211> LENGTH: 21
<212> TYPE: RNA
<213> ORGANISM: artificial sequence
<220> FEATURE:
<223> OTHER INFORMATION: synthetic nucleotide

<400> SEQUENCE: 72
uagggaaguc auccuuggcu c                                              21

<210> SEQ ID NO 73
<211> LENGTH: 21
<212> TYPE: RNA
<213> ORGANISM: artificial sequence
<220> FEATURE:
<223> OTHER INFORMATION: synthetic nucleotide

<400> SEQUENCE: 73
cugggaaguc auccuuggcu c                                              21

<210> SEQ ID NO 74
<211> LENGTH: 21
<212> TYPE: RNA
<213> ORGANISM: artificial sequence
<220> FEATURE:
<223> OTHER INFORMATION: synthetic nucleotide

<400> SEQUENCE: 74
gauauuggcg cggcucaauc a                                              21

<210> SEQ ID NO 75
<211> LENGTH: 21
```

<212> TYPE: RNA
<213> ORGANISM: artificial sequence
<220> FEATURE:
<223> OTHER INFORMATION: synthetic nucleotide

<400> SEQUENCE: 75
cugcagcauc aucaggauuc u					21

<210> SEQ ID NO 76
<211> LENGTH: 21
<212> TYPE: RNA
<213> ORGANISM: artificial sequence
<220> FEATURE:
<223> OTHER INFORMATION: synthetic nucleotide

<400> SEQUENCE: 76
cagcagcauc aucaggauuc u					21

<210> SEQ ID NO 77
<211> LENGTH: 21
<212> TYPE: RNA
<213> ORGANISM: artificial sequence
<220> FEATURE:
<223> OTHER INFORMATION: synthetic nucleotide

<400> SEQUENCE: 77
augcagcauc aucaggauuc u					21

<210> SEQ ID NO 78
<211> LENGTH: 21
<212> TYPE: RNA
<213> ORGANISM: artificial sequence
<220> FEATURE:
<223> OTHER INFORMATION: synthetic nucleotide

<400> SEQUENCE: 78
uggcagcauc aucaggauuc u					21

<210> SEQ ID NO 79
<211> LENGTH: 21
<212> TYPE: RNA
<213> ORGANISM: artificial sequence
<220> FEATURE:
<223> OTHER INFORMATION: synthetic nucleotide

<400> SEQUENCE: 79
uuguagcauc aucaggauuc c					21

<210> SEQ ID NO 80
<211> LENGTH: 21
<212> TYPE: RNA
<213> ORGANISM: artificial sequence
<220> FEATURE:
<223> OTHER INFORMATION: synthetic nucleotide

<400> SEQUENCE: 80
uugcagcauc aucaggauuc c					21

<210> SEQ ID NO 81
<211> LENGTH: 21
<212> TYPE: RNA
<213> ORGANISM: artificial sequence
<220> FEATURE:
<223> OTHER INFORMATION: synthetic nucleotide

<400> SEQUENCE: 81 caggggacc cuucagucca a          21

<210> SEQ ID NO 82
<211> LENGTH: 21
<212> TYPE: RNA
<213> ORGANISM: artificial sequence
<220> FEATURE:
<223> OTHER INFORMATION: synthetic nucleotide

<400> SEQUENCE: 82
gagggguccc cuucagucca u          21

<210> SEQ ID NO 83
<211> LENGTH: 21
<212> TYPE: RNA
<213> ORGANISM: artificial sequence
<220> FEATURE:
<223> OTHER INFORMATION: synthetic nucleotide

<400> SEQUENCE: 83
gagggguccc cuucagucca g          21

<210> SEQ ID NO 84
<211> LENGTH: 21
<212> TYPE: RNA
<213> ORGANISM: artificial sequence
<220> FEATURE:
<223> OTHER INFORMATION: synthetic nucleotide

<400> SEQUENCE: 84 aaggggguacc cuucagucca g         21

<210> SEQ ID NO 85
<211> LENGTH: 21
<212> TYPE: RNA
<213> ORGANISM: artificial sequence
<220> FEATURE:
<223> OTHER INFORMATION: synthetic nucleotide

<400> SEQUENCE: 85 uaggggggacc cuucagucca a         21

<210> SEQ ID NO 86
<211> LENGTH: 21
<212> TYPE: RNA
<213> ORGANISM: artificial sequence
<220> FEATURE:
<223> OTHER INFORMATION: synthetic nucleotide

<400> SEQUENCE: 86 gaggggacccc cuucagucca g         21

<210> SEQ ID NO 87
<211> LENGTH: 21
<212> TYPE: RNA
<213> ORGANISM: artificial sequence
<220> FEATURE:
<223> OTHER INFORMATION: synthetic nucleotide

<400> SEQUENCE: 87
ucggggcaca cuucagucca a          21

<210> SEQ ID NO 88
<211> LENGTH: 21
<212> TYPE: RNA
<213> ORGANISM: artificial sequence

```
<220> FEATURE:
<223> OTHER INFORMATION: synthetic nucleotide

<400> SEQUENCE: 88
aaacaaugcg aucccuuugg a                                              21

<210> SEQ ID NO 89
<211> LENGTH: 21
<212> TYPE: RNA
<213> ORGANISM: artificial sequence
<220> FEATURE:
<223> OTHER INFORMATION: synthetic nucleotide

<400> SEQUENCE: 89
agaccaugcg aucccuuugg a                                              21

<210> SEQ ID NO 90
<211> LENGTH: 21
<212> TYPE: RNA
<213> ORGANISM: artificial sequence
<220> FEATURE:
<223> OTHER INFORMATION: synthetic nucleotide

<400> SEQUENCE: 90
ggucagagcg aucccuuugg c                                              21

<210> SEQ ID NO 91
<211> LENGTH: 21
<212> TYPE: RNA
<213> ORGANISM: artificial sequence
<220> FEATURE:
<223> OTHER INFORMATION: synthetic nucleotide

<400> SEQUENCE: 91
agacaaugcg aucccuuugg a                                              21

<210> SEQ ID NO 92
<211> LENGTH: 21
<212> TYPE: RNA
<213> ORGANISM: artificial sequence
<220> FEATURE:
<223> OTHER INFORMATION: synthetic nucleotide

<400> SEQUENCE: 92
ggagguugac agaaugccaa a                                              21

<210> SEQ ID NO 93
<211> LENGTH: 21
<212> TYPE: RNA
<213> ORGANISM: artificial sequence
<220> FEATURE:
<223> OTHER INFORMATION: synthetic nucleotide

<400> SEQUENCE: 93
gaguuccucc aaacacuuca u                                              21

<210> SEQ ID NO 94
<211> LENGTH: 21
<212> TYPE: RNA
<213> ORGANISM: artificial sequence
<220> FEATURE:
<223> OTHER INFORMATION: synthetic nucleotide

<400> SEQUENCE: 94
gaguuccucc aaacucuuca u                                              21
```

```
<210> SEQ ID NO 95
<211> LENGTH: 21
<212> TYPE: RNA
<213> ORGANISM: artificial sequence
<220> FEATURE:
<223> OTHER INFORMATION: synthetic nucleotide

<400> SEQUENCE: 95
aaguucuccc aaacacuuca a                                              21

<210> SEQ ID NO 96
<211> LENGTH: 22
<212> TYPE: RNA
<213> ORGANISM: artificial sequence
<220> FEATURE:
<223> OTHER INFORMATION: synthetic nucleotide

<400> SEQUENCE: 96
ucguucaaga aagccugugg aa                                             22

<210> SEQ ID NO 97
<211> LENGTH: 22
<212> TYPE: RNA
<213> ORGANISM: artificial sequence
<220> FEATURE:
<223> OTHER INFORMATION: synthetic nucleotide

<400> SEQUENCE: 97
ccguucaaga aagccugugg aa                                             22

<210> SEQ ID NO 98
<211> LENGTH: 22
<212> TYPE: RNA
<213> ORGANISM: artificial sequence
<220> FEATURE:
<223> OTHER INFORMATION: synthetic nucleotide

<400> SEQUENCE: 98
ucguucaaga aagcaugugg aa                                             22

<210> SEQ ID NO 99
<211> LENGTH: 22
<212> TYPE: RNA
<213> ORGANISM: artificial sequence
<220> FEATURE:
<223> OTHER INFORMATION: synthetic nucleotide

<400> SEQUENCE: 99
acguucaaga aagcuugugg aa                                             22

<210> SEQ ID NO 100
<211> LENGTH: 22
<212> TYPE: RNA
<213> ORGANISM: artificial sequence
<220> FEATURE:
<223> OTHER INFORMATION: synthetic nucleotide

<400> SEQUENCE: 100
ccguucaaga aagccugugg aa                                             22

<210> SEQ ID NO 101
<211> LENGTH: 21
<212> TYPE: RNA
<213> ORGANISM: artificial sequence
<220> FEATURE:
<223> OTHER INFORMATION: synthetic nucleotide
```

```
<400> SEQUENCE: 101
aaucaaugcu gcacucaaug a                                              21

<210> SEQ ID NO 102
<211> LENGTH: 21
<212> TYPE: RNA
<213> ORGANISM: artificial sequence
<220> FEATURE:
<223> OTHER INFORMATION: synthetic nucleotide

<400> SEQUENCE: 102
agucaacgcu gcacuuaaug a                                              21

<210> SEQ ID NO 103
<211> LENGTH: 21
<212> TYPE: RNA
<213> ORGANISM: artificial sequence
<220> FEATURE:
<223> OTHER INFORMATION: synthetic nucleotide

<400> SEQUENCE: 103
aaucaaugcu gcacuuaaug a                                              21

<210> SEQ ID NO 104
<211> LENGTH: 21
<212> TYPE: RNA
<213> ORGANISM: artificial sequence
<220> FEATURE:
<223> OTHER INFORMATION: synthetic nucleotide

<400> SEQUENCE: 104 aaggguuuc cugagaucac a                                               21

<210> SEQ ID NO 105
<211> LENGTH: 22
<212> TYPE: RNA
<213> ORGANISM: artificial sequence
<220> FEATURE:
<223> OTHER INFORMATION: synthetic nucleotide

<400> SEQUENCE: 105
ugcgggugac cugggaaaca ua                                             22

<210> SEQ ID NO 106
<211> LENGTH: 22
<212> TYPE: RNA
<213> ORGANISM: artificial sequence
<220> FEATURE:
<223> OTHER INFORMATION: synthetic nucleotide

<400> SEQUENCE: 106
aaggugugac cugagaauca ca                                             22

<210> SEQ ID NO 107
<211> LENGTH: 22
<212> TYPE: RNA
<213> ORGANISM: artificial sequence
<220> FEATURE:
<223> OTHER INFORMATION: synthetic nucleotide

<400> SEQUENCE: 107
gugauuuuuc ucaacaagcg aa                                             22

<210> SEQ ID NO 108
```

```
<211> LENGTH: 22
<212> TYPE: RNA
<213> ORGANISM: artificial sequence
<220> FEATURE:
<223> OTHER INFORMATION: synthetic nucleotide

<400> SEQUENCE: 108
gugauuuuuc ucuacaagcg aa                                              22

<210> SEQ ID NO 109
<211> LENGTH: 22
<212> TYPE: RNA
<213> ORGANISM: artificial sequence
<220> FEATURE:
<223> OTHER INFORMATION: synthetic nucleotide

<400> SEQUENCE: 109
gugauuuuuc ucuccaagcg aa                                              22

<210> SEQ ID NO 110
<211> LENGTH: 21
<212> TYPE: RNA
<213> ORGANISM: artificial sequence
<220> FEATURE:
<223> OTHER INFORMATION: synthetic nucleotide

<400> SEQUENCE: 110
uagggcauau cuccuuuggc a                                               21

<210> SEQ ID NO 111
<211> LENGTH: 21
<212> TYPE: RNA
<213> ORGANISM: artificial sequence
<220> FEATURE:
<223> OTHER INFORMATION: synthetic nucleotide

<400> SEQUENCE: 111
uugggcaaau cuccuuuggc a                                               21

<210> SEQ ID NO 112
<211> LENGTH: 21
<212> TYPE: RNA
<213> ORGANISM: artificial sequence
<220> FEATURE:
<223> OTHER INFORMATION: synthetic nucleotide

<400> SEQUENCE: 112
ucgagcaaau cuccuuuggc a                                               21

<210> SEQ ID NO 113
<211> LENGTH: 21
<212> TYPE: RNA
<213> ORGANISM: artificial sequence
<220> FEATURE:
<223> OTHER INFORMATION: synthetic nucleotide

<400> SEQUENCE: 113
uagagcaaau cuccuuuggc a                                               21

<210> SEQ ID NO 114
<211> LENGTH: 21
<212> TYPE: RNA
<213> ORGANISM: artificial sequence
<220> FEATURE:
<223> OTHER INFORMATION: synthetic nucleotide

<400> SEQUENCE: 114
```

-continued uagggcaaau cuucuuuggc a                                21

<210> SEQ ID NO 115
<211> LENGTH: 21
<212> TYPE: RNA
<213> ORGANISM: artificial sequence
<220> FEATURE:
<223> OTHER INFORMATION: synthetic nucleotide

<400> SEQUENCE: 115
uagggcaaau cuccuuuggc a                                21

<210> SEQ ID NO 116
<211> LENGTH: 21
<212> TYPE: RNA
<213> ORGANISM: artificial sequence
<220> FEATURE:
<223> OTHER INFORMATION: synthetic nucleotide

<400> SEQUENCE: 116
cugggcaaau cuccuuuggc a                                21

<210> SEQ ID NO 117
<211> LENGTH: 21
<212> TYPE: RNA
<213> ORGANISM: artificial sequence
<220> FEATURE:
<223> OTHER INFORMATION: synthetic nucleotide

<400> SEQUENCE: 117
ucgggcaaau cuccuuuggc a                                21

<210> SEQ ID NO 118
<211> LENGTH: 21
<212> TYPE: RNA
<213> ORGANISM: artificial sequence
<220> FEATURE:
<223> OTHER INFORMATION: synthetic nucleotide

<400> SEQUENCE: 118
ccgggcaaau cuccuuuggc a                                21

<210> SEQ ID NO 119
<211> LENGTH: 21
<212> TYPE: RNA
<213> ORGANISM: artificial sequence
<220> FEATURE:
<223> OTHER INFORMATION: synthetic nucleotide

<400> SEQUENCE: 119
gcgggcaaau cuucuuuggc a                                21

<210> SEQ ID NO 120
<211> LENGTH: 21
<212> TYPE: RNA
<213> ORGANISM: artificial sequence
<220> FEATURE:
<223> OTHER INFORMATION: synthetic nucleotide

<400> SEQUENCE: 120
aagggcaaau cuccuuuggc a                                21

<210> SEQ ID NO 121
<211> LENGTH: 21
<212> TYPE: RNA

<213> ORGANISM: artificial sequence
<220> FEATURE:
<223> OTHER INFORMATION: synthetic nucleotide

<400> SEQUENCE: 121
uagggcaaau cuccuuuggc g                                            21

<210> SEQ ID NO 122
<211> LENGTH: 21
<212> TYPE: RNA
<213> ORGANISM: artificial sequence
<220> FEATURE:
<223> OTHER INFORMATION: synthetic nucleotide

<400> SEQUENCE: 122
cugggcaaau cuccuuuggc g                                            21

<210> SEQ ID NO 123
<211> LENGTH: 21
<212> TYPE: RNA
<213> ORGANISM: artificial sequence
<220> FEATURE:
<223> OTHER INFORMATION: synthetic nucleotide

<400> SEQUENCE: 123
uucggcaaau cuccuuuggc a                                            21

<210> SEQ ID NO 124
<211> LENGTH: 22
<212> TYPE: RNA
<213> ORGANISM: artificial sequence
<220> FEATURE:
<223> OTHER INFORMATION: synthetic nucleotide

<400> SEQUENCE: 124
ggaguuugug cgugaaucua au                                           22

<210> SEQ ID NO 125
<211> LENGTH: 22
<212> TYPE: RNA
<213> ORGANISM: artificial sequence
<220> FEATURE:
<223> OTHER INFORMATION: synthetic nucleotide

<400> SEQUENCE: 125
cuugucuauc ccuccugagc ua                                           22

<210> SEQ ID NO 126
<211> LENGTH: 22
<212> TYPE: RNA
<213> ORGANISM: artificial sequence
<220> FEATURE:
<223> OTHER INFORMATION: synthetic nucleotide

<400> SEQUENCE: 126
uaugucuauc ccuucugagc ug                                           22

<210> SEQ ID NO 127
<211> LENGTH: 22
<212> TYPE: RNA
<213> ORGANISM: artificial sequence
<220> FEATURE:
<223> OTHER INFORMATION: synthetic nucleotide

<400> SEQUENCE: 127
uaugucuauc ccuucugagc ua                                           22

-continued

```
<210> SEQ ID NO 128
<211> LENGTH: 22
<212> TYPE: RNA
<213> ORGANISM: artificial sequence
<220> FEATURE:
<223> OTHER INFORMATION: synthetic nucleotide

<400> SEQUENCE: 128 uaugcuauc ccuucugagc ug                                           22

<210> SEQ ID NO 129
<211> LENGTH: 22
<212> TYPE: RNA
<213> ORGANISM: artificial sequence
<220> FEATURE:
<223> OTHER INFORMATION: synthetic nucleotide

<400> SEQUENCE: 129
ucggucuauc ccuccugagc ug                                          22

<210> SEQ ID NO 130
<211> LENGTH: 22
<212> TYPE: RNA
<213> ORGANISM: artificial sequence
<220> FEATURE:
<223> OTHER INFORMATION: synthetic nucleotide

<400> SEQUENCE: 130 uuagcuauc ccuccugagc ua                                           22

<210> SEQ ID NO 131
<211> LENGTH: 22
<212> TYPE: RNA
<213> ORGANISM: artificial sequence
<220> FEATURE:
<223> OTHER INFORMATION: synthetic nucleotide

<400> SEQUENCE: 131
auugccuauc ccuccugagc ug                                          22

<210> SEQ ID NO 132
<211> LENGTH: 22
<212> TYPE: RNA
<213> ORGANISM: artificial sequence
<220> FEATURE:
<223> OTHER INFORMATION: synthetic nucleotide

<400> SEQUENCE: 132
ccuugcuauc ccuccugagc ug                                          22

<210> SEQ ID NO 133
<211> LENGTH: 22
<212> TYPE: RNA
<213> ORGANISM: artificial sequence
<220> FEATURE:
<223> OTHER INFORMATION: synthetic nucleotide

<400> SEQUENCE: 133 cuugcuauc ccuccugagc ug                                           22

<210> SEQ ID NO 134
<211> LENGTH: 22
<212> TYPE: RNA
<213> ORGANISM: artificial sequence
<220> FEATURE:
```

<223> OTHER INFORMATION: synthetic nucleotide

<400> SEQUENCE: 134
cccuucuauc ccuccugagc ua                                        22

<210> SEQ ID NO 135
<211> LENGTH: 22
<212> TYPE: RNA
<213> ORGANISM: artificial sequence
<220> FEATURE:
<223> OTHER INFORMATION: synthetic nucleotide

<400> SEQUENCE: 135
cuugucuauc ccuccugagc ua                                        22

<210> SEQ ID NO 136
<211> LENGTH: 22
<212> TYPE: RNA
<213> ORGANISM: artificial sequence
<220> FEATURE:
<223> OTHER INFORMATION: synthetic nucleotide

<400> SEQUENCE: 136
cccuucuauc ccuccugagc ua                                        22

<210> SEQ ID NO 137
<211> LENGTH: 22
<212> TYPE: RNA
<213> ORGANISM: artificial sequence
<220> FEATURE:
<223> OTHER INFORMATION: synthetic nucleotide

<400> SEQUENCE: 137
cccuucuauc ccuccugagc ua                                        22

<210> SEQ ID NO 138
<211> LENGTH: 22
<212> TYPE: RNA
<213> ORGANISM: artificial sequence
<220> FEATURE:
<223> OTHER INFORMATION: synthetic nucleotide

<400> SEQUENCE: 138
ccuuucuauc ccuccugagc ua                                        22

<210> SEQ ID NO 139
<211> LENGTH: 22
<212> TYPE: RNA
<213> ORGANISM: artificial sequence
<220> FEATURE:
<223> OTHER INFORMATION: synthetic nucleotide

<400> SEQUENCE: 139
ccugucuauc ccuccugagc ua                                        22

<210> SEQ ID NO 140
<211> LENGTH: 22
<212> TYPE: RNA
<213> ORGANISM: artificial sequence
<220> FEATURE:
<223> OTHER INFORMATION: synthetic nucleotide

<400> SEQUENCE: 140
ugugucuauc ccuccugagc ua                                        22

```
<210> SEQ ID NO 141
<211> LENGTH: 21
<212> TYPE: RNA
<213> ORGANISM: artificial sequence
<220> FEATURE:
<223> OTHER INFORMATION: synthetic nucleotide

<400> SEQUENCE: 141
ugacaaacau cucgucccca a                                            21

<210> SEQ ID NO 142
<211> LENGTH: 21
<212> TYPE: RNA
<213> ORGANISM: artificial sequence
<220> FEATURE:
<223> OTHER INFORMATION: synthetic nucleotide

<400> SEQUENCE: 142
ugacaaacau cucguuccua a                                            21

<210> SEQ ID NO 143
<211> LENGTH: 21
<212> TYPE: RNA
<213> ORGANISM: artificial sequence
<220> FEATURE:
<223> OTHER INFORMATION: synthetic nucleotide

<400> SEQUENCE: 143
aagcucagga gggauagcgc c                                            21

<210> SEQ ID NO 144
<211> LENGTH: 21
<212> TYPE: RNA
<213> ORGANISM: artificial sequence
<220> FEATURE:
<223> OTHER INFORMATION: synthetic nucleotide

<400> SEQUENCE: 144
uucgcaggag agauagcgcc a                                            21

<210> SEQ ID NO 145
<211> LENGTH: 22
<212> TYPE: RNA
<213> ORGANISM: artificial sequence
<220> FEATURE:
<223> OTHER INFORMATION: synthetic nucleotide

<400> SEQUENCE: 145
auuagauuca cgcacaaacu cg                                           22

<210> SEQ ID NO 146
<211> LENGTH: 22
<212> TYPE: RNA
<213> ORGANISM: artificial sequence
<220> FEATURE:
<223> OTHER INFORMATION: synthetic nucleotide

<400> SEQUENCE: 146
uuggggacga gauguuuugu ug                                           22

<210> SEQ ID NO 147
<211> LENGTH: 22
<212> TYPE: RNA
<213> ORGANISM: artificial sequence
<220> FEATURE:
<223> OTHER INFORMATION: synthetic nucleotide
```

<400> SEQUENCE: 147
gagccgacau guugugcaac uu								22

<210> SEQ ID NO 148
<211> LENGTH: 22
<212> TYPE: RNA
<213> ORGANISM: artificial sequence
<220> FEATURE:
<223> OTHER INFORMATION: synthetic nucleotide

<400> SEQUENCE: 148
aauggaagcc uugucagcuu au								22

<210> SEQ ID NO 149
<211> LENGTH: 22
<212> TYPE: RNA
<213> ORGANISM: artificial sequence
<220> FEATURE:
<223> OTHER INFORMATION: synthetic nucleotide

<400> SEQUENCE: 149
uaaagucaau aauaccuuga ag								22

<210> SEQ ID NO 150
<211> LENGTH: 20
<212> TYPE: RNA
<213> ORGANISM: artificial sequence
<220> FEATURE:
<223> OTHER INFORMATION: synthetic nucleotide

<400> SEQUENCE: 150
uauaagccau cuuacuaguu								20

<210> SEQ ID NO 151
<211> LENGTH: 22
<212> TYPE: RNA
<213> ORGANISM: artificial sequence
<220> FEATURE:
<223> OTHER INFORMATION: synthetic nucleotide

<400> SEQUENCE: 151
uucugcuaug uugcugcuca uu								22

<210> SEQ ID NO 152
<211> LENGTH: 22
<212> TYPE: RNA
<213> ORGANISM: artificial sequence
<220> FEATURE:
<223> OTHER INFORMATION: synthetic nucleotide

<400> SEQUENCE: 152
ucuaagucuu cuauugaugu uc								22

<210> SEQ ID NO 153
<211> LENGTH: 22
<212> TYPE: RNA
<213> ORGANISM: artificial sequence
<220> FEATURE:
<223> OTHER INFORMATION: synthetic nucleotide

<400> SEQUENCE: 153
cugucuucuc aacuucaugu ga								22

<210> SEQ ID NO 154
<211> LENGTH: 21

```
<212> TYPE: RNA
<213> ORGANISM: artificial sequence
<220> FEATURE:
<223> OTHER INFORMATION: synthetic nucleotide

<400> SEQUENCE: 154
cggcucugau accaauugau g                                              21

<210> SEQ ID NO 155
<211> LENGTH: 20
<212> TYPE: RNA
<213> ORGANISM: artificial sequence
<220> FEATURE:
<223> OTHER INFORMATION: synthetic nucleotide

<400> SEQUENCE: 155
ugacagaaga gagugagcac                                                20

<210> SEQ ID NO 156
<211> LENGTH: 21
<212> TYPE: RNA
<213> ORGANISM: artificial sequence
<220> FEATURE:
<223> OTHER INFORMATION: synthetic nucleotide

<400> SEQUENCE: 156
cgacagaaga gagugagcac a                                              21

<210> SEQ ID NO 157
<211> LENGTH: 21
<212> TYPE: RNA
<213> ORGANISM: artificial sequence
<220> FEATURE:
<223> OTHER INFORMATION: synthetic nucleotide

<400> SEQUENCE: 157
uugacagaag aaagagagca c                                              21

<210> SEQ ID NO 158
<211> LENGTH: 21
<212> TYPE: RNA
<213> ORGANISM: artificial sequence
<220> FEATURE:
<223> OTHER INFORMATION: synthetic nucleotide

<400> SEQUENCE: 158
uugacagaag auagagagca c                                              21

<210> SEQ ID NO 159
<211> LENGTH: 20
<212> TYPE: RNA
<213> ORGANISM: artificial sequence
<220> FEATURE:
<223> OTHER INFORMATION: synthetic nucleotide

<400> SEQUENCE: 159
ucccaaaugu agacaaagca                                                20

<210> SEQ ID NO 160
<211> LENGTH: 20
<212> TYPE: RNA
<213> ORGANISM: artificial sequence
<220> FEATURE:
<223> OTHER INFORMATION: synthetic nucleotide

<400> SEQUENCE: 160
```

-continued ccccaaaugu agacaaagca                    20

<210> SEQ ID NO 161
<211> LENGTH: 21
<212> TYPE: RNA
<213> ORGANISM: artificial sequence
<220> FEATURE:
<223> OTHER INFORMATION: synthetic nucleotide

<400> SEQUENCE: 161
uuuggauuga agggagcucu a                  21

<210> SEQ ID NO 162
<211> LENGTH: 21
<212> TYPE: RNA
<213> ORGANISM: artificial sequence
<220> FEATURE:
<223> OTHER INFORMATION: synthetic nucleotide

<400> SEQUENCE: 162
uuuggauuga agggagcucu u                  21

<210> SEQ ID NO 163
<211> LENGTH: 21
<212> TYPE: RNA
<213> ORGANISM: artificial sequence
<220> FEATURE:
<223> OTHER INFORMATION: synthetic nucleotide

<400> SEQUENCE: 163
uuuggauuga agggagcucc u                  21

<210> SEQ ID NO 164
<211> LENGTH: 21
<212> TYPE: RNA
<213> ORGANISM: artificial sequence
<220> FEATURE:
<223> OTHER INFORMATION: synthetic nucleotide

<400> SEQUENCE: 164
uuggacugaa gggagcuccc u                  21

<210> SEQ ID NO 165
<211> LENGTH: 21
<212> TYPE: RNA
<213> ORGANISM: artificial sequence
<220> FEATURE:
<223> OTHER INFORMATION: synthetic nucleotide

<400> SEQUENCE: 165
uuggacugaa gggagcuccu u                  21

<210> SEQ ID NO 166
<211> LENGTH: 21
<212> TYPE: RNA
<213> ORGANISM: artificial sequence
<220> FEATURE:
<223> OTHER INFORMATION: synthetic nucleotide

<400> SEQUENCE: 166
ugccuggcuc ccuguaugcc a                  21

<210> SEQ ID NO 167
<211> LENGTH: 21
<212> TYPE: RNA
<213> ORGANISM: artificial sequence
<220> FEATURE:
<223> OTHER INFORMATION: synthetic nucleotide

<400> SEQUENCE: 167
uugaaaguga cuacaucggg g                                              21

<210> SEQ ID NO 168
<211> LENGTH: 21
<212> TYPE: RNA
<213> ORGANISM: artificial sequence
<220> FEATURE:
<223> OTHER INFORMATION: synthetic nucleotide

<400> SEQUENCE: 168
ucaaugcauu gaaagugacu a                                              21

<210> SEQ ID NO 169
<211> LENGTH: 21
<212> TYPE: RNA
<213> ORGANISM: artificial sequence
<220> FEATURE:
<223> OTHER INFORMATION: synthetic nucleotide

<400> SEQUENCE: 169
ucgauaaacc ucugcaucca g                                              21

<210> SEQ ID NO 170
<211> LENGTH: 24
<212> TYPE: RNA
<213> ORGANISM: artificial sequence
<220> FEATURE:
<223> OTHER INFORMATION: synthetic nucleotide

<400> SEQUENCE: 170
uugaagagga cuuggaacuu cgau                                           24

<210> SEQ ID NO 171
<211> LENGTH: 21
<212> TYPE: RNA
<213> ORGANISM: artificial sequence
<220> FEATURE:
<223> OTHER INFORMATION: synthetic nucleotide

<400> SEQUENCE: 171
uggagaagca gggcacgugc a                                              21

<210> SEQ ID NO 172
<211> LENGTH: 21
<212> TYPE: RNA
<213> ORGANISM: artificial sequence
<220> FEATURE:
<223> OTHER INFORMATION: synthetic nucleotide

<400> SEQUENCE: 172
uggagaagca gggcacgugc g                                              21

<210> SEQ ID NO 173
<211> LENGTH: 21
<212> TYPE: RNA
<213> ORGANISM: artificial sequence
<220> FEATURE:
<223> OTHER INFORMATION: synthetic nucleotide

<400> SEQUENCE: 173
ucggaccagg cuucauccccc c                                             21

<210> SEQ ID NO 174
<211> LENGTH: 21
<212> TYPE: RNA
<213> ORGANISM: artificial sequence
<220> FEATURE:
<223> OTHER INFORMATION: synthetic nucleotide

<400> SEQUENCE: 174
ucggaccagg cuucauuccc c                                    21

<210> SEQ ID NO 175
<211> LENGTH: 21
<212> TYPE: RNA
<213> ORGANISM: artificial sequence
<220> FEATURE:
<223> OTHER INFORMATION: synthetic nucleotide

<400> SEQUENCE: 175
ugaagcugcc agcaugaucu a                                    21

<210> SEQ ID NO 176
<211> LENGTH: 21
<212> TYPE: RNA
<213> ORGANISM: artificial sequence
<220> FEATURE:
<223> OTHER INFORMATION: synthetic nucleotide

<400> SEQUENCE: 176
uuaagcugcc agcaugaucu u                                    21

<210> SEQ ID NO 177
<211> LENGTH: 22
<212> TYPE: RNA
<213> ORGANISM: artificial sequence
<220> FEATURE:
<223> OTHER INFORMATION: synthetic nucleotide

<400> SEQUENCE: 177
ugaagcugcc agcaugaucu gg                                   22

<210> SEQ ID NO 178
<211> LENGTH: 21
<212> TYPE: RNA
<213> ORGANISM: artificial sequence
<220> FEATURE:
<223> OTHER INFORMATION: synthetic nucleotide

<400> SEQUENCE: 178
ucgcuuggug caggucggga a                                    21

<210> SEQ ID NO 179
<211> LENGTH: 21
<212> TYPE: RNA
<213> ORGANISM: artificial sequence
<220> FEATURE:
<223> OTHER INFORMATION: synthetic nucleotide

<400> SEQUENCE: 179
cagccaagga ugacuugccg a                                    21

<210> SEQ ID NO 180
<211> LENGTH: 21
<212> TYPE: RNA
<213> ORGANISM: artificial sequence
<220> FEATURE:
<223> OTHER INFORMATION: synthetic nucleotide -continued

```
<400> SEQUENCE: 180
cagccaagga ugacuugccg g                                              21

<210> SEQ ID NO 181
<211> LENGTH: 21
<212> TYPE: RNA
<213> ORGANISM: artificial sequence
<220> FEATURE:
<223> OTHER INFORMATION: synthetic nucleotide

<400> SEQUENCE: 181
ugagccaagg augacuugcc g                                              21

<210> SEQ ID NO 182
<211> LENGTH: 21
<212> TYPE: RNA
<213> ORGANISM: artificial sequence
<220> FEATURE:
<223> OTHER INFORMATION: synthetic nucleotide

<400> SEQUENCE: 182
uagccaagga ugacuugccu g                                              21

<210> SEQ ID NO 183
<211> LENGTH: 21
<212> TYPE: RNA
<213> ORGANISM: artificial sequence
<220> FEATURE:
<223> OTHER INFORMATION: synthetic nucleotide

<400> SEQUENCE: 183
ugauugagcc gugucaauau c                                              21

<210> SEQ ID NO 184
<211> LENGTH: 21
<212> TYPE: RNA
<213> ORGANISM: artificial sequence
<220> FEATURE:
<223> OTHER INFORMATION: synthetic nucleotide

<400> SEQUENCE: 184
ugauugagcc gcgccaauau c                                              21

<210> SEQ ID NO 185
<211> LENGTH: 21
<212> TYPE: RNA
<213> ORGANISM: artificial sequence
<220> FEATURE:
<223> OTHER INFORMATION: synthetic nucleotide

<400> SEQUENCE: 185
uugagccgug ccaauaucac g                                              21

<210> SEQ ID NO 186
<211> LENGTH: 21
<212> TYPE: RNA
<213> ORGANISM: artificial sequence
<220> FEATURE:
<223> OTHER INFORMATION: synthetic nucleotide

<400> SEQUENCE: 186
ugauugagcc gugccaauau c                                              21

<210> SEQ ID NO 187
```

```
<211> LENGTH: 21
<212> TYPE: RNA
<213> ORGANISM: artificial sequence
<220> FEATURE:
<223> OTHER INFORMATION: synthetic nucleotide

<400> SEQUENCE: 187
agaaucuuga ugaugcugca u                                              21

<210> SEQ ID NO 188
<211> LENGTH: 21
<212> TYPE: RNA
<213> ORGANISM: artificial sequence
<220> FEATURE:
<223> OTHER INFORMATION: synthetic nucleotide

<400> SEQUENCE: 188
agaaucuuga ugaugcugca g                                              21

<210> SEQ ID NO 189
<211> LENGTH: 21
<212> TYPE: RNA
<213> ORGANISM: artificial sequence
<220> FEATURE:
<223> OTHER INFORMATION: synthetic nucleotide

<400> SEQUENCE: 189
ggaaucuuga ugaugcugca u                                              21

<210> SEQ ID NO 190
<211> LENGTH: 22
<212> TYPE: RNA
<213> ORGANISM: artificial sequence
<220> FEATURE:
<223> OTHER INFORMATION: synthetic nucleotide

<400> SEQUENCE: 190
uucgcuugca gagagaaauc ac                                             22

<210> SEQ ID NO 191
<211> LENGTH: 21
<212> TYPE: RNA
<213> ORGANISM: artificial sequence
<220> FEATURE:
<223> OTHER INFORMATION: synthetic nucleotide

<400> SEQUENCE: 191
uccaaaggga ucgcauugau c                                              21

<210> SEQ ID NO 192
<211> LENGTH: 21
<212> TYPE: RNA
<213> ORGANISM: artificial sequence
<220> FEATURE:
<223> OTHER INFORMATION: synthetic nucleotide

<400> SEQUENCE: 192
uuuggcauuc uguccaccuc c                                              21

<210> SEQ ID NO 193
<211> LENGTH: 21
<212> TYPE: RNA
<213> ORGANISM: artificial sequence
<220> FEATURE:
<223> OTHER INFORMATION: synthetic nucleotide

<400> SEQUENCE: 193
``` cugaagguguu uggggggaacu c          21

```
<210> SEQ ID NO 194
<211> LENGTH: 21
<212> TYPE: RNA
<213> ORGANISM: artificial sequence
<220> FEATURE:
<223> OTHER INFORMATION: synthetic nucleotide

<400> SEQUENCE: 194
```
cugaaguguu uggggggacu c          21

```
<210> SEQ ID NO 195
<211> LENGTH: 21
<212> TYPE: RNA
<213> ORGANISM: artificial sequence
<220> FEATURE:
<223> OTHER INFORMATION: synthetic nucleotide

<400> SEQUENCE: 195
```
uuccacagcu uucuugaacu g          21

```
<210> SEQ ID NO 196
<211> LENGTH: 21
<212> TYPE: RNA
<213> ORGANISM: artificial sequence
<220> FEATURE:
<223> OTHER INFORMATION: synthetic nucleotide

<400> SEQUENCE: 196
```
uuccacagcu uucuugaacu u          21

```
<210> SEQ ID NO 197
<211> LENGTH: 21
<212> TYPE: RNA
<213> ORGANISM: artificial sequence
<220> FEATURE:
<223> OTHER INFORMATION: synthetic nucleotide

<400> SEQUENCE: 197
```
ucauugagug cagcguugau g          21

```
<210> SEQ ID NO 198
<211> LENGTH: 21
<212> TYPE: RNA
<213> ORGANISM: artificial sequence
<220> FEATURE:
<223> OTHER INFORMATION: synthetic nucleotide

<400> SEQUENCE: 198
```
ucauugagug caucguugau g          21

```
<210> SEQ ID NO 199
<211> LENGTH: 21
<212> TYPE: RNA
<213> ORGANISM: artificial sequence
<220> FEATURE:
<223> OTHER INFORMATION: synthetic nucleotide

<400> SEQUENCE: 199
```
uguguucuca ggucaccccu u          21

```
<210> SEQ ID NO 200
<211> LENGTH: 21
<212> TYPE: RNA
```

```
<213> ORGANISM: artificial sequence
<220> FEATURE:
<223> OTHER INFORMATION: synthetic nucleotide

<400> SEQUENCE: 200
uguguucuca ggucacccu g                                               21

<210> SEQ ID NO 201
<211> LENGTH: 21
<212> TYPE: RNA
<213> ORGANISM: artificial sequence
<220> FEATURE:
<223> OTHER INFORMATION: synthetic nucleotide

<400> SEQUENCE: 201
ugccaaagga gauuugcccu g                                              21

<210> SEQ ID NO 202
<211> LENGTH: 21
<212> TYPE: RNA
<213> ORGANISM: artificial sequence
<220> FEATURE:
<223> OTHER INFORMATION: synthetic nucleotide

<400> SEQUENCE: 202
ugccaaagga gaguugcccu g                                              21

<210> SEQ ID NO 203
<211> LENGTH: 21
<212> TYPE: RNA
<213> ORGANISM: artificial sequence
<220> FEATURE:
<223> OTHER INFORMATION: synthetic nucleotide

<400> SEQUENCE: 203
ugccaaagga gauuugcccc g                                              21

<210> SEQ ID NO 204
<211> LENGTH: 21
<212> TYPE: RNA
<213> ORGANISM: artificial sequence
<220> FEATURE:
<223> OTHER INFORMATION: synthetic nucleotide

<400> SEQUENCE: 204
ugccaaagga gauuugccuc g                                              21

<210> SEQ ID NO 205
<211> LENGTH: 21
<212> TYPE: RNA
<213> ORGANISM: artificial sequence
<220> FEATURE:
<223> OTHER INFORMATION: synthetic nucleotide

<400> SEQUENCE: 205
ugccaaagga gauuugcccg g                                              21

<210> SEQ ID NO 206
<211> LENGTH: 22
<212> TYPE: RNA
<213> ORGANISM: artificial sequence
<220> FEATURE:
<223> OTHER INFORMATION: synthetic nucleotide

<400> SEQUENCE: 206
uuggggacga caucuuuugu ug                                             22
```

<210> SEQ ID NO 207
<211> LENGTH: 21
<212> TYPE: RNA
<213> ORGANISM: artificial sequence
<220> FEATURE:
<223> OTHER INFORMATION: synthetic nucleotide

<400> SEQUENCE: 207
uugacagaag agagugagca c                                              21

<210> SEQ ID NO 208
<211> LENGTH: 21
<212> TYPE: RNA
<213> ORGANISM: artificial sequence
<220> FEATURE:
<223> OTHER INFORMATION: synthetic nucleotide

<400> SEQUENCE: 208
gugacagaag agagugagca c                                              21

<210> SEQ ID NO 209
<211> LENGTH: 20
<212> TYPE: RNA
<213> ORGANISM: artificial sequence
<220> FEATURE:
<223> OTHER INFORMATION: synthetic nucleotide

<400> SEQUENCE: 209
ugacagaaga uagagagcac                                                20

<210> SEQ ID NO 210
<211> LENGTH: 21
<212> TYPE: RNA
<213> ORGANISM: artificial sequence
<220> FEATURE:
<223> OTHER INFORMATION: synthetic nucleotide

<400> SEQUENCE: 210
cugacagaag auagagagca c                                              21

<210> SEQ ID NO 211
<211> LENGTH: 21
<212> TYPE: RNA
<213> ORGANISM: artificial sequence
<220> FEATURE:
<223> OTHER INFORMATION: synthetic nucleotide

<400> SEQUENCE: 211
gcucucuagc cuucugucau c                                              21

<210> SEQ ID NO 212
<211> LENGTH: 21
<212> TYPE: RNA
<213> ORGANISM: artificial sequence
<220> FEATURE:
<223> OTHER INFORMATION: synthetic nucleotide

<400> SEQUENCE: 212
cuuugucuac aauuuuggaa a                                              21

<210> SEQ ID NO 213
<211> LENGTH: 20
<212> TYPE: RNA
<213> ORGANISM: artificial sequence
<220> FEATURE:

<223> OTHER INFORMATION: synthetic nucleotide

<400> SEQUENCE: 213 cuugucuac aauuuuggaa                                        20

<210> SEQ ID NO 214
<211> LENGTH: 22
<212> TYPE: RNA
<213> ORGANISM: artificial sequence
<220> FEATURE:
<223> OTHER INFORMATION: synthetic nucleotide

<400> SEQUENCE: 214 cuugucuac aauuuuggaa aa                                     22

<210> SEQ ID NO 215
<211> LENGTH: 21
<212> TYPE: RNA
<213> ORGANISM: artificial sequence
<220> FEATURE:
<223> OTHER INFORMATION: synthetic nucleotide

<400> SEQUENCE: 215
ucuuuggauu gaagggagcu c                                     21

<210> SEQ ID NO 216
<211> LENGTH: 20
<212> TYPE: RNA
<213> ORGANISM: artificial sequence
<220> FEATURE:
<223> OTHER INFORMATION: synthetic nucleotide

<400> SEQUENCE: 216
uuuggauuga agggagcucu                                       20

<210> SEQ ID NO 217
<211> LENGTH: 20
<212> TYPE: RNA
<213> ORGANISM: artificial sequence
<220> FEATURE:
<223> OTHER INFORMATION: synthetic nucleotide

<400> SEQUENCE: 217
uuggauugaa gggagcucua                                       20

<210> SEQ ID NO 218
<211> LENGTH: 22
<212> TYPE: RNA
<213> ORGANISM: artificial sequence
<220> FEATURE:
<223> OTHER INFORMATION: synthetic nucleotide

<400> SEQUENCE: 218
ugccuggcuc ccuguaugcc au                                    22

<210> SEQ ID NO 219
<211> LENGTH: 20
<212> TYPE: RNA
<213> ORGANISM: artificial sequence
<220> FEATURE:
<223> OTHER INFORMATION: synthetic nucleotide

<400> SEQUENCE: 219
gccuggcucc cuguaugcca                                       20

```
<210> SEQ ID NO 220
<211> LENGTH: 21
<212> TYPE: RNA
<213> ORGANISM: artificial sequence
<220> FEATURE:
<223> OTHER INFORMATION: synthetic nucleotide

<400> SEQUENCE: 220
cguacaagga gucaagcaug a                                              21

<210> SEQ ID NO 221
<211> LENGTH: 20
<212> TYPE: RNA
<213> ORGANISM: artificial sequence
<220> FEATURE:
<223> OTHER INFORMATION: synthetic nucleotide

<400> SEQUENCE: 221
ugaaagugac uacaucgggg                                                20

<210> SEQ ID NO 222
<211> LENGTH: 21
<212> TYPE: RNA
<213> ORGANISM: artificial sequence
<220> FEATURE:
<223> OTHER INFORMATION: synthetic nucleotide

<400> SEQUENCE: 222
ugaaagugac uacaucgggg u                                              21

<210> SEQ ID NO 223
<211> LENGTH: 22
<212> TYPE: RNA
<213> ORGANISM: artificial sequence
<220> FEATURE:
<223> OTHER INFORMATION: synthetic nucleotide

<400> SEQUENCE: 223
ucaaugcauu gaaagugacu ac                                             22

<210> SEQ ID NO 224
<211> LENGTH: 20
<212> TYPE: RNA
<213> ORGANISM: artificial sequence
<220> FEATURE:
<223> OTHER INFORMATION: synthetic nucleotide

<400> SEQUENCE: 224
ucaaugcauu gaaagugacu                                                20

<210> SEQ ID NO 225
<211> LENGTH: 20
<212> TYPE: RNA
<213> ORGANISM: artificial sequence
<220> FEATURE:
<223> OTHER INFORMATION: synthetic nucleotide

<400> SEQUENCE: 225
caaugcauug aaagugacua                                                20

<210> SEQ ID NO 226
<211> LENGTH: 21
<212> TYPE: RNA
<213> ORGANISM: artificial sequence
<220> FEATURE:
<223> OTHER INFORMATION: synthetic nucleotide
```

```
<400> SEQUENCE: 226
cacguguucu acuacuccaa c                                              21

<210> SEQ ID NO 227
<211> LENGTH: 22
<212> TYPE: RNA
<213> ORGANISM: artificial sequence
<220> FEATURE:
<223> OTHER INFORMATION: synthetic nucleotide

<400> SEQUENCE: 227
ucggaccagg cuucauuccc cc                                             22

<210> SEQ ID NO 228
<211> LENGTH: 22
<212> TYPE: RNA
<213> ORGANISM: artificial sequence
<220> FEATURE:
<223> OTHER INFORMATION: synthetic nucleotide

<400> SEQUENCE: 228
uucggaccag gcuucauucc cc                                             22

<210> SEQ ID NO 229
<211> LENGTH: 21
<212> TYPE: RNA
<213> ORGANISM: artificial sequence
<220> FEATURE:
<223> OTHER INFORMATION: synthetic nucleotide

<400> SEQUENCE: 229
uucggaccag gcuucauucc c                                              21

<210> SEQ ID NO 230
<211> LENGTH: 21
<212> TYPE: RNA
<213> ORGANISM: artificial sequence
<220> FEATURE:
<223> OTHER INFORMATION: synthetic nucleotide

<400> SEQUENCE: 230
ggacuguugu cuggcucgag g                                              21

<210> SEQ ID NO 231
<211> LENGTH: 20
<212> TYPE: RNA
<213> ORGANISM: artificial sequence
<220> FEATURE:
<223> OTHER INFORMATION: synthetic nucleotide

<400> SEQUENCE: 231
ugaagcugcc agcaugaucu                                                20

<210> SEQ ID NO 232
<211> LENGTH: 20
<212> TYPE: RNA
<213> ORGANISM: artificial sequence
<220> FEATURE:
<223> OTHER INFORMATION: synthetic nucleotide

<400> SEQUENCE: 232
gaagcugcca gcaugaucua                                                20

<210> SEQ ID NO 233
<211> LENGTH: 22
```

```
<212> TYPE: RNA
<213> ORGANISM: artificial sequence
<220> FEATURE:
<223> OTHER INFORMATION: synthetic nucleotide

<400> SEQUENCE: 233
augaagcugc cagcaugauc ua                                              22

<210> SEQ ID NO 234
<211> LENGTH: 22
<212> TYPE: RNA
<213> ORGANISM: artificial sequence
<220> FEATURE:
<223> OTHER INFORMATION: synthetic nucleotide

<400> SEQUENCE: 234
ugaagcugcc agcaugaucu au                                              22

<210> SEQ ID NO 235
<211> LENGTH: 22
<212> TYPE: RNA
<213> ORGANISM: artificial sequence
<220> FEATURE:
<223> OTHER INFORMATION: synthetic nucleotide

<400> SEQUENCE: 235
gugaagcugc cagcaugauc ua                                              22

<210> SEQ ID NO 236
<211> LENGTH: 21
<212> TYPE: RNA
<213> ORGANISM: artificial sequence
<220> FEATURE:
<223> OTHER INFORMATION: synthetic nucleotide

<400> SEQUENCE: 236
ugaagcugcc agcaugaucu g                                               21

<210> SEQ ID NO 237
<211> LENGTH: 21
<212> TYPE: RNA
<213> ORGANISM: artificial sequence
<220> FEATURE:
<223> OTHER INFORMATION: synthetic nucleotide

<400> SEQUENCE: 237
cccgccuugc aucaacugaa u                                               21

<210> SEQ ID NO 238
<211> LENGTH: 20
<212> TYPE: RNA
<213> ORGANISM: artificial sequence
<220> FEATURE:
<223> OTHER INFORMATION: synthetic nucleotide

<400> SEQUENCE: 238
cccgccuugc aucaacugaa                                                 20

<210> SEQ ID NO 239
<211> LENGTH: 21
<212> TYPE: RNA
<213> ORGANISM: artificial sequence
<220> FEATURE:
<223> OTHER INFORMATION: synthetic nucleotide

<400> SEQUENCE: 239
```

```
ucccgccuug caucaacuga a                                              21

<210> SEQ ID NO 240
<211> LENGTH: 20
<212> TYPE: RNA
<213> ORGANISM: artificial sequence
<220> FEATURE:
<223> OTHER INFORMATION: synthetic nucleotide

<400> SEQUENCE: 240
cagccaagga ugacuugccg                                                20

<210> SEQ ID NO 241
<211> LENGTH: 21
<212> TYPE: RNA
<213> ORGANISM: artificial sequence
<220> FEATURE:
<223> OTHER INFORMATION: synthetic nucleotide

<400> SEQUENCE: 241
ugcagccaag gaugacuugc c                                              21

<210> SEQ ID NO 242
<211> LENGTH: 20
<212> TYPE: RNA
<213> ORGANISM: artificial sequence
<220> FEATURE:
<223> OTHER INFORMATION: synthetic nucleotide

<400> SEQUENCE: 242
agccaaggau gacuugccgg                                                20

<210> SEQ ID NO 243
<211> LENGTH: 22
<212> TYPE: RNA
<213> ORGANISM: artificial sequence
<220> FEATURE:
<223> OTHER INFORMATION: synthetic nucleotide

<400> SEQUENCE: 243
cagccaagga ugacuugccg au                                             22

<210> SEQ ID NO 244
<211> LENGTH: 21
<212> TYPE: RNA
<213> ORGANISM: artificial sequence
<220> FEATURE:
<223> OTHER INFORMATION: synthetic nucleotide

<400> SEQUENCE: 244
gcagccaagg augacuugcc g                                              21

<210> SEQ ID NO 245
<211> LENGTH: 20
<212> TYPE: RNA
<213> ORGANISM: artificial sequence
<220> FEATURE:
<223> OTHER INFORMATION: synthetic nucleotide

<400> SEQUENCE: 245
agccaaggau gacuugccga                                                20

<210> SEQ ID NO 246
<211> LENGTH: 21
<212> TYPE: RNA
<213> ORGANISM: artificial sequence
```

-continued

```
<220> FEATURE:
<223> OTHER INFORMATION: synthetic nucleotide

<400> SEQUENCE: 246
agccaaggau gacuugccga u                                              21

<210> SEQ ID NO 247
<211> LENGTH: 22
<212> TYPE: RNA
<213> ORGANISM: artificial sequence
<220> FEATURE:
<223> OTHER INFORMATION: synthetic nucleotide

<400> SEQUENCE: 247
cagccaagga ugacuugccg gu                                             22

<210> SEQ ID NO 248
<211> LENGTH: 21
<212> TYPE: RNA
<213> ORGANISM: artificial sequence
<220> FEATURE:
<223> OTHER INFORMATION: synthetic nucleotide

<400> SEQUENCE: 248
agccaaggau gacuugccgg a                                              21

<210> SEQ ID NO 249
<211> LENGTH: 21
<212> TYPE: RNA
<213> ORGANISM: artificial sequence
<220> FEATURE:
<223> OTHER INFORMATION: synthetic nucleotide

<400> SEQUENCE: 249
agccaaggau gacuugccgg u                                              21

<210> SEQ ID NO 250
<211> LENGTH: 22
<212> TYPE: RNA
<213> ORGANISM: artificial sequence
<220> FEATURE:
<223> OTHER INFORMATION: synthetic nucleotide

<400> SEQUENCE: 250
agccaaggau gacuugccgg uu                                             22

<210> SEQ ID NO 251
<211> LENGTH: 22
<212> TYPE: RNA
<213> ORGANISM: artificial sequence
<220> FEATURE:
<223> OTHER INFORMATION: synthetic nucleotide

<400> SEQUENCE: 251
cagccaagga ugacuugccg ga                                             22

<210> SEQ ID NO 252
<211> LENGTH: 20
<212> TYPE: RNA
<213> ORGANISM: artificial sequence
<220> FEATURE:
<223> OTHER INFORMATION: synthetic nucleotide

<400> SEQUENCE: 252
ggcaaguugu ccuuggcuac                                                20
```

```
<210> SEQ ID NO 253
<211> LENGTH: 22
<212> TYPE: RNA
<213> ORGANISM: artificial sequence
<220> FEATURE:
<223> OTHER INFORMATION: synthetic nucleotide

<400> SEQUENCE: 253
ggcaaguugu ccuucggcua ca                                              22

<210> SEQ ID NO 254
<211> LENGTH: 20
<212> TYPE: RNA
<213> ORGANISM: artificial sequence
<220> FEATURE:
<223> OTHER INFORMATION: synthetic nucleotide

<400> SEQUENCE: 254
agccaaggau gacuugccug                                                 20

<210> SEQ ID NO 255
<211> LENGTH: 22
<212> TYPE: RNA
<213> ORGANISM: artificial sequence
<220> FEATURE:
<223> OTHER INFORMATION: synthetic nucleotide

<400> SEQUENCE: 255
uagccaagga ugacuugccu ga                                              22

<210> SEQ ID NO 256
<211> LENGTH: 21
<212> TYPE: RNA
<213> ORGANISM: artificial sequence
<220> FEATURE:
<223> OTHER INFORMATION: synthetic nucleotide

<400> SEQUENCE: 256
agccaaggau gacuugccug a                                               21

<210> SEQ ID NO 257
<211> LENGTH: 22
<212> TYPE: RNA
<213> ORGANISM: artificial sequence
<220> FEATURE:
<223> OTHER INFORMATION: synthetic nucleotide

<400> SEQUENCE: 257
uagccaagga ugacuugccu gu                                              22

<210> SEQ ID NO 258
<211> LENGTH: 22
<212> TYPE: RNA
<213> ORGANISM: artificial sequence
<220> FEATURE:
<223> OTHER INFORMATION: synthetic nucleotide

<400> SEQUENCE: 258
guagccaagg augacuugcc ug                                              22

<210> SEQ ID NO 259
<211> LENGTH: 23
<212> TYPE: RNA
<213> ORGANISM: artificial sequence
<220> FEATURE:
<223> OTHER INFORMATION: synthetic nucleotide
```

```
<400> SEQUENCE: 259
uagccaagga ugacuugccu gac                                            23

<210> SEQ ID NO 260
<211> LENGTH: 21
<212> TYPE: RNA
<213> ORGANISM: artificial sequence
<220> FEATURE:
<223> OTHER INFORMATION: synthetic nucleotide

<400> SEQUENCE: 260
uagccaagga ugacuucccu u                                              21

<210> SEQ ID NO 261
<211> LENGTH: 20
<212> TYPE: RNA
<213> ORGANISM: artificial sequence
<220> FEATURE:
<223> OTHER INFORMATION: synthetic nucleotide

<400> SEQUENCE: 261
uagccaagga ugacuugccu                                                20

<210> SEQ ID NO 262
<211> LENGTH: 20
<212> TYPE: RNA
<213> ORGANISM: artificial sequence
<220> FEATURE:
<223> OTHER INFORMATION: synthetic nucleotide

<400> SEQUENCE: 262
ugauugagcc gcgccaauau                                                20

<210> SEQ ID NO 263
<211> LENGTH: 20
<212> TYPE: RNA
<213> ORGANISM: artificial sequence
<220> FEATURE:
<223> OTHER INFORMATION: synthetic nucleotide

<400> SEQUENCE: 263
gcagcaccau uaagauucac                                                20

<210> SEQ ID NO 264
<211> LENGTH: 21
<212> TYPE: RNA
<213> ORGANISM: artificial sequence
<220> FEATURE:
<223> OTHER INFORMATION: synthetic nucleotide

<400> SEQUENCE: 264
gcagcaccau uaagauucac a                                              21

<210> SEQ ID NO 265
<211> LENGTH: 21
<212> TYPE: RNA
<213> ORGANISM: artificial sequence
<220> FEATURE:
<223> OTHER INFORMATION: synthetic nucleotide

<400> SEQUENCE: 265
ugauucucug uguaagcgaa a                                              21

<210> SEQ ID NO 266
```

```
<211> LENGTH: 20
<212> TYPE: RNA
<213> ORGANISM: artificial sequence
<220> FEATURE:
<223> OTHER INFORMATION: synthetic nucleotide

<400> SEQUENCE: 266
agcucaggag ggauagcgcc                                              20

<210> SEQ ID NO 267
<211> LENGTH: 20
<212> TYPE: RNA
<213> ORGANISM: artificial sequence
<220> FEATURE:
<223> OTHER INFORMATION: synthetic nucleotide

<400> SEQUENCE: 267
aagcucagga gggauagcgc                                              20

<210> SEQ ID NO 268
<211> LENGTH: 19
<212> TYPE: RNA
<213> ORGANISM: artificial sequence
<220> FEATURE:
<223> OTHER INFORMATION: synthetic nucleotide

<400> SEQUENCE: 268
gcucaggagg gauagcgcc                                               19

<210> SEQ ID NO 269
<211> LENGTH: 21
<212> TYPE: RNA
<213> ORGANISM: artificial sequence
<220> FEATURE:
<223> OTHER INFORMATION: synthetic nucleotide

<400> SEQUENCE: 269
agcucaggag ggauagcgcc a                                            21

<210> SEQ ID NO 270
<211> LENGTH: 20
<212> TYPE: RNA
<213> ORGANISM: artificial sequence
<220> FEATURE:
<223> OTHER INFORMATION: synthetic nucleotide

<400> SEQUENCE: 270
cgcuauccau ccugaguucc                                              20

<210> SEQ ID NO 271
<211> LENGTH: 21
<212> TYPE: RNA
<213> ORGANISM: artificial sequence
<220> FEATURE:
<223> OTHER INFORMATION: synthetic nucleotide

<400> SEQUENCE: 271
cgcuauccau ccugaguucc a                                            21

<210> SEQ ID NO 272
<211> LENGTH: 21
<212> TYPE: RNA
<213> ORGANISM: artificial sequence
<220> FEATURE:
<223> OTHER INFORMATION: synthetic nucleotide

<400> SEQUENCE: 272
```

```
acguauccuc uccuacguag c                                              21

<210> SEQ ID NO 273
<211> LENGTH: 22
<212> TYPE: RNA
<213> ORGANISM: artificial sequence
<220> FEATURE:
<223> OTHER INFORMATION: synthetic nucleotide

<400> SEQUENCE: 273
gguucaauaa agcuguggga ag                                             22

<210> SEQ ID NO 274
<211> LENGTH: 22
<212> TYPE: RNA
<213> ORGANISM: artificial sequence
<220> FEATURE:
<223> OTHER INFORMATION: synthetic nucleotide

<400> SEQUENCE: 274
ucauugagug cagcguugau gu                                             22

<210> SEQ ID NO 275
<211> LENGTH: 21
<212> TYPE: RNA
<213> ORGANISM: artificial sequence
<220> FEATURE:
<223> OTHER INFORMATION: synthetic nucleotide

<400> SEQUENCE: 275
ccugccaaag gagaguugcc c                                              21

<210> SEQ ID NO 276
<211> LENGTH: 20
<212> TYPE: RNA
<213> ORGANISM: artificial sequence
<220> FEATURE:
<223> OTHER INFORMATION: synthetic nucleotide

<400> SEQUENCE: 276
uucgaugucu agcagugcca                                                20

<210> SEQ ID NO 277
<211> LENGTH: 1185
<212> TYPE: DNA
<213> ORGANISM: artificial sequence
<220> FEATURE:
<223> OTHER INFORMATION: construct with artificial ta-siRNAs targeting
      Aequorea victoria gene encoding GFP

<400> SEQUENCE: 277
ctctagagga tccccgggta ccgggccccc cctcgaggcg cgccaagcta tcaaacaagt      60
ttgtacaaaa aagcaggctc cgcggccgcc cgcttcacca aacctaaacc taaacggcta    120
agcccgacgt caaataccaa aaagagaaaa acaagagcgc cgtcaagctc tgcaaatacg    180
atctgtaagt ccatcttaac acaaaagtga gatgggttct agatcatgt tccgccgtta    240 gatcgagtca tggtcttgtc tcatagaaag gtactttcgt ttacttcttt tgagtatcga    300
gtagagcgtc gtctatagtt agtttgagat tgcgtttgtc agaagttagg ttcaatgtcc    360
cggtccaatt ttcaccagcc atgtgtcagt tcgttccttc ccgtcctct tctttgattt    420 cgttgggtta cggatgtttt cgagatgaaa cagcattgtt tgttgtgat ttttctctac    480 aagcgaatag accatttatc ggtggatctt agaaaattat gatgtatacg ttgtgggagt    540
```

```
ttatttgtat agttcatcca tgaactagaa aagacattgg acatattcca ggatatgcaa    600
aagaaaacaa tgaatattgt tttgaatgtg ttcaagtaaa tgagattttc aagtcgtcta    660
aagaacagtt gctaatacag ttacttattt caataaataa ttggttctaa taatacaaaa    720
catattcgag gatatgcaga aaaaaagatg tttgttattt tgaaaagctt gagtagtttc    780
tctccgaggt gtagcgaaga agcatcatct actttgtaat gtaattttct ttatgttttc    840
actttgtaat tttatttgtg ttaatgtacc atggccgata tcggttttat tgaaagaaaa    900
tttatgttac ttctgttttg gctttgcaat cagttatgct agttttctta tacccttt cg    960 taagcttcct aaggaatcgt tcattgattt ccactgcttc attgtatatt aaaactttac   1020
aactgtatcg accatcatat aattctgggt caagagatga aaatagaaca ccacatcgta   1080
aagtgaaata agggtgggcg cgccgaccca gctttcttgt acaaagtggt tcgataattc   1140
cttaattaac tagttctaga gcggccgccc accgcggtgg agctc                   1185
```

<210> SEQ ID NO 278
<211> LENGTH: 1185
<212> TYPE: DNA
<213> ORGANISM: artificial sequence
<220> FEATURE:
<223> OTHER INFORMATION: construct with artificial ta-siRNAs targeting Arabidopsis gene encoding PDS

<400> SEQUENCE: 278

```
ctctagagga tccccgggta ccgggccccc cctcgaggcg cgccaagcta tcaaacaagt     60
ttgtacaaaa aagcaggctc cgcggccgcc cgcttcacca aacctaaacc taaacggcta    120
agcccgacgt caaataccaa aaagagaaaa acaagagcgc cgtcaagctc tgcaaatacg    180
atctgtaagt ccatcttaac acaaaagtga gatgggttct tagatcatgt tccgccgtta    240
gatcgagtca tggtcttgtc tcatagaaag gtactttcgt ttacttcttt tgagtatcga    300
gtagagcgtc gtctatagtt agtttgagat tgcgtttgtc agaagttagg ttcaatgtcc    360
cggtccaatt ttcaccagcc atgtgtcagt ttcgttcctt cccgtcctct tctttgattt    420
cgttgggtta cggatgtttt cgagatgaaa cagcattgtt ttgttgtgat ttttctctac    480
aagcgaatag accatttatc ggtggatctt agaaaattat aagtagcact tccccaccta    540
ttagctttgc tttggtcagc tgaactagaa aagacattgg acatattcca ggatatgcaa    600
aagaaaacaa tgaatattgt tttgaatgtg ttcaagtaaa tgagattttc aagtcgtcta    660
aagaacagtt gctaatacag ttacttattt caataaataa ttggttctaa taatacaaaa    720
catattcgag gatatgcaga aaaaaagatg tttgttattt tgaaaagctt gagtagtttc    780
tctccgaggt gtagcgaaga agcatcatct actttgtaat gtaattttct ttatgttttc    840
actttgtaat tttatttgtg ttaatgtacc atggccgata tcggttttat tgaaagaaaa    900
tttatgttac ttctgttttg gctttgcaat cagttatgct agttttctta tacccttt cg    960 taagcttcct aaggaatcgt tcattgattt ccactgcttc attgtatatt aaaactttac   1020
aactgtatcg accatcatat aattctgggt caagagatga aaatagaaca ccacatcgta   1080
aagtgaaata agggtgggcg cgccgaccca gctttcttgt acaaagtggt tcgataattc   1140
cttaattaac tagttctaga gcggccgccc accgcggtgg agctc                   1185
```

<210> SEQ ID NO 279
<211> LENGTH: 1185
<212> TYPE: DNA
<213> ORGANISM: artificial sequence
<220> FEATURE:
<223> OTHER INFORMATION: construct with artificial ta-siRNAs targeting Arabidopsis gene encoding PID

<400> SEQUENCE: 279

```
ctctagagga tccccgggta ccgggccccc cctcgaggcg cgccaagcta tcaaacaagt      60
ttgtacaaaa aagcaggctc cgcggccgcc cgcttcacca aacctaaacc taaacggcta    120
agcccgacgt caaataccaa aaagagaaaa acaagagcgc cgtcaagctc tgcaaatacg    180
atctgtaagt ccatcttaac acaaaagtga gatgggttct tagatcatgt tccgccgtta    240
gatcgagtca tggtcttgtc tcatagaaag gtactttcgt ttacttcttt tgagtatcga    300
gtagagcgtc gtctatagtt agtttgagat tgcgtttgtc agaagttagg ttcaatgtcc    360
cggtccaatt ttcaccagcc atgtgtcagt ttcgttcctt cccgtcctct tctttgattt    420
cgttgggtta cggatgtttt cgagatgaaa cagcattgtt ttgttgtgat ttttctctac    480
aagcgaatag accatttatc ggtggatctt agaaaattat caaaagtaat cgaacgccgc    540
tcattagtcg gcgcaacgaa cgaactagaa aagacattgg acatattcca ggatatgcaa    600
aagaaaacaa tgaatattgt tttgaatgtg ttcaagtaaa tgagattttc aagtcgtcta    660
aagaacagtt gctaatacag ttacttattt caataaataa ttggttctaa taatacaaaa    720
catattcgag gatatgcaga aaaaagatg tttgttattt tgaaaagctt gagtagtttc    780
tctccgaggt gtagcgaaga agcatcatct actttgtaat gtaattttct ttatgttttc    840
actttgtaat tttatttgtg ttaatgtacc atggccgata tcggttttat tgaaagaaaa    900
tttatgttac ttctgttttg gctttgcaat cagttatgct agttttctta tacccttcg     960
taagcttcct aaggaatcgt tcattgattt ccactgcttc attgtatatt aaaactttac   1020
aactgtatcg accatcatat aattctgggt caagagatga aaatagaaca ccacatcgta   1080
aagtgaaata agggtgggcg cgccgaccca gctttcttgt acaaagtggt tcgataattc   1140
cttaattaac tagttctaga gcggccgccc accgcggtgg agctc                   1185
```

<210> SEQ ID NO 280
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 280

```
gtgctctctc tcttctgtca                                                  20
```

<210> SEQ ID NO 281
<211> LENGTH: 21
<212> TYPE: RNA
<213> ORGANISM: artificial sequence
<220> FEATURE:
<223> OTHER INFORMATION: Synthetic oligonucleotide

<400> SEQUENCE: 281

```
ccaagggaag aggcagugca u                                                21
```

<210> SEQ ID NO 282
<211> LENGTH: 21
<212> TYPE: RNA
<213> ORGANISM: artificial sequence
<220> FEATURE:
<223> OTHER INFORMATION: Synthetic oligonucleotide

<400> SEQUENCE: 282

```
accagugaag aggcugugca g                                              21
```

<210> SEQ ID NO 283
<211> LENGTH: 21
<212> TYPE: RNA
<213> ORGANISM: artificial sequence
<220> FEATURE:
<223> OTHER INFORMATION: Synthetic oligonucleotide

<400> SEQUENCE: 283

```
gccagggaag aggcagugca u                                              21
```

<210> SEQ ID NO 284
<211> LENGTH: 21
<212> TYPE: RNA
<213> ORGANISM: artificial sequence
<220> FEATURE:
<223> OTHER INFORMATION: Synthetic oligonucleotide

<400> SEQUENCE: 284

```
gccggugaag aggcugugca a                                              21
```

<210> SEQ ID NO 285
<211> LENGTH: 21
<212> TYPE: RNA
<213> ORGANISM: artificial sequence
<220> FEATURE:
<223> OTHER INFORMATION: Synthetic oligonucleotide

<400> SEQUENCE: 285

```
gccggugaag aggcugugca g                                              21
```

<210> SEQ ID NO 286
<211> LENGTH: 60
<212> TYPE: DNA
<213> ORGANISM: Arabidopsis thaliana

<400> SEQUENCE: 286

```
aaacgggttc ctaatctttta tatataccctt ccatcatcaa aagaccattc attgttcact   60
```

<210> SEQ ID NO 287
<211> LENGTH: 60
<212> TYPE: DNA
<213> ORGANISM: Arabidopsis thaliana

<400> SEQUENCE: 287

```
ataaagaaag gtaagactct ttgaaataga gagagataag gttttctctt atcttcttct    60
```

<210> SEQ ID NO 288
<211> LENGTH: 60
<212> TYPE: DNA
<213> ORGANISM: Arabidopsis thaliana

<400> SEQUENCE: 288

```
tcttctcctc tcctcttatt aatctaatcc tcctccccga atatttctct gcctttagtt    60
```

<210> SEQ ID NO 289
<211> LENGTH: 60
<212> TYPE: DNA
<213> ORGANISM: Arabidopsis thaliana

<400> SEQUENCE: 289

```
ctcttctcct tcggttataa atattctctc cggttttgct tgtttaacct aaaagcctca    60
```

```
<210> SEQ ID NO 290
<211> LENGTH: 60
<212> TYPE: DNA
<213> ORGANISM: Arabidopsis thaliana

<400> SEQUENCE: 290
tctatcccca tttggctata aaagccccg acaggtctca gtttcttccc acatccaaag    60

<210> SEQ ID NO 291
<211> LENGTH: 60
<212> TYPE: DNA
<213> ORGANISM: Arabidopsis thaliana

<400> SEQUENCE: 291
tctctccatt ttggctataa aagccacaa cagggtctcc atttcttccc gcagccaatg    60

<210> SEQ ID NO 292
<211> LENGTH: 60
<212> TYPE: DNA
<213> ORGANISM: Arabidopsis thaliana

<400> SEQUENCE: 292
tttctcaact tactcctata tatatacaca ttactctcta ttttcccttt gtcacttcat    60

<210> SEQ ID NO 293
<211> LENGTH: 60
<212> TYPE: DNA
<213> ORGANISM: Arabidopsis thaliana

<400> SEQUENCE: 293
tggtctcaaa tctttcctat atatacacac cactttccat tacaccattt actcttcacc    60

<210> SEQ ID NO 294
<211> LENGTH: 60
<212> TYPE: DNA
<213> ORGANISM: Arabidopsis thaliana

<400> SEQUENCE: 294 tgttccttttt tttcttttct tttattctt ctatcacgaa tatctaaacc actataatta    60

<210> SEQ ID NO 295
<211> LENGTH: 60
<212> TYPE: DNA
<213> ORGANISM: Arabidopsis thaliana

<400> SEQUENCE: 295
acgaatatct aaaccactat aattacgact ctctatctat catttcttcc aaaacatgac    60

<210> SEQ ID NO 296
<211> LENGTH: 60
<212> TYPE: DNA
<213> ORGANISM: Arabidopsis thaliana

<400> SEQUENCE: 296
ggctacagat ttttgtcttt aaaaagccat tcaagtttca atggttttc acttttgttc    60

<210> SEQ ID NO 297
<211> LENGTH: 60
<212> TYPE: DNA
<213> ORGANISM: Arabidopsis thaliana

<400> SEQUENCE: 297
gttctaaatt tgaagcttat aaaaacccat cactactttt gcatacttgt atccgcagtg    60
```

```
<210> SEQ ID NO 298
<211> LENGTH: 60
<212> TYPE: DNA
<213> ORGANISM: Arabidopsis thaliana

<400> SEQUENCE: 298
tacctttgtt tttgctataa aaagccataa ctccttcatt ttctttagac atctcttctt    60

<210> SEQ ID NO 299
<211> LENGTH: 60
<212> TYPE: DNA
<213> ORGANISM: Arabidopsis thaliana

<400> SEQUENCE: 299
tcttgtctac atatacatat atttatatac acacatgtat ctctctcatc acaccttaa    60

<210> SEQ ID NO 300
<211> LENGTH: 60
<212> TYPE: DNA
<213> ORGANISM: Arabidopsis thaliana

<400> SEQUENCE: 300
atcccaccct taattgtttt atataaacca tttctcctcc tctctccatc accttcaatc    60

<210> SEQ ID NO 301
<211> LENGTH: 60
<212> TYPE: DNA
<213> ORGANISM: Arabidopsis thaliana

<400> SEQUENCE: 301
tttatcattt ttctcctcta tatatatgtg ccaccattcc tcttatactc ataactctcc    60

<210> SEQ ID NO 302
<211> LENGTH: 60
<212> TYPE: DNA
<213> ORGANISM: Arabidopsis thaliana

<400> SEQUENCE: 302
tcttctctct ttcccctta tatatttgta ccacatattc ctcttcaacc aaaactcttc    60

<210> SEQ ID NO 303
<211> LENGTH: 60
<212> TYPE: DNA
<213> ORGANISM: Arabidopsis thaliana

<400> SEQUENCE: 303
ctttctcttc ttccttcata tttatataca accttctctc acttatctct aactcatcct    60

<210> SEQ ID NO 304
<211> LENGTH: 60
<212> TYPE: DNA
<213> ORGANISM: Arabidopsis thaliana

<400> SEQUENCE: 304
tgttatgaga cttttagata cattttagtt ataaatatga atcaaataca ttttagttct    60

<210> SEQ ID NO 305
<211> LENGTH: 60
<212> TYPE: DNA
<213> ORGANISM: Arabidopsis thaliana

<400> SEQUENCE: 305
```
tttagataca ttttagttat aaatatgaat caaatacatt ttagttctag aagaaaaaac    60

<210> SEQ ID NO 306
<211> LENGTH: 60
<212> TYPE: DNA
<213> ORGANISM: Arabidopsis thaliana

<400> SEQUENCE: 306
accagatcta taaagtttgt tattaaaaga tagagagaga ggagggatgt agtaggccaa    60

<210> SEQ ID NO 307
<211> LENGTH: 60
<212> TYPE: DNA
<213> ORGANISM: Arabidopsis thaliana

<400> SEQUENCE: 307
catcaaagga aaattagtat aaataagcat agaggcgtcc atggattatc acagttctca    60

<210> SEQ ID NO 308
<211> LENGTH: 60
<212> TYPE: DNA
<213> ORGANISM: Arabidopsis thaliana

<400> SEQUENCE: 308
ctagcaacct agcacttata tatgtagagt ttgtgaaatt tagggcagac aagcccccac    60

<210> SEQ ID NO 309
<211> LENGTH: 60
<212> TYPE: DNA
<213> ORGANISM: Arabidopsis thaliana

<400> SEQUENCE: 309
atgcaatctt tgggcctata tatacaaacc tttccataac caaagttctc atactacaaa    60

<210> SEQ ID NO 310
<211> LENGTH: 60
<212> TYPE: DNA
<213> ORGANISM: Arabidopsis thaliana

<400> SEQUENCE: 310
atagatattt ccgtttgcta taaatgagaa agcacttaca acatacatac attctctctt    60

<210> SEQ ID NO 311
<211> LENGTH: 60
<212> TYPE: DNA
<213> ORGANISM: Arabidopsis thaliana

<400> SEQUENCE: 311
tgtttctgtt gtgtcttatt aaaagcccat cttcgtctcc gccactcatc attccctcat    60

<210> SEQ ID NO 312
<211> LENGTH: 60
<212> TYPE: DNA
<213> ORGANISM: Arabidopsis thaliana

<400> SEQUENCE: 312
tctccactac tcaatttctt cataaaaccc ccctttttat ttctctcatt ctctcttcca    60

<210> SEQ ID NO 313
<211> LENGTH: 60
<212> TYPE: DNA
<213> ORGANISM: Arabidopsis thaliana

<400> SEQUENCE: 313

```
aatttcttca taaaaccccc cttttattt ctctcattct ctcttccatc atcaccactc    60
```

<210> SEQ ID NO 314
<211> LENGTH: 60
<212> TYPE: DNA
<213> ORGANISM: Arabidopsis thaliana

<400> SEQUENCE: 314

```
tcttgagttt ttttctcttc ttaaaaacct cttcttcact tatccttctc atcattctct    60
```

<210> SEQ ID NO 315
<211> LENGTH: 60
<212> TYPE: DNA
<213> ORGANISM: Arabidopsis thaliana

<400> SEQUENCE: 315

```
tggtcatttg tgcctctata tatacaagac ataggtttat tttgtctcac acataccttt    60
```

<210> SEQ ID NO 316
<211> LENGTH: 60
<212> TYPE: DNA
<213> ORGANISM: Arabidopsis thaliana

<400> SEQUENCE: 316

```
ttgctcctct ctcctatgta taaatattcg cctcacacat agacctattt agcttcttct    60
```

<210> SEQ ID NO 317
<211> LENGTH: 60
<212> TYPE: DNA
<213> ORGANISM: Arabidopsis thaliana

<400> SEQUENCE: 317

```
tctcctcctt atcccttcta tataaacact cgtcttcttc ttcacttgat gaacagaaaa    60
```

<210> SEQ ID NO 318
<211> LENGTH: 60
<212> TYPE: DNA
<213> ORGANISM: Arabidopsis thaliana

<400> SEQUENCE: 318

```
caaatcctct ctcatctctt tctataagta tctatagcgc ctcttaaacc acaaagcatc    60
```

<210> SEQ ID NO 319
<211> LENGTH: 60
<212> TYPE: DNA
<213> ORGANISM: Arabidopsis thaliana

<400> SEQUENCE: 319

```
tatctctgac ccatcttcta tataaaccca gagcgggtaa gtcctctagt attcataagc    60
```

<210> SEQ ID NO 320
<211> LENGTH: 60
<212> TYPE: DNA
<213> ORGANISM: Arabidopsis thaliana

<400> SEQUENCE: 320

```
aactggtaga aagatctata agtacgatac accttatact tcaagagagc aagacaatgc    60
```

<210> SEQ ID NO 321
<211> LENGTH: 60
<212> TYPE: DNA
<213> ORGANISM: Arabidopsis thaliana

<400> SEQUENCE: 321
ttcgtacggt catgcctata taacacacat agtagtcttg tgggatactc atcaacaacc    60

<210> SEQ ID NO 322
<211> LENGTH: 60
<212> TYPE: DNA
<213> ORGANISM: Arabidopsis thaliana

<400> SEQUENCE: 322
ttccttctct caagggttat aaataaaacg agagcacatg aatgtaaggc atgagacata    60

<210> SEQ ID NO 323
<211> LENGTH: 60
<212> TYPE: DNA
<213> ORGANISM: Arabidopsis thaliana

<400> SEQUENCE: 323
cgagtctcga gggttataaa aagagagcac atgcatgtat ggaataaggc aaaaacatat    60

<210> SEQ ID NO 324
<211> LENGTH: 60
<212> TYPE: DNA
<213> ORGANISM: Arabidopsis thaliana

<400> SEQUENCE: 324
tgagagtagc agagttatta aatgcttcgc agaattgcag ttgcacattc actcccttct    60

<210> SEQ ID NO 325
<211> LENGTH: 60
<212> TYPE: DNA
<213> ORGANISM: Arabidopsis thaliana

<400> SEQUENCE: 325
taattcttcc tcaaaatctt ttctcttttt ttggttatat atatttgaat tttgatttat    60

<210> SEQ ID NO 326
<211> LENGTH: 60
<212> TYPE: DNA
<213> ORGANISM: Arabidopsis thaliana

<400> SEQUENCE: 326
cttcttcaac catcttcgta tttatatctt cttcttcact atgcatactc ataaactttg    60

<210> SEQ ID NO 327
<211> LENGTH: 60
<212> TYPE: DNA
<213> ORGANISM: Arabidopsis thaliana

<400> SEQUENCE: 327
tcttcatcac cctcttcgta tttatatctc cttcactctg caaacccaag aaaaaacatt    60

<210> SEQ ID NO 328
<211> LENGTH: 60
<212> TYPE: DNA
<213> ORGANISM: Arabidopsis thaliana

<400> SEQUENCE: 328
ccaaataaat caacatatat attattacac agtcacatct cttactgtgc atatatattt    60

<210> SEQ ID NO 329
<211> LENGTH: 60
<212> TYPE: DNA
<213> ORGANISM: Arabidopsis thaliana

<400> SEQUENCE: 329
acatctctta ctgtgcatat atatttagac aaacacatct ctctctctct atctctctca    60

<210> SEQ ID NO 330
<211> LENGTH: 60
<212> TYPE: DNA
<213> ORGANISM: Arabidopsis thaliana

<400> SEQUENCE: 330
gttttactat tttagcagta tatattaaga agttcagatg ttattcgatc atctgttttt    60

<210> SEQ ID NO 331
<211> LENGTH: 60
<212> TYPE: DNA
<213> ORGANISM: Arabidopsis thaliana

<400> SEQUENCE: 331
aagtcattgc gtgtctctat aaataccaca cttcaccttc ttcttcactt gcacctctca    60

<210> SEQ ID NO 332
<211> LENGTH: 60
<212> TYPE: DNA
<213> ORGANISM: Arabidopsis thaliana

<400> SEQUENCE: 332
tttttctcgt ttttttcttc ttcttctcca agaaaataga gatcgaaaag attagatcta    60

<210> SEQ ID NO 333
<211> LENGTH: 60
<212> TYPE: DNA
<213> ORGANISM: Arabidopsis thaliana

<400> SEQUENCE: 333
tttaatttgt taattatata tattttatgc acatcattgg agaaaacacc aaataggctc    60

<210> SEQ ID NO 334
<211> LENGTH: 60
<212> TYPE: DNA
<213> ORGANISM: Arabidopsis thaliana

<400> SEQUENCE: 334
tctttatcgc ttcatatata taaaagtcta catctatctc tttctaggtc actagctaga    60

<210> SEQ ID NO 335
<211> LENGTH: 60
<212> TYPE: DNA
<213> ORGANISM: Arabidopsis thaliana

<400> SEQUENCE: 335
aaaaggtttt acggtttgtg tataaaagac ttgcaatctt gagatatgtc atattgagaa    60

<210> SEQ ID NO 336
<211> LENGTH: 60
<212> TYPE: DNA
<213> ORGANISM: Arabidopsis thaliana

<400> SEQUENCE: 336
atatgtcata ttgagaactc tttagccttt ggcttctgtt cctgacactt atatagtgaa    60

<210> SEQ ID NO 337
<211> LENGTH: 60
<212> TYPE: DNA

<213> ORGANISM: Arabidopsis thaliana

<400> SEQUENCE: 337
tttcatatga gtgtatatat tcatgtacct atctctctca attgcttctc accaaaatca    60

<210> SEQ ID NO 338
<211> LENGTH: 60
<212> TYPE: DNA
<213> ORGANISM: Arabidopsis thaliana

<400> SEQUENCE: 338
tgttagatct gaggtctatt aaaatccgaa tcctttcaat ctcttctctt attccatcac    60

<210> SEQ ID NO 339
<211> LENGTH: 60
<212> TYPE: DNA
<213> ORGANISM: Arabidopsis thaliana

<400> SEQUENCE: 339
agggttttaa gccaagctta tatagcccgt cataaagaga actcatctgc ctctctctca    60

<210> SEQ ID NO 340
<211> LENGTH: 60
<212> TYPE: DNA
<213> ORGANISM: Arabidopsis thaliana

<400> SEQUENCE: 340
ctctcaatac caataaatat caccaccgtc cttctctcct atcactattc aatctatcgc    60

<210> SEQ ID NO 341
<211> LENGTH: 60
<212> TYPE: DNA
<213> ORGANISM: Arabidopsis thaliana

<400> SEQUENCE: 341
gactctttgc aataatatat aaataggcat gcagtgttag tgttgtttgt atcatgacag    60

<210> SEQ ID NO 342
<211> LENGTH: 60
<212> TYPE: DNA
<213> ORGANISM: Arabidopsis thaliana

<400> SEQUENCE: 342
acaatgcttc caattgtata tataaaacgc cagtccctcc attcttttc aaaccctaac    60

<210> SEQ ID NO 343
<211> LENGTH: 60
<212> TYPE: DNA
<213> ORGANISM: Arabidopsis thaliana

<400> SEQUENCE: 343 ctcttcccctt gtcccctata aatatctttc tatcgaccat cttccttctc acaacttcaa   60

<210> SEQ ID NO 344
<211> LENGTH: 60
<212> TYPE: DNA
<213> ORGANISM: Arabidopsis thaliana

<400> SEQUENCE: 344
aagacacgac caaatgtctt ataaatgata tttgtgttta tctccatggt aatagaaatg    60

<210> SEQ ID NO 345
<211> LENGTH: 60

```
<212> TYPE: DNA
<213> ORGANISM: Arabidopsis thaliana

<400> SEQUENCE: 345
tcatttgttg tgttgtgtat atatagtagc tctcagcaga tttgaaggat atcgaaactc    60

<210> SEQ ID NO 346
<211> LENGTH: 60
<212> TYPE: DNA
<213> ORGANISM: Arabidopsis thaliana

<400> SEQUENCE: 346
cacacacgca tatatatata aatacagaca caagccttca tatggatctt atagagatga    60

<210> SEQ ID NO 347
<211> LENGTH: 60
<212> TYPE: DNA
<213> ORGANISM: Arabidopsis thaliana

<400> SEQUENCE: 347
ccacttttat taaaactcat atatatacac tgagccatta gtccatgaat aaccaaccag    60

<210> SEQ ID NO 348
<211> LENGTH: 60
<212> TYPE: DNA
<213> ORGANISM: Arabidopsis thaliana

<400> SEQUENCE: 348
aaacactttc atcaactata tatacatact ttgctagtcc aacttccaat aactcaaaat    60

<210> SEQ ID NO 349
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 349
gctcctccca atcacccaac ccaat    25

<210> SEQ ID NO 350
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 350
ggagcggcgt tgtcgcggag aacaa    25

<210> SEQ ID NO 351
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 351
gcgtttctct tgtcccaact ctttca    26

<210> SEQ ID NO 352
<211> LENGTH: 27
<212> TYPE: DNA
<213> ORGANISM: Artificial Sequence
<220> FEATURE:
```

<223> OTHER INFORMATION: Synthetic oligonucleotide

<400> SEQUENCE: 352
ctcttgtccc aactctttca ttcacaa                                            27

<210> SEQ ID NO 353
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 353
ctccctcttc tagcaactaa ttcaaaaa                                           28

<210> SEQ ID NO 354
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 354
cctagatgga ttaagaactc aactttct                                           28

<210> SEQ ID NO 355
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 355
cagtttctat gcgtttctct taaaatttgt                                         30

<210> SEQ ID NO 356
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 356
gcgtttctct taaaatttgt cccaaaact                                          29

<210> SEQ ID NO 357
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 357
ccccatcaac atatatttat ctagttatga                                         30

<210> SEQ ID NO 358
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 358
ctagttatga cactaaataa tatgttagaa                                         30

```
<210> SEQ ID NO 359
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 359
tcctaattac ctttcacact ctacgcat                                          28

<210> SEQ ID NO 360
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 360
cactctacgc atgtgaccag gctcgaaa                                          28

<210> SEQ ID NO 361
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 361
ccactcaaac cgtcgacaaa tatgttt                                           27

<210> SEQ ID NO 362
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 362
ccgtcgacaa atatgtttca tatctctt                                          28

<210> SEQ ID NO 363
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 363
cttcgttatt gctattccct tacctcctt                                         29

<210> SEQ ID NO 364
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 364
cccttacctc ctttagttga cttgctt                                           27

<210> SEQ ID NO 365
<211> LENGTH: 28
<212> TYPE: DNA
<213> ORGANISM: Artificial Sequence
<220> FEATURE:
<223> OTHER INFORMATION: Synthetic oligonucleotide
```

<400> SEQUENCE: 365
cttcttctcg ggaggaatag aagaagaa                                28

<210> SEQ ID NO 366
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 366
ctcgggagga atagaagaag aagaagaa                                28

<210> SEQ ID NO 367
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 367
caatgcctct caattctcaa acaattaa                                28

<210> SEQ ID NO 368
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 368
ctctcaattc tcaaacaatt aaatatcgat                              30

<210> SEQ ID NO 369
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 369
cctcccaaac cattaaaaat cgattttta                               29

<210> SEQ ID NO 370
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 370
ccattaaaaa tcgattttta atttacagtt ga                           32

<210> SEQ ID NO 371
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 371
caaacctatg tgtgatatgc aacatcata                               29

<210> SEQ ID NO 372
<211> LENGTH: 30

<212> TYPE: DNA
<213> ORGANISM: Artificial Sequence
<220> FEATURE:
<223> OTHER INFORMATION: Synthetic oligonucleotide

<400> SEQUENCE: 372
gtgtgatatg caacatcata aagtatgtat                                        30

<210> SEQ ID NO 373
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 373
ccctccacta tacatacagc attctt                                            26

<210> SEQ ID NO 374
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 374
catacagcat tcttgcggtt tgatata                                           27

<210> SEQ ID NO 375
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 375
cttcttctgc agtcgctagc cctcta                                            26

<210> SEQ ID NO 376
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 376
ctgcagtcgc tagccctcta atctaaa                                           27

<210> SEQ ID NO 377
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 377
gcacagagat gacgtgttct tatcctt                                           27

<210> SEQ ID NO 378
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 378
gacgtgttct tatccttctg cagtcaa 27

<210> SEQ ID NO 379
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 379
ccatcgtcag atcaagatct atcgaaa 27

<210> SEQ ID NO 380
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 380
ggatctgaca taagcaaact gtaaaga 27

<210> SEQ ID NO 381
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 381
cctcttcttc ttcctttgtt tttctatat 29

<210> SEQ ID NO 382
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 382
cgtgtggatc tgctttgact aactcat 27

<210> SEQ ID NO 383
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 383
ccttctgtta cacttgaaga acgaatgt 28

<210> SEQ ID NO 384
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 384
gtcccccaaa aagagtttga tatctttt 28

<210> SEQ ID NO 385
<211> LENGTH: 29
<212> TYPE: DNA
<213> ORGANISM: Artificial Sequence

```
<220> FEATURE:
<223> OTHER INFORMATION: Synthetic oligonucleotide

<400> SEQUENCE: 385
gccaggcata catatataat acatataca                                          29

<210> SEQ ID NO 386
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 386
gcgtcatgac atatacatgg ttatgtaa                                           28

<210> SEQ ID NO 387
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 387
gccaggcacg actattattc catata                                             26

<210> SEQ ID NO 388
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 388 gggaacccctt aagtatgatt ggtggat                                           27

<210> SEQ ID NO 389
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 389
ccaaacctct acgcatgaac atatctt                                            27

<210> SEQ ID NO 390
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 390
gtggatcttg gcttgaatcg aatcaga                                            27

<210> SEQ ID NO 391
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 391
ctggtcaaaa accgagatca agcaaaaga                                          29
```

<210> SEQ ID NO 392
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 392
ccgagatcaa gcaaaagaga agtactgat                                              29

<210> SEQ ID NO 393
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 393
actccaaaat gtcaacgaaa cataaattt                                              29

<210> SEQ ID NO 394
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 394
ccgaatcgga tcaaacgaaa cacatca                                                27

<210> SEQ ID NO 395
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 395
gtcctgcttc tcagcaatac tcaaata                                                27

<210> SEQ ID NO 396
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 396
gtcatgaaga gcaagcagcg ctggat                                                 26

<210> SEQ ID NO 397
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 397
ccaccaatca agacctatgc tcttga                                                 26

<210> SEQ ID NO 398
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 398
catgatctct ctctatctct ctcttta                                              27

<210> SEQ ID NO 399
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 399
ggggcatgaa tttaattaca tgtgcat                                              27

<210> SEQ ID NO 400
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 400
ggcacaacct atagagaaac tggaca                                               26

<210> SEQ ID NO 401
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 401
cacccgcatt tccaagcaca tgag                                                 24

<210> SEQ ID NO 402
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 402
ccaagcacat gagggcgtt tgtagt                                                26

<210> SEQ ID NO 403
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 403
gctcatcaca caccttcatc attctct                                              27

<210> SEQ ID NO 404
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 404
ccttcatcat tctctccgac cacataa                                              27

<210> SEQ ID NO 405

```
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 405
ctcacccatt actttctctc ttgcatcat                                            29

<210> SEQ ID NO 406
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 406
ctctcttgca tcatcaaact ccaaataat                                            29

<210> SEQ ID NO 407
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 407
gaaatagctt aaccctcatg ataatcga                                             28

<210> SEQ ID NO 408
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 408
ccctcatgat aatcgatctt agcagat                                              27

<210> SEQ ID NO 409
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 409
cctcttcatg attatcagtc gcagct                                               26

<210> SEQ ID NO 410
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 410
gattatcagt cgcagctcaa tcttat                                               26

<210> SEQ ID NO 411
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 411
``` gcccctttt cttttcagtc gaaattat                                    28

<210> SEQ ID NO 412
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 412
cagtcgaaat tatagaatct agggtttct                                  29

<210> SEQ ID NO 413
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 413
tcccctcaaa agaaaaatcc ctctttaa                                   28

<210> SEQ ID NO 414
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 414
ccctctttaa atcctcttct tcttcttct                                  29

<210> SEQ ID NO 415
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 415
cgcacaacaa tgaattaatc aagactaga                                  29

<210> SEQ ID NO 416
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 416
caagactaga accacgttat caagaaga                                   28

<210> SEQ ID NO 417
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 417
accctaaacc aaagcaggat aactttat                                   28

<210> SEQ ID NO 418
<211> LENGTH: 28
<212> TYPE: DNA

<210> SEQ ID NO 419
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 418
gcaggataac tttatgtaag tagacaga                                        28

<210> SEQ ID NO 419
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 419
cccctcaaaa ggaaaagctt cactgaa                                         27

<210> SEQ ID NO 420
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 420
gcttcactga agaacatgga ctccatat                                        28

<210> SEQ ID NO 421
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 421
ggctcagaaa gacagagaga gaagaga                                         27

<210> SEQ ID NO 422
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 422
cagagagaga agagagaatg agaaaaag                                        28

<210> SEQ ID NO 423
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 423
tcgcttcact ataagaagaa taagatgaa                                       29

<210> SEQ ID NO 424
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 424
gaagaataag atgaagagga caagaatgt                                       29

<210> SEQ ID NO 425
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 425
gcaccataga cttcaccgta gcagat                                    26

<210> SEQ ID NO 426
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 426
caccgtagca gatcaagaaa gagaaaga                                  28

<210> SEQ ID NO 427
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 427
cccttgtgga cttgtcttca aaatacct                                  28

<210> SEQ ID NO 428
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 428
cctgagcaac aagttgtgca aatctca                                   27

<210> SEQ ID NO 429
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 429
ctgctactgg tacatggtat acatacaga                                 29

<210> SEQ ID NO 430
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 430
ggtatacata cagacatgaa gacgacta                                  28

<210> SEQ ID NO 431
<211> LENGTH: 32
<212> TYPE: DNA
<213> ORGANISM: Artificial Sequence
<220> FEATURE:

<223> OTHER INFORMATION: Synthetic oligonucleotide

<400> SEQUENCE: 431
ccaacataga taattgaaaa agaatgagaa ga                                    32

<210> SEQ ID NO 432
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 432
gagaagagaa atgcctcctt gtgaagctt                                        29

<210> SEQ ID NO 433
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 433
gagactctac tatcataata atcccttta                                        29

<210> SEQ ID NO 434
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 434
ccctttagac agggatatga agaaaga                                          27

<210> SEQ ID NO 435
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 435
ggtaacttta acaatcatcg catctctct                                        29

<210> SEQ ID NO 436
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 436
cgcatctctc tctcatcaga aaaggt                                           27

<210> SEQ ID NO 437
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 437
cgcgtttcac tagctatacc cacttgt                                          27

```
<210> SEQ ID NO 438
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 438
cactagctat acccacttgt atatatga                                          28

<210> SEQ ID NO 439
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 439
cttggctgca ttatactcta ctccactt                                          28

<210> SEQ ID NO 440
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 440
ggctgcatta tactctactc cacttcat                                          28

<210> SEQ ID NO 441
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 441
ggcctttttc ccacattcaa ggcttta                                           27

<210> SEQ ID NO 442
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 442
cccacattca aggctttaga tgagacaa                                          28

<210> SEQ ID NO 443
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 443
ggctcaatct cattctttaa ttttccca                                          28

<210> SEQ ID NO 444
<211> LENGTH: 31
<212> TYPE: DNA
<213> ORGANISM: Artificial Sequence
<220> FEATURE:
<223> OTHER INFORMATION: Synthetic oligonucleotide
```

<400> SEQUENCE: 444
ctcaatctca ttctttaatt tttccatgca a					31

<210> SEQ ID NO 445
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 445
ggctcaatct cattttctat ttttccat					28

<210> SEQ ID NO 446
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 446
ccatgcaaga ctctatgata caattaatt					29

<210> SEQ ID NO 447
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 447
gctcaattcc attcgttatt ccttcatgca					30

<210> SEQ ID NO 448
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 448
ccctctgata caaccaaaga ctcccatt					28

<210> SEQ ID NO 449
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 449
ggctcaacct cattctctat tcttccat					28

<210> SEQ ID NO 450
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 450
cctcattctc tattcttcca tgcaaga					27

<210> SEQ ID NO 451
<211> LENGTH: 28

```
<212> TYPE: DNA
<213> ORGANISM: Artificial Sequence
<220> FEATURE:
<223> OTHER INFORMATION: Synthetic oligonucleotide

<400> SEQUENCE: 451
ggctaccaca caagttctca ttcttcat                                          28

<210> SEQ ID NO 452
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 452
ccacacaagt tctcattctt catgtca                                           27

<210> SEQ ID NO 453
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 453
ggctaccaaa tatgattctt ctattcat                                          28

<210> SEQ ID NO 454
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 454
catctccttc taaataatgt gtacactca                                         29

<210> SEQ ID NO 455
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 455
gctactaaac atgactcttt tcgccatgt                                         29

<210> SEQ ID NO 456
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 456
ctaaacatga ctcttttcgc catgttag                                          28

<210> SEQ ID NO 457
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 457
```
ggctaccaaa tattgttctc ctattca                                          27

<210> SEQ ID NO 458
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 458
ctcctattca tctttgacat ctccttct                                         28

<210> SEQ ID NO 459
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 459
ccttggctat taaacatgac tcttttc                                          27

<210> SEQ ID NO 460
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 460
ggctattaaa catgactctt ttcgccata                                        29

<210> SEQ ID NO 461
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 461
ggctaccaaa tatgattctt ctattcat                                         28

<210> SEQ ID NO 462
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 462
gctaccaaat atgattcttc tattcatct                                        29

<210> SEQ ID NO 463
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 463
gctactaaac atgacgcttt ccgccatg                                         28

<210> SEQ ID NO 464
<211> LENGTH: 27
<212> TYPE: DNA
<213> ORGANISM: Artificial Sequence -continued

```
<220> FEATURE:
<223> OTHER INFORMATION: Synthetic oligonucleotide

<400> SEQUENCE: 464
cgctttccgc catgttagac ctctctt                                        27

<210> SEQ ID NO 465
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 465
ctcggaaaca tagtgtatct gttttgt                                        27

<210> SEQ ID NO 466
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 466
cgcaagtgag agaatgtctg taactgta                                       28

<210> SEQ ID NO 467
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 467
gtgcggatat caaaggaaac attgtaa                                        27

<210> SEQ ID NO 468
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 468
gtgtgaggag gagaagtgag aatgtctgt                                      29

<210> SEQ ID NO 469
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 469
cgcgttacct tgcataaaac cactctt                                        27

<210> SEQ ID NO 470
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 470
ccactcttgt tcgactataa tctccactt                                      29
```

<210> SEQ ID NO 471
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 471
gcgctcatcg actcttcagt tgcttat                                      27

<210> SEQ ID NO 472
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 472
actcttcagt tgcttattac accaaact                                     28

<210> SEQ ID NO 473
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 473
gccaacaacg accgtggctc cggaaat                                      27

<210> SEQ ID NO 474
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 474
cgtggctccg gaaattagtc ttccatt                                      27

<210> SEQ ID NO 475
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 475
caaacaacga cagatgagct ttcttccat                                    29

<210> SEQ ID NO 476
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 476
gctttcttcc atggatccgc cgacaa                                       26

<210> SEQ ID NO 477
<211> LENGTH: 28
<212> TYPE: DNA
<213> ORGANISM: Artificial Sequence
<220> FEATURE:
<223> OTHER INFORMATION: Synthetic oligonucleotide

```
<400> SEQUENCE: 477
gctggttgat datagggatg tatgtagt                                    28

<210> SEQ ID NO 478
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 478
agggatgtat gtagtgattt ggttttgt                                    28

<210> SEQ ID NO 479
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 479
gactgccact aacttcagaa tctgaagt                                    28

<210> SEQ ID NO 480
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 480
ctgaagtcat caacatgcta accctaat                                    28

<210> SEQ ID NO 481
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 481
cgactactgg ctgataacat ccaccaa                                     27

<210> SEQ ID NO 482
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 482
ggctagccta ttcatcgaga acctagct                                    28

<210> SEQ ID NO 483
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 483
cttaatcacc aacacagtag attgatatat                                  30

<210> SEQ ID NO 484
```

```
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 484
ccaacacagt agattgatat atttgggttt a                                      31

<210> SEQ ID NO 485
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 485
cagcgagtat taagtgtatg aacatgt                                           27

<210> SEQ ID NO 486
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 486
gcgtccgagc gtgtgtttgt acatcta                                           27

<210> SEQ ID NO 487
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 487
cctccaccaa ctcaacatct ataagca                                           27

<210> SEQ ID NO 488
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 488
ccaccaactc aacatctata agcatatt                                          28

<210> SEQ ID NO 489
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 489
ccatgactgg actgaaagaa tctcctt                                           27

<210> SEQ ID NO 490
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 490
```
gaatctcctt ctatatctat ctattttggt                                        30

<210> SEQ ID NO 491
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 491
cagattcttc tctacaattt gttttttg                                          29

<210> SEQ ID NO 492
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 492
tgggttgtga cttagagaaa gataaaac                                          28

<210> SEQ ID NO 493
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 493
gctttatagc tatttctcta ctactcaat                                         29

<210> SEQ ID NO 494
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 494
ctctactact caatctgaaa tttacatcca                                        30

<210> SEQ ID NO 495
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 495
gcaaatcttt atttgcagtt ttaaaacca                                         29

<210> SEQ ID NO 496
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 496
ccatagaaga agcaagacca cttgtat                                           27

<210> SEQ ID NO 497
<211> LENGTH: 28
<212> TYPE: DNA

```
<213> ORGANISM: Artificial Sequence
<220> FEATURE:
<223> OTHER INFORMATION: Synthetic oligonucleotide

<400> SEQUENCE: 497
cctctagttg ctatgaagaa tttgttca                                          28

<210> SEQ ID NO 498
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 498
ctctctatct ctctctcact ctaaaagt                                          28

<210> SEQ ID NO 499
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 499
gctgtgaaga actctctctc tttcaag                                           27

<210> SEQ ID NO 500
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 500
ctctctctct ttcaaggtgg gagcaat                                           27

<210> SEQ ID NO 501
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 501
ccctcatgaa aaggaacaaa agtttaaag                                         29

<210> SEQ ID NO 502
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 502
gtgttcttga aggaaaccct ctcataaaat                                        30

<210> SEQ ID NO 503
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 503
cccgcatgat caaaaaggtt aaagat                                            26
```

```
<210> SEQ ID NO 504
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 504
ctgtcgaatg taacatcgag aggtaca                                       27

<210> SEQ ID NO 505
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 505
ggagacatcc aaccaagaat attgttt                                       27

<210> SEQ ID NO 506
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 506
ccaaccaaga atattgtttc ttgagtat                                      28

<210> SEQ ID NO 507
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 507
catggggaca tttgactctc ttcttgta                                      28

<210> SEQ ID NO 508
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 508
ggggacattt gactctcttc ttgtagct                                      28

<210> SEQ ID NO 509
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 509
ggtggccact tcaacgccag aatga                                         25

<210> SEQ ID NO 510
<211> LENGTH: 28
<212> TYPE: DNA
<213> ORGANISM: Artificial Sequence
<220> FEATURE:
```

<223> OTHER INFORMATION: Synthetic oligonucleotide

<400> SEQUENCE: 510
ggacatctag tcgaattatt attgtgtt                                    28

<210> SEQ ID NO 511
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 511
gttgctagtt accaccatga acataaata                                   29

<210> SEQ ID NO 512
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 512
cagctagcta gtctactgaa tttaaaat                                    28

<210> SEQ ID NO 513
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 513
gggacatttg actttacatg ttatgtct                                    28

<210> SEQ ID NO 514
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 514
gactttacat gttatgtctc ttttgcaa                                    28

<210> SEQ ID NO 515
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 515
ggtcatgtag agcagacgaa accctaa                                     27

<210> SEQ ID NO 516
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 516
gagggagtga ggggcaaaag cgtaat                                      26

<210> SEQ ID NO 517
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 517
ccaggatctt catcttctcc ttcttct                                27

<210> SEQ ID NO 518
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 518
cttctccttc ttctgaaaac taattaaact t                           31

<210> SEQ ID NO 519
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 519
gttcattcaa acccaggaaa aaatatc                                27

<210> SEQ ID NO 520
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 520
tcaaacccag gaaaaaatat cctcatg                                27

<210> SEQ ID NO 521
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 521
ggagtcaaaa gaactctcaa ggtctttta                              29

<210> SEQ ID NO 522
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 522
gttcacatgc cactcctttg aaatttca                               28

<210> SEQ ID NO 523
<211> LENGTH: 28
<212> TYPE: DNA
<213> ORGANISM: Artificial Sequence
<220> FEATURE:
<223> OTHER INFORMATION: Synthetic oligonucleotide

```
<400> SEQUENCE: 523
ccactccttt gaaatttcac ctcctgtt                                              28

<210> SEQ ID NO 524
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 524
ccttcatgat atattgatat cttcttgtt                                             29

<210> SEQ ID NO 525
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 525
tgatatcttc ttgttattac attttgagt                                             29

<210> SEQ ID NO 526
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 526
cacgggccac ggcgttgata aaacat                                                26

<210> SEQ ID NO 527
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 527
cctgccaata gagatcttac cctgtaa                                               27

<210> SEQ ID NO 528
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 528
ccaatagaga tcttaccctg taatgcat                                              28

<210> SEQ ID NO 529
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 529
ggaagtaaag gacctgccaa tggaga                                                26

<210> SEQ ID NO 530
<211> LENGTH: 26
```

```
<212> TYPE: DNA
<213> ORGANISM: Artificial Sequence
<220> FEATURE:
<223> OTHER INFORMATION: Synthetic oligonucleotide

<400> SEQUENCE: 530
gccaatggag aggcgcccta aaacta                                          26

<210> SEQ ID NO 531
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 531
gcctgccaat agaaagatgc cctatta                                         27

<210> SEQ ID NO 532
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 532
gccctattac tgctccgctt atcgta                                          26

<210> SEQ ID NO 533
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 533
tcgcccagta atccaaccat acattat                                         27

<210> SEQ ID NO 534
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 534
cccagtaatc caaccataca ttatctct                                        28

<210> SEQ ID NO 535
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 535
gaggattcgc cctgtaatgc tttcta                                          26

<210> SEQ ID NO 536
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 536
```

```
gccctgtaat gctttctacc aagaaat                                    27

<210> SEQ ID NO 537
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 537
ctgccaatgg tgatcttgcc ctgtaat                                    27

<210> SEQ ID NO 538
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 538
ggtgatcttg ccctgtaatg catattca                                   28

<210> SEQ ID NO 539
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 539
cgaagacaga tctggtaaaa atcgaaa                                    27

<210> SEQ ID NO 540
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 540
gacagatctg gtaaaaatcg aaaagaca                                   28

<210> SEQ ID NO 541
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 541
gagccactct cgatatataa tactacaa                                   28

<210> SEQ ID NO 542
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 542
ccaggggaca gatgcttcgt ttact                                      25

<210> SEQ ID NO 543
<211> LENGTH: 27
<212> TYPE: DNA
<213> ORGANISM: Artificial Sequence
```

-continued

```
<220> FEATURE:
<223> OTHER INFORMATION: Synthetic oligonucleotide

<400> SEQUENCE: 543
gggacagatg cttcgtttac tcgacat                               27

<210> SEQ ID NO 544
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 544
gccccttctt atatcgagtc aacaaaa                               27

<210> SEQ ID NO 545
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 545
gccactccga aaaccttcta aagcat                                26

<210> SEQ ID NO 546
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 546
ctccgaaaac cttctaaagc atctgaaa                              28

<210> SEQ ID NO 547
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 547
ttggcttaga catttctttc tttgatc                               27

<210> SEQ ID NO 548
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 548
gatcgcttct tatcatctcg tctgtt                                26

<210> SEQ ID NO 549
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 549
gctctctccc tctctacgtc tatttat                               27
```

<210> SEQ ID NO 550
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 550
ccctctctac gtctatttat ctatcta                                        27

<210> SEQ ID NO 551
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 551
gcgccatgtt gtgtgatcgt gtcat                                          25

<210> SEQ ID NO 552
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 552
tcgtgtcatg agcgtatgtt atgtata                                        27

<210> SEQ ID NO 553
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 553
gccttctgtc atcaccttttt atttgct                                       27

<210> SEQ ID NO 554
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 554
gctttattgt ctctttttta agcttttgat                                     30

<210> SEQ ID NO 555
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 555
acccgttatt tgccatcacc catctt                                         26

<210> SEQ ID NO 556
<211> LENGTH: 28
<212> TYPE: DNA
<213> ORGANISM: Artificial Sequence
<220> FEATURE:
<223> OTHER INFORMATION: Synthetic oligonucleotide -continued

```
<400> SEQUENCE: 556
ttgccatcac ccatcttttt cacatatt                                           28

<210> SEQ ID NO 557
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 557
accgtgatga cgttatatgg agatttt                                            27

<210> SEQ ID NO 558
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 558
ggagattttg ttgatgttac gaacgtgtgt at                                      32

<210> SEQ ID NO 559
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 559
gggagctcct tttcttcttc tcttaat                                            27

<210> SEQ ID NO 560
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 560
gctccttttc ttcttctctt aattagtc                                           28

<210> SEQ ID NO 561
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 561
ctcccagttt gtctgcagat gcatgt                                             26

<210> SEQ ID NO 562
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 562
ggaggcagcg gttcatcgat ctctt                                              25

<210> SEQ ID NO 563
```

```
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 563
cgctgcttgc tcttcatgac ttttgt                                          26

<210> SEQ ID NO 564
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 564
tgctcttcat gactttttgtt taattgata                                      29

<210> SEQ ID NO 565
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 565
gccttcaatc actctggaga aactaca                                         27

<210> SEQ ID NO 566
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 566
ctggagaaac tacaaaacct tgattatta                                       29

<210> SEQ ID NO 567
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 567
cccctcaatt atatcgcttc gatctt                                          26

<210> SEQ ID NO 568
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 568
cgcttcgatc tttccttctt tgagta                                          26

<210> SEQ ID NO 569
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 569
```
cccctcaact tacacgtttt gcttct                                          26

<210> SEQ ID NO 570
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 570
gcttctcaat cttcaagacc aatcgtt                                         27

<210> SEQ ID NO 571
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 571
ccctcaacct attttatcgc attttca                                         28

<210> SEQ ID NO 572
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 572
ctcagttctc accccattca aaacct                                          26

<210> SEQ ID NO 573
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 573
cacctgctaa tgattgtagc atgaagga                                        28

<210> SEQ ID NO 574
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 574
gtagcatgaa ggagaagaag aagaaga                                         27

<210> SEQ ID NO 575
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 575
cggagtccga ggtgaaaaaa taagga                                          26

<210> SEQ ID NO 576
<211> LENGTH: 27
<212> TYPE: DNA

<210> SEQ ID NO 576
<211> LENGTH: 27
<212> TYPE: DNA
<213> ORGANIZM: Artificial Sequence
<220> FEATURE:
<223> OTHER INFORMATION: Synthetic oligonucleotide

<400> SEQUENCE: 576
ggatccaact atcagatctg acacaat              27

<210> SEQ ID NO 577
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 577
ctctagatat ctctatccgt tatatcata             29

<210> SEQ ID NO 578
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 578
tccgttatat catatcatca tcatgatta             29

<210> SEQ ID NO 579
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 579
cctaaccaca tatcatatat atcatcatc             29

<210> SEQ ID NO 580
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 580
aggggttgct ttgtagtatc gttgaaa              27

<210> SEQ ID NO 581
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 581
gcttcgttct ctattcttcc atgttaga             28

<210> SEQ ID NO 582
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 582
gtcatgaatc ggacttatca tgtcaca              27

<210> SEQ ID NO 583
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 583
gcgaattttt tggcttacgg tttttcga            28

<210> SEQ ID NO 584
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 584
ggcttacggt tttcgattt gaatgat            27

<210> SEQ ID NO 585
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 585
ggcagtctcc ttggctatct tgaca            25

<210> SEQ ID NO 586
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 586
cattcacgtt atacctgttt ttctttct            28

<210> SEQ ID NO 587
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 587
ctcaactcag atatttacct tcatccaa            28

<210> SEQ ID NO 588
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 588
ggtgagcgaa tgttgacgat ttttgga            27

<210> SEQ ID NO 589
<211> LENGTH: 27
<212> TYPE: DNA
<213> ORGANISM: Artificial Sequence
<220> FEATURE:

<223> OTHER INFORMATION: Synthetic oligonucleotide

<400> SEQUENCE: 589
ggcttactta tctagggtct tttttc                                    27

<210> SEQ ID NO 590
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 590
ctagggtctt tttttccatt ttcatcat                                  28

<210> SEQ ID NO 591
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 591
tcggtagctt cctcttcgat cgtat                                     25

<210> SEQ ID NO 592
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 592
cctcttcgat cgtatggcaa atttct                                    26

<210> SEQ ID NO 593
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 593
cttccactcc ggtcaaaggg tttcat                                    26

<210> SEQ ID NO 594
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 594
agggtttcat gaccggagac atcaa                                     25

<210> SEQ ID NO 595
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 595
acccctcatg atttgatata taaagatag                                 29

```
<210> SEQ ID NO 596
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 596
cggtgaatac tactaagatc taagtttg                                    28

<210> SEQ ID NO 597
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 597
ctcccggacc cattcaacgg attt                                        24

<210> SEQ ID NO 598
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 598
ccgcaggtcg agacgagatt ttatat                                      26

<210> SEQ ID NO 599
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 599
ctcttggtgt cattctggcg tagtga                                      26

<210> SEQ ID NO 600
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 600
gtgaccacca ttgcagccgt tttat                                       25

<210> SEQ ID NO 601
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 601
ggaactcccg atgtcatttg gtgat                                       25

<210> SEQ ID NO 602
<211> LENGTH: 27
<212> TYPE: DNA
<213> ORGANISM: Artificial Sequence
<220> FEATURE:
<223> OTHER INFORMATION: Synthetic oligonucleotide
```

```
<400> SEQUENCE: 602
ggtgatgcca agccatgtat gtaaaat                                        27

<210> SEQ ID NO 603
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 603
cttggcaccc acaggctata ttaatta                                        27

<210> SEQ ID NO 604
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 604
cgagcggtgt agtcaacggt tga                                            23

<210> SEQ ID NO 605
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 605
gctgtgggaa aacatgacaa ttcag                                          25

<210> SEQ ID NO 606
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 606
cagggtttta ctccattgat tcacttgt                                       28

<210> SEQ ID NO 607
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 607
cacccctgct gagctctttc tcta                                           24

<210> SEQ ID NO 608
<211> LENGTH: 27
<212> TYPE: DNA
<213> ORGANISM: Artificial Sequence
<220> FEATURE:
<223> OTHER INFORMATION: Synthetic oligonucleotide
```

```
<400> SEQUENCE: 608
aggctggctt ttactcattt accaaat                                          27

<210> SEQ ID NO 609
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 609
ctgcaccaac atattaatat gattaatca                                        29

<210> SEQ ID NO 610
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 610
cagaatctga ggaataacaa aggattct                                         28

<210> SEQ ID NO 611
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 611
gcctcgcaat gcttcactaa cgttat                                           26

<210> SEQ ID NO 612
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 612
ggggttattc atttctccaa tatccaa                                          27

<210> SEQ ID NO 613
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 613
gagcgccggc gaaaaaagtc tct                                              23

<210> SEQ ID NO 614
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 614
cgacgattgt cattagaaga gtcgta                                           26
```

US 9,334,506 B2

METHOD TO TRIGGER RNA INTERFERENCE

REFERENCE TO RELATED APPLICATIONS

This is a division of U.S. patent application Ser. No. 13/827,450, filed Mar. 14, 2013 and issued as U.S. Pat. No. 9,018,002 on Apr. 28, 2015; which is a continuation of U.S. patent application Ser. No. 13/216,942, filed Aug. 24, 2011 and issued as U.S. Pat. No. 8,476,422 on Jul. 2, 2013; which is a continuation of U.S. patent application Ser. No. 11/334,776, filed Jan. 6, 2006 and issued as U.S. Pat. No. 8,030,473 on Oct. 4, 2011; which claims the benefit of U.S. provisional application No. 60/642,126, filed Jan. 7, 2005. Each of these prior applications is incorporated herein by reference in its entirety.

STATEMENT OF GOVERNMENT SUPPORT

This invention was made with United States government support pursuant to grant MCB-0209836 from the National Science Foundation, grant A143288 from the National Institutes of Health, and grant 2005-35319-15280 from the USDA; the United States government has certain rights in the invention.

FIELD

This disclosure relates to methods of regulating gene expression in vivo in plant, fungi, and invertebrate cells, as well as constructs and compositions useful in such methods. Further, it relates to RNAi-inducing nucleic acid constructs having a microRNA or siRNA target sequence (initiator sequence) and one or more siRNA-generating sequences directed to one or more target genes or RNAs, whereby the siRNA-generating sequences are in 21-nucleotide register with the cleavage site guided by the microRNA or siRNA initiator.

BACKGROUND

Mechanisms that suppress the expression of specific cellular genes, viruses or mobile genetic elements (such as transposons and retroelements) are critical for normal cellular function in a variety of eukaryotes. A number of related processes, discovered independently in plants (Matzke et al., *Curr. Opin. Genet. Dev.* 11:221-227, 2001), animals (Fire et al., *Nature,* 391:806-811, 1998) and fungi (Cogoni, *Annu. Rev. Microbiol.* 55:381-406, 2001), result in the RNA-directed inhibition of gene expression (also known as RNA silencing). Each of these processes is triggered by molecules containing double-stranded RNA (dsRNA) structure, such as transcripts containing inverted repeats or double-stranded RNA intermediates formed during RNA virus replication. Non-dsRNAs, also referred to as aberrant RNAs, may also function as initiators of RNA silencing. Such aberrant RNAs may be converted into dsRNAs by silencing-associated RNA-dependent RNA polymerases (RDRs), which have been identified in plants, fungi and *C. elegans* (Tuschl, *ChemBiochem,* 2:239-245, 2001).

Two major classes of small RNAs have been characterized: short interfering RNAs (siRNAs) and microRNAs (miRNAs). The primary transcripts that eventually form miRNAs are transcribed from non-protein-coding miRNA genes. These transcripts form hairpin structures that are then processed by Dicer (or by Dicer-like activities in plants) to yield small RNA duplexes containing 2-base overhangs at each 3' end. The mature single-stranded miRNA approximately 20-22 nucleotides in length forms by dissociation of the two strands in the duplex, and is selectively incorporated into the RNA-Induced Silencing Complex, or RISC (Zamore, *Science,* 296:1265-1269, 2002; Tang et al., *Genes Dev.,* 17:49-63, 2003; Xie et al., *Curr. Biol.* 13:784-789, 2003).

siRNAs are similar in chemical structure to miRNAs, however siRNAs are generated by the cleavage of relatively long double-stranded RNA molecules by Dicer or DCL enzymes (Zamore, *Science,* 296:1265-1269, 2002; Bernstein et al., *Nature,* 409:363-366, 2001). In animals and plants, siRNAs are assembled into RISC and guide the sequence specific ribonucleolytic activity of RISC, thereby resulting in the cleavage of mRNAs, viral RNAs or other RNA target molecules in the cytoplasm. In the nucleus, siRNAs also guide heterochromatin-associated histone and DNA methylation, resulting in transcriptional silencing of individual genes or large chromatin domains.

MicroRNAs in plants and animals function as posttranscriptional regulators of genes involved in a wide range of cellular processes (Bartel, *Cell* 116:281-297, 2004; He & Hannon, *Nat Rev Genet.* 5:522-531, 2004). In the plant *Arabidopsis thaliana*, miRNAs regulate mRNAs encoding at least twelve families of transcription factors, several miRNA metabolic factors, and proteins involved in stress responses, metabolism, and hormone signaling (Jones-Rhoades & Bartel, *Mol Cell* 14:787-799, 2004; Kasschau et al., *Dev Cell* 4:205-217, 2003; Llave et al., *Science* 297:2053-2056, 2002b; Vazquez et al., *Curr Biol* 14:346-351, 2004a; Xie et al., *Curr Biol* 13:784-789, 2003). Plant miRNAs target a disproportionately high number of genes with functions in developmental processes, including developmental timing, control of cell proliferation, meristem cell function, and patterning. Global disruption of miRNA biogenesis or function, or specific disruption of miRNA-target interactions, can result in severe developmental abnormalities (Achard et al., *Development* 131:3357-3365, 2004; Chen, *Science* 303:2022-2025, 2004; Emery et al., *Curr Biol* 13:1768-1774, 2003; Juarez et al., *Nature* 428:84-88, 2004; Kidner & Martienssen, *Nature* 428:81-84, 2004; Laufs et al., *Development* 131:4311-4322, 2004; Mallory et al., *Curr Biol* 14:1035-1046, 2004; Palatnik et al., *Nature* 425:257-263, 2003; Tang et al., *Genes & Dev* 17:49-63 2003; Vaucheret et al., *Genes Dev* 18:1187-1197, 2004), indicating that miRNA-based regulation is crucial for normal growth and development. This idea is reinforced by the conservation of most miRNAs and their corresponding targets through significant evolutionary time (Bartel, *Cell* 116:281-297, 2004). MicroRNAs have been identified by direct cloning methods and computational prediction strategies (Jones-Rhoades & Bartel, *Mol Cell* 14:787-799, 2004; Llave et al., *Plant Cell* 14:1605-1619, 2000a; Park et al., *Curr Biol* 12:1484-1495, 2002; Reinhart et al., *Genes Dev* 16:1616-1626, 2002; Sunkar & Zhu, *Plant Cell* 16:2001-2019, 2004).

Plant miRNAs usually contain near-perfect complementarity with target sites, which are found most commonly in protein-coding regions of the genome. As a result, most (but not all) plant miRNAs function to guide cleavage of targets through a mechanism similar to the siRNA-guided mechanism associated with RNAi (Jones-Rhoades & Bartel, *Mol Cell* 14:787-799, 2004; Kasschau et al., *Dev Cell* 4:205-217, 2003; Llave et al., *Science* 297:2053-2056, 2002; Tang et al., *Genes & Dev* 17:49-63 2003). In contrast, animal miRNAs contain relatively low levels of complementarity to their target sites, which are most commonly found in multiple copies within 3' untranslated regions of the target transcript (Lewis et al., *Cell* 115:787-798, 2003; Rajewsky & Socci, *Dev Biol*

267:529-535, 2004; Stark et al., *PLoS Biol* 1:E60, 2003). Most animal miRNAs do not guide cleavage, but rather function to repress expression at the translational or co-translational level (Ambros, *Cell* 113:673-676, 2003; He & Hannon, *Nat Rev Genet.* 5:522-531, 2004). At least some plant miRNAs may also function as translational repressors (Aukerman & Sakai, *Plant Cell* 15:2730-2741, 2003; Chen, *Science* 303:2022-2025, 2004). Translation repression is not an inherent activity of animal miRNAs, as miRNAs will guide cleavage if presented with a target containing high levels of complementarity (Doench et al., *Genes Dev* 17:438-442, 2003; Hutvagner & Zamore, *Science* 297:2056-2060, 2002; Yekta et al., *Science* 304:594-596, 2004; Zeng et al., *Proc Natl Acad Sci USA* 100:9779-9784, 2003).

MicroRNAs form through nucleolytic maturation of genetically defined RNA precursors that adopt imperfect, self-complementary foldback structures. Processing yields a duplex intermediate (miRNA/miRNA*) that ultimately provides the miRNA strand to the effector complex, termed RISC (Khvorova et al., *Cell* 115:209-216, 2003; Schwarz et al., *Cell* 115:199-208, 2003). Plants contain four DICER-LIKE (DCL) proteins, one of which (DCL1) is necessary for maturation of most or all miRNA precursors (Kurihara & Watanabe, *Proc Natl Acad Sci USA* 101:12753-12758, 2004; Park et al., *Curr Biol* 12:1484-1495, 2002; Reinhart et al., *Genes Dev* 16:1616-1626, 2002; Schauer et al., *Trends Plant Sci* 7:487-491, 2002). The DCL1 protein contains an RNA helicase and two RNaseIII-like domains, a central PAZ domain and C-terminal dsRNA binding motifs. Animal miRNA precursor processing requires Drosha, another RNaseIII domain protein, and Dicer in sequential nucleolytic steps (Lee et al., *Nature* 425:415-419, 2003). HEN1 participates in miRNA biogenesis or stability in plants via a 3' methylase activity (Boutet et al., *Curr Biol* 13:843-848, 2003; Park et al., *Curr Biol* 12:1484-1495, 2002). The dsRNA-binding HYL1 protein is necessary for miRNA biogenesis in cooperation with DCL1 and HEN1 in the nucleus. Based on sequence similarity, HYL1 has been suggested to function like animal R2D2, which is required post-processing during RISC assembly (Han et al., *Proc Natl Acad Sci USA* 101:1093-1098, 2004; Liu et al., *Science* 301:1921-1925, 2003; Pham et al., *Cell* 117:83-94, 2004; Tomari et al., *Science* 306:1377-1380, 2004; Vazquez et al., *Curr Biol* 14:346-351, 2004a). In animals, Exportin-5 (Exp5) regulates the transport of pre-miRNAs from the nucleus to the cytoplasm by a Ran-GTP-dependent mechanism (Bohnsack et al., *RNA* 10:185-191, 2004; Lund et al., *Science* 303:95-98, 2003; Yi et al., *Genes Dev* 17:3011-3016, 2003). In *Arabidopsis*, HST may provide a related function to transport miRNA intermediates to the cytoplasm (Bollman et al., *Development* 130:1493-1504, 2003). Active miRNA-containing RISC complexes in plants almost certainly contain one or more ARGONAUTE proteins, such as AGO1 (Fagard et al., *Proc Natl Acad Sci USA* 97:11650-11654, 2000; Vaucheret et al., *Genes Dev* 18:1187-1197, 2004). Argonaute proteins in animals were shown recently to provide the catalytic activity for target cleavage (Liu et al., *Science* 305:1437-1441, 2004; Meister et al., *Mol Cell* 15:185-197, 2004).

In addition to miRNAs, plants also produce diverse sets of endogenous 21-25 nucleotide small RNAs. Most of these differ from miRNAs in that they arise from double-stranded RNA (rather than imperfect foldback structures), in some cases generated by the activity of RNA-DEPENDENT RNA POLYMERASEs (RDRs). *Arabidopsis* DCL2, DCL3, DCL4, RDR1, RDR2 and RDR6 have known roles in siRNA biogenesis (Dalmay et al., *Cell* 101:543-553, 2000; Mourrain et al., *Cell* 101:533-542, 2000; Peragine et al., *Genes & Dev* 18:2369-2379, 2004; Vazquez et al., *Mol Cell* 16:69-79, 2004b; Xie et al., *PLoS Biol* 2:642-652, 2004; Yu et al., *Mol Plant Microbe Interact* 16:206-216, 2003). For example, DCL3 and RDR2 cooperate in the heterochromatin-associated RNAi pathway, resulting in ~24-nucleotide siRNAs from various retroelements and transposons, 5S rDNA loci, endogenous direct and inverted repeats, and transgenes containing direct repeats (Xie et al., *PLoS Biol* 2:642-652, 2004; Zilberman et al., *Science* 299:716-719, 2003). RDR6 functions in posttranscriptional RNAi of sense transgenes, some viruses, and specific endogenous mRNAs that are targeted by trans-acting siRNAs (ta-siRNAs) (Dalmay et al., *Cell* 101:543-553, 2000; Mourrain et al., *Cell* 101:533-542, 2000; Peragine et al., *Genes & Dev* 18:2369-2379, 2004; Vazquez et al., *Mol Cell* 16:69-79, 2004b; Yu et al., *Mol Plant Microbe Interact* 16:206-216, 2003). Ta-siRNAs arise from transcripts that are recognized by RDR6, in cooperation with SGS3, as a substrate to form dsRNA. The dsRNA is processed accurately in 21-nucleotide steps by DCL1 to yield a set of "phased" ta-siRNAs. These ta-siRNAs interact with target mRNAs to guide cleavage by the same mechanism as do plant miRNAs (Peragine et al., *Genes & Dev* 18:2369-2379, 2004; Vazquez et al., *Mol Cell* 16:69-79, 2004).

There is a need to develop methods and constructs that can be used to induce targeted RNAi in vivo. It is to such methods and constructs, and related compositions, that this disclosure is drawn.

SUMMARY OF THE DISCLOSURE

Provided herein are methods of generating one or more siRNAs in vivo; also provided are constructs and compositions useful in the methods. The methods do not depend on DNA or other synthetic nucleic acid molecules that contain inverted duplications (repeats) or dual promoters to form perfect or largely double-stranded RNA. Rather, the methods employ constructs that yield single-stranded RNA transcripts, and take advantage of endogenous (native or heterologous) or in vivo-produced miRNAs or siRNAs to initiate production of siRNAs from an engineered RNAi-triggering cassette. The miRNAs or siRNAs guide cleavage of the transcript and set the register (phase) for production of siRNAs (usually 21 nucleotides in length) encoded adjacent to the initiation cleavage site within the construct. The methods result in specific formation of siRNAs of predictable size and register (phase) relative to the initiation cleavage site. The method can be used to produce specific siRNAs in vivo for inactivation or suppression of one or more target genes or other entities, such as pathogens or pests (e.g., viruses, bacteria, nematodes). No exogenous hairpin or foldback structure is required in the provided constructs in order to generate siRNAs or to carry out RNAi-like inhibition of target gene(s).

Also provided are methods, and constructs for use in such methods, where the siRNAs are produced in a tissue-specific, cell-specific, or other regulated manner.

Further, transformed cells and organisms that contain a transgene including at least one RNAi-triggering cassette are also provided by this disclosure. For instance, transgenic fungi, invertebrate animals, and plants are provided that contain at least one RNAi-triggering cassette, which, when transcribed, produces at least one siRNA molecule complementary to a target sequence to be inhibited in that organism.

The foregoing and other features and advantages will become more apparent from the following detailed description of several embodiments, which proceeds with reference to the accompanying figures.

BRIEF DESCRIPTION OF THE FIGURES

(FIG. 1A) Flowchart for miRNA target identification. The number of small RNAs (or targets) passing a filter is shown in parentheses. Predicted targets are classified into 5 bins based on validation data. The false negative rate in Bins 1 and 2 are based on 66 and 28 targets in the 'Rule development set', respectively (see Table 3). (FIG. 1B) Percent of mismatched and G:U base-pairs at each position of the Rule development set targets. Position 1 corresponds to the 5' end of the miRNA. (FIG. 1C) Minimum Free Energy (MFE) ratio of the Rule development set target duplexes. Black circles indicate Rule development set validated targets, open circles indicate rule development set targets only predicted computationally. (FIG. 1D) Number of predicted target genes for a given miRNA-target duplex score, filtered by duplexes with an MFE ratio ≥0.73. Total predicted targets (open triangles) and captured targets in the Rule development set (open circles) are shown. Total targets in the Rule development set (94) is indicated by the dashed line.

(FIG. 2A) Target duplexes from Bin 1 validated in this study. (FIG. 2B) Duplexes for predicted miRNA targets in Bin 3.

(FIG. 3A) Protein-coding miRNA targets. The miRNA-target duplex is highlighted, with the fraction of cloned PCR products terminating at a given position in the target validation assay (Llave et al., *Science* 297:2053-2056, 2002) indicated above the duplex. The distribution of cleavage products across all five predicted miR399 target sites is displayed above the schematic representation of At2g33770. (FIG. 3B) Non-coding miRNA targets predicted by the EST database search. Each of these targets corresponds to a ta-siRNA-generating primary transcript.

(FIG. 4A) Phenotype of hst-15 and rdr6-15 mutants. Rosettes (Col-0, rdr6-15, hst-15), first true leaf (Col-0, rdr6-15), bolt and flower (Col-0, hst-15) are shown. For array data in (b-e), normalized intensity is plotted as log 2 of the fold change relative to the control sample for each mutant, thus zero represents no change in transcript abundance. (FIG. 4B) Profile of 81 of 94 miRNA target transcripts predicted previously and in this study (Bins 1 and 2, FIG. 1). (FIG. 4C) Profile of 12 of 18 miRNA target genes predicted in this study. The solid lines indicate new targets from existing target families (Bin 3, FIG. 1), and the dashed lines indicate novel miRNA targets (Bin 4, FIG. 1). Non-validated targets in Bin 5 are not shown. (FIG. 4D) Profile of transcripts significantly co-affected (P>0.01) in dcl1-7, hen1-1, and rdr6-15. (FIG. 4E) Profile of 93 predicted miRNA target transcripts (light lines), and PCA component 1 (dark line). (FIG. 4F) Cladogram of the small RNA biogenesis mutant series. The correlation among groups (r×100) is shown at each node. (FIG. 4G) Scatterplots of all genes showing normalized intensity values representing fold change (hyl1-2 vs. hst-15, dcl1-7 vs. hen1-1, hyl1-2 vs. dcl3-1).

FIG. 5A-E. In-phase processing of trans-acting siRNAs directed by miR173 as the initiator. (FIG. 5A-5C) Diagrammatic representation of the three TAS1 and on TAS2 loci. The naming convention used is TAS (for Trans-Acting SiRNA). Ta-siRNAs with functional evidence are shown by the systematic nomenclature (see text for details). The 21 nucleotide phase is indicated by brackets, with the first position starting from the miR173-guided cleavage site. The relative positions from the cleavage site are designated 3'D1, 3'D2, etc. Positions for which small RNAs are represented in the ASRP sequence database are listed with the ASRP ID number. Relative positions of the At2g39675 and At3g39680 loci in *Arabidopsis* chromosome 2 are shown in (FIG. 5C). (FIG. 5D) Detection and validation of ta-siRNAs by small RNA blot analysis. Small RNAs were detected using specific oligo probes, except At3g39680 antisense small RNAs which were detected with a 469 nucleotide radiolabeled RNA transcript. (FIG. 5E) Validation of siR255 target genes by 5' RACE, and predicted Ag3g39681 (TAS2). 3'D6(−) targeted PPR genes.

(FIG. 6A) Diagrammatic representation of the miR390 target locus, TAS3 (At3g17185). Labeling is as in FIG. 5, but with the 21-nucleotide phased positions designated 5'D1, 5'D2, etc., starting at the miR390-guided cleavage site. The two siRNAs that are predicted to guide cleavage of ARF3 and ARF4 are indicated. (FIG. 6B) Detection and validation of ta-siRNAs from the TAS3 locus. (FIG. 6C) T-Coffee program alignment of TAS3 orthologs in plants showing conservation of predicted TAS3 ta-siRNAs and miR390 target site. High levels of conservation are designated by light shading. (FIG. 6D) PLOTCON program similarity score (21 nt window) derived from alignment of 18 ARF3 and ARF4 genes from 16 species, over a 600 nt region. Two highly conserved regions are indicated by A and B, which are TAS3 ta-siRNA target sites. Below, validation of small RNA directed cleavage of ARF3 and ARF4 by 5' RACE. The predicted TAS3-derived ta-siRNAs are shown below complementary regions of ARF3 and ARF4 sequences. (FIG. 6E) Consensus phylogenetic tree of the ARF family, showing miRNA and ta-siRNA regulated branches. Bayesian posterior probability was 100 except for labeled nodes.

(FIG. 8A) Prediction flowchart for miRNA validation. The number of small RNAs passing a filter is shown in parentheses. (FIG. 8B) Predicted secondary structure of miRNA precursors validated in this study. (FIG. 8C, FIG. 8D) Small RNA blot analysis of miRNAs. miR159 and miR167 are shown as traditional miRNA controls, AtSN1 is shown as an siRNA control. Ethidium bromide-stained gel (tRNA and 5S RNA zone) is shown at the bottom. Wildtype controls (Col-0 and La-er) are shown next to respective miRNA metabolism mutants (FIG. 8C) and ta-siRNA biogenesis mutants (rdr6-11 and sgs3-11) or transgenic plants expressing viral silencing (FIG. 8D).

(FIG. 9A) Schematic representation of a generic MIRNA transcript (top), and control SCL6-IV mRNA (middle) and miR171-guided cleavage product (bottom). The relative positions of oligonucleotides used in 5'RACE reactions are shown. (FIG. 9B) RLM-5'RACE reactions using poly(A)+-selected RNA that was pretreated with calf intestinal phosphatase (CIP) plus tobacco acid pyrophosphatase (TAP, even-numbered lanes) or with buffer (odd-numbered lanes) prior to adaptor ligation. The 5'RACE products for SCL6-IV-specific RNAs (lanes1-4) and three MIRNA loci (lanes 5-10) were resolved on a 2% agarose gel. Gene-specific primers used for 5'RACE are indicated above each lane.

FIG. 10A-C. MIRNA gene transcript start sites and core promoter elements. (FIG. 10A) Base frequency at MIRNA transcription initiation sites (n=63). (FIG. 10B) Genomic sequences (−50 to +10 relative to start sites) around 63 start sites (bold capital letters 10 in from the 3' end of each sequence) from 47 *Arabidopsis* MIRNA loci. Putative TATA motifs (bold) are indicated. These sequences correspond to SEQ ID NOs: 286-348. (FIG. 10C) Occurrence of high-scoring TATA motifs within a 250-nucleotide (−200 to +50) genomic context for 63 MIRNA transcripts.

FIG. 12A; PDS: FIG. 12C; PID: FIG. 12D). The GFP gene was silenced by the artificial GFP ta-siRNAs in a miR173-dependent manner (FIG. 12B). The same miR173 and ta-siRNA255 controls were used for PDS, PID, and GFP siRNA assays.

(FIG. 14A and FIG. 14B) Constructs with wild-type miR173 target sites. Constructs were expressed or coexpressed as indicated above the blot panels. The small RNAs detected in blot assays are shown to the right of each panel. Duplicate biological samples were analyzed for most treatments. (FIG. 14C) Constructs with mutagenized target site or miR173 sequences. Target site and miRNA combinations tested are illustrated schematically above the blot panels. Mutagenized positions are in bold. The miR173res1 probe hybridized to both the miR173 and miR173res1 sequences.

BRIEF DESCRIPTION OF THE SEQUENCE LISTING

Figure 1A:
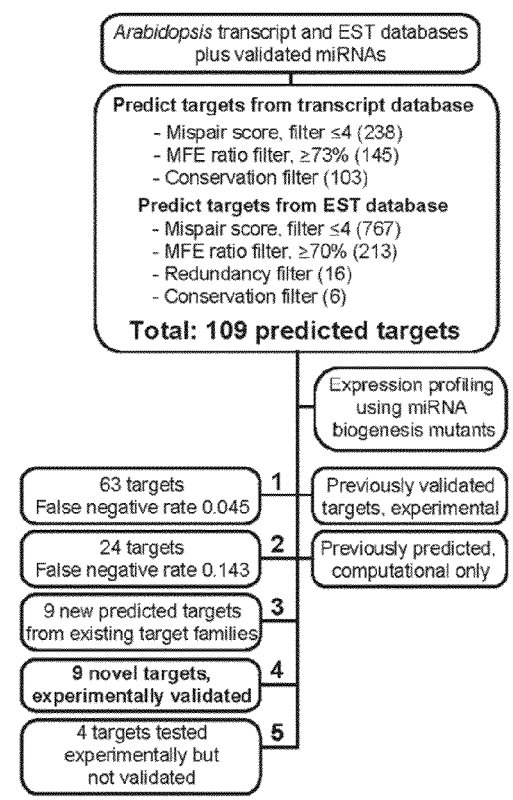
FIG. 1A-1D. Refined prediction and validation of miRNA target genes in *Arabidopsis*.

The nucleic acid sequences listed below are shown using standard letter abbreviations for nucleotide bases, as defined in 37 C.F.R. §1.822. Only one strand of each nucleic acid sequence is shown, but the complementary strand is understood as included in embodiments where it would be appropriate. The Sequence Listing is submitted as an ASCII text file named SeqList.txt, created on Apr. 24, 2014, ~120 KB, which is incorporated by reference herein. In the accompanying Sequence Listing:

SEQ ID NOs: 1-142 and 281-285 are representative target (initiator) sequences. The initiator sequences are shown as RNA; it is understood that the corresponding DNA sequence would comprise a T in place of any U. The sequences are broken out based on the miRNA complementary to the provided initiator (target) sequences. The corresponding miRNA sequence can be deduced for each target sequence; it is the reverse complement formed of RNA.

SEQ ID NOs: 143-154 are predicted miRNA candidates (shown as RNA) that were tested experimentally, and which are discussed in Example 5.

SEQ ID NOs: 155-206 are miRNA sequences (shown as RNA), which are discussed in Example 5.

SEQ ID NOs: 207-276 are validated miRNA sequences cloned from *Arabidopsis* small RNA libraries (shown as RNA), and which are discussed in Example 5.

SEQ ID NO: 277 is the nucleic acid sequence of an artificial ta-siRNA locus targeting *Arabidopsis* gene encoding GFP.

SEQ ID NO: 278 is the nucleic acid sequence of an artificial ta-siRNA locus targeting *Arabidopsis* gene encoding phytoene desaturase (PDS).

SEQ ID NO: 279 is the nucleic acid sequence of an artificial ta-siRNA locus targeting *Arabidopsis* gene encoding PINOID (PID).

SEQ ID NO: 280 is an example of a sequence that would be contained in DNA construct containing SEQ ID NO: 1 as an initiator sequence.

SEQ ID NOs: 286-348 are genomic sequences (−50 to +10 relative to start sites) of 63 start sites in 47 *Arabidopsis* miRNA loci. These are shown graphically in FIG. 10B.

SEQ ID NOs: 349 to 614 are primers used in 3'RACE confirmation sequencing.

DETAILED DESCRIPTION

I. Abbreviations

AGO Argonaute
asRNA antisense RNA
cDNA complementary DNA
DCL dicer-like
dsRNA double-stranded RNA
GFP green fluorescent protein
LKR lysine ketoglutarate reductase
miRNA microRNA
nt nucleotide
PID PINOID
PDS phytoene desaturase
PTGS post-transcriptional gene silencing
RDR RNA-dependent RNA polymerase
RISC RNA-induced silencing complex
RNAi RNA interference
siRNA small interfering RNA
ssRNA single-stranded RNA
ta-siRNA trans-acting siRNA
TGS transcriptional gene silencing II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, by VCH Publishers, Inc., 1995 (ISBN 1-56081-569-8).

In order to facilitate review of the various embodiments of the invention, the following non-limiting explanations of specific terms are provided:

21-Nucleotide Phasing: An incremental 21-nucleotide register, starting at an initiator cleavage site, in which cleavage is mediated by a RISC guided by either a miRNA or siRNA. Phasing defines a set of 21 nucleotide segments in linear, end-to-end orientation, either to the 5' or 3' side of the initiator cleavage site, or both. Formation of the 21-nucleotide siRNAs in phase with the cleavage site depends on the activity of a DICER or DICER-LIKE enzyme.

Agent: Any substance, including, but not limited to, an antibody, chemical compound, small molecule, therapeutic, nucleic acid, peptide mimetic, peptide, or protein. An agent can increase or decrease the level of miRNA or siRNA expression or production.

Agronomic trait: Characteristic of a plant, which characteristics include, but are not limited to, plant morphology, physiology, growth and development, yield, nutritional enhancement, disease or pest resistance, or environmental or chemical tolerance are agronomic traits. In the plants of this disclosure, the expression of identified recombinant DNA, e.g. for gene suppression, confers an agronomically important trait, e.g. increased yield. An "enhanced agronomic trait" refers to a measurable improvement in an agronomic trait including, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Increased yield may result from improved utilization of key biochemical compounds, such as nitrogen, phosphorus and carbohydrate, or from improved responses to environmental stresses, such as cold, heat, drought, salt, and attack by pests or pathogens. Recombinant DNA used in this disclosure can also be used to provide plants having improved growth and development, and ultimately increased yield, as the result of modified expression of plant growth regulators or modification of cell cycle or photosynthesis pathways.

Altering level of production or expression: Changing, either by increasing or decreasing, the level of production or expression of a nucleic acid sequence or an amino acid sequence (for example a polypeptide, an siRNA, a miRNA, an mRNA, a gene), as compared to a control level of production or expression.

Antisense, Sense, and Antigene: DNA has two antiparallel strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA (asRNA) is a molecule of RNA complementary to a sense (encoding) nucleic acid molecule.

Amplification: When used in reference to a nucleic acid, this refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744, 311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. For instance, binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples.

Complementarity and percentage complementarity: Molecules with complementary nucleic acids form a stable duplex or triplex when the strands bind, or hybridize, to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with (are complementary to) the bases in a second nucleic acid strand. Complementarity is conveniently described by the percentage, i.e., the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

Sufficient complementarity means that a sufficient number of base pairs exist between the oligonucleotide and the target sequence to achieve detectable binding, and disrupt or reduce expression of the gene product(s) encoded by that target sequence. When expressed or measured by percentage of base pairs formed, the percentage complementarity that fulfills this goal can range from as little as about 50% complementarity to full, (100%) complementarity. In some embodiments, sufficient complementarity is at least about 50%, about 75% complementarity, or at least about 90% or 95% complementarity. In particular embodiments, sufficient complementarity is 98% or 100% complementarity.

A thorough treatment of the qualitative and quantitative considerations involved in establishing binding conditions that allow one skilled in the art to design appropriate oligonucleotides for use under the desired conditions is provided by Beltz et al., *Methods Enzymol* 100:266-285, 1983, and by Sambrook et al. (ed.), *Molecular Cloning: A Laboratory Manual*, $2^{nd}$ ed., v:1-3, Cold Spring Harbor Laboratory Press, Cold Spring Harbor, N.Y., 1989.

Complementary: The base pairing that occurs between two distinct nucleic acid sequences or two distinct regions of the same nucleic acid sequence.

Control level: The level of a molecule, such as a polypeptide or nucleic acid, normally found in nature under a certain condition and/or in a specific genetic background. In certain embodiments, a control level of a molecule can be measured in a cell or specimen that has not been subjected, either directly or indirectly, to a treatment. A control level is also referred to as a wildtype or a basal level. These terms are understood by those of ordinary skill in the art.

Control plant: A control plant, i.e. a plant that does not contain a recombinant DNA that confers (for instance) an enhanced agronomic trait in a transgenic plant, is used as a baseline for comparison to identify an enhanced agronomic trait in the transgenic plant. A suitable control plant may be a non-transgenic plant of the parental line used to generate a transgenic plant. A control plant may in some cases be a transgenic plant line that comprises an empty vector or marker gene, but does not contain the recombinant DNA, or does not contain all of the recombinant DNAs in the test plant.

DICER-LIKE (DCL): Plant homologs of the animal protein DICER. Both DICER and DCL enzymes catalyze formation of small RNA duplexes from larger precursor RNA molecules. By way of example, *Arabidopsis thaliana* contains four DCL genes (DCL1-DCL4). DCL1 for instance catalyzes processing of fold-back precursors for miRNAs (GenBank Accession No. NM_099986; locus position At1g01040).

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Encode: A polynucleotide is said to encode a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expression: The process by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased).

Fluorophore: A chemical compound, which when excited by exposure to a particular wavelength of light, emits light (i.e., fluoresces), for example at a different wavelength than that to which it was exposed. Fluorophores can be described in terms of their emission profile, or "color." Green fluorophores, for example Cy3, FITC, and Oregon Green, are characterized by their emission at wavelengths generally in the range of 515-540$\lambda$. Red fluorophores, for example Texas Red, Cy5 and tetramethylrhodamine, are characterized by their emission at wavelengths generally in the range of 590-690$\lambda$.

Encompassed by the term "fluorophore" are luminescent molecules, which are chemical compounds which do not require exposure to a particular wavelength of light to fluoresce; luminescent compounds naturally fluoresce. Therefore, the use of luminescent signals eliminates the need for an external source of electromagnetic radiation, such as a laser. An example of a luminescent molecule includes, but is not limited to, aequorin (Tsien, *Ann. Rev. Biochem.* 67:509, 1998).

Examples of fluorophores are provided in U.S. Pat. No. 5,866,366. These include: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcoumarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride);

4-(4'-dimethylaminophenylazo)benzoic acid (DABCYL); 4-dimethylaminophenyl-azophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores include thiol-reactive europium chelates that emit at approximately 617 nm (Heyduk and Heyduk, *Analyt. Biochem.* 248:216-227, 1997; *J. Biol. Chem.* 274:3315-3322, 1999).

Still other fluorophores include cyanine, merocyanine, styryl, and oxonyl compounds, such as those disclosed in U.S. Pat. Nos. 5,268,486; 5,486,616; 5,627,027; 5,569,587; and 5,569,766, and in published PCT patent application no. US98/00475, each of which is incorporated herein by reference. Specific examples of fluorophores disclosed in one or more of these patent documents include Cy3 and Cy5, for instance.

Other fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al., herein incorporated by reference) and derivatives thereof. Other fluorophores are known to those skilled in the art, for example those available from Molecular Probes (Eugene, Oreg.).

Gene Silencing: Gene silencing refers to lack of (or reduction of) gene expression as a result of, though not limited to, effects at a genomic (DNA) level such as chromatin re-structuring, or at the post-transcriptional level through effects on transcript stability or translation. Current evidence suggests that RNA interference (RNAi) is a major process involved in transcriptional and posttranscriptional gene silencing.

Because RNAi exerts its effects at the transcriptional and/or post-transcriptional level, it is believed that RNAi can be used to specifically inhibit alternative transcripts from the same gene.

Heterologous: A type of sequence that is not normally (i.e. in the wild-type sequence) found adjacent to a second sequence. In one embodiment, the sequence is from a different genetic source, such as a virus or organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. In RNA molecules, G also will bond to U. Complementary refers to the base pairing that occurs between two distinct nucleic acid sequences or two distinct regions of the same nucleic acid sequence.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference. The following is an exemplary set of hybridization conditions and is not meant to be limiting.

Very High Stringency (Detects Sequences that Share 90% Sequence Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share 80% Sequence Identity or Greater)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share Greater than 50% Sequence Identity)
  Hybridization: 6×SSC at RT to 55° C. for 16-20 hours
  Wash at least twice: 2×-3×SSC at RT to 55° C. for 20-30 minutes each.

Initiator sequence: A nucleotide sequence of about 21 nucleotides in length that, when present in an RNA molecule, serves as a cleavage site that is recognized by a RISC guided by a miRNA or siRNA. Cleavage at an initiator sequence (usually between the tenth and eleventh nucleotide counted from the 3' end of the initiator sequence) sets the 21-nucleotide phasing within one or both RNA molecules that result after cleavage. These cleavage products, after conversion to double-stranded RNA, are subject to processing by Dicer or DCL enzymes usually in 21-nucleotide intervals upstream and/or downstream of the initiator sequence. In an engineered nucleic acid cassette as described herein, such in-phase cleavages release siRNAs from the cassette. Representative initiator sequences, also referred to as miRNA target sequences, are shown herein, including SEQ ID NOs: 1-142 and 281-285. Additional initiator sequences will be known to those of ordinary skill in the art. See, for instance, sequences listed in the public database miRBase::Sequences (available on-line through the Sanger Institute website, microma.sanger.ac.uk/sequences/index.shtml); sequences in that database through Release 7.1 (October 2005) are included herein by reference.

In the following table of target (initiator) sequences (Table 1), the initiator cleavage site is indicated by a "~" symbol. The sequences are broken out based on the miRNA families. The corresponding miRNA sequence(s) or miRNA family sequences are largely complementary to the target sequences. The gene name indicates a representative plant species for each sequence: At=*Arabidopsis thaliana*; Gh=*Gossypium hirsutum*; Gm=*Glycine max*; Hv=*Hordeum vulgare*; Le=*Lycopersicum esculentum*; Lj=*Lotus japonicus*;

Mc=*Mesembryanthemum crystallinum*; Mt=*Medicago truncatula*; Os=*Oryza sativa*; Pg=*Pennisetum glaucum*; Pt=*Populus tremula*; Pv=*Plumbago zeylanica*; Sb=*Sorghum bicolor*; So=*Saccharum officinarum*; Tc=*Theobroma cacao*; Ta=*Triticum aesitivum*; Vv=*Vitis vinifera*; Zm=*Zea mays*. Additional plants containing these sequences are discussed below. Validated miRNA target sequences have been confirmed experimentally using a cleavage site assay (Llave et al., *Science* 297:2053-2056, 2002); predicted sequences have yet to be examined experimentally and identified in vivo, but were predicted computationally. Sequences that are known only in *Arabidopsis* are indicated.

TABLE 1

| Gene | Target Sequence | Status | SEQ ID # |
|---|---|---|---|
| miR156 family target sequences - all plants ||||
| At1g27370 | GUGCUCUCUC~UCUUCUGUCA | Validated | 1 |
| At1g53160 | CUGCUCUCUC~UCUUCUGUCA | Validated | 2 |
| At2g33810 | UUGCUUACUC~UCUUCUGUCA | Predicted | 3 |
| At3g15270 | CCGCUCUCUC~UCUUCUGUCA | Predicted | 4 |
| miR159 family target sequences - all plants ||||
| At5g06100 | UGGAGCUCCCU~UCAUUCCAAU | Validated | 5 |
| At2g26960 | UCGAGUUCCU~UCAUUCCAAU | Predicted | 6 |
| At4g26930 | AUGAGCUCUCU~UCAAACCAAA | Predicted | 7 |
| At2g26950 | UGGAGCUCCCU~UCAUUCCAAG | Predicted | 8 |
| At2g32460 | UAGAGCUUCCU~UCAAACCAAA | Predicted | 9 |
| At3g60460 | UGGAGCUCCAU~UCGAUCCAAA | Predicted | 10 |
| At5g55020 | AGCAGCUCCCU~UCAAACCAAA | Predicted | 11 |
| PvMYB | CAGAGCUCCCU~UCACUCCAAU | Predicted | 12 |
| VvMYB | UGGAGCUCCCU~UCACUCCAAU | Predicted | 13 |
| HvMYB33 | UGGAGCUCCCU~UCACUCCAAG | Predicted | 14 |
| OsMYB33 | UGGAGCUCCCU~UUAAUCCAAU | Predicted | 15 |
| miR160 family target sequences - all plants ||||
| At1g77850 | UGGCAUGCAGG~GAGCCAGGCA | Validated | 16 |
| At2g28350 | AGGAAUACAGG~GAGCCAGGCA | Validated | 17 |
| At4g30080 | GGGUUUACAGG~GAGCCAGGCA | Validated | 18 |
| OsARF | AGGCAUACAGG~GAGCCAGGCA | Predicted | 19 |
| LjARF | AAGCAUACAGG~GAGCCAGGCA | Predicted | 20 |
| miR161 family target sequences - *Arabidopsis* ||||
| At5g41170 | ACCUGAUGUAA~UCACUUUCAA | Validated | 21 |
| At1g06580 | CCCGGAUGUAA~UCACUUUCAG | Validated | 22 |
| At1g63150 | UUGUUACUUUC~AAUGCAUUGA | Validated | 23 |
| At5g16640 | CCCUGAUGUAU~UUACUUUCAA | Predicted | 24 |
| At1g62590 | UAGCACGUUC~AAUGCAUUGA | Predicted | 25 |
| At1g62670 | CCCUGAUGUAU~UCACUUUCAG | Predicted | 26 |
| At1g62860 | CCCUGAUGUUG~UUACUUUCAG | Predicted | 27 |
| At1g62910 | UAGUCACUUUC~AGCGCAUUGA | Predicted | 28 |
| At1g62930 | UCCAAAUGUAG~UCACUUUCAG | Predicted | 29 |
| At1g63080 | UCCAAAUGUAG~UCACUUUCAA | Predicted | 30 |
| At1g63130 | UCCAAAUGUAG~UCACUUUCAG | Predicted | 31 |
| At1g63400 | UCCAAAUGUAG~UCACUUUCAA | Predicted | 32 |
| At1g63230 | UUGUAACUUUC~AGUGCAUUGA | Predicted | 33 |
| At1g63330 | UAGUCACGUUC~AAUGCAUUGA | Predicted | 34 |
| At1g63630 | UUGUUACUUUC~AGUGCAUUGA | Predicted | 35 |
| At1g64580 | CCCUGAUGUUG~UCACUUUCAC | Predicted | 36 |
| At2g41720 | UUGUUACUUAC~AAUGCAUUGA | Predicted | 37 |
| At1g63070 | UAGUCUUUUUC~AACGCAUUGA | Predicted | 38 |
| miR162 family target sequences - all plants ||||
| At1g01040 | CUGGAUGCAGA~GGUAUUAUCGA | Validated | 39 |
| PtDCL1 | CUGGAUGCAGA~GGUCUUAUCGA | Predicted | 40 |
| OsDCL1 | CUGGAUGCAGA~GGUUUUAUCGA | Predicted | 41 |
| miR163 family target sequences - *Arabidopsis* ||||
| At1g66700 | AUCGAGUUCCAAG~UCCUCUUCAA | Validated | 42 |
| At1g66720 | AUCGAGUUCCAGG~UCCUCUUCAA | Validated | 43 |
| At3g44860 | AUCGAGUUCCAAG~UUUUCUUCAA | Validated | 44 |
| miR164 family target sequences - all plants ||||
| At1g56010 | AGCACGUACCC~UGCUUCUCCA | Validated | 45 |
| At5g07680 | UUUACGUGCCC~UGCUUCUCCA | Validated | 46 |
| At5g53950 | AGCACGUGUCC~UGUUUCUCCA | Validated | 47 |
| At5g61430 | UCUACGUGCCC~UGCUUCUCCA | Validated | 48 |
| At5g39610 | CUCACGUGACC~UGCUUCUCCG | Predicted | 49 |
| OsNAC1 | CGCACGUGACC~UGCUUCUCCA | Predicted | 50 |
| MtNAC | CUUACGUGUCC~UGCUUCUCCA | Predicted | 51 |
| GmNAC | CUUACGUGCCC~UGCUUCUCCA | Predicted | 52 |
| LeNAC | GCCACGUGCAC~UGCUUCUCCA | Predicted | 53 |
| miR165/166 family target sequences - all plants ||||
| At1g30490 | UUGGGAUGAAG~CCUGGUCCGG | Validated | 54 |
| At5g60690 | CUGGGAUGAAG~CCUGGUCCGG | Validated | 55 |
| At1g52150 | CUGGAAUGAAG~CCUGGUCCGG | Validated | 56 |
| PtHDZIPIII | CCGGGAUGAAG~CCUGGUCCGG | Predicted | 57 |

TABLE 1-continued

| Gene | Target Sequence | Status | SEQ ID # |
|---|---|---|---|
| miR167 family target sequences - all plants | | | |
| At1g30330 | GAGAUCAGGCU~GGCAGCUUGU | Validated | 58 |
| At5g37020 | UAGAUCAGGCU~GGCAGCUUGU | Validated | 59 |
| OsARF6 | AAGAUCAGGCU~GGCAGCUUGU | Predicted | 60 |
| miR168 family target sequences - all plants | | | |
| At1g48410 | UUCCCGAGCUG~CAUCAAGCUA | Validated | 61 |
| miR169 family target sequences - all plants | | | |
| At1g17590 | AAGGGAAGUCA~UCCUUGGCUG | Validated | 62 |
| At1g54160 | ACGGGAAGUCA~UCCUUGGCUA | Validated | 63 |
| At1g72830 | AGGGGAAGUCA~UCCUUGGCUA | Validated | 64 |
| At3g05690 | AGGCAAAUCAU~CUUUGGCUCA | Validated | 65 |
| At3g20910 | GCGGCAAUUCA~UUCUUGGCUU | Validated | 66 |
| At5g12840 | CCGGCAAAUCA~UUCUUGGCUU | Predicted | 67 |
| At3g14020 | AAGGGAAGUCA~UCCUUGGCUA | Predicted | 68 |
| ZmHAP2 | GUGGCAACUCA~UCCUUGGCUC | Predicted | 69 |
| VvHAP2 | UGGGCAAUUCA~UCCUUGGCUU | Predicted | 70 |
| OsHAP2 | AUGGCAAAUCA~UCCUUGGCUU | Predicted | 71 |
| GmHAP2 | UAGGGAAGUCA~UCCUUGGCUC | Predicted | 72 |
| GhHAP2 | CUGGGAAGUCA~UCCUUGGCUC | Predicted | 73 |
| miR170/171 family target sequences - all plants | | | |
| At2g45160 | GAUAUUGGCGC~GGCUCAAUCA | Validated | 74 |
| miR172 family target sequences - all plants | | | |
| At4g36920 | CUGCAGCAUCA~UCAGGAUUCU | Validated | 75 |
| At2g28550 | CAGCAGCAUCA~UCAGGAUUCU | Validated | 76 |
| At5g60120 | AUGCAGCAUCA~UCAGGAUUCU | Validated | 77 |
| At5g67180 | UGGCAGCAUCA~UCAGGAUUCU | Validated | 78 |
| At2g39250 | UUGUAGCAUCA~UCAGGAUUCC | Predicted | 79 |
| At3g54990 | UUGCAGCAUCA~UCAGGAUUCC | Predicted | 80 |
| miR319 family target sequences - all plants | | | |
| At4g18390 | CAGGGGGACCC~UUCAGUCCAA | Validated | 81 |
| At1g53230 | GAGGGGUCCCC~UUCAGUCCAU | Validated | 82 |
| At3g15030 | GAGGGGUCCCC~UUCAGUCCAG | Validated | 83 |
| At2g31070 | AAGGGGUACCC~UUCAGUCCAG | Validated | 84 |
| At1g30210 | UAGGGGGACCC~UUCAGUCCAA | Validated | 85 |
| OsPCF5 | GAGGGGACCCC~UUCAGUCCAG | Predicted | 86 |
| OsPCF8 | UCGGGGCACAC~UUCAGUCCAA | Predicted | 87 |

TABLE 1-continued

| Gene | Target Sequence | Status | SEQ ID # |
|---|---|---|---|
| miR393 family target sequences - all plants | | | |
| At1g12820 | AAACAAUGCGA~UCCCUUUGGA | Validated | 88 |
| At4g03190 | AGACCAUGCGA~UCCCUUUGGA | Validated | 89 |
| At3g23690 | GGUCAGAGCGA~UCCCUUUGGC | Validated | 90 |
| At3g62980 | AGACAAUGCGA~UCCCUUUGGA | Validated | 91 |
| miR394 family target sequences - all plants | | | |
| At1g27340 | GGAGGUUGACA~GAAUGCCAAA | Validated | 92 |
| miR395 family target sequences - all plants | | | |
| At5g43780 | GAGUUCCUCCA~AACACUUCAU | Validated | 93 |
| At3g22890 | GAGUUCCUCCA~AACUCUUCAU | Predicted | 94 |
| At5g10180 | AAGUUCUCCCA~AACACUUCAA | Predicted | 95 |
| miR396 family target sequences - all plants | | | |
| At2g22840 | UCGUUCAAGAA~AGCCUGUGGAA | Validated | 96 |
| At2g36400 | CCGUUCAAGAA~AGCCUGUGGAA | Validated | 97 |
| At4g24150 | UCGUUCAAGAA~AGCAUGUGGAA | Validated | 98 |
| At2g45480 | ACGUUCAAGAA~AGCUUGUGGAA | Validated | 99 |
| At3g52910 | CCGUUCAAGAA~AGCCUGUGGAA | Predicted | 100 |
| miR397 family target sequences - all plants | | | |
| At2g29130 | AAUCAAUGCUG~CACUCAAUGA | Validated | 101 |
| At2g38080 | AGUCAACGCUG~CACUUAAUGA | Validated | 102 |
| At2g60020 | AAUCAAUGCUG~CACUUAAUGA | Validated | 103 |
| miR398 family target sequences - all plants | | | |
| At1g08830 | AAGGGGUUUCC~UGAGAUCACA | Validated | 104 |
| At2g28190 | UGCGGGUGACC~UGGGAAACAUA | Validated | 105 |
| At3g15640 | AAGGUGUGACC~UGAGAAUCACA | Validated | 106 |
| miR173 family target sequences - Arabidopsis | | | |
| At1g50055 | GUGAUUUUCUC~AACAAGCGAA | Validated | 107 |
| At2g39675 | GUGAUUUUCUC~UACAAGCGAA | Validated | 108 |
| At3g39680 | GUGAUUUUCUC~UCCAAGCGAA | Validated | 109 |
| miR399 family target sequences - all plants | | | |
| At2g33770 | UAGGGCAUAUC~UCCUUUGGCA | Validated | 110 |
| At2g33770 | UUGGGCAAAUC~UCCUUUGGCA | Validated | 111 |
| At2g33770 | UCGAGCAAAUC~UCCUUUGGCA | Validated | 112 |
| At2g33770 | UAGAGCAAAUC~UCCUUUGGCA | Validated | 113 |
| At2g33770 | UAGGGCAAAUC~UCUUUUGGCA | Predicted | 114 |
| OsE2UBC | UAGGGCAAAUC~UCCUUUGGCA | Predicted | 115 |
| OsE2UBC | CUGGGCAAAUC~UCCUUUGGCA | Predicted | 116 |
| OsE2UBC | UCGGGCAAAUC~UCCUUUGGCA | Predicted | 117 |

TABLE 1-continued

| Gene | Target Sequence | Status | SEQ ID # |
|---|---|---|---|
| OsE2UBC | CCGGGCAAAUC~UCCUUUGGCA | Predicted | 118 |
| PtE2UBC | GCGGGCAAAUC~UUCUUUGGCA | Predicted | 119 |
| MtE2UBC | AAGGGCAAAUC~UCCUUUGGCA | Predicted | 120 |
| TaE2UBC | UAGGGCAAAUC~UCCUUUGGCG | Predicted | 121 |
| TaE2UBC | CUGGGCAAAUC~UCCUUUGGCG | Predicted | 122 |
| TaE2UBC | UUCGGCAAAUC~UCCUUUGGCA | Predicted | 123 |
| miR403 family target sequences - dicots | | | |
| At1g31280 | GGAGUUUGUGC~GUGAAUCUAAU | Validated | 124 |
| miR390 family target sequences - all plants | | | |
| At3g17185 | CUUGUCUAUCCC~UCCUGAGCUA | Validated | 125 |
| SbTAS3 | UAUGUCUAUCCC~UUCUGAGCUG | Predicted | 126 |
| SoTAS3 | UAUGUCUAUCCC~UUCUGAGCUA | Predicted | 127 |
| ZmTAS3a | UAUGUCUAUCCC~UUCUGAGCUG | Predicted | 128 |
| OsTAS3 | UCGGUCUAUCCC~UCCUGAGCUG | Predicted | 129 |
| PgTAS3 | UUAGUCUAUCCC~UCCUGAGCUA | Predicted | 130 |
| VvTAS3 | AUUGCCUAUCCC~UCCUGAGCUG | Predicted | 131 |
| TcTAS3 | CCUUGCUAUCCC~UCCUGAGCUG | Predicted | 132 |
| LeTAS3 | CUUGUCUAUCCC~UCCUGAGCUG | Predicted | 133 |
| ZmTAS3b | CCCUUCUAUCCC~UCCUGAGCUA | Predicted | 134 |
| PtTAS3 | CUUGUCUAUCCC~UCCUGAGCUA | Predicted | 135 |
| OsTAS3b | CCCUUCUAUCCC~UCCUGAGCUA | Predicted | 136 |
| TaTAS3 | CCCUUCUAUCCC~UCCUGAGCUA | Predicted | 137 |
| HvTAS3 | CCUUUCUAUCCC~UCCUGAGCUA | Predicted | 138 |
| PtTAS3b | CCUGUCUAUCCC~UCCUGAGCUA | Predicted | 139 |
| McTAS3 | UGUGUCUAUCCC~UCCUGAGCUA | Predicted | 140 |
| miR447 family target sequences - Arabidopsis | | | |
| At5g60760 | UGACAAACAUC~UCGUCCCCAA | Validated | 141 |
| At3g45090 | UGACAAACAUC~UCGUUCCUAA | Predicted | 142 |
| miR408 family target sequences - all plants | | | |
| At2g02850 | CCAAGGGAAGA~GGCAGUGCAU | Predicted | 281 |
| At2g30210 | ACCAGUGAAGA~GGCUGUGCAG | Validated | 282 |
| At2g47020 | GCCAGGGAAGA~GGCAGUGCAU | Predicted | 283 |
| At5g05390 | GCCGGUGAAGA~GGCUGUGCAA | Predicted | 284 |
| At5g07130 | GCCGGUGAAGA~GGCUGUGCAG | Predicted | 285 |

Between Jan. 7, 2005 and Jan. 7, 2006, the following changes were made to nomenclature related to nucleic acid molecules described herein:

Systematic Names Assigned to TAS Loci by the *Arabidopsis* Information Resource (TAIR)

At2g39680 antisense (TAS1511) has become At2g39681 (TAS2)

AU235820 (TAS255a) has become At1g50055 (TAS1b)

CD534192 (TAS255b) has become At2g27400 (TAS1a)

TAS255c has become At2g39675 (TAS1c)

At3g17185 (ASR) has become At3g17185 (TAS3)

Official miRNA Name Assigned by the miRNA Registry (miRBase)

ASRP1890 has become miR447

These nomenclature changes are reflected in this document.

Interfering with or inhibiting (expression of a target sequence): This phrase refers to the ability of a small RNA, such as an siRNA or a miRNA, or other molecule, to measurably reduce the expression and/or stability of molecules carrying the target sequence. A target sequence can include a DNA sequence, such as a gene or the promoter region of a gene, or an RNA sequence, such as an mRNA. "Interfering with or inhibiting" expression contemplates reduction of the end-product of the gene or sequence, e.g., the expression or function of the encoded protein or a protein, nucleic acid, other biomolecule, or biological function influenced by the target sequence, and thus includes reduction in the amount or longevity of the mRNA transcript or other target sequence. In some embodiments, the small RNA or other molecule guides chromatin modifications which inhibit the expression of a target sequence. It is understood that the phrase is relative, and does not require absolute inhibition (suppression) of the sequence. Thus, in certain embodiments, interfering with or inhibiting expression of a target sequence requires that, following application of the small RNA or other molecule (such as a vector or other construct encoding one or more small RNAs), the sequence is expressed at least 5% less than prior to application, at least 10% less, at least 15% less, at least 20% less, at least 25% less, or even more reduced. Thus, in some particular embodiments, application of a small RNA or other molecule reduces expression of the target sequence by about 30%, about 40%, about 50%, about 60%, or more. In specific examples, where the small RNA or other molecule is particularly effective, expression is reduced by 70%, 80%, 85%, 90%, 95%, or even more.

Isolated: A biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

MicroRNA (miRNA): Small, non-coding RNA gene products of approximately 21 nucleotides long and found in diverse organisms, including animals and plants. miRNAs structurally resemble siRNAs except that they arise from structured, foldback-forming precursor transcripts derived from miRNA genes. Primary transcripts of miRNA genes form hairpin structures that are processed by the multidomain RNaseIII-like nuclease DICER and DROSHA (in animals) or DICER-LIKE1 (DCL1; in plants) to yield miRNA duplexes. The mature miRNA is incorporated into RISC complexes after duplex unwinding. Plant miRNAs interact with their RNA targets with perfect or near perfect complementarity.

Mutation: A heritable change in DNA sequence. Mutations include a frame-shift, a point mutation, a missense mutation, a silent mutation, a polymorphism, a nonsense mutation, a deletion, a null mutation, a truncation, an elongation, an amino acid substitution, or an insertion. A mutant is an organism or cell carrying a mutation. The mutant can be genetically engineered or produced naturally.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in an oligonucleotide/polynucleotide. A nucleotide sequence refers to the sequence of bases in an oligonucleotide/polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine is also a base that can be integrated into DNA or RNA in a nucleotide (dITP or ITP, respectively).

Oligonucleotide: An oligonucleotide is a plurality of nucleotides joined by phosphodiester bonds, between about 6 and about 300 nucleotides in length. An oligonucleotide analog refers to compounds that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA.

Operably linked. A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In specific embodiments, operably linked nucleic acids as discussed herein are aligned in a linear concatamer capable of being cut into 21-mer fragments, at least one of which is a siRNA.

Ornamental plant: A plant that is grown for visual display. Numerous plants are commonly recognized as ornamental. These include, for example, indoor or outdoor nursery plants, house and garden plants, and florist crops, each of which may include without limitation trees, shrubs, perennials, bulbs, annuals, groundcovers, turf grasses, herbs, or native plants.

Ortholog: Two nucleic acid or amino acid sequences are orthologs of each other if they share a common ancestral sequence and diverged when a species carrying that ancestral sequence split into two species. Orthologous sequences are also homologous sequences.

Polymerization: Synthesis of a nucleic acid chain (oligonucleotide or polynucleotide) by adding nucleotides to the hydroxyl group at the 3'-end of a pre-existing RNA or DNA primer using a pre-existing DNA strand as the template. Polymerization usually is mediated by an enzyme such as a DNA or RNA polymerase. Specific examples of polymerases include the large proteolytic fragment of the DNA polymerase I of the bacterium *E. coli* (usually referred to as Kleenex polymerase), *E. coli* DNA polymerase I, and bacteriophage T7 DNA polymerase. Polymerization of a DNA strand complementary to an RNA template (e.g., a cDNA complementary to a mRNA) can be carried out using reverse transcriptase (in a reverse transcription reaction).

For in vitro polymerization reactions, it is necessary to provide to the assay mixture an amount of required cofactors such as $M^{++}$, and dATP, dCTP, dGTP, dTTP, ATP, CTP, GTP, UTP, or other nucleoside triphosphates, in sufficient quantity to support the degree of polymerization desired. The amounts of deoxyribonucleotide triphosphate substrates required for polymerizing reactions are well known to those of ordinary skill in the art. Nucleoside triphosphate analogues or modified nucleoside triphosphates can be substituted or added to those specified above.

Polypeptide: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

Post-Transcriptional Gene Silencing (PTGS): A form of gene silencing in which the inhibitory mechanism occurs after transcription. This can result in either decreased steady-state level of a specific RNA target or inhibition of translation (Tuschl, *ChemBiochem,* 2:239-245, 2001). In the literature, the terms RNA interference (RNAi) and posttranscriptional cosuppression are often used to indicate posttranscriptional gene silencing.

Primer: Primers are relatively short nucleic acid molecules, usually DNA oligonucleotides six nucleotides or more in length. Primers can be annealed to a complementary target DNA strand ("priming") by nucleic acid hybridization to form a hybrid between the primer and the target DNA strand, and then the primer extended along the target DNA strand by a nucleic acid polymerase enzyme. Pairs of primers can be used for amplification of a nucleic acid sequence, e.g., by nucleic-acid amplification methods known to those of ordinary skill in the art.

A primer is usually single stranded, which may increase the efficiency of its annealing to a template and subsequent polymerization. However, primers also may be double-stranded. A double-stranded primer can be treated to separate the two strands, for instance before being used to prime a polymerization reaction (see for example, *Nucleic Acid Hybridization. A Practical Approach*, Hames and Higgins, eds., IRL Press, Washington, 1985). By way of example, a double-stranded primer can be heated to about 90°-100° C. for about 1 to 10 minutes.

Promoter: An array of nucleic acid control sequences which direct transcription of a nucleic acid. A promoter includes necessary nucleic acid sequences near the start site of transcription, such as, in the case of an RNA polymerase II type promoter, a TATA element. Optionally, a promoter may include an enhancer and/or a repressor element. Enhancer and repressor elements can be located adjacent to, or distal to the promoter, and can be located as much as several thousand base pairs from the start site of transcription. Representative examples of promoters that can be used in the present disclosure are described herein.

Protein: A biological molecule, for example a polypeptide, expressed by a gene and comprised of amino acids.

Purified: The term purified does not require absolute purity; rather, it is intended as a relative term. Thus, for example, a purified protein preparation is one in which the protein referred to is more pure (has fewer impurities) than the protein in its natural environment within a cell.

Recombinant: A recombinant nucleic acid is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acids, e.g., by genetic engineering techniques.

Regulatable promoter: A promoter whose activity is regulated by an agent, such as a transcription factor, a chemical compound, or a nucleic acid molecule.

Regulating gene expression: The process of controlling the expression of a gene by increasing or decreasing the expression, production, or activity of an agent that affects gene expression. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

RNA: A typically linear polymer of ribonucleic acid monomers, linked by phosphodiester bonds. Naturally occurring RNA molecules fall into three general classes, messenger (mRNA, which encodes proteins), ribosomal (rRNA, components of ribosomes), and transfer (tRNA, molecules responsible for transferring amino acid monomers to the ribosome during protein synthesis). Messenger RNA includes heteronuclear (hnRNA) and membrane-associated polysomal RNA (attached to the rough endoplasmic reticulum). Total RNA refers to a heterogeneous mixture of all types of RNA molecules.

RNA-dependent RNA polymerase (RDR): Enzyme that polymerizes formation of RNA using a single-stranded RNA template. This frequently results in formation of a double-stranded RNA molecule. Examples of *Arabidopsis* RDRs include RDR1, RDR2 and RDR6 (Xie et al., *PLoS Biol* 2:642-652, 2004). RDRs required for viral replication are also encoded by many viruses (Kao et al., *Virology* 287:251-260, 2001).

RNA interference (RNAi): Gene silencing mechanisms that involve small RNAs (including miRNA and siRNA) are frequently referred to under the broad term RNAi. Natural functions of RNAi include protection of the genome against invasion by mobile genetic elements such as transposons and viruses, and regulation of gene expression.

RNA interference results in the inactivation or suppression of expression of a gene within an organism. RNAi can be triggered by one of two general routes. First, it can be triggered by direct cellular delivery of short-interfering RNAs (siRNAs, usually ~21 nucleotides in length and delivered in a dsRNA duplex form with two unpaired nucleotides at each 3' end), which have sequence complementarity to a RNA that is the target for suppression. Second, RNAi can be triggered by one of several methods in which siRNAs are formed in vivo from various types of designed, expressed genes. These genes typically express RNA molecules that form intra- or intermolecular duplexes (dsRNA) which are processed by natural enzymes (DICER or DCL) to form siRNAs. In some cases, these genes express "hairpin"-forming RNA transcripts with perfect or near-perfect base-pairing; some of the imperfect hairpin-forming transcripts yield a special type of small RNA, termed microRNA (miRNA). In either general method, it is the siRNAs (or miRNAs) that function as "guide sequences" to direct an RNA-degrading enzyme (termed RISC) to cleave or silence the target RNA. In some cases, it is beneficial to integrate an RNAi-inducing gene into the genome of a transgenic organism. An example would be a plant that is modified to suppress a specific gene by an RNAi-inducing transgene. In most methods that are currently in practice, RNAi is triggered in transgenic plants by transgenes that express a dsRNA (either intramolecular or hairpin, or intermolecular in which two transcripts anneal to form dsRNA).

RNA silencing: A general term that is used to indicate RNA-based gene silencing or RNAi.

Sequence identity: The similarity between two (or more) nucleic acid sequences, or two (or more) amino acid sequences, is expressed in terms of the similarity between the sequences, otherwise referred to as sequence identity or homology. Sequence identity is frequently measured in terms of percentage identity (or similarity or homology); the higher the percentage, the more similar the two sequences are. Homologs or orthologs of a specified protein, and the corresponding cDNA sequence, will possess a relatively high degree of sequence identity when aligned using standard methods. This homology will be more significant when the orthologous proteins or cDNAs are derived from species which are more closely related (e.g., different plant sequences), compared to species more distantly related (e.g., human and *Arabidopsis* sequences).

Typically, orthologs are at least 50%, at least 70%, at least 75%, at least 80%, at least 85%, at least 90%, at least 91%, at least 93%, at least 95%, or at least 98% identical at the nucleotide level and at least 50%, at least 70%, at least 75%, at least 80%, at least 85%, at least 90%, at least 91%, at least 93%, at least 95%, or at least 98% identical at the amino acid level when comparing a protein to an orthologous protein.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16:10881-10890, 1988; Huang et al. *Computer Appls. Biosciences* 8:155-165, 1992; and Pearson et al. *Meth. Mol. Bio.* 24:307-331, 1994. Altschul et al. (*J. Mol. Biol.* 215:403-410, 1990) present a detailed consideration of sequence alignment methods and homology calculations. Multiple sequences can be aligned, for instance, using programs such as CLUSTAL-W or TCoffee.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 91%, at least 92%, at least 93%, at least 94% or at least 95% sequence identity. When less than the entire sequence is being compared for sequence identity, homologs will typically possess at least 75% sequence identity over short windows of 10-20 amino acids, and may possess sequence identities of at least 85% or at least 90% or 95% or more depending on their similarity to the reference sequence. Methods for determining sequence identity over such short windows are described at the NCBI website, frequently asked questions (FAQ) page. One of ordinary skill in the art will appreciate that these sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) *Molecular Cloning: A Laboratory Manual*, CSHL, New York and Tijssen (1993) *Laboratory Techniques in Biochemistry and Molecular Biology—Hybridization with Nucleic Acid Probes* Part I, Chapter 2, Elsevier, New York. Nucleic acid molecules that hybridize under stringent conditions to a human p28ING5 gene sequence will typically hybridize to a probe based on either an entire human p28ING5 gene or selected portions of the gene under wash conditions of 2×SSC at 50° C.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Silencing agent or molecule: A specific molecule, which can exert an influence on a cell in a sequence-specific manner to reduce or silence the expression or function of a target, such as a target gene or protein. Examples of silence agents include nucleic acid molecules such as naturally occurring or synthetically generated small interfering RNAs (siRNAs), naturally occurring or synthetically generated microRNAs (miRNAs), naturally occurring or synthetically generated dsRNAs, and antisense sequences (including antisense oligonucleotides, hairpin structures, and antisense expression vectors), as well as constructs that code for any one of such molecules.

Specific binding agent: An agent that binds substantially only to a defined target. Thus a protein-specific binding agent binds substantially only the specified protein.

Small interfering RNA (siRNA): RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity.

Target nucleic acid (to be inhibited): Any nucleic acid containing a sequence that interacts with a miRNA or siRNA, or that has the potential to yield a sequence that interacts with a miRNA or siRNA (for example, through transcription of a locus). The target can be a cellular nucleic acid, such as a mRNA that encodes an essential or non-essential protein, or a foreign nucleic acid, such as a virus-derived or transgene-derived RNA molecule. The target can be a DNA sequence corresponding to a promoter, or a sequence corresponding to any expressed region of a genome, for instance.

Trans-acting siRNAs: A subclass of siRNAs that function like miRNAs to repress expression of target genes, yet have unique biogenesis requirements. Trans-acting siRNAs form by transcription of ta-siRNA-generating genes, cleavage of the transcript through a guided RISC mechanism, conversion of one of the cleavage products to dsRNA, and processing of the dsRNA by DCL enzymes. ta-siRNAs are unlikely to be predicted by computational methods used to identify miRNA because they fail to form a stable foldback structure. Data provided herein demonstrate that ta-siRNAs are not an *Arabidopsis* oddity, but are conserved among distantly related plant species and have been maintained over a long evolutionary period.

A ta-siRNA precursor is any nucleic acid molecule, including single-stranded or double-stranded DNA or RNA, that can be transcribed and/or processed to release a ta-siRNA.

Transcriptional gene silencing (TGS): A phenomenon that is triggered by the formation of dsRNA that is homologous with gene promoter regions and sometimes coding regions. TGS results in DNA and histone methylation and chromatin remodeling, thereby causing transcriptional inhibition rather than RNA degradation. Both TGS and PTGS depend on dsRNA, which is cleaved into small (21-25 nucleotides) interfering RNAs (Eckhardt, *Plant Cell*, 14:1433-1436, 2002; Aufsatz et al., *Proc. Natl. Acad. Sci. U.S.A.*, 99:16499-16506, 2002).

Transgenic (plant/fungus/cell/other entity): This term refers to a plant/fungus/cell/other entity that contains recombinant genetic material not normally found in entities of this type and which has been introduced into the entity in question (or into progenitors of the entity) by human manipulation. Thus, a plant that is grown from a plant cell into which recombinant DNA is introduced by transformation is a transgenic plant, as are all offspring of that plant that contain the introduced transgene (whether produced sexually or asexually).

Triggering RNA: RNA transcript of an siRNA generating locus which is converted into a dsRNA molecule by an RNA-dependent RNA polymerase (RDR) in vivo.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

An siRNA-triggering or RNAi-triggering nucleic acid cassette is provided, which cassette comprises an initiator sequence consisting of about 20 to 25 nucleotides, the initiator sequence having an initiation cleavage site between the tenth and eleventh nucleotide counted from the 3' end of the initiator sequence; and at least one gene suppressing segment in about 21-nucleotide register (or phase) counted either upstream or downstream from the initiation cleavage site, wherein the gene suppressing segment or its complement is substantially complementary to an RNA transcribed from a target gene selected for siRNA inhibition. Also provided are expression vectors which include at least one such nucleic acid cassette operably linked to a promoter.

Specific example initiator sequences are provided herein, for instance, in SEQ ID NOs: 1-142 and 281-285.

Also provided are siRNA- or RNAi-triggering nucleic acids (both cassettes and vectors) that comprise two or more gene suppressing segments. In embodiments having two or more gene suppressing segments, these segments optionally can be directed to (complementary with) two or more different genes or other target sequences selected for siRNA inhibition.

Cells and organisms into which have been introduced a vector or cassette of this disclosure are also provided, as are parts of multicellular organisms that contain such transgenic nucleic acids. Thus, another specific embodiment is a seed for a transgenic plant that expresses RNA for suppressing a target gene, wherein said seed and plant comprise recombinant DNA from which there is transcribed a first RNA comprising an initiator segment consisting of 20-25 nucleotides wherein an initiation cleavage site is located between the tenth and eleventh nucleotide counted from the 3' end of the initiator segment and wherein said initiator segment is linked to or overlaps with at least one gene suppressing segment of 21-nucleotides in precise 21-nucleotide register counted either upstream or downstream from the initiation cleavage site, wherein said gene suppressing segment or it complement is complementary to mRNA transcribed from said target gene.

Yet other embodiments are seed for a transgenic plant further comprising DNA from which there is transcribed a second RNA that hybridizes to said first RNA at said initiation cleavage site. By way of example, the second RNA in some instances is an exogenous miRNA, or a miRNA transcribed from a native plant gene or a heterologous gene or any gene not native to the plant. Seed are also provided for a transgenic plant wherein the first RNA comprises two or more gene suppressing segments.

Optionally, the target gene in any provided organism can be endogenous to that organism. For instance, the target gene may be an endogenous plant gene, an endogenous fungal gene, or an endogenous invertebrate gene, in plant, fungal, or invertebrate embodiments, respectively. There is also therefore provided a seed for a transgenic plant of the disclosure, wherein the plant is corn and the endogenous plant gene encodes lysine ketoglutarate reductase.

Alternatively, the target gene could be exogenous to the transgenic organism, for instance it could be a gene of a pathogen or a pest, such as a plant pathogen or plant pest. In specific examples, such plant pest is a nematode or insect or such pant pathogen is a virus or fungus. In one particular embodiment, a seed for a transgenic plant is provided wherein said plant is soybean and said plant pest is soybean cyst nematode.

In yet another provided seed for a transgenic plant of the disclosure, the recombinant DNA comprises a promoter functional in said plant and operably linked to DNA coding for the first RNA. Such a promoter in some cases is characterized as being a constitutive promoter, an inducible promoter, a tissue specific promoter, a ubiquitous promoter or a combination thereof.

Also provided are seed for a transgenic plant as described, wherein the plant is a corn, soybean, cotton, canola, wheat or rice plant.

Optionally, in any of the provided embodiments of seed for a transgenic plant, the recombinant DNA further comprises nucleotides for expressing at least one protein.

Also provided herein are methods of inhibiting expression of a target gene in a cell, the method comprising exposing the cell to an effective amount of a RNAi-triggering or siRNA-triggering nucleic acid cassette or a vector as described. The cell can be, for instance, a plant cell, a fungal cell, or an invertebrate cell. It is particularly contemplated that the cell could be in vitro or in vivo, for instance, contained in a multicellular organism.

Yet another method is provided, which is a method of inducing production of at least one siRNA in a cell. This method involves transforming the cell with a recombinant nucleic acid molecule comprising a nucleic acid cassette as described herein, wherein the recombinant nucleic acid molecule directs expression of a mRNA from the nucleic acid cassette, which mRNA is processed in the cell to produce at least one siRNA, thereby inducing the production of at least one siRNA in the cell.

Another method is provided, which is a method of inhibiting activity of a target gene in a plant cell. This method involves transforming the plant cell with a recombinant nucleic acid molecule comprising a nucleic acid cassette as described herein, wherein at least one gene suppressing segment of the nucleic acid cassette is specific for the target gene; and expressing the nucleic acid molecule, thereby producing in the plant cell at least one siRNA specific for the target gene which inhibits activity of the target gene in the plant cell.

Another method is a method of inhibiting activity of a target gene in a plant seed, comprising providing in cells of said plant a recombinant nucleic acid molecule comprising a nucleic acid cassette of the disclosure, wherein at least one gene suppressing segment of the nucleic acid cassette is specific for the target gene and wherein said cassette comprises a seed-specific promoter operably linked to said initiator sequence and said at least one gene suppressing segment; a recombinant DNA with a seed specific promoter operably linked to DNA transcribing an miRNA that hybridizes to said initiator sequence at said initiation cleavage site; both.

IV. Methods of Triggering RNA Interference (RNAi)

Plants and animals use small RNAs [microRNAs (miRNAs) and siRNAs] as guides for posttranscriptional and epigenetic regulation of target genes. In plants, miRNAs and trans-acting (ta) siRNAs form through distinct biogenesis pathways, although they both interact with target transcripts and guide cleavage. An integrated approach to identify targets of *Arabidopsis thaliana* miRNAs and ta-siRNAs revealed several new classes of small RNA-regulated genes. These included conventional genes, such as the RNAi factor Argonaute2 (miR403), an E2-ubiquitin conjugating enzyme (miR399), and two Auxin Response Factors (TAS3 ta-siRNAs). Five ta-siRNA-generating transcripts were identified as targets of miR173 or miR390. Rather than functioning to negatively regulate these transcripts, miR173- and miR390- guided cleavage was shown to set the 21-nucleotide phasing for ta-siRNA precursor processing. These data support a model in which miRNA-guided formation of a 5' or 3' terminus within pre-ta-siRNA transcripts, followed by RDR6-dependent formation of dsRNA and DCL1-mediated processing, yields phased ta-siRNAs that negatively regulate other genes.

In Example 1, new *Arabidopsis* miRNA and ta-siRNA targets are identified through an integrated strategy that included computational, genome-wide expression profiling and experimental validation components. Through identification of genes significantly upregulated in miRNA or ta-siRNA biogenesis mutants (hyl1-2, hst-15, dcl1-7, hen1-1, and rdr6-2) using microarrays, data is presented herein that demonstrates identification of genes potentially regulated by miRNAs and ta-siRNAs. Two genes, ARF3 and ARF4, were found to contain a duplicated conserved 21 sequence. Analysis of an *Arabidopsis* sequence, conserved across angiosperms, identified small RNAs typical of ta-siRNAs that could target ARF3 and ARF4 mRNAs.

As taught herein, RNAi can be induced using transgenes or other delivered genes or constructs that encode non-dsRNA-forming transcripts. This method exploits the occurrence of natural siRNAs and miRNAs that can: 1) interact with the delivered transcript through base-pairing, 2) engage a natural dsRNA-forming enzyme termed an RNA-dependent RNA polymerase (RDR), and 3) engage natural DICER-LIKE (e.g., DCL1) enzymes to form siRNAs in precise and predictable register. The siRNAs that form under this mechanism can function to suppress target mRNA expression if the target contains a high degree of sequence complementarity to the siRNAs. One advantage of this method is that it circumvents the need to deliver a dsRNA-forming entity or transgene to initiate the RNAi process of gene suppression.

The methods described herein also enable RNAi to target multiple mRNAs or other target RNAs, depending on the specific siRNA units designed into the construct. The method also permits highly specific siRNA formation rather than non-specific siRNA formation (which results in an increased chance of off-target effects) using conventional dsRNA-forming constructs. The method also may take advantage of naturally occurring miRNAs and siRNAs with tissue- or cell-specific expression characteristics to drive tissue- and cell-specificity of RNAi. Alternatively, a heterologous miRNA or siRNA can be added to the cell (for instance by providing an expression cassette encoding such molecule) in order to provide the receptive element necessary to mediate cleavage and release of siRNAs from a RNAi-triggering nucleic acid cassette.

Also provided herein are nucleic acid constructs that generate, in vivo, siRNAs useful for triggering RNAi-like responses. Representative methods for producing such constructs, as well as guidelines for selecting elements included therein, are provided.

V. Initiator Sequences and Identification Thereof

When present in an RNA molecule, an initiator sequence serves as a site that interacts with a miRNA or siRNA, which guides cleavage through the activity of RISC. Cleavage at an initiator sequence cleavage site (usually between the tenth and eleventh nucleotide counting from the 3' end of the initiator sequence) sets the 21-nucleotide register within the RNA molecule, resulting in additional cleavages of the RNA molecule by the Dicer or DCL protein at usually 21-nucleotide intervals upstream and/or downstream of the initiator sequence. In an engineered RNAi-triggering nucleic acid cassette as described herein, such additional, in-phase cleavages release siRNAs from RNA molecules that are transcribed from the cassette. Representative initiator sequences in RNA form, also referred to as miRNA target sequences, are shown in SEQ ID NOs: 1-142 and 281-285.

Any sequence in an RNA molecule to which a siRNA or miRNA can bind by complementarity, or any sequence in a DNA molecule that encodes for such a sequence in an RNA molecule, can serve as an initiator sequence. In addition to representative initiator sequences provided herein, methods are provided for identifying additional sequences from other genes, other plant species, or any other organisms. An integrated system is provided herein for identifying new miRNA and ta-siRNA targets. This system involves computational, genome-wide expression profiling and experimental validation components. As demonstrated in Example 1, the system reliably identifies prospective initiator sequences, which are target sites for miRNAs. Representative initiator sequences, including many identified and validated using the computational system provided, are shown in SEQ ID NO: 1-142 and 281-285.

In general, an initial pool of predicted target sites for validated miRNAs was created by FASTA searches using a +15/−10 scoring matrix of the TAIR AGI transcript database, limited to 4 mispairs, 4 G:U pairs, to a total of seven, with 100,000 results obtained for the reverse complement of each small RNA. A single, one nucleotide gap was allowed. In the embodiment described in Example 1, the miRNA target prediction algorithm used to score these sites was developed based on 94 experimentally validated and predicted family members of miRNA-target site duplexes, including 66 targets validated in previous studies plus 28 family members with conserved miRNA target sites (Target Rule Set).

Three filters based on the Target Rule Set were applied sequentially. In each case, base one was considered to be the first nucleotide from the 5' end of the miRNA. First, targets with a mismatch score greater than four were excluded. The Minimum Free Energy ($\Delta G_{MFE}$) of a perfect miRNA-target duplex was determined by computationally attaching a perfectly complementary target sequence to a small RNA using a four base "gap" linker sequence (----). The free energy each miRNA-predicted target site ($\Delta G_{target}$) was determined by computationally linking the target sequence to the small RNA, from which the MFE ratio was calculated ($\Delta G_{target}/\Delta G_{MFE}$). All thermodynamic values were calculated using RNAFold in the Vienna RNA package. Remaining targets with an MFE ratio less than 0.73 were excluded. Conservation of the target sequence was determined by using the region containing the target sequence in a BLAST search against target transcripts, for instance, the *Arabidopsis* transcript and EST databases, NCBI EST database, and *O. sativa* Unigene database in Example 1, and removing any targets with no matches with less than three base changes in the target sequence. Duplicate target sites (identical genes) for related miRNA family members were combined in the final target gene set.

VI. Selection of Initiation Sequence for RNAi-Triggering Constructs

Any nucleic acid sequence that will serve to mediate cleavage by a miRNA- or siRNA-guided RISC mechanism may be used as the initiator sequence in constructs provided herein. Examples of such sequences are provided herein, for instance in SEQ ID NOs: 1-142 and 281-285. It is noted that the presented sequences are RNA sequences. It will be apparent to one of ordinary skill in the art that DNA constructs, such as DNA constructs used in transformation of target cells, will contain the DNA equivalent of the listed RNA sequences.

By way of example, SEQ ID NO: 1 is GUGCUCUCUCU-CUUCUGUCA (shown 5' to 3'). The corresponding miRNA sequence (also shown 5' to 3') is UGACAGAA-GAGAGUGAGCAC (SEQ ID NO: 155); this is the reverse complement of the target/initiation sequence shown in SEQ ID NO: 1. A DNA construct containing an initiator sequence corresponding to SEQ ID NO: 1 would include the following sequence: 5'-GTGCTCTCTCTCTTCTGTCA-3' (SEQ ID NO: 280), which may be generated in double-stranded format depending on the embodiment. In such a DNA construct, the transcription site and strandedness would be designed so the initiator sequence is produced as shown in SEQ ID NO: 1. This enables the native or provided, corresponding miRNA to bind by complementarity to the initiator sequence.

It is noted that, in many embodiments, the initiator sequence and a first gene suppressing element may overlap. This arises because the register that is set by the initiator cleavage site begins at that site. Thus, the nucleotides of the 5' or 3' portion of the initiator sequence will be incorporated into the first 21-mer gene suppressing element (e.g., siRNA) produced. This is illustrated, for instance, in FIGS. 5A-C, FIG. 6A, and FIG. 7.

Many miRNAs and their corresponding target sequences (also referred to herein as initiator sequences) are highly conserved among distantly related species. In plants in particular, target sequences that are recognized by related miRNAs in different species differ only by one to three bases, making computational prediction of target sites by similarity searches relatively straightforward (Jones-Rhoades & Bartel, *Mol Cell* 14:787-799, 2004). Owing to the high level of conservation of miRNAs, a functional miRNA target site from one plant species is likely to be functional in a species which expresses the targeting miRNA. For example, miRNA target genes from *Arabidopsis* expressed in *Nicotiana* are cleaved by endogenous miRNAs (Llave et al., *Science* 297: 2053-2056, 2002). In *Oryza* and *Populus*, for which near-complete genomic sequence information exists, homologous miRNA and/or target genes have been identified for 20 of 25 validated miRNA families in *Arabidopsis*. For these 20 conserved miRNA families, conserved homologous miRNA and/or target genes have also been found in several other plant species with less complete sequence information.

By way of example, in Table 2, miRNAs are grouped by related families (one to three nucleotide differences), or by targets of the miRNA family. Presence of the miRNA or target in a listed plant genus is indicated by an "X". In generating this table, miRNA genes were considered to be conserved if the homologous sequence was within 1-3 nucleotides of the *Arabidopsis* sequence, formed a stable foldback structure, and did not encode an identifiable protein. Target sites were considered to be conserved if the target gene in the specified genus encodes a protein similar to the *Arabidopsis* target gene.

TABLE 2

Conservation of miRNAs and target genes in plants.

| Genus | miR156/157 miRNA | miR156/157 Target | miR158 miRNA | miR158 Target | miR159 miRNA | miR159 Target | miR160 miRNA | miR160 Target | miR161 miRNA | miR161 Target | miR162 miRNA | miR162 Target | miR163 miRNA | miR163 Target | miR164 miRNA | miR164 Target | miR165/166 miRNA | miR165/166 Target |
|---|---|---|---|---|---|---|---|---|---|---|---|---|---|---|---|---|---|---|
| *Acorus* | | X | | | | | | | | | | | | | | | | X |
| *Aegilops* | | | | | | | | | | | | | | | | | | |
| *Allium* | | X | | | | | | | | | | | | | | | | |
| *Amborella* | | | | | | | | | | | | | | | | | | |
| *Antirrhinum* | X | X | | | X | | | | | | | | | | X | | X | |
| *Apium* | | | | | | | | | | | | | | | | | | |
| *Arabidopsis* | X | X | X | | X | X | X | X | X | X | X | X | X | X | X | X | X | X |
| *Arachis* | | | | | | | | | | | | | | | | | | |
| *Beta* | | | | | | | | | | | | | | | | | | X |
| *Betula* | | | | | | | | | | | | | | | | | | |
| *Brassica* | X | | | | X | | | | | | | | | | X | | | |
| *Brugeria* | | | | | | | | | | | | | | | | | | |
| *Capsicum* | | X | | | X | | | | | | | | | | | | | X |
| *Ceratopteris* | X | | | | | X | | | | | | | | | | X | | |
| *Citrus* | | X | | | | | | | | | X | | | | | | | |
| *Cryptomeria* | | | | | | | | | | | | | | | | | | |
| *Cycas* | | | | | | | | | | | | | | | | | | |
| *Descurainia* | | | | | | | | | | | | | | | | | | |
| *Eschscholzia* | | X | | | | X | | | | | | | | | | | | |
| *Eucalyptus* | | | | | | | | | | | | | | | | | | |
| *Glycine* | X | X | | X | X | X | X | | X | | | | | X | X | X | | |
| *Gossypium* | | X | | | X | X | | | | | | | | X | | | | |
| *Hedyotis* | | | | | | | | | | | | | | | | X | | |
| *Helianthus* | X | X | | | | | | | | | | | | | | | | |
| *Hordeum* | | X | | X | X | X | | | | | | | | | X | | | |
| *Ipomoea* | | X | | | X | | | | | | | | | | X | | | |
| *Lactuca* | | X | | | X | | | | | | | | | | X | | X | |
| *Linum* | | | | | | | | | | | | | | | | | | |
| *Liriodendron* | X | | | X | X | | | | | | | | | X | X | | | |
| *Lotus* | X | | | | | X | | X | | | | | | | | | | |
| *Lupinus* | | | | | | | | X | | | | | | | | | | |
| *Lycopersicon* | | X | | | X | X | | | | | | | | | X | | X | |
| *Malus* | | | | | | | | | | | | | | | | | | |
| *Manihot* | | | | | | | | | | | | | | | | | | |
| *Messmbryanthemum* | | | | | | | | | | | | | | | | | | |
| *Medicago* | X | | | X | X | X | X | | X | | | | | X | X | | | |
| *Nicotiana* | | X | X | | X | X | X | | | | | | | | X | | X | |
| *Nuphar* | | X | | | | | | | | | | | | | | | | |

TABLE 2-continued

Conservation of miRNAs and target genes in plants.

| Genus | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Oryza | X | X | | X | X | X | X | | X | X | | X | | X | X |
| Pennisetum | | | | | X | | | | | | | | | | |
| Persea | | | | | | | | | | | | | | | |
| Phaseolus | | X | | | X | | | | | | | | | | |
| Phycomitrella | X | | | | X | | | | | | | | | | |
| Picea | | | | | | | | | | | | | | | |
| Pinus | | X | | | | | X | | | | | | | | X |
| Poncirus | | | | | | | | | | | | | | | X |
| Populus | X | X | | X | X | X | X | | X | X | | X | X | X | X |
| Prunus | | X | | | X | | X | | | | | | | | |
| Robinia | | | | | | | | | | | | | | | |
| Rosa | | | | | | | | | | | | | | | |
| Saccharum | X | X | | X | X | | X | | | | | | | | X |
| Schedonorus | | | | X | | | | | | | | | | | |
| Sueada | | | | | | | | | | | | | | | |
| Secale | | | | | | | X | | | | | | | | |
| Sesamum | X | | | | | | | | | | | | | | |
| Solanum | X | X | | | X | | X | | | | | | | | X |
| Sorghum | X | X | | X | X | X | | | X | | | X | | X | X |
| Stevia | | | | | | | | | | | | | | | |
| Thellungiella | | | | | | | | | | | | | | | |
| Theobroma | | | | | | | | | | | | | | | |
| Triphysaria | | | | | | | | | | | | | | | |
| Triticum | X | X | | X | X | X | X | | | | | X | | X | X |
| Vitis | X | X | | X | X | | | | X | | | | X | | |
| Zea | X | X | | X | X | X | | | | | | | | X | X |
| Zinnia | | | | | | | | | | | | | | | |

| Genus | miR167 miRNA | miR167 Target | miR168 miRNA | miR168 Target | miR169 miRNA | miR169 Target | miR170/171 miRNA | miR170/171 Target | miR172 miRNA | miR172 Target | miR173 miRNA | miR173 Target | miR319 miRNA | miR319 Target | miR390/391 miRNA | miR390/391 Target | miR393 miRNA | miR393 Target |
|---|---|---|---|---|---|---|---|---|---|---|---|---|---|---|---|---|---|---|
| Acorus | | | | | | | | | | | | | | | | | | X |
| Aegilops | | X | | | | | | | | | | | | | | | | |
| Allium | | | | | | | X | | | X | | | | | | | | |
| Amborella | | | | | | | | | | | | | | | | | | |
| Antirrhinum | | | | | | | | | | X | | | | X | X | X | | |
| Apium | | | | | | | | | | | | | | | | | | |
| Arabidopsis | X | X | X | X | X | X | X | X | X | X | X | X | X | X | X | X | X | X |
| Arachis | | | | | | | | | | | | | | | | | | |
| Beta | | | | | | | | | | | | | | | | | | |
| Betula | | | X | | | | | | | | | | | | | | | |
| Brassica | | X | | | | | X | | | X | | | X | | | | | |
| Brugeria | | | | | | | | | | | | | | | X | X | | |
| Capsicum | | | | | | | | | | | | | | | | | | X |
| Ceratopteris | | X | | X | | | X | | X | X | | | | X | | | | |
| Citrus | X | | | | | | | | | X | | | | | | X | | X |
| Cryptomeria | X | | | | | | | | | | | | | | | | | |
| Cycas | | | | | | | | | | | | | | | | | | |
| Descurainia | | | | | X | | | | | X | | | | | | | | |
| Eschscholzia | | | | | | | | | | | | | | | | X | | |
| Eucalyptus | | | | | | | | | | | | | | | | | | X |
| Glycine | X | X | X | | X | X | X | X | X | | X | X | X | X | X | | X | X |
| Gossypium | | | | | | X | | | | X | | | X | X | X | | X | X |
| Hedyotis | | | X | X | | | X | | | | | | | | | | | |
| Helianthus | | X | | | | | | | | | | | | | | | | X |
| Hordeum | | X | | | X | X | X | | X | | X | X | X | X | | | | X |
| Ipomoea | | X | | | | | | | | | | | X | | | | | |
| Lactuca | | X | | | | | | | | X | | | X | | | | | |
| Linum | | | | | | | | | | | | | | | | | | |
| Liriodendron | X | | X | | X | | X | | X | | | X | X | | | | | |
| Lotus | | X | | | | | | X | | | | | X | X | | | X | |
| Lupinus | | X | | | | | | | | | | | | | | | | |
| Lycopersicon | | X | X | | | | | | X | X | | | X | X | X | | | |
| Malus | | | | | | | | | | | | | | | | X | | |
| Manihot | | | | | | | | | | | | | | | X | X | | |
| Messmbryanthemum | | | | | | | | | | | | | | | X | X | | |
| Medicago | | X | | | X | X | | X | | X | X | | | | | | X | X |
| Nicotiana | X | X | X | | X | | X | | X | | | | X | | | | | |
| Nuphar | | | | | | | | | | X | | | | | | | | |
| Oryza | X | X | X | | X | X | X | X | X | X | | | X | X | X | X | X | X |
| Pennisetum | | | | | | | | | | | | | | | | | | |
| Persea | | | | | | | | | | | | | | | X | X | | X |
| Phaseolus | X | | | | | | | | | | | | X | | | | | |
| Phycomitrella | | | | | | | | | | | | | | | X | | X | |
| Picea | | | | | | | | | | | | | | | X | X | | |
| Pinus | | X | | | | | | | | | | | | | | X | | X |
| Poncirus | | X | | | | | | | | | | | | | | | | |

TABLE 2-continued

Conservation of miRNAs and target genes in plants.

| Genus | | | | | | | | | | | | | | | | | | |
|---|---|---|---|---|---|---|---|---|---|---|---|---|---|---|---|---|---|---|
| Populus | X | X | X |   | X | X | X |   | X |   |   |   | X | X | X | X | X | X |
| Prunus |   | X |   |   |   |   |   |   |   |   |   |   |   |   |   |   |   | X |
| Robinia |   |   |   |   |   |   |   |   |   |   |   |   |   |   |   |   |   |   |
| Rosa |   |   |   |   |   |   |   |   |   |   |   |   |   |   |   |   |   |   |
| Saccharum | X | X | X |   | X |   |   | X |   | X |   |   | X | X | X | X |   | X |
| Schedonorus |   |   |   |   |   |   |   |   |   |   |   |   |   |   |   |   |   |   |
| Sueada |   |   |   |   | X |   |   |   |   |   |   |   |   |   |   |   |   |   |
| Secale |   |   |   |   |   |   |   |   |   |   |   |   |   |   |   |   |   |   |
| Sesamum |   |   |   |   |   |   |   |   |   |   |   |   |   |   |   |   |   |   |
| Solanum |   | X | X |   | X |   | X | X | X |   |   |   | X |   | X |   |   | X |
| Sorghum | X | X | X |   | X |   | X | X | X |   |   |   | X | X | X | X | X | X |
| Stevia |   |   |   |   |   |   |   |   |   |   |   |   |   |   |   |   |   |   |
| Thellungiella |   |   |   |   |   |   |   |   |   |   |   |   |   |   |   |   |   |   |
| Theobroma |   |   |   |   |   |   |   | X |   |   |   |   |   | X | X |   |   | X |
| Triphysaria |   |   |   |   |   |   |   |   |   |   |   |   |   |   |   |   |   | X |
| Triticum | X | X | X | X | X | X | X |   | X |   |   | X | X | X | X | X |   | X |
| Vitis |   | X | X |   | X |   |   | X |   | X |   |   | X | X | X | X |   | X |
| Zea | X | X | X | X | X | X | X |   | X |   |   |   | X | X | X | X | X | X |
| Zinnia |   | X |   |   |   |   | X |   | X |   |   |   |   |   |   |   |   |   |

| Genus | miR394 miRNA | miR394 Target | miR395 miRNA | miR395 Target | miR396 miRNA | miR396 Target | miR397 miRNA | miR397 Target | miR398 miRNA | miR398 Target | miR399 miRNA | miR399 Target | miR403 miRNA | miR403 Target |
|---|---|---|---|---|---|---|---|---|---|---|---|---|---|---|
| Acorus |   |   |   |   | X |   | X |   |   |   | X |   |   |   |
| Aegilops |   |   |   |   |   |   | X |   |   |   |   |   |   |   |
| Allium |   |   |   |   | X |   | X |   |   |   | X |   |   |   |
| Amborella |   |   |   |   |   |   | X |   |   |   | X |   |   |   |
| Antirrhinum |   |   |   |   |   |   |   |   |   |   |   |   |   |   |
| Apium |   |   |   |   |   |   |   |   |   |   | X |   |   |   |
| Arabidopsis | X | X | X | X | X | X | X | X | X | X | X | X | X | X |
| Arachis |   |   |   |   |   |   |   |   |   |   | X |   |   |   |
| Beta |   |   |   |   | X |   |   |   | X |   | X |   |   |   |
| Betula |   |   |   |   |   |   |   |   |   |   |   |   |   |   |
| Brassica |   |   |   |   | X | X | X |   |   |   | X |   |   |   |
| Brugeria |   |   |   |   |   |   |   |   |   |   |   |   |   |   |
| Capsicum |   |   |   |   | X |   | X |   |   |   | X |   |   |   |
| Ceratopteris |   |   |   |   |   |   |   |   |   |   |   |   |   |   |
| Citrus |   |   |   |   | X |   | X |   |   | X | X |   |   |   |
| Cryptomeria |   |   |   |   | X |   |   |   |   |   | X |   |   |   |
| Cycas |   |   |   |   |   |   | X |   |   |   |   |   |   |   |
| Descurainia |   |   |   |   |   |   |   |   |   |   |   |   |   |   |
| Eschscholzia |   |   | X |   |   |   | X |   |   |   | X |   |   |   |
| Eucalyptus |   |   |   |   |   |   |   |   |   |   |   |   |   |   |
| Glycine | X | X | X | X | X | X |   |   | X | X | X |   |   |   |
| Gossypium |   |   | X |   |   |   | X |   | X |   | X |   |   |   |
| Hedyotis |   |   |   |   | X |   |   |   |   |   | X |   |   |   |
| Helianthus |   |   | X |   |   |   |   |   |   | X | X |   |   |   |
| Hordeum |   |   |   |   | X |   | X | X |   |   | X |   | X |   |
| Ipomoea |   |   | X |   | X |   |   |   |   |   |   |   |   |   |
| Lactuca |   |   | X |   | X |   | X |   |   | X | X |   |   |   |
| Linum |   |   | X |   |   |   |   |   |   |   |   |   |   |   |
| Liriodendron | X |   |   |   |   | X | X |   |   |   | X |   |   |   |
| Lotus |   |   |   |   | X |   | X |   | X | X | X |   | X |   |
| Lupinus |   |   |   |   | X |   |   |   |   |   |   |   |   |   |
| Lycopersicon |   |   |   |   | X |   | X |   | X |   | X |   |   | X |
| Malus |   |   |   |   |   |   |   |   |   |   |   |   |   |   |
| Manihot |   |   |   |   |   |   |   |   |   |   |   |   |   |   |
| Messmbryanthemum |   |   |   |   |   | X |   |   |   |   |   |   |   |   |
| Medicago |   |   | X | X |   | X |   | X | X | X | X | X |   |   |
| Nicotiana |   | X |   |   | X | X |   | X | X | X | X |   |   |   |
| Nuphar |   |   |   |   |   |   | X |   |   |   |   |   |   |   |
| Oryza |   |   | X | X |   | X | X | X |   | X | X |   | X |   |
| Pennisetum |   |   | X |   |   |   |   |   |   |   |   |   |   |   |
| Persea |   |   |   |   |   |   |   |   |   |   |   |   |   |   |
| Phaseolus |   |   |   |   |   |   | X |   |   |   | X |   |   |   |
| Phycomitrella |   |   |   |   |   |   |   |   |   |   |   |   |   |   |
| Picea |   |   |   |   |   |   |   |   |   |   | X |   |   |   |
| Pinus |   |   |   |   |   |   | X |   | X |   | X |   |   |   |
| Poncirus |   |   |   |   |   | X |   |   |   |   |   |   |   |   |
| Populus | X | X | X | X | X | X | X | X | X | X | X | X | X |   |
| Prunus |   |   |   |   |   |   | X |   |   |   | X |   |   |   |
| Robinia | X |   |   |   |   |   |   |   |   |   |   |   |   |   |
| Rosa |   |   |   |   |   | X |   |   |   |   |   |   |   |   |
| Saccharum |   |   | X |   |   | X | X | X |   |   | X |   |   |   |
| Schedonorus |   |   |   |   |   |   |   |   |   |   |   |   |   |   |
| Sueada |   |   |   |   |   |   |   |   |   |   |   |   |   |   |
| Secale |   |   |   |   |   |   |   |   |   |   |   |   |   |   |

TABLE 2-continued

Conservation of miRNAs and target genes in plants.

| Genus | | | | | | | | | | | |
|---|---|---|---|---|---|---|---|---|---|---|---|
| Sesamum | | | | | | | | X | | | |
| Solanum | | X | | X | X | X | | | X | | | X |
| Sorghum | X | X | X | X | X | X | | | X | X | X |
| Stevia | | | | X | | | | | | | |
| Thellungiella | | | | X | | | | | | | |
| Theobroma | | | | | | | | | | | |
| Triphysaria | | | | | | | | X | | | |
| Triticum | X | X | X | X | X | X | X | | X | | X |
| Vitis | | | | | X | | X | | X | | |
| Zea | X | X | X | | X | X | | X | X | X | |
| Zinnia | | | | | | | | X | X | | |

VII. Selection of Gene Suppressing Elements and Targets for RNAi-Triggering Constructs A gene suppressing element is any nucleotide sequence which leads to the downregulation of the final functional product of a gene, either RNA or protein. For RNAi, this sequence is a 20 to 25 nucleotide RNA with complementarity to the gene to be suppressed.

Beneficial characteristics of a gene suppressing element useful for inclusion "in register" in an RNAi-triggering cassette are those known to produce a functional (measurably effective for reducing expression of a target gene/sequence) siRNA sequence. Empirical studies such as described herein can be used to identify gene suppressing elements. There are also art-recognized guidelines that provide predictive RISC incorporation rules (Khvorova et al., *Cell* 115:209-216, 2003; Schwarz et al., *Cell* 115:199-208, 2003), Specific gene suppressive elements can be designed depending on the target sequences (e.g., gene(s), regulatory sequence or invasive or pathogenic entities) to be suppressed. Gene suppressive elements (usually about 21 nucleotides in length), complementary to a target (e.g., gene transcript) to be suppressed, are included the RNAi-triggering cassette, in register, in either sense or antisense orientation starting from the initiation cleavage site. At least eight, possibly more, unique (or duplicated) sequences can be included either upstream or downstream of the initiation cleavage site. Beyond the eighth register, processing by DICER or DCL enzymes may become less precise, and the 21-nucleotide is more likely to be compromised. Even so, gene suppressive elements beyond eight can be optionally included in constructs, including elements that are not in precise 21-nucleotide register.

Gene suppressive elements contained in the RNAi-inducing cassette can be designed to target one or more genes, with one or more unique target sequences. Potential targets might include, but are not limited to, pathogens, toxins, genes that lead to production of undesirable flavors and/or odors, reproductive genes which could facilitate pollination or increase crop yield, color or pigment genes, transcription factors, pathogen response genes, and genes involved in cold/water/drought and other environmental stresses. Related gene families, pathway-related genes, or quantitative trait loci also may be targeted, for instance in a single RNAi-inducing cassette or a set of such cassettes. Such family-directed cassettes are useful in the down regulation of all (or select) members of a gene family, all (or select) members in a biosynthetic pathway, and so forth, thereby yielding coordinated downregulation of sets of genes.

Additional gene suppressive elements that are contemplated are directed to the genes of pathogens or pests associated with the resultant target organism; endogenous genes of the target organism that are involved in response to such pathogens or pests; and exogenous (heterologous) transgenes provided to the target organism (separately or in a single construct containing the RNAi-triggering cassette) to influence infection or infestation or association of such pathogens or pests.

Gene suppressive elements also can be from any endogenous gene that it is desired to downregulate. Genes that negatively influence a characteristic (that cause an unpleasant flavor, aroma, etc.) of the target organism; genes that lead to production of a toxin, allergen, or other detrimental component (e.g., erucic acid in an oil seed; hazardous allergens in peanuts; toxic compounds in potatoes, apricots); genes involved in reproduction (where inhibition will result in increased vegetative production in a plant, for instance); genes involved in male fertility in plants (in order to produce male-sterile, non-selfing plants); genes that enhance vegetative growth (where reproductive growth is desired over seed production, such as in leaf crops like lettuce and spinach); genes that govern or influence color (for instance, the color of leaves or bracts, flowers, stems, fruit, and so forth, where it is desired to change the color); genes that govern or influence susceptibility to stress (such as cold stress, water or drought stress, shear stress, and so forth); and transcription factors (where it is desired to influence a downstream gene or set of genes the expression of which is influenced by the transcription factor) are all examples of conceived of targets for suppression using the methods and constructs described herein.

It is further contemplated that transgenic plants produced using methods and cassettes described herein can be further enhanced with stacked traits, e.g. a crop having an enhanced agronomic trait resulting from gene suppression from an siRNA-triggering nucleic acid cassette in combination with DNA expressing a protein supplementing the agronomic trait, or conferring another trait such as herbicide and/or pest resistance traits. For example, a trait can be enhanced by simultaneous suppression of one gene and over expression of another gene to provide transgenic corn with an enhance level of the amino acid lysine. Transgenic corn with recombinant DNA for expression of the gene encoding dihydodipicolinate synthase in the lysine synthetic pathway and suppression of the gene encoding lysine ketoglutarate reductase (LKR) in the lysine catabolic pathway has enhanced lysine as compared to control plants. Following the methods of this disclosure, the suppression of LKR can be effected by identifying a 21-nucleotide segment of the gene encoding LKR for insertion into an siRNA-triggering nucleic acid cassette. To effect the enhanced lysine trait preferentially in seed tissue, seed specific promoters are used to express the siRNA-triggering nucleic acid cassette and/or to express the RNA that hybridizes to the initiation cleavage site in the initiator segment.

The siRNA-triggering nucleic acid cassettes can also be stacked with DNA imparting other traits of agronomic interest including DNA providing herbicide resistance or insect resistance such as using a gene from *Bacillus thuringensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Persons of ordinary skill in the art are enabled in providing stacked traits by reference to U.S. patent application publications 2003/0106096A1 and 2002/0112260A1 and U.S. Pat. Nos. 5,034,322; 5,776,760; 6,107,549 and 6,376,754 and to insect/nematode/virus resistance by reference to U.S. Pat. Nos. 5,250,515; 5,880,275; 6,506,599; 5,986,175 and U.S. Patent Application Publication 2003/0150017 A1, all of which are incorporated herein by reference.

VIII. Constructs for Triggering RNAi

RNAi-inducing constructs contain an initiator (target) sequence and one or more gene-suppressing elements in-phase or near-phase to the initiation cleavage site in the in initiator (target) sequence. These are operably linked to a promoter or other regulatory sequence which governs transcription from the RNAi-triggering cassette (comprising the initiator sequence with an initiator cleavage site and at least one gene suppressing element upstream or downstream of the initiator sequence and that may optionally overlap a portion of the initiator sequence) in order to generate a single-stranded RNA comprising one or more elements that, when cleaved in register or nearly in register from the in initiator cleavage site, yield one or more siRNA.

DNA constructs for plant transformation are assembled using methods well known to persons of ordinary skill in the art, and typically comprise a promoter operably linked to DNA, the expression of which provides an enhanced trait, e.g. by gene suppression using an siRNA-triggering (or RNAi-triggering) nucleic acid cassette alone or in combination with a DNA for expressing a protein or another RNA molecule. Other construct components may include additional regulatory elements, such as 5' introns for enhancing transcription, 3' untranslated regions (such as polyadenylation signals and sites), DNA for transit or signal peptides.

Vectors suitable for stable transformation of culturable cells are well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. A number of vectors suitable for stable transformation of plant cells or for the establishment of transgenic plants have been described in, e.g., Pouwels et al. (*Cloning Vectors: A Laboratory Manual,* 1985, Suppl., 1987), Weissbach and Weissbach (*Meth. Plant Mol. Bio.*, Academic Press, 1989) and Gelvin et al. (*Plant Molecular Biology Manual*, Kluwer Academic Publishers, 1990). In addition, on of ordinary skill in the art is aware of the components useful in a transformation vector, and will be able to select and assemble such components in order to tailor make a vector for their specific use.

Typically, transformation and expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Also included in most expression vectors will be a promoter, which is an array of nucleic acid control sequences which direct transcription of a nucleic acid. A promoter includes necessary nucleic acid sequences near the start site of transcription, such as, in the case of an RNA polymerase II type promoter, a TATA element. Optionally, a promoter may include an enhancer and/or a repressor element Enhancer and repressor elements can be located adjacent to, or distal to the promoter, and can be located as much as several thousand base pairs from the start site of transcription. Examples of promoters that can be used in the present disclosure include, but are not limited to the Cauliflower mosaic virus 35S promoter, SV40 promoter, the CMV enhancer-promoter, the CMV enhancer/β-actin promoter, and the tissue-specific promoter probasin. Other promoter sequences that can be used to construct nucleic acids and practice methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In certain embodiments, a promoter is a strong promoter, which promotes transcription of RNA at high levels, for example at levels such that the transcriptional activity of the promoter generally accounts for about 5% or more of the transcriptional activity of all transcription within a cell. The strength of a promoter is often tissue-specific and thus may vary from one cell type to another. Examples of strong promoters include, but are not limited to: viral promoters (such as CaMV 35S or CoYMV), ubiquitin promoter (such as Ubi-1 from maize), actin promoter (e.g, Act from rice), nopaline synthase promoter, and the octopine synthase promoter, pEMU promoter, MAS promoter, or a H3 histone promoter.

In another embodiment, a promoter is a tissue-specific, cell-specific, or developmental stage-specific promoter, which promotes transcription in a single cell or tissue type, a narrow range of cells or tissues, or in one or more specific developmental stages, or at least promotes measurably more transcription in such. Examples of such promoters include, but are not limited to: anther-specific, embryo-specific, endosperm-specific, floral-specific, leaf-specific, meristem-specific, nodule-specific, phloem-specific, seed-specific, stem-specific, stomata-specific, trichome-specific, root-specific, tapetum-specific, and xylem-specific promoters. See, for instance, Carpenter et al., *The Plant Cell* 4:557-571, 1992; Denis et al., *Plant Physiol.* 101:1295-1304, 1993; Opperman et al., *Science* 263:221-223, 1993; Stockhause et al., *The Plant Cell* 9:479-489, 1997; Roshal et al., *EMBO J.* 6:1155, 1987; Schernthaner et al., *EMBO J.* 7:1249, 1988; and Bustos et al., *Plant Cell* 1:839, 1989.

Inducible promoters or gene-switches are used to both spatially and temporally regulate gene expression. By allowing the time and/or location of gene expression to be precisely regulated, gene-switches or inducible promoters may control deleterious and/or abnormal effects caused by overexpression or non-localized gene expression. Thus, for a typical inducible promoter in the absence of the inducer, there would be little or no gene expression while, in the presence of the inducer, expression should be high (i.e., off/on). Examples of stimulus-responsive promoters include, but are not limited to hormone-responsive promoters (e.g, ethanol inducible alcR-encoded transcriptional activator (ALCR), a promoter derived from alcA), light-inducible promoters (such as a rbcS promoter), metal-inducible promoters, heat-shock promoters, wound-inducible and stress-inducible (e.g., drought stress, salt stress, shear stress, nutrient stress) promoters. Others are activated by chemical stimuli, such as IPTG or Tetracycline (Tet), or galactose. Other promoters are responsive to pathogen infection or insect damage.

A number of controllable gene expression systems have been devised, including those regulated by light (e.g., the pea rbcS-3A promoter, Kuhlemeier et al., *The Plant Cell*, 1:471-478, 1989, and the maize rbcS promoter, Schaffner and Sheen, *Plant Cell* 3:997, 1991), heat (Callis et al., *Plant Physiol.* 88:965, 1988; Ainley and Key, *Plant Mol. Biol.*, 14:949-967, 1990; Holtorf et al., *Plant Mol. Biol.* 29:637-646, 1995), pathogens (PR1-a; Williams et al., *Biotechnology* 10:540-543, 1992; Gatz, *Annu. Rev. Plant Physiol. Plant Mol. Biol.* 48:89-108, 1997), herbicide safeners (In2-2, GST-27; DeVeylder et al., *Plant Cell Physiol.* 38:568-577, 1997), light (Kuhlemeier et al., *Plant Cell* 1:471-478, 1989), wounding (Firek et al. *Plant Mol. Biol.* 22:129-212, 1993), ethanol (Salter et al., *Plant J.* 16:127-132, 1998), phytohormones (Li et al., *Plant Cell* 3:1167-1175, 1991), steroids (Aoyama and Chua, *Plant J.*, 11:605-612, 1997), wounding (e.g., wunI, Siebertz et al., *Plant Cell* 1:961, 1989), hormones, such as abscisic acid (Marcotte et al., *Plant Cell* 1:969, 1989); chemicals such as methyl jasminate or salicylic acid (see Gatz et al., *Ann. Rev. Plant Physiol. Plant Mol. Biol.* 48:89-108, 1997), and tetracycline (Gatz et al., *Plant J.* 2:397-404, 1992; Weinmann et al., *Plant J.*, 5:559-569, 1994; Sommer et al., *Plant Cell Rep.* 17:891-896, 1998) (from Granger & Cyr, *Plant Cell Reports* 20:227-234, 2001).

It is specifically contemplated that useful promoters will include promoters present in plant genomes as well as promoters from other sources, including nopaline synthase (nos) promoter and octopine synthase (ocs) promoters carried on tumor-inducing plasmids of *Agrobacterium tumefaciens*, caulimovirus promoters such as the cauliflower mosaic virus or figwort mosaic virus promoters. For instance, see U.S. Pat. Nos. 5,322,938 and 5,858,742 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 5,420,034 which discloses a napin promoter, U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Pat. No. 6,635,806 which discloses a coixin promoter, U.S. 2002/0192813 A1 which discloses 5',3' and intron elements useful in the design of effective plant expression vectors, U.S. 2004/0216189 A1 which discloses a maize chloroplast aldolase promoter, and U.S. 2004/0123347 A1 which discloses water-deficit inducible promoters, all of which are incorporated herein by reference. These and numerous other promoters that function in plant cells are known to those skilled in the art and available for use in recombinant polynucleotides of the present disclosure to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects, sufficient expression in plant seed tissues is desired to effect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) *Genetics* 129:863-872), glutelin 1 (Russell (1997) supra), and peroxiredoxin antioxidant (Per1) (Stacy et al. (1996) *Plant Mol. Biol.* 31(6): 1205-1216).

Recombinant DNA constructs prepared in accordance with this disclosure will often include a 3' element that typically contains a polyadenylation signal and site, especially if the recombinant DNA is intended for protein expression as well as gene suppression. Well-known 3' elements include those from *Agrobacterium tumefaciens* genes such as nos 3', tml 3', tmr 3', tms 3', ocs 3', tr7 3', e.g. disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

Constructs and vectors may also include a transit peptide for targeting of a gene target to a plant organelle, particularly to a chloroplast, leucoplast or other plastid organelle. For descriptions of the use of chloroplast transit peptides see U.S. Pat. No. 5,188,642 and U.S. Pat. No. 5,728,925, incorporated herein by reference. For description of the transit peptide region of an *Arabidopsis* EPSPS gene useful in the provided constructs; see Klee et al (MGG 210:437-442, 1987).

For expression of constructs in fungi such as yeast, there are a variety of promoters to choose from for various purposes. The following are provided by way of example, and are not meant to be in any way limiting:

The Gal 1,10 Promoter:

This promoter is inducible by galactose. It can be used to turn expression of an associated nucleic acid on and off, for instance in order to follow the time dependent effects of expression. The Gal promoter is slightly leaky, and so is appropriate where it is not essential to have absolutely no expression of the passenger gene in the absence of galactose. The Gal 1 gene and Gal 10 gene are adjacent and transcribed in opposite directions from the same promoter region. The regulatory region containing the UAS sequences can be cut out on a DdeI Sau3A fragment and placed upstream of any other gene to confer galactose inducible expression and glucose repression.

PGK, GPD and ADH1 Promoters:

These are high expression constitutive promoters. PGK=phosphoglycerate kinase, GPD=glyceraldehyde 3 phosphate dehydrogenase, ADH1=alcohol dehydrogenase.

ADH2 Promoter:

This gene is glucose repressible and it is strongly transcribed on non-fermentable carbon sources (similar to GAL 1,10, except not inducible by galactose).

CUP1 Promoter:

This is the metalothionein gene promoter. It is activated by copper or silver ions added to the medium. The CUP1 gene is one of a few yeast genes that is present in yeast in more than one copy. Depending on the strain, there can be up to eight copies of this gene. By way of example, a gene, when placed under CUP1 regulation, should e provided with a degree of control of the level of expression based on the amount of copper (or silver) in the medium. Copper is toxic and any cells should be tested to see how well they tolerate copper before making a CUP1 construct.

PHO5 Promoter:

This promoter is derived from a gene that encodes an acid phosphatase. It is induced by low or no phosphate in the medium. The phosphatase is secreted in the chance it will be able to free up some phosphate from the surroundings. When phosphate is present, no PHO5 message can be found. When phosphate is absent, the promoter is strongly turned on.

Steroid Inducible Expression:

Keith Yamamoto's lab has developed an inducible system in yeast similar to the ecdysone system for mammalian cells. The rat glucocorticoid receptor gene has been inserted behind the constitutive GPD promoter to express the rat glucocorticoid receptor in yeast. A second vector was made with three glucocorticoid response elements upstream of the CYC1 gene minimal promoter (cytochrome c gene). A cloning site was placed after this so a selected gene or other engineered construct could be placed under control of the 3GRE/CYC1 promoter. Both vectors are high copy vectors. This system works well with dose dependent expression, when steroid hormone is added to the medium. Response time is rapid with $t_{1/2}$ of 7-9 minutes after addition of hormone.

Heat Shock Expression:

By placing the UAS from a heat shock gene in front of the minimal CYC1 promoter, any gene or synthetic construct can be placed under heat shock induction. This is a specialized requirement usually used in studies of heat shock response, or in regulation of RNAi under different temperature regimens.

GAL1-10 Promoter:

This promoter is highly regulatable by galactose, such that there is a basal level on glucose, but over 100 fold increase when cells are placed in galactose medium.

The yeast GAL genes form one of the most intensely studied model systems for eukaryotic gene regulation. The structural genes, e.g. GAL1 and GAL10, are induced to very high level expression in galactose by the action of the activator Gal4p. Gal4p binds to activation sequences (UASG) that lie up stream of GAL genes and activates transcription in a process that depends on gene-proximal TATA elements and involves numerous coactivators and general transcription factors including TBP. The activation function of Gal4p is modulated by Gal80p, an inhibitory regulator that binds specifically to the activation domain of Gal4p, thus preventing gene activation in nongalactose carbon sources.

In certain embodiments, the provided constructs or methods are used or carried out in animal cells, particularly cells from the nematode *C. elegans*. In such embodiments, promoters or other regulatory sequences that function in animal cells are useful. Myriad animal promoters are well known to those of ordinary skill in the art, including constitutive promoters and inducible or repressible promoters, as well as promoters that show cell or tissue specificity or other regulated expression. Where a siRNA triggering cassette is expressed in *C. elegans* or a cell from a *C. elegans* organism, optionally a *C. elegans* promoter can be used. See, for instance published U.S. application Ser. No. 10/239,249 (2003-0177507) and Ser. No. 09/422,569 (2003-0023997), which describe the use of various promoters for construct expression in the invertebrate animal *C. elegans*. Specific examples of *C. elegans* promoters include the following: unc-54, hsp16-2, unc-119, $G_{oA1}$ and sel-12. It is also appropriate to use heterologous promoters in animal cells, including cells from (or in) *C. elegans* organisms. Additional promoters and/or regulatory sequences are discussed elsewhere in this document.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

Screenable markers are also used for cell transformation, such as fungus or plant cell transformation, including color markers such as genes encoding β-glucuronidase (gus) or anthocyanin production, or fluorescent markers such as genes encoding luciferase or green fluorescence protein (GFP).

IX. In Vitro Production of Oligonucleotides

Though it is often appropriate to produce RNAi triggering constructs through genetic engineering techniques such as those discussed above, in some instances components of such constructs can be advantageously produced using in vitro chemical synthesis.

In vitro methods for the synthesis of oligonucleotides are well known to those of ordinary skill in the art; such conventional methods can be used to produce IROs for the disclosed methods. The most common method for in vitro oligonucleotide synthesis is the phosphoramidite method, formulated by Letsinger and further developed by Caruthers (Caruthers et al., *Chemical synthesis of deoxyoligonucleotides*, in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach*, IRL Press, 1984.

In general, the synthesis reactions proceed as follows: First, a dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleoside to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for instances, U.S. Pat. Nos. 4,415,732, 4,458,066, 4,500,707, 4,973,679, and 5,132,418. Oligonucleotide synthesizers that employ this or similar methods are available commercially (e.g., the PolyPlex oligonucleotide synthesizer from Gene Machines, San Carlos, Calif.). In addition, many companies will perform such synthesis (e.g., Sigma-Genosys, TX; Operon Technologies, CA; Integrated DNA Technologies, IA; and TriLink BioTechnologies, CA).

Oligonucleotides are conveniently available commercially up to approximately 125 nucleotides; beyond this length the efficiency and purification drops. Modified nucleotides can be incorporated into an oligonucleotide essentially as described above for non-modified nucleotides.

Methods described above, or other methods known to those of ordinary skill in the art, can be used to produce oligonucleotides comprising an initiation sequence, a gene suppressing element, or combinations thereof, for instance. Such oligonucleotides can be used to construct RNA-trigger nucleic acid cassettes, for instance.

X. Plants for Production of siRNAs

The presence of the cellular systems described herein necessary to respond to initiator sequences, and thereby produce siRNAs from the described constructs, appears to be nearly universal within the plant and fungal kingdoms. These systems are also present in some invertebrates, such as *C. elegans*. At the molecular level for instance, DCL and RDR homologs have been found in a variety of plant and fungi species, as well as *C. elegans*. Thus, expression of target genes using the synthetic siRNA-bearing constructs (RNAi-triggering nucleic acid molecules) described herein may be modified, particularly inhibited, in a wide range of target organisms and cells of such organisms. These include plants, including both monocotyledonous and dicotyledonous plants. The described system for inducing RNAi finds equal application in fungal systems, including filamentous (mold-type) and some yeast-type fungi, as well as *C. elegans*, a representative invertebrate animal.

Representative, non-limiting example plants include *Arabidopsis*; field crops (e.g. alfalfa, barley, bean, clover, corn, cotton, flax, lentils, maize, pea, rape/canola, rice, rye, safflower, sorghum, soybean, sunflower, tobacco, and wheat); vegetable crops (e.g. asparagus, beet, *brassica* generally, broccoli, Brussels sprouts, cabbage, carrot, cauliflower, celery, cucumber (cucurbits), eggplant, lettuce, mustard, onion, pepper, potato, pumpkin, radish, spinach, squash, taro, tomato, and zucchini); fruit and nut crops (e.g. almond, apple, apricot, banana, blackberry, blueberry, cacao, cassava, cherry, citrus, coconut, cranberry, date, hazelnut, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); tree woods and ornamentals (e.g. alder, ash, aspen, azalea, birch, boxwood, camellia, carnation, chrysanthemum, elm, fir, ivy, jasmine, juniper, oak, palm, poplar, pine, redwood, rhododendron, rose and rubber).

XI. Delivery of Constructs to Target Cells

Once a nucleic acid molecule (e.g., synthetic construct) encoding at least one siRNA for use in RNAi is generated, standard techniques may be used to express the encoded siRNA molecule(s) in transgenic plants, yeast, or animals. The basic approach is to clone, for instance, the synthetic siRNA construct into a transformation vector, such that it is operably linked to control sequences (e.g., a promoter) that direct expression of the nucleic acid in target cells. The transformation vector is then introduced into the target cells by one of a number of techniques (e.g., electroporation) and progeny containing the introduced nucleic acid construct are selected. In some embodiments, all or part of the transformation vector will stably integrate into the genome of the target cell. That part of the transformation vector that integrates into the target cell and that contains the introduced synthetic siRNA construct and associated sequences for controlling expression (the introduced "transgene") may be referred to as the recombinant expression cassette.

Selection of progeny, for instance, progeny plants, yeast, or invertebrate cells, containing the introduced transgene may be based upon the detection of an altered phenotype. Such a phenotype may result directly from the synthetic construct cloned into the transformation vector or may be manifested as enhanced (or reduced) resistance to a chemical agent (such as an antibiotic) as a result of the inclusion of a selectable marker gene incorporated into the transformation vector.

Examples of the modification of plant characteristics by transformation with cloned cDNA sequences are replete in the technical and scientific literature. Selected examples, which serve to illustrate the knowledge in this field of technology, include: U.S. Pat. No. 5,451,514; U.S. Pat. No. 5,750,385; U.S. Pat. No. 5,583,021; U.S. Pat. No. 5,589,615; U.S. Pat. No. 5,268,526; U.S. Pat. No. 5,741,684; U.S. Pat. No. 5,773,692; WO 96/13582; published U.S. application Ser. No. 10/450,412 (2004-0139494), Ser. No. 09/850,846 (2002-0147168). These examples include descriptions of transformation vector selection, transformation techniques and the assembly of constructs designed to express or over-express the introduced nucleic acid.

In light of the foregoing and the provision herein of methods for producing siRNA-producing synthetic constructs governed by described initiator sequences, one of ordinary skill in the art will be able to introduce such nucleic acid constructs into plants, fungi, and animals (particularly invertebrates) in order to produce specimens exhibiting RNAi of one or more target genes.

XII. Plant Transformation, Regeneration, and Selection

Transformation and regeneration of both monocotyledonous and dicotyledonous plant cells is routine, and the most appropriate transformation technique will be determined by the practitioner. The choice of method will vary with the type of plant to be transformed; those skilled in the art will recognize the suitability of particular methods for given plant types.

Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

Following transformation and regeneration of plants with the transformation vector, transformed plants may be selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein, and other methods appropriate to the synthetic construct of the transgene, to determine whether the passenger siRNA(s) are being produced, and/or whether the target gene(s) are measurably inhibited by RNAi as a result of the introduced transgene.

Numerous methods for transforming plant cells with recombinant DNA are known in the art and may be used. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, e.g. to replace an existing gene in the genome, to use an existing promoter in the plant genome, or to insert a recombinant polynucleotide at a predetermined site known to be active for gene expression. Several site specific recombination systems exist which are known to function in plants include cre-lox as disclosed in U.S. Pat. No. 4,959,317 and FLP-FRT as disclosed in U.S. Pat. No. 5,527,695, both incorporated herein by reference.

Transformation methods are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants, e.g. various media and recipient target cells, transformation of immature embryos and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants including a hybrid plants line for screening of plants having an enhanced agronomic trait. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line. A transgenic plant with recombinant DNA providing an enhanced agronomic trait, e.g. enhanced yield, can be crossed with a transgenic plant line having other recombinant DNA that confers another trait, e.g. herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA. Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line.

In the practice of transformation DNA is typically introduced into only a small percentage of target cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Cells that survive exposure to the selective agent, or cells that have been scored positive in a screening assay, may be cultured in regeneration media and allowed to mature into plants. Developing plantlets can be transferred to plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, e.g. self-pollination is commonly used with transgenic corn. The regenerated transformed plant or its progeny seed or plants can be tested for expression of the recombinant DNA and screened for the presence of enhanced agronomic trait(s).

XIII. Transgenic Plants and Seeds

Transgenic plant seed provided herein are grown to generate transgenic plants having an enhanced trait as compared to a control plant. Such seed for plants with enhanced agronomic trait(s) is identified by screening transformed plants, progeny, or progeny seed for the enhanced trait(s). For efficiency, a screening program is beneficially used to evaluate multiple transgenic plants (events) comprising the recombinant DNA, e.g. multiple plants from 2 to 20 or more transgenic events.

Transgenic plants grown from transgenic seed provided herein demonstrate improved agronomic traits that contribute to increased yield or other trait that provides increased plant value, including, for example, improved seed quality. Of particular interest are plants having enhanced yield resulting from improved plant growth and development, stress tolerance, improved seed development, higher light response, improved flower development, or improved carbon and/or nitrogen metabolism Many transgenic events which survive to fertile transgenic plants that produce seeds and progeny plants will not exhibit an enhanced agronomic trait. Screening is necessary to identify the transgenic plant having enhanced agronomic traits from populations of plants transformed as described herein by evaluating the trait in a variety of assays to detect an enhanced agronomic trait. These assays also may take many forms, including but not limited to, analyses to detect changes in the chemical composition, biomass, physiological properties, morphology of the plant.

XIV. Targets for RNAi

The target gene can be in any cell derived from or contained in any organism. The organism can be a plant, an animal, or fungus, as described herein. The target gene may be a cellular gene (i.e., derived from a cell, as opposed to a virus or other exogenous source), an endogenous gene (i.e., a cellular gene found in the genome), a transgene (i.e., a gene construct inserted at an ectopic site in the genome of the cell), or a gene from a pathogen or invasive entity which is capable of infecting or infesting an organism from which the cell is derived. Specific, non-limiting examples of target genes include genes encoding: structural or regulatory molecules; enzymes; toxins; transcription factors; chromatin factors; metabolic factors; secreted factors; mRNA expressed by pathogens; reproductive factors; pigments; pathogen response factors; environmental stress factors; allergens; and so forth. Also contemplated are target genes that are involved in reproduction, particularly male fertility in plants, and genes that enhance vegetative growth. Targets also can be selected from non-coding regions of the genome of the target organism.

In addition to endogenous gene and non-gene targets, it is contemplated that the RNAi-triggering constructs and methods described herein can be used to inhibit expression of pathogen or parasite genes, for instance gene sequences expressed by bacterial, viral, other pathogen, animal pest, or plant pest (e.g., nematode) targets. By way of example, such gene inhibition in the context of an organism infected or infested with such pathogenic target could be used to combat the pathogen. Treatment of pathogens using such a system could be preventative, wherein the RNAi-triggering construct(s) are introduced before there is known infection or introduction of the pathogenic organism. In such embodiments, the presence of the RNAi-triggering system is intended to prevent, reduce, or ameliorate a subsequent infection or contamination with the target pathogen or other microorganism. Alternatively, infected or infested organisms could be treated after the microorganism(s) are present. In such embodiments, the RNAi-triggering system is intended to treat or eradicate the infection/infestation.

In yet other embodiments, an RNAi-triggering system is introduced to provide inhibitory control over a transgenic target gene sequence, or set of transgenic sequences, for instance that have been introduced into a transgenic plant, fungus, or other cell. Such targets might include transgenes that confer desirable or undesirable traits to the target organism. Representative non-limiting examples of categories of transgenes are discussed herein; any transgene could serve as a target, and specific targets will be best selected by the practitioner.

Inhibition of target gene expression or activity can be measured by monitoring the levels of target gene mRNA or proteins encoded by the target gene. Examples of known techniques used to measure mRNA levels include RNA solution hybridization, nuclease protection, Northern blot analysis, and reverse transcription which can be used in combination with polymerase chain reaction. Examples of techniques used to measure target gene protein levels include antibody binding, enzyme linked immunosorbent assay (ELISA), Western blot analysis, immunoassays (e.g. radioimmunoassay), and fluorescence activated cell sort (FACS).

Depending on the particular target gene and the level of production of the siRNA, increasing the production of siRNA(s), for example through expression from a transgene described herein, may provide partial or complete loss of expression, or function, of the target gene. The inhibition in target gene expression in different embodiments is at least a 5%, at least a 10%, at least a 20%, at least a 30%, at least a 50%, at least a 75%, at least an 80%, at least an 85%, at least a 90%, at least a 95%, or a 100% inhibition in target gene expression.

XV. Regulated RNAi

The RNAi-triggering systems described herein can further be employed to exploit differentially regulated systems within a target, for instance in order to provide cell-specific, tissue-specific, or developmentally specific RNAi of one or more specific genes. In particular, miRNAs frequently accumulate in specific cell-types or tissues (e.g. Palatnik et al., *Nature* 425:257-263, 2003) or are induced under specific conditions, such as nutrient or abiotic stress (Jones-Rhoades & Bartel, *Mol Cell* 14:787-799, 2004). Thus, cell-, tissue-, or conditional RNAi may be regulated by cell-, tissue- or condition-specific miRNA or siRNA expression by employing a target sequence (initiator sequence) that interacts with a specific regulated small RNA to guide cleavage of the target sequence in the desired expression pattern. Representative miRNAs and functions associated with their target(s) are listed in Table 4.

Alternatively, or in combination, regulated RNAi can also be achieved using expression cassettes that are only transcribed, or preferentially transcribed, in certain cells, tissues, conditions, and so forth. Represented promoters useful for such regulated expression are discussed herein.

The following examples are provided to illustrate certain particular features and/or embodiments. These examples should not be construed to limit the invention to the particular features or embodiments described.

EXAMPLE 1

MiRNA-Directed Phasing During Trans-Acting siRNA Biogenesis in Plants

Small RNA Blot Analysis

Low molecular weight RNA (5 μg) from *Arabidopsis* inflorescence tissue was used for miRNA and endogenous siRNA analysis as described (Allen et al., *Nat Genet.* 36:1282-1290, 2004). Mutant lines for dcl1-7, dcl2-1, dcl3-1, rdr1-1, rdr2-1, hen1-1, hyl1-2, rdr6-11, rdr6-15, and sgs3-11 were described previously (Allen et al., *Nat Genet.* 36:1282-1290, 2004; Park et al., *Curr Biol* 12:1484-1495, 2002; Peragine et al., *Genes & Dev* 18:2369-2379, 2004; Vazquez et al., *Curr Biol* 14:346-351, 2004a; Xie et al., *PLoS Biol* 2:642-652, 2004). The hst-15 allele used was the SALK_079290 T-DNA insertion line from ABRC, which contains a T-DNA at position 1584 from the start codon. Probes for miR159, miR167, and AtSN1-siRNA blots were described previously (Llave et al., *Plant Cell* 14:1605-1619, 2000a; Zilberman et al., *Science* 299:716-719, 2003). All other miRNAs were detected using end-labeled DNA oligonucleotides. Probes for ta-siRNA loci were PCR amplified from Col-0 genomic DNA, cloned into pGEMT-Easy, and verified by sequencing. Radiolabeled probes incorporating $^{32}$P-UTP were made by T7 RNA polymerase transcription, to obtain strand specific small RNA probes. Probes were as follows: TAS3 locus, Chr3:5862146-5862295; At3g39680 (TAS2) locus, Chr2:16546831-16547300.

Computational Prediction of miRNA Targets

An initial pool of predicted target sites for validated miRNAs was created by FASTA searches using a +15/−10 scoring matrix of the TAIR AGI transcript database, limited to 4 mispairs, 4G:U pairs, to a total of seven, with 100,000 results obtained for the reverse complement of each small RNA. A single, one nucleotide gap was allowed. The miRNA target prediction algorithm used to score these sites was developed based on 94 experimentally validated and predicted family members of miRNA-target site duplexes, including 55 targets validated in previous studies, 11 new validated targets, plus 28 family members with conserved miRNA target sites (Target Rule Set, Table 3). Three filters based on the Target Rule Set were applied sequentially. In each case, base one is considered to be the first nucleotide from the 5' end of the miRNA. First, targets with a mismatch score greater than four were excluded. The Minimum Free Energy ($\Delta G_{MFE}$) of a perfect miRNA-target duplex was determined by computationally attaching a perfectly complementary target sequence to a small RNA using a four base "gap" linker sequence (----). The free energy each miRNA-predicted target site ($\Delta G_{target}$) was determined by computationally linking the target sequence to the small RNA, from which the MFE ratio was calculated ($\Delta G_{target}/\Delta G_{MFE}$). All thermodynamic values were calculated using RNAFold in the Vienna RNA package. Remaining targets with an MFE ratio less than 0.73 were excluded. Conservation of the target sequence was determined by using the region containing the target sequence in a BLAST search against the *Arabidopsis* transcript and EST databases, NCBI EST database, and *O. sativa* Unigene database, and removing any targets with no matches with less than three base changes in the target sequence. Duplicate target sites (identical genes) for related miRNA family members were combined in the final target gene set.

TABLE 3

Summary of miRNA target gene predictions represented in FIG. 1

| | Systematic name[a] | Common name[a] | Gene family | miRNA family | Rule Development Set | Score[b] | MFE Ratio | Pass/Fail | Original prediction reference |
|---|---|---|---|---|---|---|---|---|---|
| | | | | Bin 1. Previously predicted miRNA target genes, experimentally validated | | | | | |
| 1 | At1g27370 | SPL10 | SPL | miR156 | yes | 3 | 0.808 | Pass | c |
| 2 | At5g43270 | SPL2 | SPL | miR156 | yes | 3 | 0.842 | Pass | c |
| 3 | At1g53160 | SPL4 | SPL | miR157 | yes | 3 | 0.820 | Pass | c |
| 4 | At5g06100 | MYB33 | MYB | miR159 | yes | 3 | 0.787 | Pass | c; d |
| 5 | At3g11440 | MYB65 | MYB | miR159 | yes | 3 | 0.787 | Pass | c; d |
| 6 | At1g77850 | ARF17 | ARF | miR160 | yes | 0.5 | 0.990 | Pass | c |
| 7 | At2g28350 | ARF10 | ARF | miR160 | yes | 2 | 0.844 | Pass | c |
| 8 | At4g30080 | ARF16 | ARF | miR160 | yes | 2.5 | 0.863 | Pass | c |
| 9 | At1g06580 | | PPR | miR161.1 | yes | 3 | 0.713 | Fail | c |
| 10 | At1g63150 | | PPR | miR161.2 | yes | 1.5 | 0.856 | Pass | c |
| 11 | At5g41170 | | PPR | miR161.1 | yes | 1 | 0.792 | Pass | c |
| 12 | At1g1040 | DCL1 | DCL | miR162 | yes | 2 | 1.000 | Pass | e |
| 13 | At1g66690 | | SAMT | miR163 | yes | 1 | 0.898 | Pass | d |
| 14 | At1g66700 | | SAMT | miR163 | yes | 1 | 0.898 | Pass | d |
| 15 | At1g66720 | | SAMT | miR163 | yes | 2 | 0.886 | Pass | f |
| 16 | At3g44860 | | SAMT | miR163 | yes | 3 | 0.765 | Pass | f |
| 17 | At1g56010 | NAC1 | NAC | miR164 | yes | 2 | 0.823 | Pass | c |
| 18 | At3g15170 | CUC1 | NAC | miR164 | yes | 3 | 0.856 | Pass | c |
| 19 | At5g07680 | | NAC | miR164 | yes | 2 | 0.849 | Pass | c |
| 20 | At5g53950 | CUC2 | NAC | miR164 | yes | 3 | 0.856 | Pass | c |
| 21 | At5g61430 | | NAC | miR164 | yes | 2 | 0.849 | Pass | c |
| 22 | At1g30490 | PHV | HD-ZipIII | miR166 | yes | 3 | 0.860 | Pass | c |
| 23 | At1g52150 | AtHB15 | HD-ZipIII | miR166 | yes | 2.5 | 0.867 | Pass | c |
| 24 | At2g34710 | PHB | HD-ZipIII | miR166 | yes | 3 | 0.860 | Pass | c |
| 25 | At5g60690 | REV/IFL1 | HD-ZipIII | miR166 | yes | 3 | 0.860 | Pass | c |

TABLE 3-continued

Summary of miRNA target gene predictions represented in FIG. 1

| | | | | | | | | | |
|---|---|---|---|---|---|---|---|---|---|
| 26 | At1g30330 | ARF6 | ARF | miR167 | yes | 3.5 | 0.844 | Pass | c; d |
| 27 | At5g37020 | ARF8 | ARF | miR167 | yes | 4 | 0.779 | Pass | c; d |
| 28 | At1g48410 | AGO1 | AGO | miR168 | yes | 4 | 0.735 | Pass | c |
| 29 | At1g17590 | | HAP2 | miR169 | yes | 2.5 | 0.866 | Pass | c |
| 30 | At1g54160 | | HAP2 | miR169 | yes | 3 | 0.840 | Pass | c |
| 31 | At1g72830 | HAP2c | HAP2 | miR169 | yes | 2.5 | 0.834 | Pass | b |
| 32 | At3g05690 | HAP2b | HAP2 | miR169 | yes | 3 | 0.746 | Pass | b |
| 33 | At3g20910 | | HAP2 | miR169 | yes | 4 | 0.735 | Pass | b |
| 34 | At5g06510 | | HAP2 | miR169 | yes | 3 | 0.746 | Pass | b |
| 35 | At2g45160 | SCL6(II) | SCL | miR171 | yes | 0 | 1.000 | Pass | g; c |
| 36 | At3g60630 | SCL6(III) | SCL | miR171 | yes | 0 | 1.000 | Pass | g; c |
| 37 | At4g00150 | SCL6(IV) | SCL | miR171 | yes | 0 | 1.000 | Pass | g; c |
| 38 | At2g28550 | TOE1/RAP2.7 | AP2 | miR172 | yes | 3.5 | 0.857 | Pass | d |
| 39 | At4g36920 | AP2 | AP2 | miR172 | yes | 2.5 | 0.896 | Pass | d |
| 40 | At5g60120 | TOE2 | AP2 | miR172 | yes | 1.5 | 0.928 | Pass | d |
| 41 | At5g67180 | TOE3 | AP2 | miR172 | yes | 3.5 | 0.896 | Pass | d |
| 42 | At1g30210 | TCP24 | TCP | miR319 | yes | 3.5 | 0.792 | Pass | i |
| 43 | At1g53230 | TCP3 | TCP | miR319 | yes | 4 | 0.751 | Pass | i |
| 44 | At2g31070 | TCP10 | TCP | miR319 | yes | 3.5 | 0.777 | Pass | i |
| 45 | At3g15030 | TCP4 | TCP | miR319 | yes | 3.5 | 0.777 | Pass | i |
| 46 | At4g18390 | TCP2 | TCP | miR319 | yes | 3.5 | 0.792 | Pass | i |
| 47 | At1g12820 | | TIR/F-box | miR393 | yes | 2 | 0.862 | Pass | b |
| 48 | At3g23690 | bHLH077 | bHLH | miR393 | yes | 3 | 0.871 | Pass | b |
| 49 | At3g26810 | | TIR/F-box | miR393 | yes | 2 | 0.862 | Pass | b |
| 50 | At3g62980 | TIR1 | TIR/F-box | miR393 | yes | 2.5 | 0.876 | Pass | b |
| 51 | At4g03190 | | TIR/F-box | miR393 | yes | 3.5 | 0.761 | Pass | b |
| 52 | At1g27340 | | F-box | miR394 | yes | 1 | 0.820 | Pass | b |
| 53 | At5g43780 | APS4 | ATP sulfurylase | miR395 | yes | 2 | 0.792 | Pass | b |
| 54 | At3g22890 | APS1 | ATP sulfurylase | miR395 | yes | 3.5 | 0.744 | Pass | b |
| 55 | At2g22840 | GRF1 | GRF | miR396 | yes | 3.5 | 0.861 | Pass | b |
| 56 | At2g36400 | GRF3 | GRF | miR396 | yes | 3 | 0.861 | Pass | b |
| 57 | At2g45480 | GRF9 | GRF | miR396 | yes | 4 | 0.861 | Pass | b |
| 58 | At4g24150 | GRF8 | GRF | miR396 | yes | 3.5 | 0.861 | Pass | b |
| 59 | At4g37740 | GRF2 | GRF | miR396 | yes | 3.5 | 0.861 | Pass | b |
| 60 | At5g53660 | GRF7 | GRF | miR396 | yes | 3.5 | 0.861 | Pass | b |
| 61 | At2g29130 | | Laccase | miR397 | yes | 3.5 | 0.755 | Pass | b |
| 62 | At2g38080 | | Laccase | miR397 | yes | 2.5 | 0.877 | Pass | b |
| 63 | At5g60020 | | Laccase | miR397 | yes | 2.5 | 0.828 | Pass | b |
| 64 | At3g15640 | | Cytochrome C oxidase | miR398 | yes | 3 | 0.804 | Pass | b |
| 65 | At1g08830 | CSD1 | Copper superoxide dismutase | miR398 | yes | 5 | 0.712 | Fail | b |
| 66 | At2g28190 | CSD2 | Copper superoxide dismutase | miR398 | yes | 6.5 | 0.761 | Fail | b |
| Bin 2. Previously predicted miRNA target gene, computational prediction only[c] | | | | | | | | | |
| 1 | At1g27360 | SPL11 | SPL | miR156 | yes | 3 | 0.808 | Pass | c |
| 2 | At1g69170 | SPL6 | SPL | miR156 | yes | 3 | 0.808 | Pass | c |
| 3 | At2g33810 | SPL3 | SPL | miR156 | yes | 3 | 0.808 | Pass | c |
| 4 | At2g42200 | SPL9 | SPL | miR156 | yes | 2 | 0.832 | Pass | c |
| 5 | At3g57920 | SPL15 | SPL | miR156 | yes | 2 | 0.832 | Pass | c |
| 6 | At5g50570 | SPL13 | SPL | miR156 | yes | 2 | 0.832 | Pass | c |
| 7 | At5g50670 | | SPL | miR156 | yes | 2 | 0.832 | Pass | c |
| 8 | At3g15270 | SPL5 | SPL | miR157 | yes | 4 | 0.778 | Pass | c |
| 9 | At2g26950 | MYB104 | MYB | miR159 | yes | 4 | 0.880 | Pass | c; d |
| 10 | At2g32460 | MYB101 | MYB | miR159 | yes | 3.5 | 0.802 | Pass | c |
| 11 | At3g60460 | MYB125 | MYB | miR159 | yes | 3.5 | 0.786 | Pass | c |
| 12 | At5g55020 | MYB120 | MYB | miR159 | yes | 3.5 | 0.732 | Pass | c; d |
| 13 | At2g26960 | MYB81 | MYB | miR159 | yes | 4.5 | 0.719 | Fail | c |
| 14 | At4g26930 | MYB97 | MYB | miR159 | yes | 4 | 0.729 | Fail | c |
| 15 | At1g62670 | | PPR | miR161.1 | yes | 3 | 0.765 | Pass | c |
| 16 | At1g64580 | | PPR | miR161.1 | yes | 3.5 | 0.787 | Pass | c |
| 17 | At1g62720 | | PPR | miR161.1 | yes | 5 | 0.754 | Fail | c |
| 18 | At1g63080 | | PPR | miR161.2 | yes | 4 | 0.732 | Pass | c |
| 19 | At1g63400 | | PPR | miR161.2 | yes | 2 | 0.846 | Pass | c |
| 20 | At5g16640 | | PPR | miR161.2 | yes | 2.5 | 0.715 | Fail | c |
| 21 | At3g44870 | | SAMT | miR163 | yes | 3 | 0.765 | Pass | f |
| 22 | At5g39610 | | NAC | miR164 | yes | 3.5 | 0.763 | Pass | b |
| 23 | At4g32880 | AtHB8 | HD-Zip | miR166 | yes | 3 | 0.860 | Pass | c |
| 24 | At5g12840 | HAP2a | HAP2 | miR169 | yes | 3 | 0.735 | Pass | b |
| 25 | At2g39250 | SNZ | AP2 | miR172 | yes | 2.5 | 0.922 | Pass | h |
| 26 | At3g54990 | SMZ | AP2 | miR172 | yes | 1.5 | 0.954 | Pass | h |
| 27 | At4g14680 | APS3 | ATP sulfurylase | miR395 | yes | 3.5 | 0.744 | Pass | b |
| 28 | At3g52910 | GRF4 | GRF | miR396 | yes | 3 | 0.861 | Pass | b |
| | At3g28460 | | unclassified | miR173 | | 7 | 0.760 | Fail, not conserved | d |
| | At2g40760 | | Rhodenase-like | miR396 | | 5.5 | 0.700 | Fail, not conserved | b |

TABLE 3-continued

Summary of miRNA target gene predictions represented in FIG. 1

| | | | | | | | |
|---|---|---|---|---|---|---|---|
| At4g27180 | ATK2 | Kinesin-like protein B | miR396 | 6.5 | 0.527 | Fail, not conserved | b |
| At5g12250 | | Beta-6 tubulin | miR397 | 10 | 0.698 | Fail, not conserved | b |
| At3g54700 | | phosphate transporter | miR399 | 3.5 | 0.743 | Fail, not conserved | b |

Bin 3. New predicted miRNA target genes from existing target families

| | Systematic name[a] | Common name[a] | Gene family | miRNA family | Score[b] | MFE Ratio | Pass/Fail |
|---|---|---|---|---|---|---|---|
| 1 | At1g62860 | | PPR | miR161.1 | 4 | 0.749 | Pass |
| 2 | At1g63330 | | PPR | miR161.2 | 1 | 0.852 | Pass |
| 3 | At1g62590 | | PPR | miR161.2 | 1 | 0.852 | Pass |
| 4 | At1g63630 | | PPR | miR161.2 | 2.5 | 0.859 | Pass |
| 5 | At1g62930 | | PPR | miR161.2 | 3 | 0.882 | Pass |
| 6 | At1g63130 | | PPR | miR161.2 | 3 | 0.882 | Pass |
| 7 | At1g62910 | | PPR | miR161.2 | 3 | 0.882 | Pass |
| 8 | At1g63230 | | PPR | miR161.2 | 3 | 0.735 | Pass |
| 9 | At3g14020 | | HAP2 | miR169 | 2 | 0.859 | Pass |

Bin 4. Novel miRNA target genes, experimentally validated

| | Systematic name[a] | Common name[a] | Gene family | miRNA family | Score[b] | MFE Ratio | Pass/Fail | Associated ESTs |
|---|---|---|---|---|---|---|---|---|
| 1 | At5g60760 | | 2PGK | miR447 | 3.5 | 0.807 | Pass | |
| 2 | At5g10180 | AST68 | Sulfate transporter | miR395 | 3 | 0.760 | Pass | |
| 3 | At2g27400 | TAS1a | | miR173 | 2.5 | 0.768 | Pass | CD534192, CD534180 |
| 4 | At1g50055 | TAS1b | | miR173 | 4.5 | | Fail | |
| 5 | At2g39675 | TAS1c | | miR173 | 2.5 | 0.768 | Pass | |
| 6 | At2g39681 | TAS2 | | miR173 | 2.5 | 0.768 | Pass | BE521498 |
| 7 | At3g17185 | TAS3 | | miR390 | 3.5 | 0.755 | Pass | AV534298, AI998599, BX838290, AA651246 |
| 8 | At2g33770 | | E2-UBC | miR399 | 3.5 | 0.763 | Pass | |
| 8 | At1g31280 | AGO2 | AGO | miR403 | 1 | 0.948 | Pass | BP648434, AU230620 |

Bin 5. Predicted miRNA target genes tested experimentally but not validated

| | Systematic name[a] | Common name[a] | Gene family | miRNA family | Score | MFE Ratio | Pass/Fail | Original prediction reference |
|---|---|---|---|---|---|---|---|---|
| 1 | At1g64100 | | PPR | miR158 | 4 | 0.733 | Pass | c |
| 2 | At3g03580 | | PPR | miR158 | 3.5 | 0.770 | Pass | |
| 3 | At2g03210 | FUT2 | FUT | miR158 | 4 | 0.731 | Pass | |
| 4 | At2g03220 | FUT1 | FUT | miR158 | 4 | 0.737 | Pass | |

[a]Systematic and common names for genes were from TAIR (available on the World Wide Web at arabidopsis.org) and AGRIS (available on-line at arabidopsis.med.ohio-state.edu/AtTFDB/index.jsp);
[b]Score was derived from a modified version of the scoring system developed by Jones-Rhoades et al., 2004.
References: b: Jones-Rhoades et al., 2004; c: Rhoades et al., 2002; d: Park et al., 2002; e: Xie et al., 2003; f: Allen et al., 2004; g: Llave et al., 2002; h: Schmid et al., 2003; i:

Targets for ARF3 and ARF4 were predicted by aligning nucleotide sequences from orthologs from 17 selected species using TCoffee. Similarity over a 21 nucleotide window (characteristic of a miRNA target site) was plotted using PLOTCON in the EMBOSS software suite. Regions beyond the two predicted target sites showing low nucleotide conservation were removed for clarity. Orthologs of the At3g17185 were identified using BLAST, with ESTs only in the predicted miRNA orientation chosen. All selected ESTs were analyzed for the presence of an ARF gene or other conserved ORF by BLASTX analysis against an *Arabidopsis* protein database, and any match eliminated. ESTs were aligned using TCoffee, and the poorly conserved region surrounding the putative miRNAs removed.

Microarray Analysis

Inflorescence tissue (stages 1-12) was collected in triplicate, with three bulked plants for each genotype per replicate. Controls for dcl1-1 and hen1-1 were La-er, controls for hyl1-2, hst-15, dcl2-1, dcl3-1, rdr1-1, rdr2-1, and rdr6-15 were Col-0. RNA was extracted using Trizol, followed by purification using the Plant RNeasy Midi kit (Qiagen). Biotinylated cRNA was synthesized from 5 μg total RNA using the MessageAmp kit (Ambion). Twenty micrograms (20 μg) of concentration-adjusted cRNA were fragmented and hybridized to ATH1 GeneChip arrays according to the manufacturer's protocol (Affymetrix). Samples were normalized using RMA Express (Bolstad et al., *Bioinformatics* 19, 185-193, 2003), and imported into Genespring v7 (Silicon Genetics) for analysis. Hierarchical clustering was performed using the standard clustering algorithm.

5' RACE Analysis of miRNA Directed Cleavage of Target Genes

Cleavage sites of miRNA target genes were mapped using the Invitrogen GeneRacer 5' RACE procedure as described previously (Kasschau et al., *Dev Cell* 4:205-217, 2003; Llave et al., *Science* 297:2053-2056, 2002). Gene specific primers were designed approximately 500 nucleotides downstream of the predicted cleavage site. These primers were used in combination with an adapter specific primer to amplify cleavage products by PCR. Purified PCR products were cloned into pGEM-T Easy.

Phylogeny Reconstruction Methods

The phylogenetic tree for the ARF family was generated by aligning the conserved ARF domain using TCoffee, followed by Bayesian reconstruction of a consensus family tree (Allen et al., *Nat Genet.* 36:1282-1290, 2004).

Results

Computational Prediction and Validation of New miRNA Targets

A rigorous set of computationally predicted and validated targets for most *Arabidopsis* miRNA families has emerged (Table 4 and Table 3) (Aukerman & Sakai, *Plant Cell* 15:2730-2741, 2003; Chen, *Science* 303:2022-2025, 2004; Emery et al., *Curr Biol* 13:1768-1774, 2003; Jones-Rhoades & Bartel, *Mol Cell* 14:787-799, 2004; Kasschau et al., *Dev Cell* 4:205-217, 2003; Llave et al., *Science* 297:2053-2056, 2002b; Mallory et al., *Curr Biol* 14:1035-1046, 2004; Palatnik et al., *Nature* 425:257-263, 2003; Park et al., *Curr Biol* 12:1484-1495, 2002; Rhoades et al., *Cell* 110:513-520, 2002; Tang et al., *Genes & Dev* 17:49-63, 2003; Vaucheret et al., *Genes Dev* 18:1187-1197, 2004; Vazquez et al., *Curr Biol* 14:346-351, 2004a; Xie et al., *Curr Biol* 13:784-789, 2003). However, clear targets for several miRNAs (miR158, miR173, miR390/391, miR399, miR403 and miR447) are not yet known.

TABLE 8B

Locus specific expression of 99 predicted MIRNA genes coding for validated *Arabidopsis* microRNAs

| Locus | 5' RACE | 3' RACE | Cloned in ASRP | Other Refs. |
|---|---|---|---|---|
| MIR156a | Yes | nt | 228 | [11] |
| MIR156b | No | No | | |
| MIR156c | Yes | nt | | |
| MIR156d | No | nt | | |
| MIR156e | Yes | nt | | |
| MIR156f | Yes | nt | | |
| MIR156g | No | No | | |
| MIR156h | No | No | | |
| MIR157a | No | Yes | 9 (1) | |
| MIR157b | No | Yes | | |
| MIR157c | Yes | nt | | |
| MIR157d | Yes | nt | | |
| MIR158a | No | nt | 18 (3) | [11] |
| MIR158b | No | No | | |
| MIR159a | Yes | nt | 225 | [8-12] |
| MIR159b | Yes | nt | 7 | |
| MIR159c | No | No | | |

TABLE 8B-continued

Locus specific expression of 99 predicted MIRNA genes coding for validated *Arabidopsis* microRNAs

| Locus | 5' RACE | 3' RACE | Cloned in ASRP | Other Refs. |
|---|---|---|---|---|
| MIR319a | Yes | nt | 5 | |
| MIR319b | Yes | nt | | |
| MIR319c | No | nt | | |
| MIR160a | Yes | nt | 103 (1) | [11] |
| MIR160b | Yes | nt | | |
| MIR160c | Yes | nt | | |
| MIR161 | Yes | nt | 334 | [1, 6, 11] |
| MIR162a | Yes | Yes | 4 | [11] |
| MIR162b | Yes | Yes | | |
| MIR163 | Yes | nt | 1 | [1, 5, 10, 11] |
| MIR164a | Yes | nt | 2 | [11] |
| MIR164b | Yes | nt | | |
| MIR164c | No | nt | 0 (2) | |
| MIR165a | Yes | nt | 30 | [11] |
| MIR165b | No | No | | |
| MIR166a | Yes | nt | 307 (1) | |
| MIR166b | Yes | nt | | |
| MIR166c | Yes | nt | | |
| MIR166d | Yes | nt | | |
| MIR166e | No | Yes | | |
| MIR166f | No | Yes | | |
| MIR166g | No | No | | |
| MIR167a | Yes | nt | 173 | [6, 10, 11, 13] |
| MIR167b | Yes | nt | | |
| MIR167c | No | No | | |
| MIR167d | No | nt | 7 | |
| MIR168a | No | nt | 22 (7) | [11, 13] |
| MIR168b | No | No | | |
| MIR169a | Yes | nt | 619 (1) | [11] |
| MIR169b | No | nt | 128 (1) | |
| MIR169c | Yes | nt | | |
| MIR169d | No | No | 22 | |
| MIR169e | No | No | | |
| MIR169f | No | No | 22 | [11] |
| MIR169g | No | No | | |
| MIR169h | Yes | nt | 458 | |
| MIR169i | No | nt | | |
| MIR169j | No | No | | |
| MIR169k | No | No | | |
| MIR169l | Yes | nt | | |

TABLE 8B-continued

Locus specific expression of 99 predicted
MIRNA genes coding for validated *Arabidopsis* microRNAs

| | | | | |
|---|---|---|---|---|
| MIR169m | No | nt | | |
| MIR169n | Yes | nt | | |
| MIR170 | Yes | nt | 1 | [6, 7, 11, 12] |
| MIR171a | Yes | nt | 35 | |
| MIR171b | Yes | nt | 2 | |
| MIR171c | Yes | nt | | |
| MIR172a | Yes | nt | 0 (2) | [2, 3, 10] |
| MIR172e | Yes | nt | | |
| MIR172b | Yes | nt | | |
| MIR172c | Yes | nt | 1 | |
| MIR172d | No | No | | |
| MIR173 | No | nt | 1 (1) | [10] |
| MIR390a | No | nt | 122 (2) | [12] |
| MIR390b | No | nt | | |
| MIR391 | No | nt | 7 (1) | |
| MIR393a | No | No | | [4, 12] |
| MIR393b | No | No | | |
| MIR394a | Yes | nt | | [4] |
| MIR394b | No | No | | |
| MIR395a | No | No | | [4] |
| MIR395b | No | No | | |
| MIR395c | Yes | nt | | |
| MIR395d | No | No | | |
| MIR395e | Yes | nt | | |
| MIR395f | No | No | | |
| MIR396a | Yes | nt | 0 (1) | [4] |
| MIR396b | No | No | | |
| MIR397a | No | nt | 1 | [4, 12] |
| MIR397b | Yes | nt | | |
| MIR398a | No | nt | | [4, 12] |
| MIR398b | No | Yes | 4 | |
| MIR398c | Yes | nt | | |
| MIR399a | No | No | | [4, 12] |
| MIR399b | Yes | nt | 1 | |
| MIR399c | Yes | nt | | |
| MIR399d | Yes | nt | | |
| MIR399e | No | No | | |
| MIR399f | No | nt | | |
| MIR403 | Yes | Yes | 1 | [12] |
| MIR447a | Yes | nt | 1 | |
| MIR447b | Yes | nt | | |
| MIR447c | Yes | nt | | | nt, not tested.
References cited are: 1. Allen et al., *Nat Genet* 36:1282-1290, 2004; 2. Aukerman & Sakai, *Plant Cell* 15:2730-2741, 2003; 3. Chen, *Science* 303:2022-2025, 2004; 4. Jones-Rhoades & Bartel, *Mol Cell* 14:787-799, 2004; 5. Kurihara & Watanabe, *Proc Natl Acad Sci U S A* 101:12753-12758, 2004; 6. Llave et al., *Plant Cell* 14:1605-1619, 2002; 7. Llave et al., *Science* 297:2053-2056, 2002; 8. Mette et al., *Plant Physiol* 130:6-9, 2002; 9. Palatnik et al., *Nature* 425:257-263, 2003; 10. Park et al., *Curr Biol* 12:1484-1495, 2002;
11. Reinhardt et al., *Genes Dev.* 16:1616-1626, 2002; 12. Sunkar and Zhu *Plant Cell* 16:2001-2019, 2004; 13. *Arabidopsis* EST clones were identified for MIR167d (GenBank accession AU239920) and MIR168a (H77158).

To further extend and refine the analysis of miRNA targets in plants, we developed a set of computational "rules" for *Arabidopsis* miRNA-target interactions involving 22 miRNA families. These were used to produce a target prediction set that was experimentally tested (FIG. 1A). The rule development set included 66 experimentally validated targets and 28 previously predicted targets that are closely related to validated family members. Among the 66 validated targets were 55 previously published targets and 11 new validated targets.

Figure 2A:
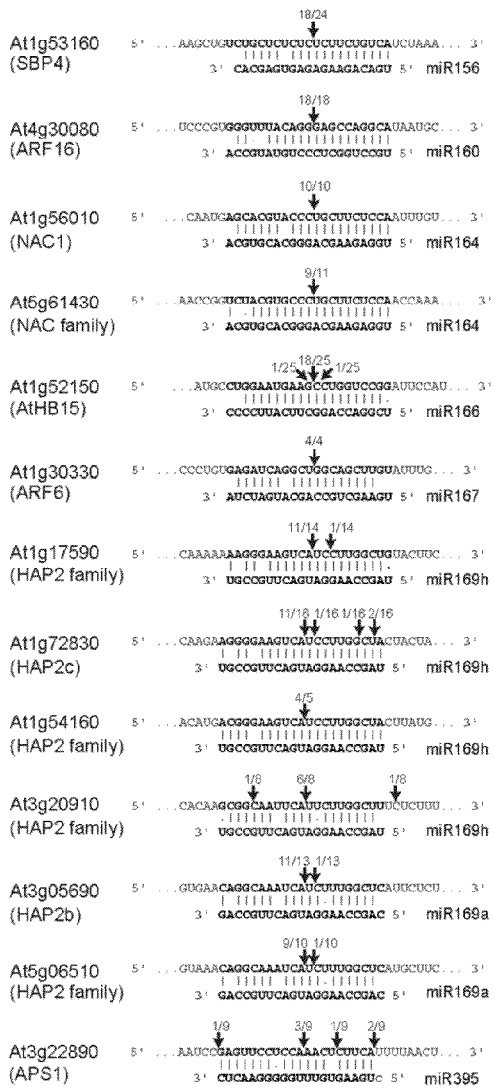
FIG. 2A-2B. miRNA-target duplexes.
Figure 2B:
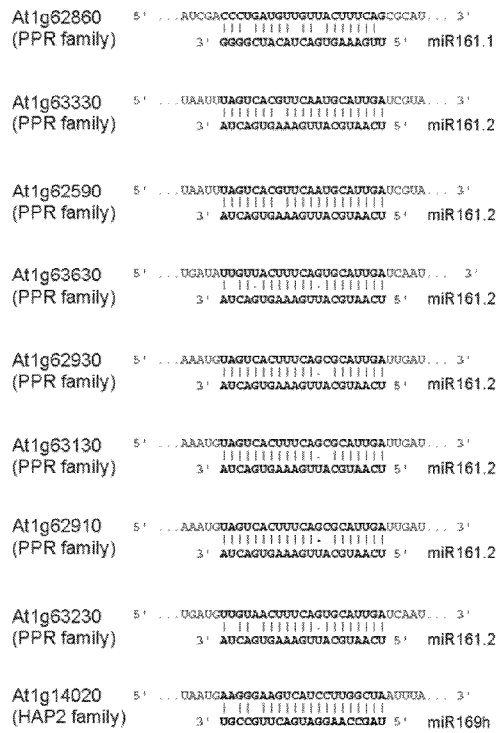

Experimental validation of targets involved 5'RACE assays to detect a cleavage site opposite of position 10 from the 5' end of the miRNA (Kasschau et al., *Dev Cell* 4:205-217, 2003; Llave et al., *Science* 297:2053-2056, 2002). Detection of a cleavage product with a 5' terminus corresponding to the predicted miRNA-guided cleavage site is strong evidence in support of target site function. Validated targets included genes from multigene families in which closely related paralogs were shown previously to be miRNA targets (Bins 1 and 3, FIG. 2A), and nine novel targets discussed in detail below (Bin 4, FIGS. 3A and 3B).

Figure 1B:
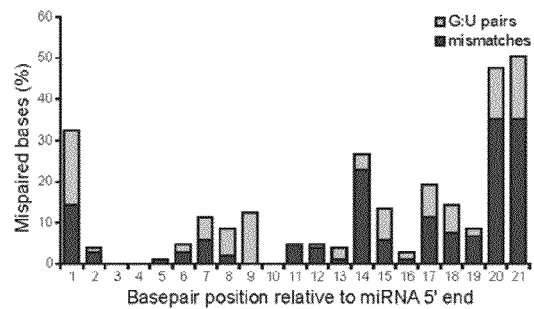
Figure 1C:
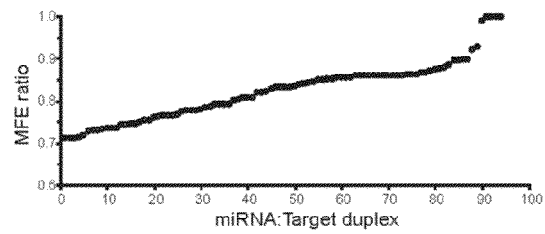

Two parameters were analyzed for rule development. First, the occurrence of mispaired bases between miRNAs and targets was analyzed. All miRNA-target duplexes within the rule set contained four or fewer unpaired bases, four or fewer G:U pairs, up to one single-nucleotide bulge, and a total of seven or fewer unpaired plus G:U positions. The positions of mispairs were examined by plotting the percentage of mismatched and G:U pairs at each target nucleotide position (counting from the 3' end) (FIG. 1B). Nucleotide pairs at positions 2-13 formed a core segment with relatively few mismatches relative to positions 1 and 14-21. This core segment is longer than the core segment of animal miRNA-target duplexes (positions 2-8) (Lewis et al., *Cell* 115:787-798, 2003). A mispair scoring system, modified from that used by Jones-Rhoades and Bartel (*Mol Cell* 14:787-799, 2004), was applied to account for the reduced occurrence of mispairs within the core segment. Mismatched pairs or single nucleotide bulges were each scored as 1 and G:U pairs were scored as 0.5. Mismatches and G:U pair scores were doubled within the core segment. A score of ≤4 captured 91 of 94 targets in the rule development set for a false negative rate of 0.03.

Figure 1D:
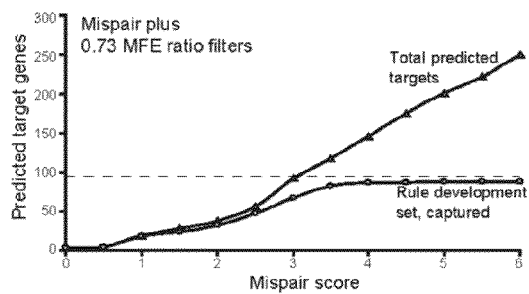

Second, a relative thermodynamic parameter was investigated. The minimum free energy (MFE) of a hypothetical duplex containing each of the 94 targets paired with a perfectly complementary sequence ($\Delta G_{MFE}$) was calculated and compared to the free energy calculated for the actual miRNA-target duplex ($\Delta G_{target}$). The MFE ratio ($\Delta G_{target}/\Delta G_{MFE}$) was calculated for each duplex in the rule set. Eighty-nine of the duplexes in the rule set had an MFE ratio ≥0.73 (FIG. 1C), corresponding to a false negative rate of 0.05. Combining the mispair (≤4) and MFE ratio (≥0.73) limits in a series of filters resulted in capture of 87 targets from the rule set (false negative rate=0.07). The mispair and MFE ratio limits were applied in searches using all validated miRNAs from the 25 families (Table 4) and the *Arabidopsis* transcript database, resulting in 145 prospective targets (FIG. 1D).

Target sequence conservation across species and between closely related paralogs was applied as a final filter. For all miRNAs that were conserved between monocots and dicots (or between dicot families), predicted target sites were required to be similarly conserved (Jones-Rhoades & Bartel, *Mol Cell* 14:787-799, 2004). For non-conserved miRNAs, target sites were required to be present within more than one paralog in *Arabidopsis*. When applied to the rule development set, the respective conservation filters resulted in loss of no genes. Application of the conservation filter to the 145 genes that passed the mispair and MFE ratio filters resulted in 103 genes (FIG. 1A).

To further extend the chances for target identification, an miRNA target search was also done using the *Arabidopsis*

EST database. The same mispair and conservation filters were used, but the MFE ratio filter limit was lowered to 0.70 to account for known sequencing errors within the EST dataset. A redundancy filter was added to subtract all prospective target genes that also passed the target search using the transcript database. Six new prospective targets were identified in the EST search, resulting in a total of 109 predicted targets. These were assigned to several bins (FIG. 1A, Table 3). Bin 1 contained 63 of 66 previously validated targets that contributed to the rule set. Bin 2 contained 24 of the 28 predicted targets from the rule set. Thus, the overall false negative rate was 0.07. Bin 3 contained nine new predicted targets from existing target gene families. These previously nonpredicted targets included eight pentatricopeptide repeat (PPR) genes targeted by miR161.1 and miR161.2, a HAP2a gene (At1g14020) targeted by miR169, and a sulfate transporter (AST68, At5g10180) gene targeted by miR395. Bin 4 contained nine novel targets that were experimentally validated and analyzed in detail (see following sections). Bin 5 contained four genes that were predicted to interact with miR158, but each of these failed the 5'RACE validation assay. If it is assumed that Bin 5 genes represent all incorrect predictions from this search, then the false positive rate was 0.04.

Figure 3A:
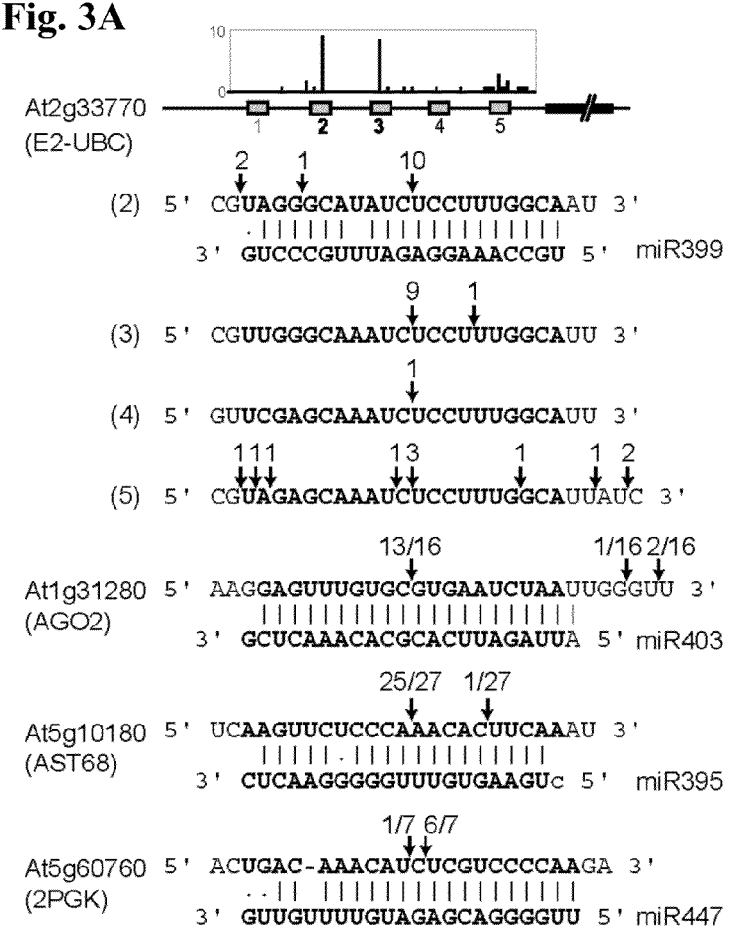
FIG. 3A-3B. Validation of miRNA targets by 5'RACE.

Genes encoding an E2-ubiquitin conjugating enzyme (E2-UBC, At2g33770), Argonaute2 (AGO2, At1g31280), and a 2-phosphoglycerate kinase (2PGK, At5g60760) were validated as targets of miR399, miR403 and miR477, respectively, and represent the only conventional genes in Bin 4 (FIG. 3A). Possibly because of computational searches using a transcript database containing a misannotated E2-UBC, miR399 was predicted previously to target a different mRNA encoding a phosphate transporter (At3g54700) (Jones-Rhoades & Bartel, *Mol Cell* 14:787-799, 2004). This gene was not predicted in our analysis, and the 5'RACE assay failed to reveal a miR399-guided cleavage product. The E2-UBC target, which was identified here and predicted by Sunkar and Zhu (*Plant Cell* 16:2001-2019, 2004) only using EST databases, contains up to five miR399-interacting sites in the 5' untranslated region (UTR). Cleavage products were detected with 5' termini corresponding to cleavage at four of these sites, most prominently sites 2 and 3 (FIG. 3A). Orthologous E2-UBC genes in rice and at least three other plant species each contain 3-5 conserved target sites. This is the only example of both a 5'UTR target position and multiple miRNA-target sites in plant genes. The miR403-target site was identified within the 3'UTR of the AGO2 transcript from *Arabidopsis* and several other dicot families, but not in orthologous AGO2 transcripts from monocots. This is the second miRNA-targeted AGO family member identified, as AGO1 was shown to be targeted by miR168. Whereas AGO1 is required for miRNA activity (Vaucheret et al., *Genes Dev* 18:1187-1197, 2004), presumably within RISC, a function for AGO2 is currently not known. The 2PGK gene (At5g60760) was validated as an miR447 target (FIG. 3A), and joins a growing list of plant miRNA targets that encode proteins with metabolic functions (Jones-Rhoades & Bartel, *Mol Cell* 14:787-799, 2004).

The five remaining Bin 4 genes were validated as miR173 and miR390 targets (FIG. 3B), and were predicted only from EST database due to their unusual nature. These are discussed in detail below.

Expression Profiling of Predicted miRNA Targets

Figure 4A:
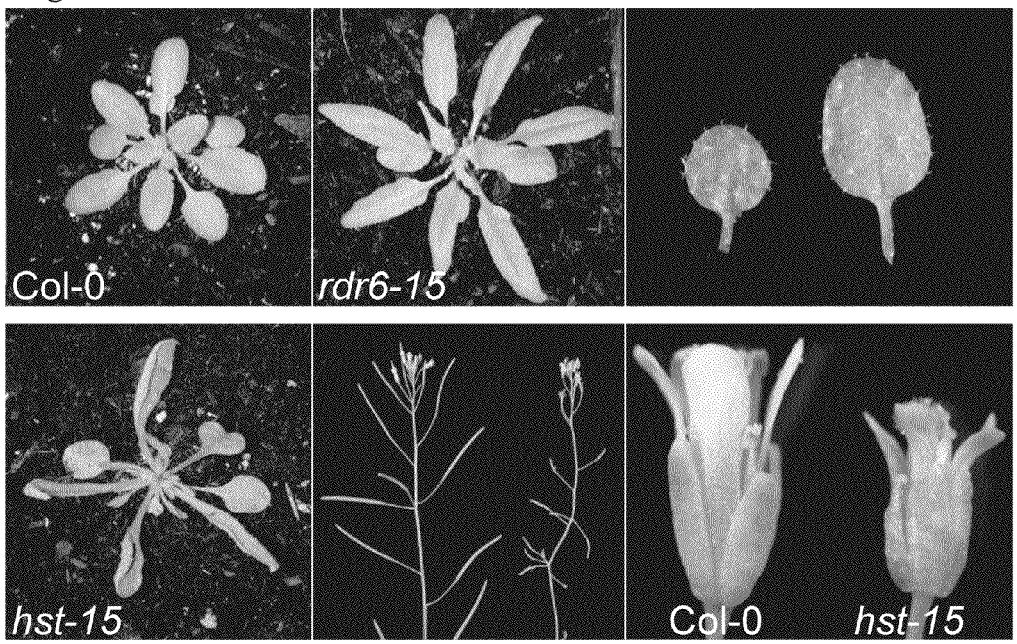
FIG. 4A-G. Characterization and expression profiling of *Arabidopsis* small RNA biogenesis mutants.

Most miRNAs of plants direct cleavage of their targets. Loss-of-function mutations in miRNA metabolic or biogenesis genes, therefore, frequently result in elevated target transcript levels (Kasschau et al., *Dev Cell* 4:205-217, 2003; Palatnik et al., *Nature* 425:257-263, 2003; Vazquez et al., *Curr Biol* 14:346-351, 2004a; Xie et al., *Curr Biol* 13:784-789, 2003). To systematically analyze the effects of miRNA and endogenous siRNA defects on validated and predicted miRNA target genes in *Arabidopsis*, expression profiling was done using nine mutant (condition) plants and two control plants. The mutants included miRNA-defective dcl1-7, hen1-1 and hyl1-2 (Park et al., *Curr Biol* 12:1484-1495, 2002; Schauer et al., *Trends Plant Sci* 7:487-491, 2002; Vazquez et al., *Curr Biol* 14:346-351, 2004a), which were shown to reduce or eliminate accumulation of miRNAs. A new insertion mutant, hst-15, with predicted defects in nucleocytoplasmic transport of miRNA and ta-siRNA precursors (Bollman et al., *Development* 130:1493-1504, 2003) was used. Using inflorescence tissue, hst-15 had only modest or no effects on miRNA accumulation. However, as shown using the hst-1 mutant (Bollman et al., *Development* 130: 1493-1504, 2003; Peragine et al., *Genes & Dev* 18:2369-2379, 2004), hst-15 had several developmental abnormalities, including a more rapid juvenile to adult phase change, leaf curling and epinasty, altered silique phyllotaxy and small flowers (FIG. 4A). The hst-15 transcript accumulated to low levels specifically in the hst-15 mutant plant; this was in contrast to the dcl1-7 transcript, which was upregulated in each of the miRNA-defective mutants due to loss of miR162-mediated feedback regulation (Xie et al., *Curr Biol* 13:784-789, 2003).

The mutant series also included five siRNA-defective mutants. The dcl3-1 and rdr2-1 mutants lack chromatin RNAi-associated, 24-nucleotide siRNAs, dcl2-1 and rdr1-1 mutants have defects in antiviral siRNA biogenesis, and the rdr6-15 mutant is defective in to-siRNA biogenesis (Peragine et al., *Genes & Dev* 18:2369-2379, 2004; Vazquez et al., *Mol Cell* 16:69-79, 2004b; Xie et al., *PLoS Biol* 2:642-652, 2004). The rdr6-15 mutant contains a new insertion allele, but displays most of the same properties of previously characterized rdr6 mutants (Allen et al., *Nat Genet* 36:1282-1290, 2004). Specifically, rdr6-15 plants display rapid juvenile-to-adult phase change and accompanying morphological defects (FIG. 4A), and accumulate low levels of rdr6-15 transcript.

Figure 4B:
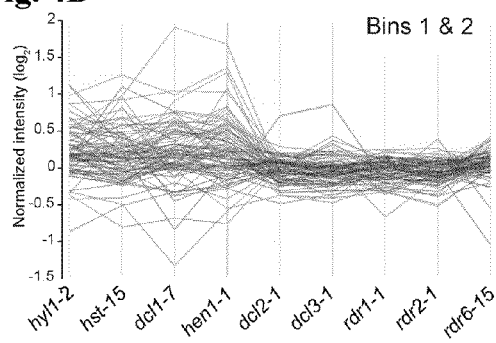
Figure 4C:
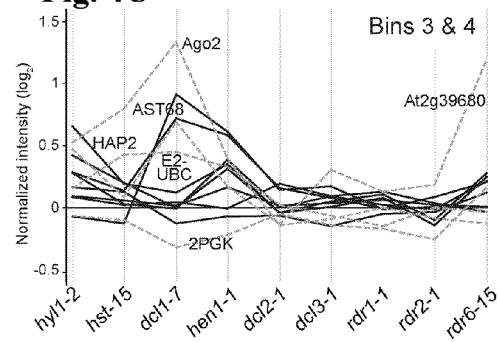
Figure 4D:
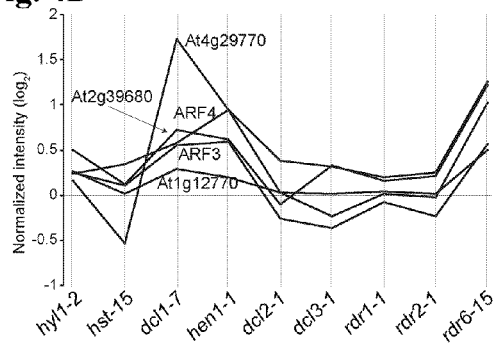

Expression profiling was done with triplicate biological samples on Affymetrix ATH1 arrays. Because DCL1, HEN1, HYL1, and likely HST, are required for miRNA biogenesis or function, we predicted that miRNA target genes would be upregulated coordinately in the corresponding mutants and largely unaffected in the siRNA biogenesis mutants. As a group, previously validated and predicted target genes (Bin 1+2 genes) generally behaved as anticipated, although clearly not all genes were upregulated in the miRNA mutants (FIG. 4B). Of the 81 genes present on the ATH1 array, 27 were significantly (P<0.01, ANOVA) upregulated in two or more of the miRNA mutants, although only 16 genes were significantly upregulated in all four miRNA mutants. Transcripts for MYB101 (miR159 target At2g32460) and a NAC domain gene (miR164 target At5g61430) were significantly (P<0.01, ANOVA) downregulated in the miRNA mutants, suggesting they may be negatively regulated by a factor that is under miRNA control. Targets from Bins 3+4, of which only 12 were represented on the array, were generally upregulated in the miRNA mutants but unaffected by the siRNA mutants, although the At2g39680 transcript (antisense to validated miR173 target) was significantly upregulated in rdr6-15 as well as in miRNA-defective mutant plants (FIG. 4C). In addition, a list of genes that were affected (P<0.01, ANOVA) in each of the dcl1-7, hen1-1 and rdr6-15 mutants was generated. This list contained five genes [At4g29770, At2g39680, At5g60450 (Auxin Response Factor4, ARF4), At2g33860 (ARF3) and At1g12770], all of which were up-regulated in the three mutants (FIG. 4D). These genes were predicted to be either miRNA targets that were also subject to a RDR6-dependent RNAi pathway, or ta-siRNA targets. Three of these genes were shown to yield transcripts that function as ta-siRNA targets (At4g29770, ARF3 and ARF4), one a predicted ta-siRNA target (At1g12770), and one a novel type of miRNA target (At2g39680).

Figure 4E:
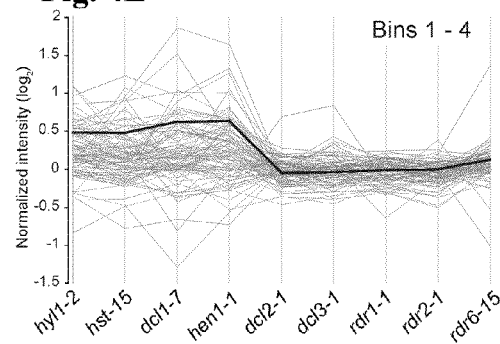
Figure 4F:
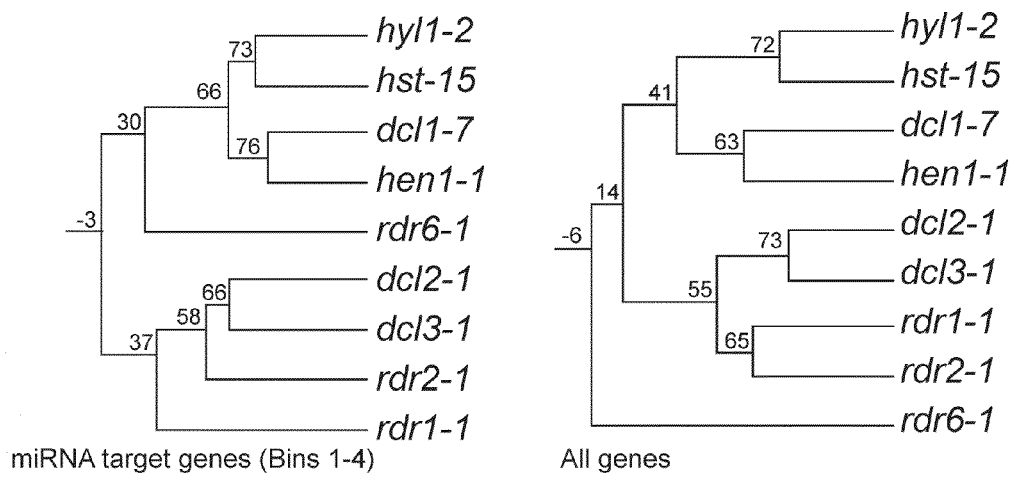

To analyze the variation patterns among all predicted and validated miRNA targets, two analyses were done. First, a Principal Components Analysis (PCA) was done using expression data from Bins 1-4. An eigenvector that accounted for 65% of the variation among conditions revealed that the miRNA mutants were unified as having target-upregulation effects, and the siRNA mutants were unified as having no effects (FIG. 4E). No other eigenvector accounted for more than 9% of the variation. Among 30 genes highly correlated to the primary eigenvector (r>0.95), 6 were validated targets, plus one 2PGK gene (At3g45090) closely related to the validated miR477 target. The predicted miR477 target site in At3g45090 failed the MFE ratio (0.69), although the expression profile suggests that At3g45090 is a miRNA target. Second, an unsupervised hierarchical clustering analysis was done, and correlated conditions were displayed as an expression tree. The four miRNA-defective mutants grouped within one clade, with dcl1-7 and hen1-1 forming a subclade distinct from an hst-15/hyl1-2 subclade (FIG. 4F). The dcl1-1, dcl2-1, rdr1-1 and rdr2-1 mutants formed a distinct expression clade.

Figure 3B:
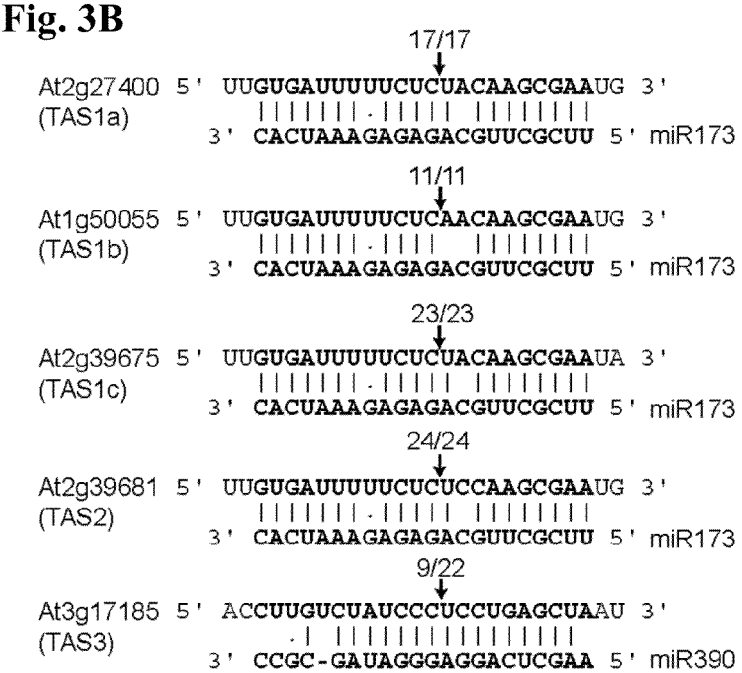
Figure 4G:
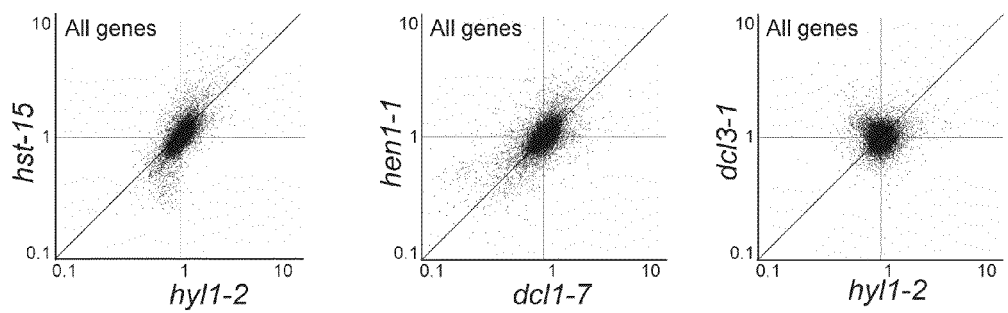

To compare more broadly the effects of miRNA and siRNA defects on the *Arabidopsis* transcriptome, condition pairs were analyzed using scatterplots. Also, a similar clustering analysis was done as for targets, using all genes. Expression values (fold-change relative to controls) for genes that are coordinately affected in two mutants should remain on the diagonal, whereas genes that are differentially affected in two mutants fall above or below the diagonal. Based on this approach, the effects of hyl1-2 were most similar to the effects of hst-15, and the effects of dcl1-7 were most similar to the effects of hen1-1 (FIG. 4G). In contrast, there was little similarity between transcriptome-wide effects of any of the miRNA mutants and siRNA mutants, as exemplified by the hyl1-2/dcl3-1 comparisons (FIG. 4G). Among all conditions, the miRNA-defective mutants grouped within one clade, and the siRNA mutants formed a distinct clade (FIG. 4F). With all genes considered, the rdr6-15 mutant did not group with either miRNA- or siRNA-defective mutants. Thus, with the major exceptions described below, the expression profiling data indicate that miRNA-mediated regulation of targets and downstream genes is largely independent of the siRNA pathways.

miR173 Guides in-Phase Processing of Precursor Transcripts for Ta-siRNAs at Several Loci Four miR173 targets were predicted based on the EST database but not the annotated transcript database. One of these predicted targets was antisense relative to the annotated gene At2g39680. Two other miR173 target sites were predicted based on ESTs AU235820 and CD534192 from paralogous loci; a third paralogous locus also contained the conserved miR173 site. miR173 target validation data for transcripts deriving from each of these four loci were obtained (FIG. 3B). None of the miR173 target transcripts contained extended, conserved protein-coding sequences.

Inspection and analysis of the four loci yielding miR173-targeted transcripts revealed that each was a confirmed or predicted ta-siRNA-generating locus (FIG. 5). The three paralogous loci, termed TAS1a, TAS1b and TAS1c yielded siR255 and several similar sequences (siR289, siR752, and siR850, also referred to as siR289, siR752 and siR850, respectively) in tandem, 21-nucleotide arrays. These ta-siRNAs were characterized previously and shown to require DCL1, RDR6, SGS3, and AGO1 (Peragine et al., *Genes & Dev* 18:2369-2379, 2004; Vazquez et al., *Mol Cell* 16:69-79, 2004). siR255 (formally TAS1a 3'D6(+), TAS1b 3'D6(+), TAS1c 3'D3(+)) was shown to target transcripts from the related genes At4g29760, At4g29770, and At5g18040 (functions unknown) for degradation in a manner similar to plant miRNAs. This was consistent with the expression profiling data, in which At4g29770 was one of five genes up-regulated in dcl1-7, hen1-1, and rdr6-15 plants (FIG. 4D). The fourth miR173 target locus, TAS2 (which was antisense to annotated At2g39680), possessed the hallmarks of a ta-siRNA-generating site, including the derivation of five cloned small RNAs representing both polarities in accurate, 21-nucleotide register (FIG. 5C) and up-regulation in dcl1-7, hen1-1, and rdr6-15 plants (FIG. 4D). The TAS2 (At3g39680) locus mapped approximately 2 kb away from, and in the same orientation as, TAS1c At2g39675, raising the possibility that both ta-siRNA sets arise from the same precursor transcript (FIG. 5C). Relative to miRNAs, siR255 and siR1511 small RNAs were relatively abundant as they corresponded to the $19^{th}$ and $10^{th}$ most frequently cloned sequences, respectively, from the small RNA libraries in the ASRP database (Table 5).

TABLE 5

Highly represented small RNAs in the ASRP database

| Rank | Small RNA Family | ASRP no. | Total sequences |
|------|------------------|----------|-----------------|
| 1 | miR169 | 1430 | 25570 |
| 2 | miR156 | 1423 | 14029 |
| 3 | miR169 | 1751 | 6491 |
| 4 | miR161.2 | 563 | 6227 |
| 5 | miR160 | 1426 | 4752 |
| 6 | miR159 | 1425 | 4567 |
| 7 | miR169 | 1514 | 3944 |
| 8 | miR166 | 934 | 3482 |
| 9 | miR167 | 5 | 2893 |
| 10 | siR1511 ta-siRNA | 1511 | 1901 |
| 11 | miR390 | 754 | 1373 |
| 12 | miR169 | 1802 | 874 |
| 13 | miR169 | 1749 | 685 |
| 14 | miR169 | 1761 | 660 |
| 15 | miR168 | 1429 | 642 |
| 16 | miR390 | 1703 | 589 |
| 17 | miR169 | 276 | 457 |
| 18 | miR169 | 1757 | 405 |
| 19 | siR255 ta-siRNA | 255 | 321 |
| 20 | miR169 | 1775 | 299 |

Figure 5C:
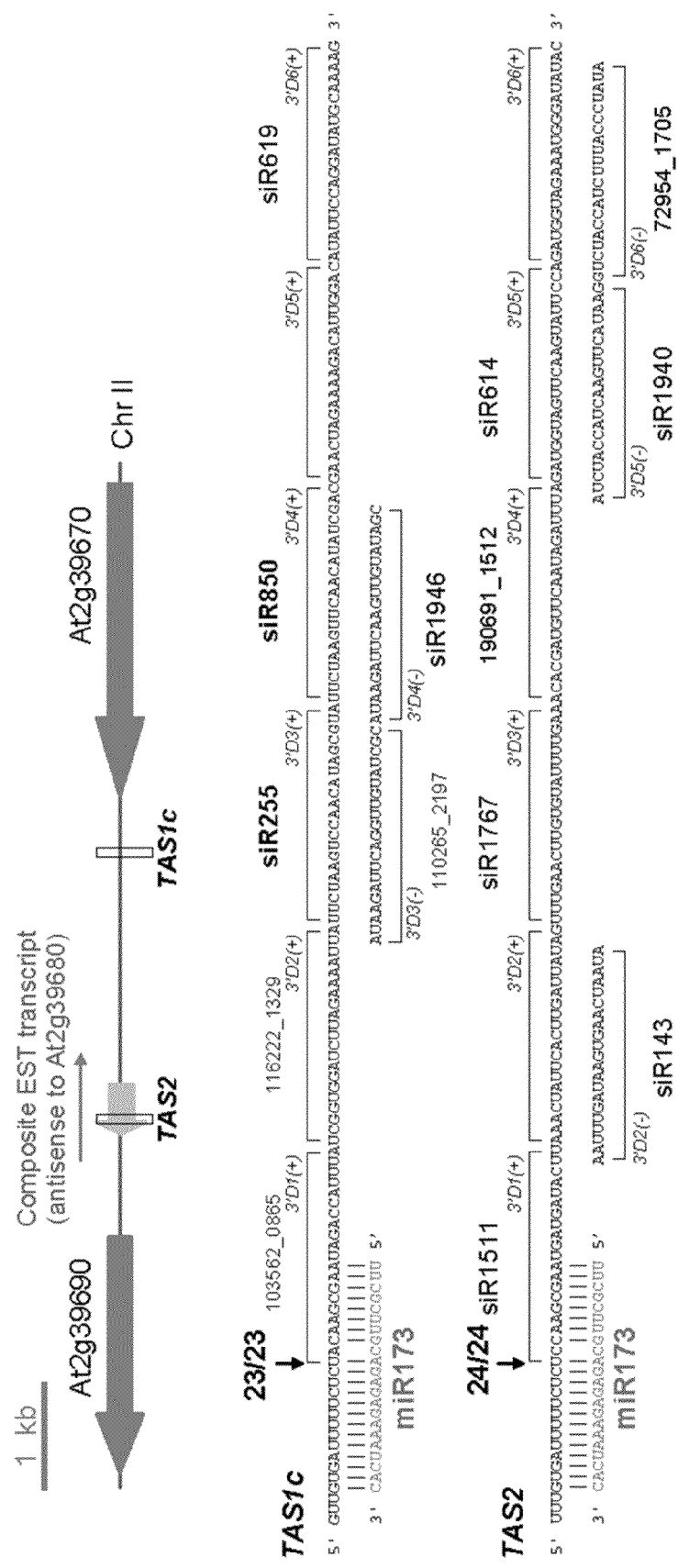
Figure 5D:
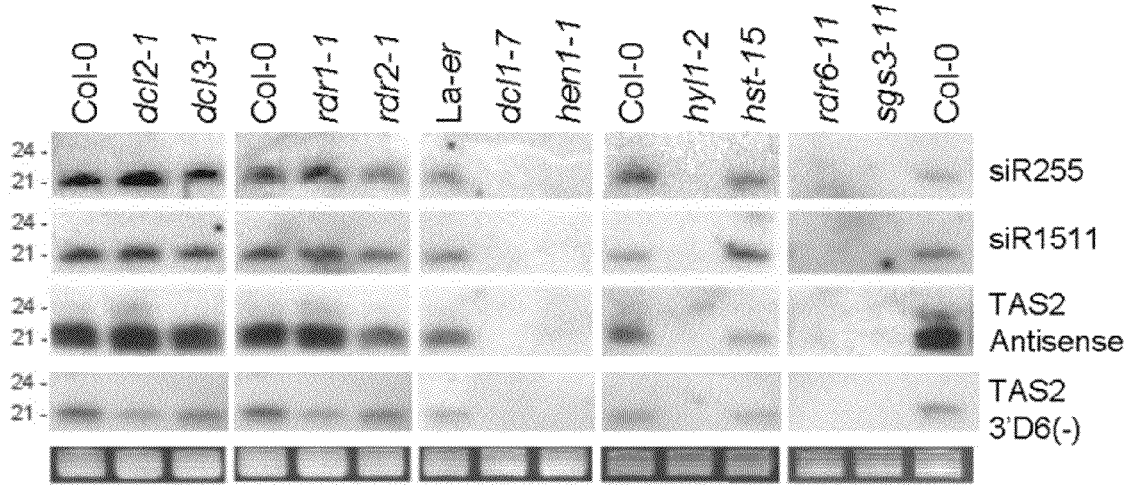

To confirm that TAS2 is a ta-siRNA-generating locus, and to extend the analysis of biogenesis requirements of this class of small RNA, TAS2-derived small RNAs and siR255 from the miRNA- and siRNA-defective mutants were analyzed in blot assays. Small RNAs from the opposite strand at the TAS2 locus were also analyzed. Accumulation of each small RNA was lost or diminished in dcl1-7, hen1-1, hyl1-2, rdr6-11 and sgs3-11, but not in hst-15 (FIG. 5D). Accumulation levels were unaffected in dcl2-1, dcl3-1, rdr1-1 and rdr2-1 mutants (FIG. 5D). These data confirm that TAS2 is a ta-siRNA-generating locus.

The biogenesis data were consistent with a model in which ta-siRNA precursor transcripts are recognized by RDR6/SGS3 and converted (at least partially) to dsRNA forms, which are then processed by DCL1 in phased, 21-nucleotide intervals to form ta-siRNA duplexes. Setting the correct register must be a critical step in this pathway, as out-of-register processing would yield small RNAs with insufficient complementarity to their targets. We hypothesized that miR173- guided cleavage of precursor transcripts generates a terminus that, after RDR6/SGS3-dependent conversion to dsRNA, functions as a start point for successive DCL1-mediated cleavage events in 21-nucleotide intervals. This hypothesis predicts that the predominant ta-siRNAs will form with a 21-nucleotide phase starting at the miR173 cleavage site. A systematic coding system, in which hypothetical DCL1 cleavage products from the miR173-targeted strand [3'D1(+), 3'D2(+), 3'D3(+), etc.] and opposite strand [3'D1(−), 3'D2(−), 3'D3(−), etc.] were assigned a strict phasing relative to miR173 target sites, was devised (FIG. 5A, B, C).

Figure 5E:
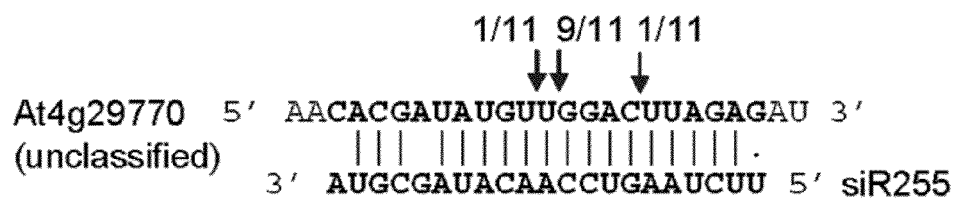
Figure 5E:
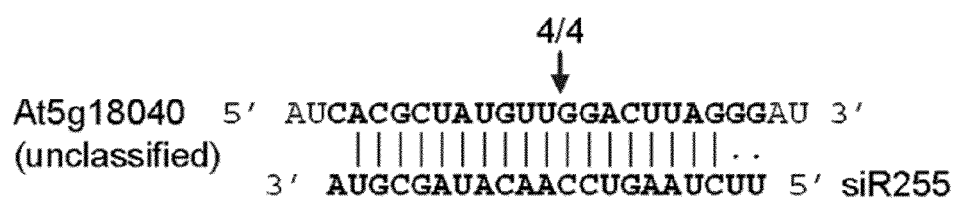
Figure 5E:
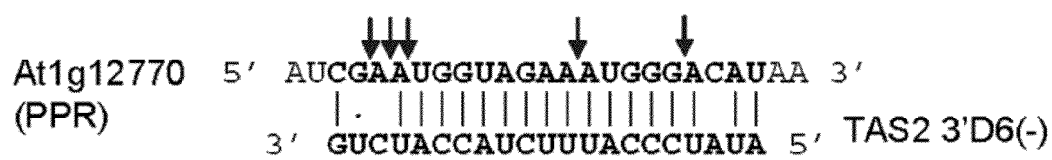
Figure 5E:
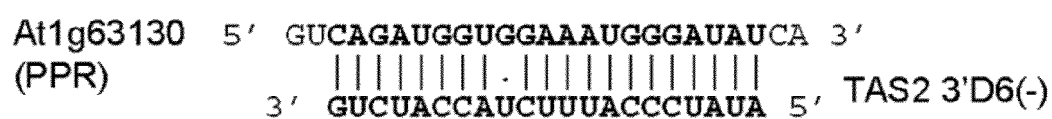

Each of the nine cloned ta-siRNAs identified collectively at the four miR173-targeted loci mapped precisely to the phasing interval set by miR173-guided cleavage (FIG. 5A, B, C). As predicted from the known properties of Dicer-like enzymes, small RNAs from the non-targeted strand (for example, siR143 and siR1946) were offset by two nucleotides relative to the complementary sequence on the target strand. The register was maintained at each locus through at least the 3'D6 position, and at TAS1a through the 3'D8 position. A total of 19 unique small RNAs, from positions 3'D1 to 3'D8, had 5' ends formed by accurate in-phase cleavage but 3' ends offset by one or two nucleotides. Slight variation of this nature was expected, as *Arabidopsis* miRNA populations frequently contain processing variants that differ by one or a few nucleotides. In addition to TAS1-derived siRNAs (e.g. siR255), which were confirmed to guide cleavage of mRNA targets (FIG. 5E), a hypothetical ta-siRNA from the 3'D6(−) position at the TAS2 locus was predicted to interact with at least two PPR gene transcripts (At1g12770 and At1g63130, FIG. 5E). At1g12770 was one of the five dcl1-1, hen1-1 and rdr6-15-upregulated genes (FIG. 4D), which was consistent with identity as a ta-siRNA target, although we were unable to validate a cleavage site at the predicted position within the transcript (FIG. 5E).

miR390 Guides in-Phase Processing of Ta-siRNAs Regulating ARF3 and ARF4

The predicted target of miR390 was a transcript from the annotated gene At3g17185 (FIG. 6A), for which no function was assigned previously. The hypothetical protein encoded by this gene is small (50 residues) and contains no recognizable motifs, raising the possibility that At3g17185 is a misannotated, protein-noncoding locus. The miR390 target site was validated by 5'RACE analysis (9/22 PCR products sequenced), although a second cleavage site 33 nucleotides away was detected at approximately the same rate (11/22 PCR products).

The hypothesis that At3g17185 is a ta-siRNA-generating locus targeted by miR390 was tested by analysis of small RNAs from the locus, and prediction and validation of putative ta-siRNA target genes. Two low-abundance, cloned small RNAs from sequences to the 5' side of the miR390 cleavage site were identified (FIG. 6A). siR1769 derived precisely from the 5'D1(+) position, whereas siR1778 was out-of-register (relative to the miR390-guided cleavage site) between the −5'D7 and 5'D8 positions. Blot assays using strand- or sequence-specific radiolabeled probes to detect small RNAs arising from between the 5'D5 to the 5'D11 positions revealed that DCL1-, HEN1- and RDR6- and SGS3-dependent, 21-nucleotide small RNAs arose from both strands (FIG. 6B). Thus, the At3g17185 locus forms transcripts that yield small RNAs with biogenesis requirements consistent with other ta-siRNAs. In addition to 21-nucleotide RNAs, this locus also yielded detectable 24-nucleotide RNAs, which were clearly DCL3- and RDR2-dependent and RDR6- and SGS3-independent (FIG. 6B).

Potential targets of sequenced and hypothetical ta-siRNAs from the At3g17185 locus were identified through several computational and experimental validation steps. First, phylogenetic conservation of the miR390 target site, which was predicted to set the phasing for ta-siRNA precursor processing, was analyzed. Transcripts and ESTs from each of 17 species of monocot and dicot plants contained a miR390 target site, which was uniquely conserved relative to immediate flanking sequence in each case (FIG. 6C). Second, functional ta-siRNAs and their targets were predicted to be phylogenetically conserved across an equivalent evolutionary distance. In *Arabidopsis*, two highly conserved, tandem 21-nucleotide sequences were detected at positions that nearly co-aligned with the hypothetical 5'D7(+) and 5'D8(+) positions relative to the miR390 cleavage site (FIG. 6C). These two intervals contained near-identical copies of the same sequence, which was conserved among all transcripts that contained a miR390 target site (FIG. 6C). The spacing between the conserved, tandem sequences and the miR390 target site varied between the 5'D7(+) and 5'D8(+) positions in different species. In all plants, however, the tandem sequences and the miR390 target site varied between the 5'D7(+)/5'D8(+) and the 5'D3(+)/5'D4(+) positions in different species. In all plants, however, the tandem sequences started in either perfect 21-nucleotide register (5/19 species) or one-nucleotide offset (14/19 species) relative to the miR390 cleavage site.

Third, using the rules developed for miRNA target prediction, four genes (ARF1, ARF2, ARF3, and ARF4) were predicted to be targets of these conserved ta-siRNAs. Both ARF3 and ARF4 genes behaved as ta-siRNA targets, as each was up-regulated in dcl1-7, hen1-1 and rdr6-15 mutant plants (FIG. 4D). Both ARF3 and ARF4 genes from 16 species contained two regions ('A' and 'B') of complementarity to the predicted ta-siRNAs (FIG. 6D); the 'A' site was also conserved in ARF1 and ARF2 genes across all plant species tested. And fourth, the 'A' site in both ARF3 and ARF4 was validated as a ta-siRNA target site by 5'RACE. In contrast to most miRNA target sites, the ARF3 and ARF4 'A' site contained several minor cleavage products in addition to the product formed by cleavage at the canonical target position (FIG. 6D). Evidence supporting ta-siRNA targeting at the 'B' site within the ARF4 transcript was also obtained (FIG. 6D). Thus, the ta-siRNA-generating locus was named TAS3.

Figure 6A:
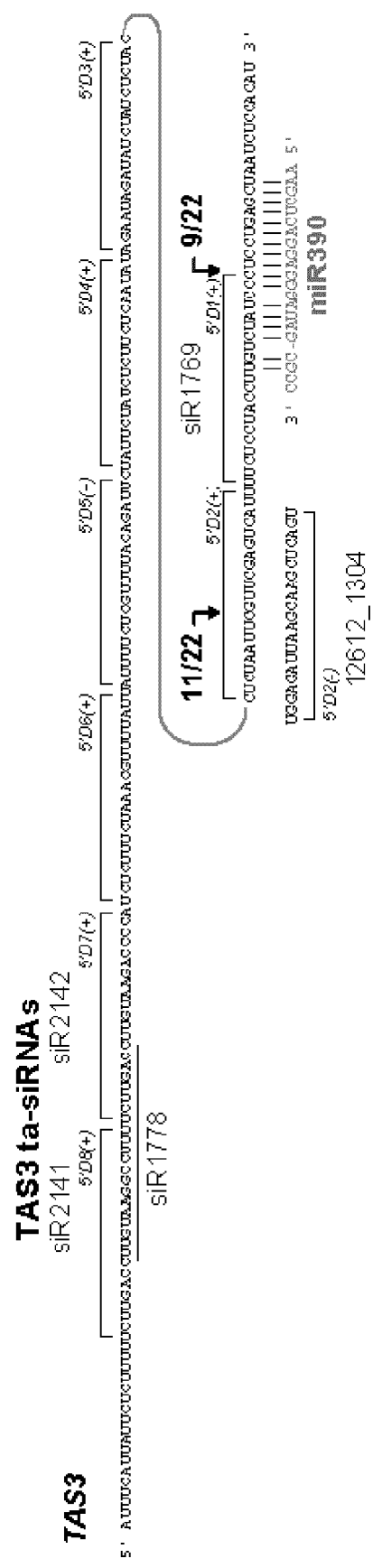
FIG. 6A-E. In-phase processing of TAS3-derived trans-acting siRNAs guided by miR390.
Figure 6B:
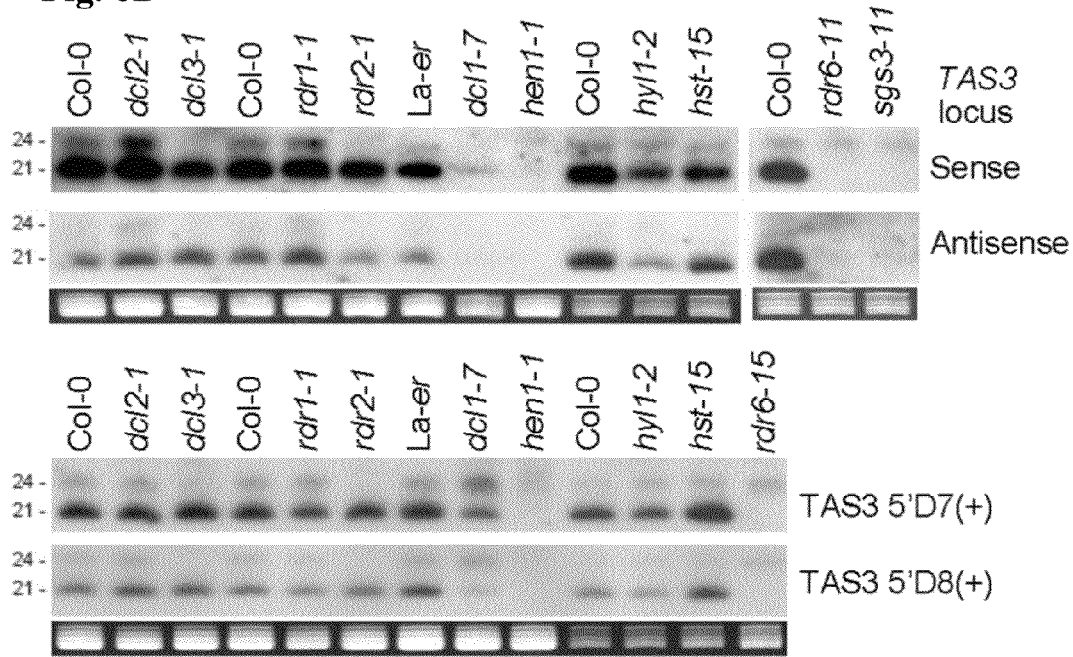
Figure 6C:
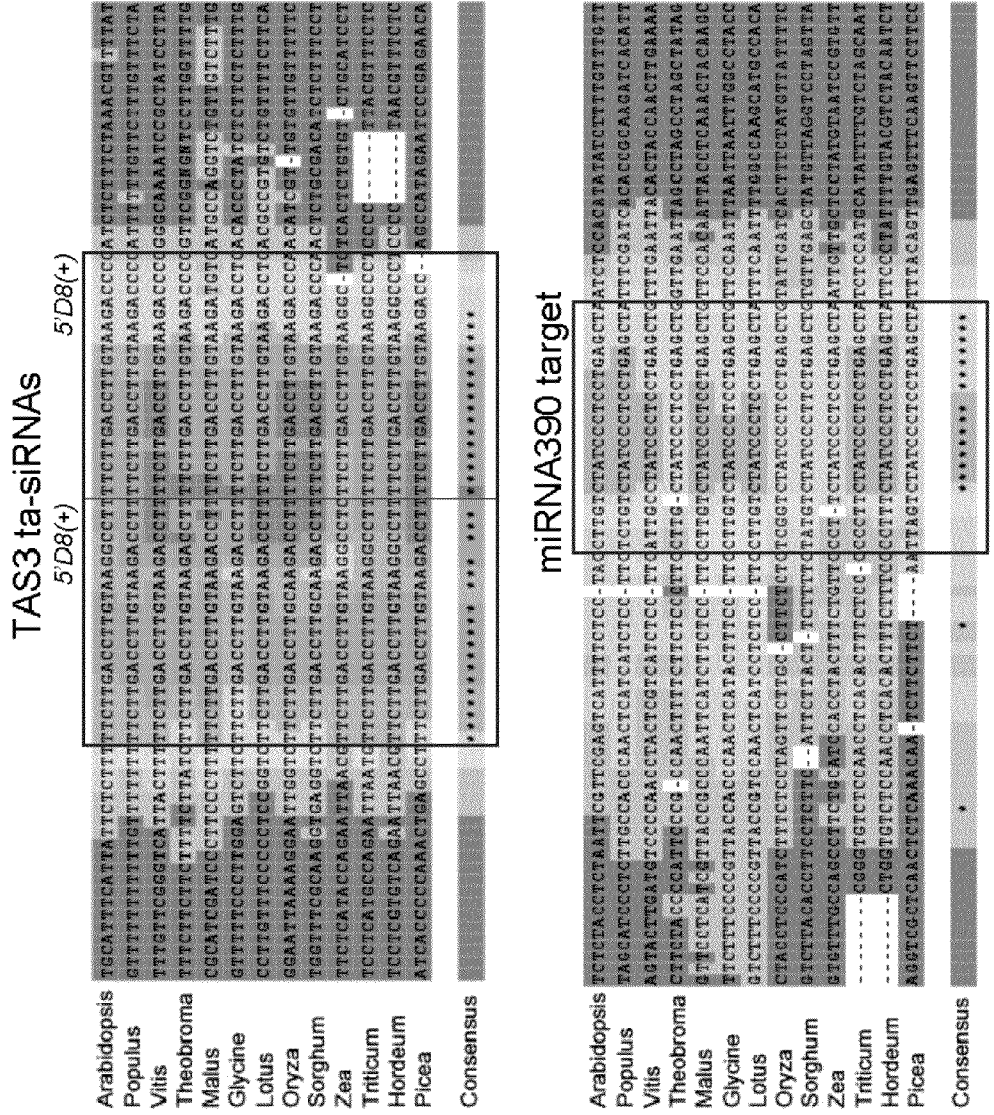
Figure 6D:
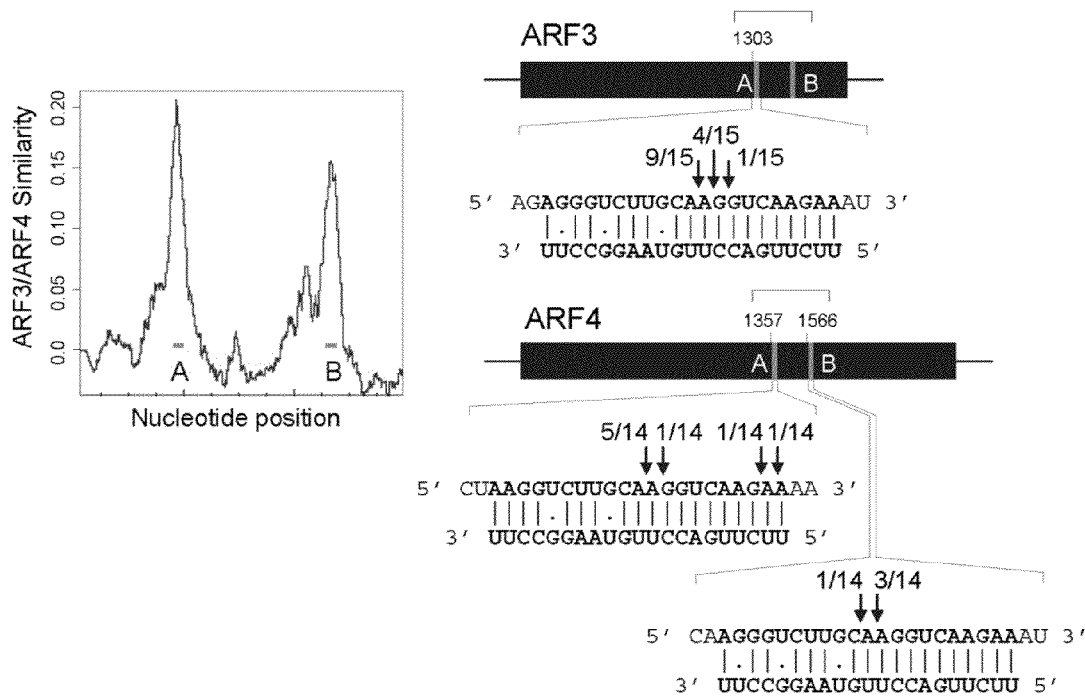
Figure 6E:
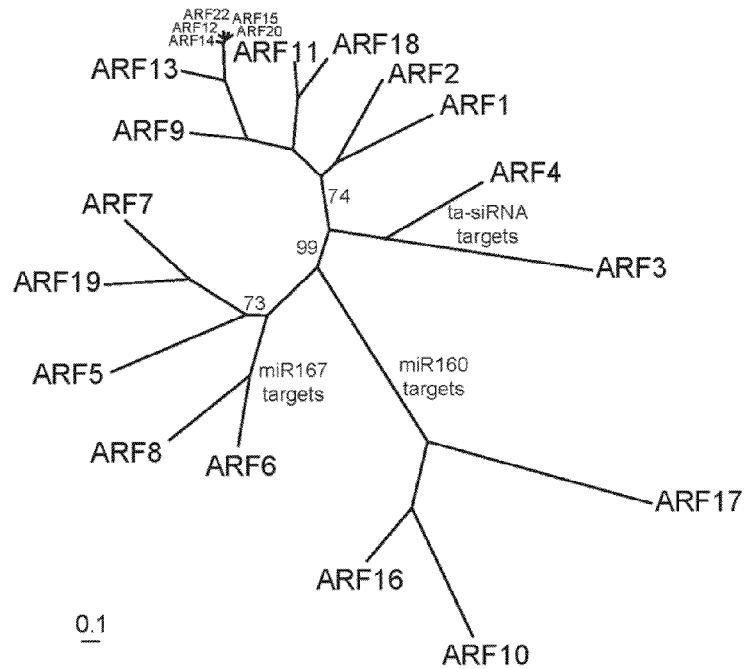

Although a small RNA from the TAS3 5'D2(−) position was not cloned, a hypothetical ta-siRNA from this position may account for the second TAS3 transcript cleavage site mapped by 5'RACE (FIG. 6A). This cleavage site occurs precisely at the position predicted if TAS3 5'D2(−) guided cleavage by a RISC-like mechanism. This cleavage site would also set the phase for ta-siRNA precursor processing to generate siR1778. This suggests that ta-siRNAs have the potential to interact with transcripts from which they originate as well as mRNA targets.

Discussion

Combined with previous data, most notably from Jones-Rhoades et al., we are now aware of 25 validated miRNA families, 53 unique miRNA sequences and 99 potential MIRNA loci in *A. thaliana*. Seventy-three genes have now been validated experimentally as targets for miRNAs in 24 families. Fifty-three targets were validated in previous studies. Twenty predicted targets of eleven miRNAs were validated or confirmed in this study (FIG. 5, Table 3). These included mRNAs for SBP4 (miR156), Auxin Response Factor 16 (ARF16; miR160), two NAC domain proteins (miR164), AtHB15 (miR165/166), ARF6 (miR167), six HAP2 family proteins (miR169), E2-UBC (miR399), AGO2 (miR403), 2PGK (miR447), and five non-coding genes (miR173 and miR390).

miRNAs are processed from genes that produce a primary transcript that forms a stable foldback structure, processed by DCL1, and therefore requires no polymerase and produces no antisense small RNAs. Trans-acting siRNAs have similar biogenesis requirements as miRNAs, but lack a stable foldback structure (Peragine et al., *Genes & Dev* 18:2369-2379, 2004; Vazquez et al., *Mol Cell* 16:69-79, 2004b). As a result, they require a polymerase, most likely RDR6, for second strand generation. Two defining characteristics of ta-siRNAs are the presence of antisense 21-nucleotide small RNAs, and a linear, in-phase processing of both sense and small RNAs. Unlike other classes of siRNAs, ta-siRNAs can be incorporated into RISC and trigger site-specific cleavage of target genes, similar to miRNAs. Both miRNAs and ta-siRNAs are uniquely insensitive to DCL2, DCL3, RDR1, and RDR2. In the absence of a comprehensive profile of biogenesis mutants, it is impossible to properly catalog small RNA function. Using this strict set of criteria, we characterized four miRNA families, two of which were previously identified.

Our target prediction algorithm confirmed the robust predictions for the majority of validated miRNAs. Additional targets were validated within this group, including eight targets residing in the untranslated region of the target messenger RNA, including SPL4, an E2-UBC gene At2g33770, and six HAP2 transcripts. Notably, most miR156 targets are located in the coding region of SPL transcripts, whereas two reside immediately downstream of the stop codon in the 3' UTR, SPL3 and SPL4 (Rhoades et al., *Cell* 110:513-520, 2002). Interestingly, two splicing variants of SPL4 exist, one with the miR156 target site (AU227430, BP595743) and one that lacks the target site (BX814070.1), although the coding sequence is unchanged. Potentially the alternately spliced variant of SPL4 would allow an additional level of miRNA-mediated control. The E2-UBC gene is unique in that it contains five miR399 targets in its 5' UTR. The multiple miR399 target sites are conserved among distantly related plant species. The multiple sites might be necessary for miRNA targeting in the 5' UTR to increase the chance of cleavage before ribosomes could clear the miRNA from the mRNA, although the nature of multi-site regulation remains to be determined.

We identified six novel miRNA target loci in the *Arabidopsis* EST database using a computational prediction algorithm developed based on validated miRNA-target characteristics. Previous computational searches for miRNA targets in plants have only used transcript databases, as a result missing these target genes (Jones-Rhoades & Bartel, *Mol Cell* 14:787-799, 2004). The miR403 target, Ago2, is the second Argonaute family gene to be miRNA regulated. *Arabidopsis* Ago2 does not have a close ortholog in mammals, and its role in small RNA function is unknown (Carmell et al., *Genes Dev* 16:2733-2742, 2002; Mochizuki et al., *Cell* 110:689-699, 2002). The remaining five miRNA targets from the EST database search are non-protein coding loci, all of which produce 21-nucleotide small RNAs, in phase with the miRNA cleavage site. Four loci were validated to generate functional ta-siRNAs, including a family of unclassified genes, as well as ARF3 and ARF4. The ta-siRNA target genes were upregulated in dcl1-7, hen1-1, and rdr6-15, which could provide a diagnostic test for ta-siRNA target genes. Both miR390 and the TAS3 locus are conserved among distantly related plants. A complete profile of small RNA coding-genes will require thorough complementary molecular and computational approaches, perhaps with consideration of conserved 21-nucleotide regions in annotated intergenic regions. Potentially, identification of non-protein coding genes will be facilitated by genome tiling data (Yamada et al., *Science* 302:842-846, 2003) in combination with small RNA cloning and biogenesis profiling.

Figure 7:
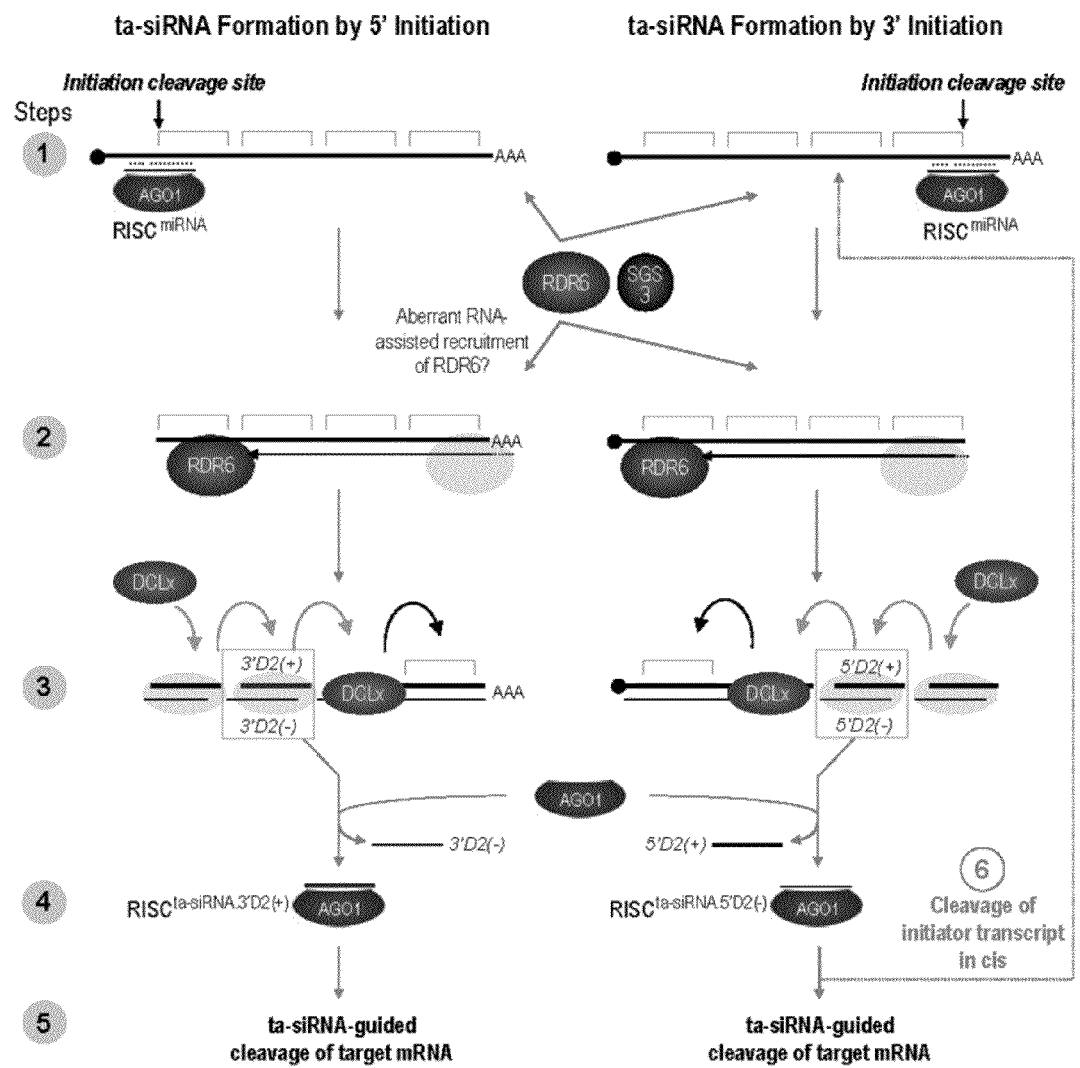
FIG. 7. Model for miRNA-directed formation of ta-siRNAs

We propose a model in which miRNA cleavage initiates the starting phase for ta-siRNA production (FIG. 7). The primary miRNA targeted cleavage of an RNA Polymerase II transcript (step 1) recruits a RISC complex to the RNA. In addition, RDR6 and SGS3 could be recruited by the RISC:miRNA: target complex. Cleavage by the miRNA at a specific position creates a unique initiation position. Following cleavage, RDR6/SGS3 polymerize a second strand (step 2), creating a double stranded RNA (dsRNA). Either the 5' (e.g. TAS3) or 3' (e.g. TAS1 and TAS2) cleavage product can be utilized as the RDR6 template. In either case, DCL processing of 21-nucleotide siRNA duplexes (step 3) proceeds in-phase from the primary miRNA cleavage site. Dicer in animals is known to catalyze cleavage from a free end (Zhang et al., *Cell* 118:57-68, 2004). We did not identify any in-phase small RNAs beyond nine phases from the miRNA cleavage initiation site, suggesting either the RDR6/SGS3 complex or the DCL1 complex is not highly processive. One strand of the siRNA duplex is loaded back into a RISC complex, following the known siRNA incorporation rules (Khvorova et al., *Cell* 115: 209-216, 2003; Schwarz et al., *Cell* 115:199-208, 2003). Following RISC incorporation of the ta-siRNA (step 4), ta-siRNAs function like miRNAs to facilitate cleavage of target genes in trans (step 5).

The regulatory role of miRNAs for all target genes previously identified is to repress target gene expression, through either cleavage or by blocking translation. Our results suggest that miRNAs also act as a positive regulator of ta-siRNA biogenesis through recruitment of RISC and initiation of unique and highly specific phasing for DCL1-mediated processing. Although we have only found evidence for a single active ta-siRNA (or highly similar tandem sequence repeat), multiple, phased ta-siRNAs could provide an advantage through generation of multiple, independent regulatory (ta-siRNA-forming) units from a single locus. The discovery that a miRNA:ta-siRNA:target regulon is conserved among distantly related plants shows that this type of regulation is not specific to *Arabidopsis*, opening the possibility of an entirely new class of small RNA mediated gene regulation.

EXAMPLE 2

MiRNA-Directed Biogenesis of Ta-siRNAs In Vivo

To experimentally test the hypothesis that ta-siRNA biogenesis is initiated by miRNA-guided cleavage of primary transcripts, TAS1 and TAS2 were co-expressed transiently with MIR173 in *Nicotiana benthamiana*. If miR173 is required for siR255 production, as predicted herein, then siR255 should be formed only in the presence of miR173. At least some of the material in this example was published in Allen et al. (*Cell* 121:207-221, 2005), which is incorporated herein by reference in its entirety.

Figure 14A:
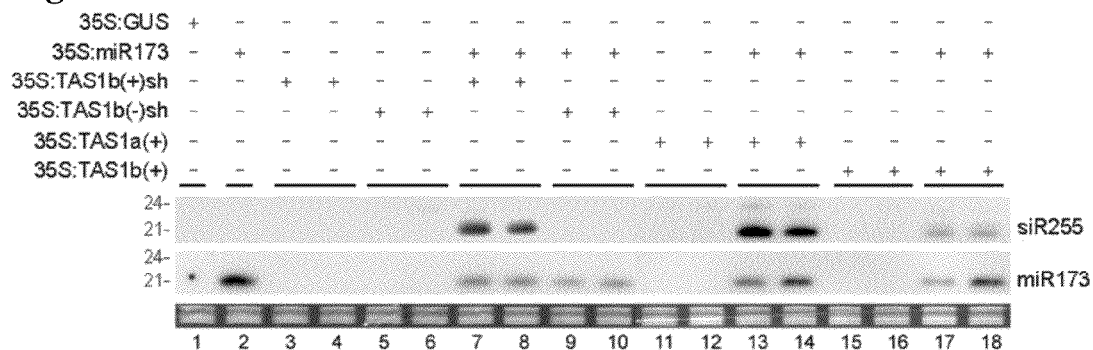
FIG. 14A-C. Reconstruction of TAS1a, TAS1b, TAS1c, and TAS2 ta-siRNA Biogenesis in a Transient Expression Assay using *N. benthamiana*.
Figure 14B:
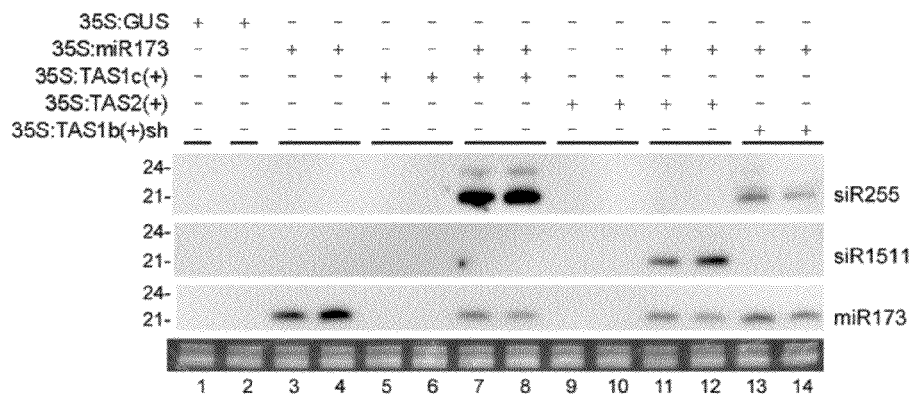

Expression cassettes containing the TAS1a, TAS1b, TAS1c and TAS2 loci (which all include both an initiator sequence, containing an initiator cleavage site, and a gene suppressing element) were delivered into *Nicotiana benthamiana* plant cells (Llave et al., *Plant Cell* 14:1605-1619, 2002; Palatnik et al., *Nature* 425:257-263, 2003) in the presence or absence of an expression cassette containing miR173, and ta-siRNA accumulation was scored. Expression of full-length TAS1b [35S:TAS1b(+)], a short version of TAS1b [35S:TAS1b(+)sh], and full-length TAS1a [35S:

TAS1a(+)] resulted in siR255 accumulation only in the presence of a construct (35S:miR173) expressing miR173 (FIG. 14A, lanes 7, 8, 13, 14, 17, 18). Likewise, siR255 from the TAS1c construct [35S:TAS1c(+)], and siR1511 from the TAS2 construct [35S:TAS2(+)], both accumulated only in the presence of the miR173 construct (FIG. 14B, lanes 7, 8, 11, 12). ta-siRNAs were not detected after expression of any of the TAS1 or TAS2 constructs alone (FIG. 14A, lanes 3, 4, 11, 12, 15, 16; FIG. 14B, lanes 5, 6, 9, 10), or after expression of the miR173-non-targeted strand of the short version of TAS1b [35S:TAS1b(–)sh] in either the presence or absence of miR173 (FIG. 14A, lanes 5, 6, 9, 10). In the presence of miR173, siR255 accumulated to levels up to 7.6 fold higher using the TAS1a(+) and TAS1c(+) constructs compared to the TAS1b(+) constructs. This may reflect a relatively poor miR173-TAS1b interaction, which involves two mismatched positions near the target cleavage site (FIG. 5B).

Figure 14C:
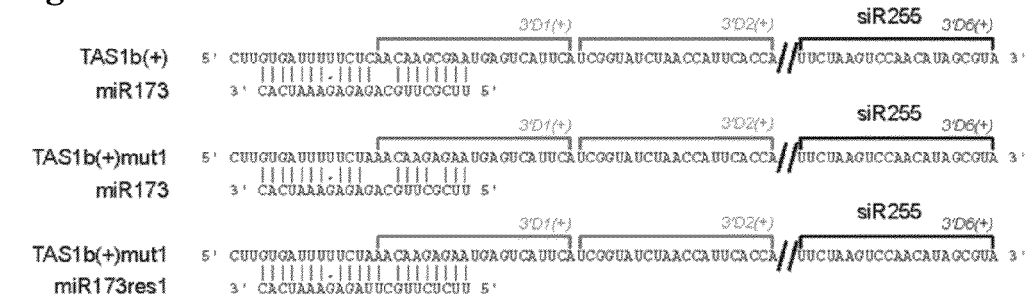
Figure 14C:
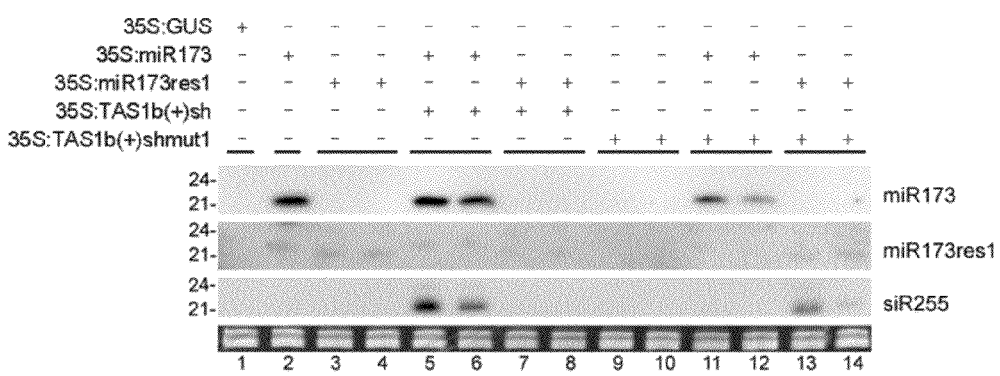

To confirm that ta-siRNA biogenesis requires miRNA-directed targeting of primary transcripts, a TAS1b mutant construct [35S:TAS1b(+)shmut1] with a disrupted miR173 target site was expressed in the presence of miR173. The TAS1b mutant was also expressed in the presence of a modified miR173 construct (35S:miR173res1) containing base substitutions to restore interaction with the TAS1b mutant (FIG. 14C, top). Mutations affecting the TAS1b target site or miR173 resulted in the loss of siR255 biogenesis (FIG. 14C, lanes 7, 8, 11, 12). In contrast, siR255 accumulation was restored when the TAS1b mutant was co-expressed with the miR173res1 construct (FIG. 14C, lanes 13, 14).

Thus, in each independent experiment, siRNAs from each locus were detected (by RNA blot assay) only in the presence of a construct that formed miR173 (FIG. 14). Mutations that disrupted the miR173 target site in the TAS1b construct eliminated siRNA (siR255) formation. However, mutations in the miR173 sequence to restore complementarity with the mutated target sequence restored the formation of siR255 (FIG. 14). These data support the model that states ta-siRNA biogenesis requires a miRNA-guided initiation cleavage. It also demonstrates that an expression cassette containing an initiator sequence and a gene suppressing element can direct production of a siRNA in the presence of an expression cassette containing a miRNA. Stated another way, these data show that a functional miRNA target site in the ta-siRNA primary transcript is required to trigger ta-siRNA formation.

See also Example 6, below, for additional details.

EXAMPLE 3

Plant Transformation Vectors/Plasmids

This example illustrates the construction of plasmids for transferring recombinant DNA into plant cells which can be regenerated into transgenic plants, e.g., expressing in a plant siRNA for suppression of an endogenous gene. See also Example 6, below.

A recombinant DNA construct for plant transformation construct 1A is fabricated for use in preparing recombinant DNA for transformation into corn tissue comprising the a selectable marker expression cassette, a siRNA-triggering cassette and a cleavage initiating cassette. The marker expression cassette comprises a rice actin 1 promoter element(s) operably linked to sequence(s) encoding a chloroplast transit peptide from *Arabidopsis thaliana* ShkG gene and an aroA protein from *Agrobacterium tumefaciens*, strain CP4, followed by a 3' region of an *Agrobacterium tumefaciens* nopaline synthase gene (nos). The siRNA-triggering cassette is positioned tail to tail with the marker expression cassette and comprises 5' regulatory DNA from a maize seed specific promoter L3 (as disclosed in U.S. Pat. No. 6,433,252) operably linked to DNA encoding RNA comprising an initiator sequence that is highly complementary to a microRNA such as miR173 (or any microRNA or siRNA, including any listed herein) and at least one 21-nucleotide segment from LKR. An initiation cleavage cassette is positioned head to head with the marker expression cassette and comprises a maize seed specific promoter L3 and DNA expressing a microRNA (e.g., miR173) that guides cleavage of the initiation cleavage site in the siRNA-triggering cassette. Construct 1A is useful for plant transformation, e.g. by microprojectile bombardment. Transgenic corn callus is produced by microprojectile bombardment of construct 1A using methods disclosed in U.S. Pat. No. 6,399,861.

A plasmid vector 1B for use in *Agrobacterium*-mediated methods of plant transformation is prepared by inserting construct 1A into a plasmid between left and right T-DNA border sequences from *Agrobacterium*. Outside of the T-DNA borders the plasmid also contains origin of replication DNA to facilitate replication of the plasmid in both *E. coli* and *Agrobacterium tumefaciens* and a spectinomycin/streptomycin resistance gene for selection in both *E. coli* and *Agrobacterium*. Transgenic corn callus is produced by *Agrobacterium*-mediated transformation of plasmid vector 1B using methods disclosed in U.S. Pat. No. 5,591,616.

Transgenic corn plants are regenerated from transgenic callus produced by microprojectile bombardment and *Agrobacterium*-mediated transformation; callus is placed on media to initiate shoot development in plantlets which are transferred to potting soil for initial growth in a growth chamber at 26° C. followed by growth on a mist bench before transplanting to 5 inch pots where plants are grown to maturity. The plants are self fertilized and seed is harvested for screening as seed, seedlings or progeny R2 plants or hybrids, e.g. for yield trials in the screens indicated above. Transgenic plants with higher levels of lysine resulting from suppressed levels of LKR and which are homozygous for the recombinant DNA are identified. The homozygous plants are self pollinated to produce transgenic seed with the recombinant DNA comprising siRNA-triggering cassettes.

EXAMPLE 4

Inhibition of Plant Pest Genes

This example illustrates the construction of plasmids for transferring recombinant DNA into plant cells which can be regenerated into transgenic described herein, particularly expressing in a plant siRNA for suppression of genes in a plant pest.

Recombinant DNA constructs 2A, 2B and 2C are fabricated for soybean transformation by microprojectile bombardment essentially like construct 1A except that the promoter used in the siRNA-triggering cassette and the initiation cleavage cassette is a root tissue-expressing promoter and the 21-nucleotide segment is derived from DNA encoding soybean cyst nematode proteins as disclosed in US Patent Application Publication 2004/0098761 A1. In construct 2A the 21-nucleotide segment is from a major sperm protein; in construct 2B the 21-nucleotide segment is from a chitin synthase; and in construct 2C the 21-nucleotide segment is from an RNA polymerase II. Soybean is transformed by microprojectile bombardment using constructs 2A, 2B and 2C using methods as disclosed in U.S. Pat. No. 5,914,451 and transgenic soybean plants are regenerated which exhibit resistance to soybean cyst nematode infestation as compared to control plants.

Plasmid vectors 2D, 2E and 2F for use in *Agrobacterium*-mediated methods of plant transformation are prepared by inserting constructs 2A, 2B and 2C, respectively, into plasmids with T-DNA borders similar to plasmid vector. Soybean is transformed by *Agrobacterium*-mediated transformation of plasmid vectors 2D, 2E and 2F using methods disclosed in U.S. Pat. No. 6,384,301 and transgenic soybean plants are regenerated which exhibit resistance to soybean cyst nematode infestation as compared to control plants.

EXAMPLE 5

Expression of *Arabidopsis thaliana* MIRNA Genes

Recent molecular cloning and computational analyses have identified nearly one hundred potential genetic loci for MIRNA genes in the *Arabidopsis thaliana* genome. However, information about the structure and expression of these genes is generally lacking. The transcriptional start site for each of 63 miRNA precursor transcripts from 52 MIRNA (99 total loci tested) was mapped. A portion of the loci yielded multiple transcripts from alternative start sites, and some contained introns between the foldback structure and the 5' end. Analysis of a representative set of transcripts revealed characteristics consistent with transcription by Pol II. A canonical TATA box motif was identified computationally upstream of the start site(s) at some MIRNA loci. The 5' mapping data were combined with miRNA cloning and 3'-PCR data to definitively validate expression some of known MIRNA genes. These data provide a molecular basis to explore regulatory mechanisms of miRNA expression in plants.

Material from this example was published as Xie et al., *Plant Physiol.* 138(4):2145-2154, 2005; Epub 2005 Jul. 22, which is incorporated herein by reference in its entirety.

MicroRNAs (miRNAs) are ~21-nucleotide noncoding RNAs that post-transcriptionally regulate expression of target genes in multicellular plants and animals (Bartel, *Cell* 116: 281-297, 2004). Mature miRNAs are generated through multiple processing steps from longer precursor transcripts that contain imperfect foldback structures. In animals, MIRNA genes are transcribed by RNA polymerase II (pol II) (Bracht et al., *RNA* 10:1586-1594, 2004; Cai et al., *RNA* 10:1957-1966, 2004; Lee et al., *EMBO J.* 23:4051-4060, 2004), yielding a primary transcript (pri-miRNA) that is processed initially by nuclear RNaseIII-like Drosha (Lee et al., *Nature* 425:415-419, 2003). The resulting pre-miRNA transcripts are transported to the cytoplasm and processed by Dicer to yield mature-size miRNAs (Lee et al., *EMBO J.* 21:4663-4670, 2002). Less is known about the miRNA biogenesis pathway in plants, although most or all miRNAs require Dicer-like1 (DCL1) (Park et al., *Curr Biol* 12:1484-1495, 2002; Reinhart et al., *Genes Dev* 16:1616-1626, 2002). The lack of a Drosha ortholog in plants, and the finding that DCL1 functions at multiple steps during biogenesis of miR163, suggest that the plant miRNA pathway may differ from the animal pathway (Kurihara & Watanabe, *Proc Natl Acad Sci USA* 101:12753-12758, 2004). MiRNAs in both animals and plants incorporate into an effector complex known as RNA-induced Silencing Complex (RISC) and guide either translation-associated repression or cleavage of target mRNAs (Bartel, *Cell* 116:281-297, 2004).

Computational and molecular cloning strategies revealed over 100 potential MIRNA genes belonging to at least 27 families in the *Arabidopsis* genome (Llave et al., *Plant Cell* 14:1605-1619, 2002; Mette et al., *Plant Physiol* 130:6-9, 2002; Park et al., *Curr Biol* 12:1484-1495, 2002; Reinhart et al., *Genes Dev* 16:1616-1626, 2002; Jones-Rhoades & Bartel, *Mol Cell* 14:787-799, 2004; Sunkar & Zhu, *Plant Cell* 16:2001-2019, 2004; Wang et al., *Genome Biol* 5:R65, 2004). These miRNA families target mRNAs encoding proteins that include a variety of transcription factors involved in development, DCL1 and the RISC factor ARGONAUTE1(AGO1), components of the SCF complex involved in ubiquitin-mediated protein degradation, and several other classes of metabolic and stress-related factors (Rhoades et al., *Cell* 110:513-520, 2002; Xie et al., *Curr Biol* 13:784-789, 2003; Jones-Rhoades & Bartel, *Mol Cell* 14:787-799, 2004; Sunkar & Zhu, *Plant Cell* 16:2001-2019, 2004; Vaucheret et al., *Genes Dev* 18:1187-1197, 2004) (see also Example 1). Based on tissue distribution and limited in situ expression data, most plant miRNAs are likely regulated at spatial and/or temporal levels during development (Chen, *Science* 303:2022-2025, 2004; Juarez et al., *Nature* 428:84-88, 2004; Kidner & Martienssen, *Nature* 428:81-84, 2004). Overexpression or knockout of MIRNA genes, or expression of MIRNA genes outside of their normal expression domains, can lead to severe developmental defects (Aukerman & Sakai, *Plant Cell* 15:2730-2741, 2003; Palatnik et al., *Nature* 425:257-263, 2003; Achard et al., *Development* 131:3357-3365, 2004; Chen, *Science* 303:2022-2025, 2004; Juarez et al., *Nature* 428:84-88, 2004; Kidner & Martienssen, *Nature* 428:81-84, 2004; Laufs et al., *Development* 131:4311-4322, 2004; Mallory et al., *Curr Biol* 14:1035-1046, 2004a; Mallory et al., *EMBO J.* 23:3356-3364, 2004; McHale & Koning, *Plant Cell* 16:1730-1740, 2004; Emery et al., *Curr Biol* 13:1768-1774, 2003; Zhong & Ye, *Plant Cell Physiol* 45:369-385, 2004). Understanding the mechanisms governing MIRNA gene expression patterns and integration into regulatory networks will be necessary for a clear understanding of the biological function of miRNAs.

In this example, several new *Arabidopsis* miRNAs were identified by a computationally assisted cloning approach and the use of mutants that contained miRNA-enriched pools of small RNAs. Expression of 99 MIRNA genes in *Arabidopsis* was examined experimentally. First, features associated with transcription initiation of MIRNA genes were analyzed, revealing core promoter, start sites and other properties that were consistent with a pol II mechanism of transcription. And second, a survey of expression of each known MIRNA locus was done to identify functional MIRNA genes.

Materials and Methods

Cloning of *A. Thaliana* Small RNAs and miRNA Prediction.

Extraction of low molecular weight RNA and library construction was done as described (Llave et al., *Plant Cell* 14:1605-1619, 2000; Lau, *Science* 294:858-862, 2001). RNA was extracted from three-day post germination seedlings, embryos from developing siliques, aerial tissues including rosette leaves and apical meristems, or stage 1 to 12 enriched inflorescence from wildtype Columbia-0, and jaw-D, rdr2-1 and dcl3-1 mutants described previously (Palatnik et al., *Nature* 425:257-263, 2003; Xie et al., *PLoS Biol* 2:642-652, 2004). Seedling libraries were constructed for Col-0, rdr2-1, and dcl3-1, embryo libraries for rdr2-1, aerial libraries for jaw-D, and inflorescence libraries for Col-0 and rdr2-1. Sequences were filtered to remove organellar, rRNA, and those not present in *A. thaliana*. Remaining small RNAs between 18 and 26 nucleotides were deposited in the ASRP database (available on-line at asrp.cgrb.oregonstate.edu/). Candidate miRNA prediction used a set of six filters. First, structural RNAs were filtered before entry into the ASRP database by manual scoring of BLAST hits to known rRNA, tRNA, and organellar RNA. Second, small RNAs from repeats identified using RepeatMasker (Jurka, *Trends Genet* 16:418-420, 2000) or from predicted protein-coding genes and pseudogenes only were removed. Third, a small RNA cluster filter was applied to remove small RNAs within 500 nt of another small RNA in the opposite orientation. The fourth filter removed any small RNA outside the typical size (20-22 nucleotides). Fifth, characteristics including the minimum paired bases of the miRNA:miRNA* duplex in the reference set (≥16), maximum foldback size (350 nucleotides), and a requirement for the miRNA and its duplex to be on a single stem were determined. Foldbacks in which the miRNA: miRNA duplex contained more than three contiguous unpaired bases were excluded. The RNAFold in the Vienna RNA Package was used to predict potential duplexes containing the small RNA, and those with duplexes not meeting the above criteria were excluded (Hofacker, *Nucleic Acids Res* 31:3429-3431, 2003). Sixth, validated miRNAs and closely related family members, as well as small RNAs processed from a miRNA locus (including miRNA*) were identified by FASTA and comparison of small RNA loci on the ASRP genome browser. These small RNAs were annotated as family members of validated miRNAs, and removed from the predicted miRNA pool.

Small RNA Blot Analysis.

Low molecular weight RNA (5 µg) from *A. thaliana* inflorescence tissue was used for miRNA and endogenous siRNA analysis. Mutant lines for dcl1-7, dcl2-1, dcl3-1, rdr1-1, rdr2-1, hen1-1, hyl1-2, rdr6-11, rdr6-15, and sgs3-11 were described previously (Park et al., *Curr Biol* 12:1484-1495, 2002; Allen et al., *Nat Genet.* 36:1282-1290, 2004; Peragine et al., *Genes & Dev* 18, 2368-2379, 2004; Vazquez et al., *Curr Biol* 14:346-351, 2004; Xie et al., *PLoS Biol* 2:642-652, 2004). The hst-15 allele used was the SALK_079290 T-DNA insertion line from ABRC, which contains a T-DNA at position 1584 from the start codon. Probes for miR159, miR167, and AtSN1-siRNA blots were described previously (Llave et al., *Plant Cell* 14:1605-1619, 2002; Zilberman et al., *Science* 299:716-719, 2003). All other miRNAs were detected using end-labeled DNA oligonucleotides. Probes for ta-siRNA loci were PCR amplified from Col-0 genomic DNA, cloned into pGEMT-Easy, and verified by sequencing. Radiolabeled probes incorporating $^{32}$P-UTP were made by T7 RNA polymerase transcription, to obtain strand specific small RNA probes. Probes were as follows: At1g17185 locus, Chr3: 5862146-5862295; At2g39680 locus, Chr2:16546831-16547300.

5'RACE Mapping of MIRNA Transcripts

Two *Arabidopsis thaliana* (Col-0) sample preparations were used for RNA isolation: inflorescence tissues from 4-week old plants grown under greenhouse condition and 4-day old seedlings grown on MS media in a growth chamber. Total RNA was extracted using TRIzol reagent (Invitrogen) followed by column purification using a RNA/DNA midi kit (Qiagen). The extracts were subjected to two rounds of purification using Oligotex (Qiagen) for the enrichment of poly (A)$^+$ RNA. The 5' ends of MIRNA transcripts were mapped by a RNA ligase-mediated 5'RACE (RLM-5'RACE, Invitrogen). Complementary DNA (cDNA) was synthesized with poly(A)+-enriched RNA (125 ng/reaction), which was first treated with calf intestine phosphatase and tobacco acid pyrophosphatase (CIP+TAP), using random oligonucleotide hexamers as primers. A cDNA pool containing equal amounts of cDNA from each tissue was used as template in 5'RACE PCR with a primer (Invitrogen) specific to the RNA adaptor sequence and a locus-specific reverse primer. In cases where no product was detected, a second-round PCR was done using a 5' nested primer and a locus-specific nested primer. The default annealing temperature in the touchdown PCR reaction was 65° C. For a MIRNA locus with a negative 5'RACE result after the second-round PCR, two additional PCR reactions with the nested primers were done with altered annealing temperatures. The PCR products from a positive 5'RACE were gel-purified and cloned into pGEM-Teasy vector. A minimum of 6 clones were sequenced for each PCR product.

The RLM-5'RACE procedure was used to analyze the presence or absence of a cap structure on several miRNA transcripts. A capped mRNA [Scarecrow-like6-IV (SCL6-IV)] and a non-capped RNA (miR171-guided cleavage product of SCL6-IV mRNA) were used as control RNAs. Parallel RLM-5'RACE reactions were done using poly(A)+-enriched RNA that was CIP+TAP treated and non-treated, which was selective for amplification of 5' ends that contained or lacked a cap structure, respectively.

For some miRNA transcripts, 3'RACE was done using poly(A)+-enriched RNA. cDNA was synthesized using an adaptor-tagged oligo(dT) primer. Two gene-specific forward primers were designed for each locus tested. The identity of the 3'RACE products were confirmed by sequencing. The sequences of the locus-specific primers are provided in SEQ ID NOs: 349 to 614, and were published in Supplementary Table 2 in Xie et al., *Plant Physiol.* 138(4):2145-2154, 2005; Epub 2005 Jul. 22.

Computational Identification of Conserved Upstream Sequence Motifs

A 60-bp (−50 to +10) genomic sequence flanking the start site for 63 transcripts from 47 MIRNA loci was analyzed using BioProspector, a Gibbs sampling-based motif-finding program (Liu et al., 2004). Searches with a motif width of 6-8 nucleotides were done. In all cases, TATA-like sequences were identified as the only conserved motif. A second search (8-nucleotide width) was done using an extended MIRNA upstream region (−200 to +50) to analyze the distribution of the putative TATA motif using MotifMatcher, with the 8-nucleotide motif matrix generated by BioProspector as a sample motif (Ao et al., *Science* 305:1743-1746, 2004). Up to three matches to the TATA motif were allowed.

Results and Discussion

Identification and Validation of *Arabidopsis* miRNAs

Several small RNA libraries were constructed from wild-type (Col-0) *A. thaliana* seedling and inflorescence tissues, and from aerial tissues of jaw-D plants that over express miR-JAW (miR319) (Palatnik et al., *Nature* 425:257-263, 2003). Among all 2357 sequences analyzed collectively from these libraries, only 32.7% corresponded to known or subsequently validated miRNA families. Most of the remaining small RNAs corresponded to diverse sets of endogenous small RNAs arising from repeated sequences such as transposons, retroelements, simple sequence repeats, inverted duplications, rDNA genes and other genic and intergenic sequences (Llave et al., *Plant Cell* 14:1605-1619, 2002; Xie et al., *PLoS Biol* 2:642-652, 2004). To genetically enrich for miRNAs, small RNA libraries were constructed from embryo, seedling, and inflorescence tissues of rdr2-1 mutant plants, and from seedlings of dcl3-1 mutant plants. These plants contain relatively low levels of ~24-nucleotide siRNAs from repeated sequences, but maintain normal levels of miRNAs (Xie et al., *PLoS Biol* 2:642-652, 2004). Among 3164 sequences analyzed collectively from the rdr2-1 and dcl3-1 libraries, 70.5% corresponded to previously characterized miRNAs, representing a 2.2-fold overall enrichment relative to the wild-type libraries. Endogenous siRNAs from known repeat families (identified from RepBase) were reduced 43.9-fold in the mutant libraries. The majority of the remaining small RNAs corresponded to sequences from two rdr2-independent small RNA-generating loci, or from rRNA genes. Unique miRNA and endogenous siRNA sequences from all libraries are available in the *Arabidopsis* Small RNA Project (ASRP) database (available on-line at asrp.cgrb.oregonstate.edu).

Figure 8A:
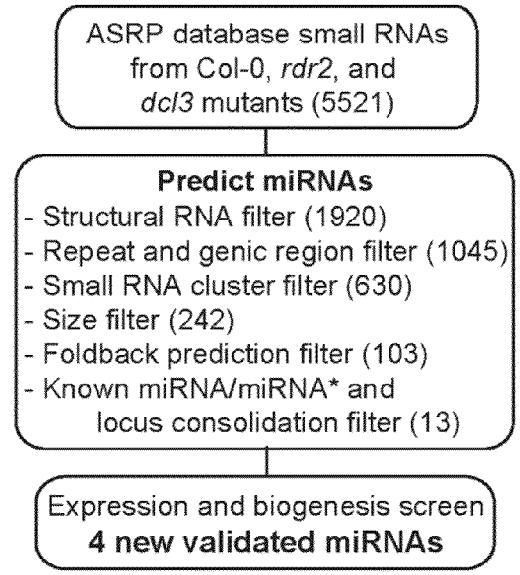
FIG. 8A-D. Validation of miRNAs in *A. thaliana*.
Figure 8B:
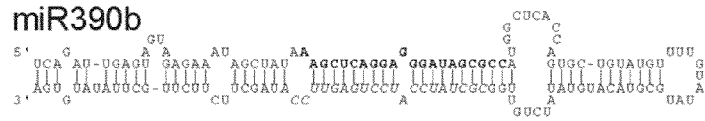
Figure 8B:
Figure 8B:
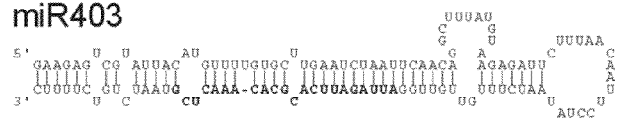
Figure 8B:
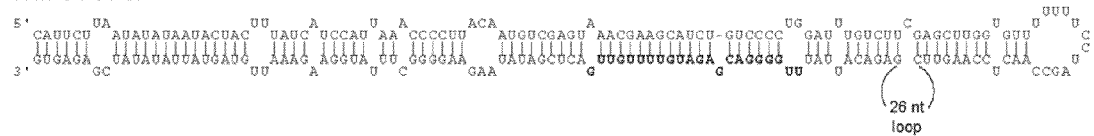

To identify new miRNAs in the cloned libraries, the small RNA sequences were subjected to a series of five computational filters (FIG. 8A). The filters were designed using the properties of a founder set of published, validated *Arabidopsis* miRNAs with codes within the range of miR156-miR399 (excluding miR390 and miR391; RFAM). Among the 48 unique miRNA sequences from 92 loci (22 validated miRNA families) in the founder set, 34 miRNA sequences from 71 loci (19 families) were in the cloned database. The initial filters eliminated all small RNA sequences deriving from structural RNA genes, other annotated genes and repetitive loci identified by RepeatMasker (FIG. 8A). Sequences originating from loci that yielded multidirectional clusters of small RNAs, which is a hallmark of many siRNA-generating loci, were eliminated. Small RNAs that were not 20-22 nucleotides in length, based on the cloned sequence, were also removed. Small RNAs originating from loci that lacked the potential to form a miRNA precursor-like foldback structure, consisting of a stem in which 16 or more positions within the putative miRNA-miRNA* duplex region were paired, were excluded. To test the sensitivity of these filters, the complete founder set of miRNAs was processed through the five filters. All but three passed, corresponding to a false negative rate of 0.032. miR163 failed because it is 24 nucleotides long, and miR166 from two loci failed because of 6 mispaired miRNA positions within the foldback stem. From the cloned dataset, a total of 103 small RNAs passed the five filters (FIG. 8A). These did not correspond to 103 unique loci, however, as many miRNA-generating loci yield multiple processed forms that are offset by one or a few nucleotides. Elimination of all sequences corresponding to founder miRNAs yielded a set of 18 small RNAs, corresponding to 13 genetic loci, as candidate new miRNAs (FIG. 8A). This set included miR390, miR391, miR403 and miR447 (FIG. 8B). Six of the 18 small RNAs corresponded to a cluster of processing variants from the two miR390 loci.

Given the high sensitivity of the computational filters using the founder set, a second set of published *Arabidopsis* sequences with miRNA designations were analyzed. These have not been subjected to extensive experimental validation as miRNAs. This set includes all sequences with codes between miR400-miR420 (Sunkar & Zhu, *Plant Cell* 16:2001-2019, 2004; Wang et al., *Genome Biol* 5:R65, 2004), except miR403. In contrast to the founder set, most of the small RNAs in the second set failed at one or more steps. Six small RNAs (miR401, 405a-d, 407, 416) were identified as transposon-derived, two (miR402, 408) were from annotated genes, and ten (miR401, 404, 406, 408, 413, 414, 417-420) failed the foldback prediction criteria. Given the high computational failure rate (0.84) of this set, which was 26-fold higher than the false negative rate of the founder set, it is likely that many or most of these are endogenous siRNAs and not bona fide miRNAs.

Figure 8C:
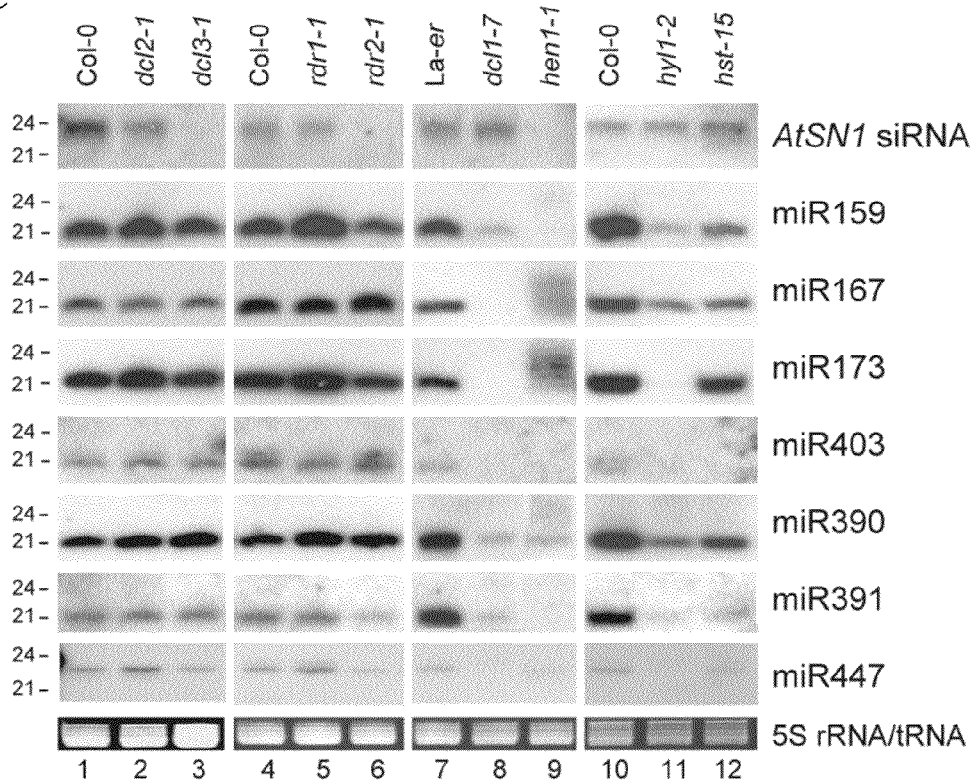
Figure 8D:
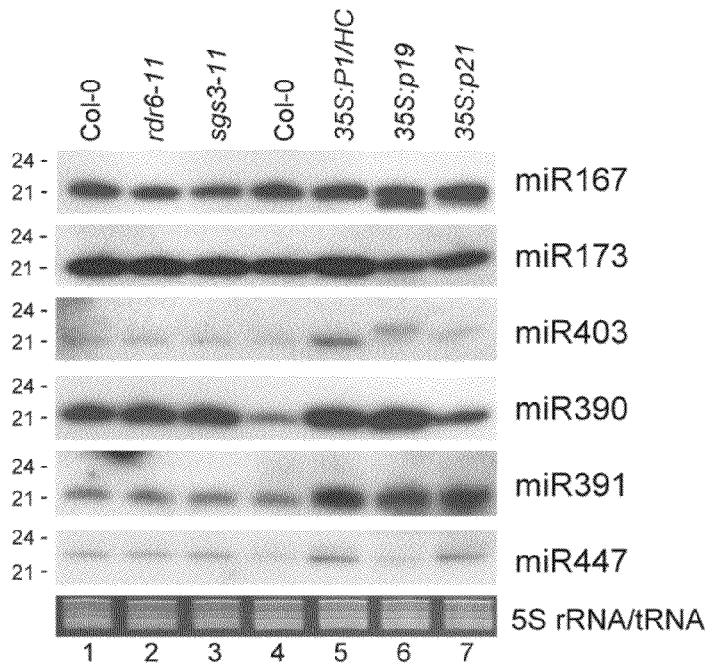

Candidate miRNAs from each of the 13 loci identified in the computational analysis were subjected to validation blot assays using a series of *Arabidopsis* miRNA-defective (dcl1, hyl1, hen1, and hst) and siRNA-defective (dcl2, dcl3, rdr1, rdr2, rdr6 or sgs3) mutants (Reinhart et al., *Genes Dev* 16:1616-1626, 2002; Kasschau et al., *Dev Cell* 4:205-217, 2003; Jones-Rhoades & Bartel, *Mol Cell* 14:787-799, 2004; Vazquez et al., *Curr Biol* 14:346-351, 2004; Xie et al., *PLoS Biol* 2:642-652, 2004). In addition, small RNAs were analyzed in transgenic plants expressing three viral RNAi suppressors (P1/HC-Pro, p19 and p21), which frequently enhance the level of miRNA accumulation (Mallory et al., *Proc Natl Acad Sci USA* 99:15228-15233, 2002; Kasschau et al., *Dev Cell* 4:205-217, 2003; Papp et al., *Plant Physiol* 132:1382-1390, 2003; Chapman et al., *Genes Dev.* 18:1179-86, 2004) but decrease the level of ta-siRNA accumulation. Previously validated miR159, miR167 and miR173, and AtSN1-derived siRNAs were analyzed in parallel as controls. Reproducible signals were detected in Col-0 and La-er control plants only using probes for miR390, miR391, miR403 and miR447 (FIG. 8C). Each of these accumulated to relatively low levels in the dcl1-7, hen1-1 and hyl1-2 mutants, but accumulated to normal or near-normal levels in the dcl2-1, dcl3-1, rdr1-1, rdr2-1, rdr6-11 and sgs3-11 mutants (FIG. 8C,D). The hst-15 mutant accumulated nearly normal amounts of the four candidates as well as the three miRNA controls (FIG. 8C), indicating that miRNA accumulation in the tissues tested was relatively insensitive to loss of HST function. MiR390, miR391, miR403 and miR447 were either up-regulated or unaffected by each of the three viral suppressor proteins (FIG. 8D). Based on structural and biogenesis criteria, we conclude that miR390, miR391, miR403 and miR447 are bona fide miRNAs. Small RNAs from the remaining eight loci (Table 6) were not detected in blot assays and were not characterized further.

TABLE 6

Predicted miRNA candidates tested experimentally

| Locus | ASRP no. | Sequence | miRNA validation | miRNA name, notes |
|---|---|---|---|---|
| 1, 2 | 754[a] | AAGCUCAGGAGGGAUAGCGCC SEQ ID NO: 143 | yes | miR390 |
| 3 | 1728 | UUCGCAGGAGAGAUAGCGCCA SEQ ID NO: 144 | yes | miR391 |
| 4 | 359 | AUUAGAUUCACGCACAAACUCG SEQ ID NO: 145 | yes | miR403 |
| 5 | 1890 | UUGGGGACGAGAUGUUUUGUUG SEQ ID NO: 146 | yes | miR447 |
| 6 | 382 | GAGCCGACAUGUUGUGCAACUU SEQ ID NO: 147 | no | not detected |
| 7 | 991 | AAUGGAAGCCUUGUCAGCUUAU SEQ ID NO: 148 | no | not detected |
| 8 | 1072 | UAAAGUCAAUAAUACCUUGAAG SEQ ID NO: 149 | no | not detected |
| 9 | 1345 | UAUAAGCCAUCUUACUAGUU SEQ ID NO: 150 | no | not detected |
| 10 | 1744 | UUCUGCUAUGUUGCUGCUCAUU SEQ ID NO: 151 | no | not detected |
| 11 | 1928 | UCUAAGUCUUCUAUUGAUGUUC SEQ ID NO: 152 | no | not detected |
| 12 | 1943 | CUGUCUUCUCAACUUCAUGUGA SEQ ID NO: 153 | no | not detected |
| 13 | 2028 | CGGCUCUGAUACCAAUUGAUG SEQ ID NO: 154 | no | not detected |

[a]Four processing variants from the two miR390 loci were cloned.

MiR390 and miR391 are related miRNAs that differ by five nucleotides, whereas miR403 and miR447 are distinct from all other known miRNAs. If miR390 and miR391 are assigned to the same family, then *Arabidopsis* contains 25 experimentally validated families of miRNAs encoded by up to 99 genes (Table 7). Among these families, 19 are conserved between dicots and monocots. One family (miR403) is conserved among families within dicots, and five families (miR158, miR161, miR163, miR173 and miR447) have been identified only in *Arabidopsis*.

TABLE 7

*Arabidopsis* miRNA families

| miRNA families | miRNA family | Locus | Sequence[a] | ASRP library[b] Col-0 | rdr2/dcl3 | Plant species[c] | Target family | SEQ ID NO. |
|---|---|---|---|---|---|---|---|---|
| 1 | miR156 | a-f | UGACAGAAGAGAGUGAGCAC | + | + | At, Bn, Gm, Ha, Hv, Lj, Mt, Nt, Os, Pta, Ptr, Sb, Si, So, St, Vv, Zm | SBP | 155 |
|   | miR156 | g | CGACAGAAGAGAGUGAGCACA | − | − | At |   | 156 |
|   | miR156 | h | UUGACAGAAGAAAGAGAGCAC | − | − | At |   | 157 |
|   | miR157 | a-d | UUGACAGAAGAUAGAGAGCAC | − | + | At, Ptr |   | 158 |
| 2 | miR158 | a | UCCCAAAUGUAGACAAAGCA | + | − | At | PPR | 159 |
|   |   | b | CCCCAAAUGUAGACAAAGCA | − | − | At |   | 160 |
| 3 | miR159 | a | UUUGGAUUGAAGGGAGCUCUA | + | + | At, Gm, Hv*, Lj, Mt, Os, Pg*, Ptr, So*, Sb*, Ta*, Vv, Zm | MYB | 161 |
|   | miR159 | b | UUUGGAUUGAAGGGAGCUCUU | − | + | At |   | 162 |
|   | miR159 | c | UUUGGAUUGAAGGGAGCUCCU | − | − | At |   | 163 |
|   | miR319 | a-b | UUGGACUGAAGGGAGCUCCCU | + | + | At, Bo, Gm, Lt, Os, Ptr, Ta | TCP | 164 |
|   | miR319 | c | UUGGACUGAAGGGAGCUCCUU | − | − | At, Os |   | 165 |
| 4 | mir160 | a-c | UGCCUGGCUCCCUGUAUGCCA | + | + | At, Gm, Os, Ptr, Tt, Zm | ARF | 166 |
| 5 | miR161.1 | a | UUGAAAGUGACUACAUCGGGG | + | + | At | PPR | 167 |
|   | miR161.2 | a | UCAAUGCAUUGAAAGUGACUA | + | + | At |   | 168 |
| 6 | miR162 | a-b | UCGAUAAACCUCUGCAUCCAG | + | + | At, Gm, Ll, Mt, Os, Ptr, Vv | DCL | 169 |
| 7 | miR163 | a | UUGAAGAGGACUUGGAACUUC-GAU | + | − | At | SAMT | 170 |
| 8 | miR164 | a-b | UGGAGAAGCAGGGCACGUGCA | − | + | At, Pb, Ta | NAC | 171 |
|   | miR164 | c | UGGAGAAGCAGGGCACGUGCG | + | + | At |   | 172 |
| 9 | miR165 | a-b | UCGGACCAGGCUUCAUCCCCC | − | + | At, Hc, Ptr | HD-ZIPIII | 173 |
|   | miR166 | a-g | UCGGACCAGGCUUCAUUCCCC | + | + | At, Gm, Hv, In*, Mt, Os, Ptr, Sb, Zm |   | 174 |
| 10 | miR167 | a-b | UGAAGCUGCCAGCAUGAUCUA | + | + | At, Gm, Os, Pc*, Ptr, Zm | ARF | 175 |
|   | miR167 | c | UUAAGCUGCCAGCAUGAUCUU | − | − | At |   | 176 |
|   | miR167 | d | UGAAGCUGCCAGCAUGAUCUGG | + | + | At, Gm, In, Ptr, So |   | 177 |

TABLE 7-continued

*Arabidopsis* miRNA families

| miRNA families | miRNA family | Locus | Sequence[a] | ASRP library[b] Col-0 | rdr2/dcl3 | Plant species[c] | Target family | SEQ ID NO. |
|---|---|---|---|---|---|---|---|---|
| 11 | miR168 | a-b | UCGCUUGGUGCAGGUCGGGAA | + | + | At, Bp, Gm, Ht, Hv, Le, Os, Ptr, Sb, So, St, Vv, Zm | AGO1 | 178 |
| 12 | miR169 | a | CAGCCAAGGAUGACUUGCCGA | + | + | At, Gm, Os, Ptr, Ptr | HAP2 | 179 |
|  | miR169 | b-c | CAGCCAAGGAUGACUUGCCGG | + | + | At, Gm, Os, Ptr, Zm |  | 180 |
|  | miR169 | d-g | UGAGCCAAGGAUGACUUGCCG | + | + | At, Ptr |  | 181 |
|  | miR169 | h-n | UAGCCAAGGAUGACUUGCCUG | + | + | At, Ls, Os, Pb, Ptr, Sb, So, Ta |  | 182 |
| 13 | miR170 | a | UGAUUGAGCCGUGUCAAUAUC | − | + | At | SCR | 183 |
|  | miR171 | a | UGAUUGAGCCGCGCCAAUAUC | + | + | At, Os, Ptr, Ta, Zm |  | 184 |
|  | miR171.2 | b-c | UUGAGCCGUGCCAAUAUCACG | + | − | At, Os, Ptr, Ta, Zm |  | 185 |
|  | miR171.1 | c | UGAUUGAGCCGUGCCAAUAUC | − | + | At, Gm, Hc, Hv, Os, Ptr, Ta, Zm |  | 186 |
| 14 | miR172 | a-b | AGAAUCUUGAUGAUGCUGCAU | − | + | At, Gm, Le, Os, Ptr, St | AP2 | 187 |
|  | miR172 | c-d | AGAAUCUUGAUGAUGCUGCAG | + | − | At, Cs |  | 188 |
|  | miR172 | e | GGAAUCUUGAUGAUGCUGCAU | − | + | At, Os, Ptr |  | 189 |
| 15 | miR173 | a | UUCGCUUGCAGAGAGAAAUCAC | − | + | At | TAS1, TAS2 | 190 |
| 16 | miR390 | a-b | AAGCUCAGGAGGGAUAGCGCC | + | + | At, Os, Ptr, St, Zm | TAS3 | 143 |
|  | miR391 | a | UUCGCAGGAGAGAUAGCGCCA | − | + | At |  | 144 |
| 17 | miR393 | a-b | UCCAAAGGGAUCGCAUUGAUC | − | − | At, Os, Ptr | T1R1/ F-box bHLH | 191 |
| 18 | miR394 | a-b | UUUGGCAUUCUGUCCACCUCC | − | − | At, Gm, Os, Ptr, Rp | F-box | 192 |
| 19 | miR395 | a, d-e | CUGAAGUGUUUGGGGGAACUC | − | − | At, Gm, Os, Ptr, Ta | ATPS | 193 |
|  | miR395 | b-c, f | CUGAAGUGUUUGGGGGGACUC | − | − | At |  | 194 |
| 20 | miR396 | a | UUCCACAGCUUUCUUGAACUG | − | + | At, Bv, Gm, Mc, Os, Ptr, Ppe, Ptr, So, St, Zm | GRF | 195 |
|  | miR396 | b | UUCCACAGCUUUCUUGAACUU | − | − | At, Bn, Gm, Mc, Os, Ptr, St |  | 196 |

TABLE 7-continued

Arabidopsis miRNA families

| miRNA families | miRNA family | Locus | Sequence[a] | ASRP library[b] Col-0 | ASRP library[b] rdr2/dcl3 | Plant species[c] | Target family | SEQ ID NO. |
|---|---|---|---|---|---|---|---|---|
| 21 | miR397 | a | UCAUUGAGUGCA<u>G</u>CGUUGAUG | − | + | At, Hv, Os, Ptr | laccase | 197 |
| | miR397 | b | UCAUUGAGUGCA<u>U</u>CGUUGAUG | − | − | At | | 198 |
| 22 | miR398 | a | UGUGUUCUCAGGUCACCCCU<u>U</u> | − | − | At, Cs, Gm, Lj, Mt, Os, Ptr | CSD | 199 |
| | miR398 | b-c | UGUGUUCUCAGGUCACCCCU<u>G</u> | − | + | At, Gm, Ha, Ls, Mt, Nb, Os, Zm* | CytC | 200 |
| 23 | miR399 | a | UGCCAAAGGAGA<u>U</u>UUGCC<u>C</u>UG | − | − | At | E2-UBC | 201 |
| | miR399 | b, c | UGCCAAAGGAGA<u>G</u>UUGCC<u>C</u>UG | − | + | At, Mt, Os, Ptr, Sb | | 202 |
| | miR399 | d | UGCCAAAGGAGA<u>U</u>UUGCC<u>C</u>CG | − | − | At, Os | | 203 |
| | miR399 | e | UGCCAAAGGAGA<u>U</u>UUGCC<u>U</u>CG | − | − | At | | 204 |
| | miR399 | f | UGCCAAAGGAGA<u>U</u>UUGCC<u>C</u>GG | − | − | At, Os | | 205 |
| 24 | miR403 | a | aUUAGAUUCACGCACAAACUCG | + | − | At, Ptr | AGO2 | 145 |
| 25 | miR447 | a-b | UUGGGGACGA<u>G</u>AUGUUUUGUUG | − | + | At | 2PGK | 146 |
| | miR447 | c | UUGGGGACGA<u>C</u>AUCUUUUGUUG | − | − | | | 206 |

[a]miRNAs are grouped by related families, with differences among families underlined;
[b]Col-0 libraries included Col-0 seedling, aerial, and inflorescence tissues, plus jaw-d sequences, rdr2/dcl3 contained seedling libraries from both mutants, and inflorescence tissues of rdr2;
[c]Presence of miRNA in genomic sequence is indicated in regular text, EST sequences are in bold, see information available on the World Wide Web at sanger.ac.ul/Software/Rfam/mirna/index.shtml for primary stem sequences; sequences with 1-2 base changes from the Arabidopsis sequence are indicated by an asterisk.

*Arabidopsis* miRNA Precursors Exhibit Characteristics of Pol II Transcripts

Figure 9A:
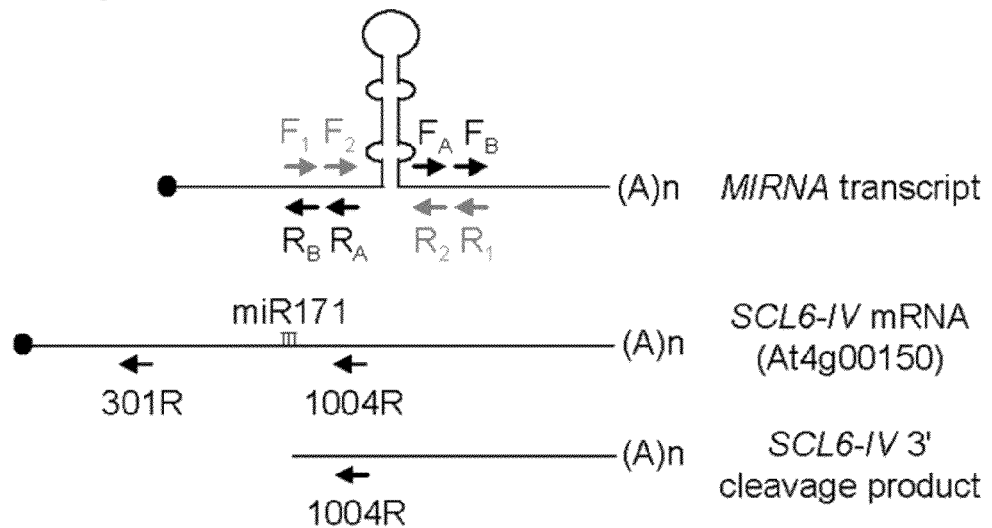
FIG. 9A-B. Strategy to map *Arabidopsis* MIRNA gene transcription start sites.
Figure 9B:
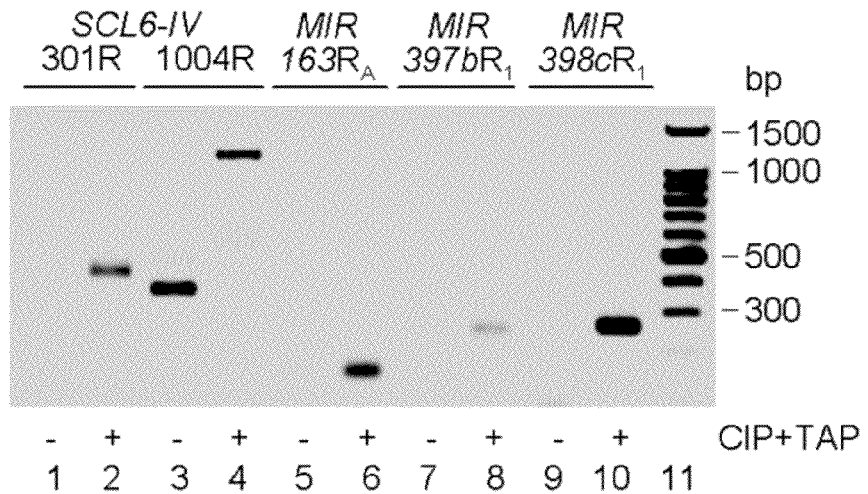

To determine if a reference set of *Arabidopsis thaliana* MIRNA gene transcripts contain 5' cap structures typical of RNA pol II transcripts, a series of RNA ligase-mediated 5'RACE reactions were done using poly(A)$^+$-selected RNA that was pretreated with either calf intestine phosphatase plus tobacco acid pyrophosphatase (CIP+TAP) or buffer alone. Only transcripts containing a 5' cap should ligate to adapters, and subsequently amplify by PCR, following CIP+TAP treatment. Transcripts lacking a cap should ligate and amplify only from the sample treated with buffer alone. As controls, capped Scarecrow-like6-IV (SCL6-IV, At4g00150) transcript and miR171-guided 3' cleavage product from SCL6-IV (containing a 5' monophosphate) were analyzed using gene specific primer sets (FIG. 9A) (Llave et al., *Science* 297:2053-2056, 2002). CIP+TAP-dependent 5'RACE products of the predicted size, ~400 and ~1,110 bp, were detected using 5'-proximal and cleavage site-proximal primer sets, respectively (FIG. 9B, lanes 2 and 4). Buffer-dependent 5'RACE product was detected only using the cleavage site-proximal primer set (FIG. 9B, lanes 1 and 3). Using locus-specific primer sets for MIR163, MIR397b and MIR398c, CIP+TAP-dependent products but not buffer-dependent products were detected (FIG. 9B, lanes 5-10), indicating that the 5' end of each miRNA transcript was capped. For 47 out of the 92 *Arabidopsis* MIRNA loci tested, 5'RACE products from poly (A)$^+$-selected and 5' capped RNA were detected (see below and Table 8). Combined with previous data for MIR172b and MIR163, and the evidence for a poly(A) tail on miRNA precursor transcripts, plant MIRNA genes are likely transcribed by an RNA pol II mechanism. These data are also consistent with recent analyses of MIRNA gene transcripts from animals (Bracht et al., *RNA* 10:1586-1594, 2004; Cai et al., *RNA* 10:1957-1966, 2004; Lee et al., *EMBO J.* 23:4051-4060, 2004).

Identification of a Core Promoter Element for *Arabidopsis* MIRNA Genes

Products of 5'RACE reactions were detected using locus-specific primers for 52 of 99 MIRNA genes tested. Transcription start sites were inferred by sequence analysis of the cloned PCR products. At several loci, such as MIR171a, MIR172b, and MIR172e, multiple 5'RACE products were detected and up to three clusters of alternative transcription start sites were identified (Table 8).

TABLE 8A

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR156 | 233 | 1423 | a | 2 | 10683613 | 106683632 | UGACAGAAGAGAGUGAGCAC SEQ ID NO: 155 |
| | | | b | 4 | 15074951 | 15074970 | |
| | | | c | 4 | 15415497 | 15415516 | |
| | | | d | 5 | 3456714 | 3456733 | |
| | | | e | 5 | 3867214 | 3867233 | |
| | | | f | 5 | 9136129 | 9136148 | |
| miR156 | 3 | 1662 | d | 5 | 3456714 | 3456734 | UUGACAGAAGAGAGUGAGCAC SEQ ID NO: 207 |
| miR156 | 1 | 1783 | e | 5 | 3867213 | 3867233 | GUGACAGAAGAGAGUGAGCAC SEQ ID NO: 208 |
| | | | f | 5 | 9136128 | 9136148 | |
| miR156 | 1 | 1950 | a | 2 | 10683612 | 106683632 | UGACAGAAGAGAGUGAGCAC SEQ ID NO: 155 |
| | | | b | 4 | 15074951 | 15074971 | |
| | | | c | 4 | 15415496 | 15415516 | |
| | | | d | 5 | 3456713 | 3456733 | |
| | | | e | 5 | 3867214 | 3867234 | |
| | | | f | 5 | 9136129 | 9136149 | |
| miR157 | 1 | 1424 | a | 1 | 24916958 | 24916939 | UGACAGAAGAUAGAGAGCAC SEQ ID NO: 209 |
| | | | b | 1 | 24924768 | 24924787 | |
| | | | c | 3 | 6244698 | 6244679 | |
| | | | d | 1 | 18030676 | 18030657 | |
| miR157 | 6 | 1770 | a | 1 | 24916959 | 24916939 | UUGACAGAAGAUAGAGAGCAC SEQ ID NO: 158 |
| | | | b | 1 | 24924767 | 24924787 | |
| | | | c | 3 | 6244699 | 6244679 | |
| miR157 | 2 | 1952 | d | 1 | 18030677 | 18030657 | CUGACAGAAGAUAGAGAGCAC SEQ ID NO: 210 |
| miR157* | 1 | 1782 | a | 1 | 24916888 | 24916868 | GCUCUCUAGCCUUCUGUCAUC SEQ ID NO: 211 |
| | | | b | 1 | 24924838 | 24924858 | |
| miR158 | 18 | 142 | a | 3 | 3366373 | 3366354 | UCCCAAAUGUAGACAAAGCA SEQ ID NO: 159 |
| miR158* | 1 | 1727 | a | 3 | 3366396 | 3366416 | CUUUGUCUACAAUUUUGGAAA SEQ ID NO: 212 |
| miR158* | 1 | 1735 | a | 3 | 3366397 | 3366416 | CUUUGUCUACAAUUUUGGAA SEQ ID NO: 213 |
| miR158* | 1 | 2007 | a | 3 | 3366395 | 3366416 | CUUUGUCUACAAUUUUGGAAAA SEQ ID NO: 214 |
| miR159 | 224 | 1425 | a | 1 | 27716915 | 27716895 | UUUGGAUUGAAGGGAGCUCUA SEQ ID NO: 161 |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR159 | 7 | 1747 | b | 1 | 6220806 | 6220826 | UUUGGAUUGAAGGGAGCUCUU SEQ ID NO: 162 |
| miR159 | 1 | 1756 | b | 1 | 6220804 | 6220824 | UCUUUGGAUUGAAGGGAGCUC SEQ ID NO: 215 |
|  |  |  | a | 1 | 27716917 | 27716897 |  |
| miR159 | 2 | 1800 | a | 1 | 27716915 | 27716896 | UUUGGAUUGAAGGGAGCUCU SEQ ID NO: 216 |
|  |  |  | b | 1 | 6220806 | 6220825 |  |
| miR159 | 1 | 2011 | a | 1 | 27716914 | 27716895 | UUGGAUUGAAGGGAGCUCUA SEQ ID NO: 217 |
| miR319 | 5 | 1665 | a | 4 | 12353119 | 12353139 | UUGGACUGAAGGGAGCUCCCU SEQ ID NO: 164 |
|  |  |  | b | 5 | 16677717 | 16677697 |  |
| miR160 | 101 | 1426 | a | 2 | 16347360 | 16347380 | UGCCUGGCUCCCUGUAUGCCA SEQ ID NO: 166 |
|  |  |  | b | 4 | 9888999 | 98889019 |  |
|  |  |  | c | 5 | 19026405 | 19026385 |  |
| miR160 | 1 | 1752 | a | 2 | 16347360 | 16347381 | UGCCUGGCUCCCUGUAUGCCAU SEQ ID NO: 218 |
| miR160 | 1 | 1754 | a | 2 | 16347360 | 16347381 | GCCUGGCUCCCUGUAUGCCA SEQ ID NO: 219 |
|  |  |  | b | 4 | 9888999 | 98889019 |  |
|  |  |  | c | 5 | 19026404 | 19026385 |  |
| miR160* | 1 | 1941 | c | 5 | 19026322 | 19026342 | CGUACAAGGAGUCAAGCAUGA SEQ ID NO: 20 |
| miR161.1 | 4 | 111 | a | 1 | 17829398 | 17829418 | UUGAAAGUGACUACAUCGGGG SEQ ID NO: 167 |
| miR161.1 | 1 | 497 | a | 1 | 17829399 | 17829418 | UGAAAGUGACUACAUCGGGG SEQ ID NO: 221 |
| miR161.1 | 10 | 1746 | a | 1 | 17829399 | 17829419 | UGAAAGUGACUACAUCGGGGU SEQ ID NO: 222 |
| miR161.2 | 307 | 563 | a | 1 | 17829390 | 17829410 | UCAAUGCAUUGAAAGUGACUA SEQ ID NO: 168 |
| miR161.2 | 6 | 1707 | a | 1 | 17829390 | 17829411 | UCAAUGCAUUGAAAGUGACUAC SEQ ID NO: 223 |
| miR161.2 | 5 | 1712 | a | 1 | 17829390 | 17829409 | UCAAUGCAUUGAAAGUGACU SEQ ID NO: 224 |
| miR161.2 | 1 | 213 | a | 1 | 17829391 | 17829410 | CAAUGCAUUGAAAGUGACUA SEQ ID NO: 225 |
| miR162 | 4 | 395 | a | 5 | 2634957 | 2634937 | UCGAUAAACCUCUGCAUCCAG SEQ ID NO: 169 |
|  |  |  | b | 5 | 7740613 | 7740633 |  |
| miR163 | 1 | 1390 | a | 1 | 24888022 | 24888045 | UUGAAGAGGACUUGGAACUUCGAU SEQ ID NO: 170 |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR164 | 2 | 1427 | a | 2 | 19527840 | 19527860 | UGGAGAAGCAGGGCACGUGCA SEQ ID NO: 171 |
|  |  |  | b | 5 | 287583 | 287603 |  |
| miR164* | 2 | 1812 | c | 5 | 9852751 | 9852771 | CACGUGUUCUACUACUCCAAC SEQ ID NO: 226 |
| miR165 | 30 | 1428 | a | 1 | 78952 | 78932 | UCGGACCAGGCUUCAUCCCCC SEQ ID NO: 173 |
|  |  |  | b | 4 | 368876 | 368856 |  |
| miR166 | 299 | 934 | a | 2 | 19183311 | 19183331 | UCGGACCAGGCUUCAUUCCCC SEQ ID NO: 174 |
|  |  |  | b | 3 | 22933276 | 22933296 |  |
|  |  |  | c | 5 | 2838738 | 2838758 |  |
|  |  |  | d | 5 | 2840709 | 2840729 |  |
|  |  |  | e | 5 | 16792772 | 16792752 |  |
|  |  |  | f | 5 | 17533605 | 17533625 |  |
|  |  |  | g | 5 | 25522108 | 25522128 |  |
| miR166 | 5 | 1743 | a | 2 | 19183311 | 19183332 | UCGGACCAGGCUUCAUUCCCCC SEQ ID NO: 227 |
|  |  |  | b | 3 | 22933276 | 22933297 |  |
|  |  |  | c | 5 | 2838738 | 2838759 |  |
|  |  |  | d | 5 | 2840709 | 2840730 |  |
| miR166 | 2 | 1764 | a | 2 | 19183310 | 19183331 | UUCGGACCAGGCUUCAUUCCCC SEQ ID NO: 228 |
| miR166 | 1 | 1779 | a | 2 | 19183310 | 19183330 | UUCGGACCAGGCUUCAUUCCC SEQ ID NO: 229 |
| miR166* | 1 | 1955 | a | 2 | 19183198 | 19183218 | GGACUGUUGUCUGGCUCGAGG SEQ ID NO: 230 |
|  |  |  | b | 3 | 22933187 | 22933207 |  |
| miR167 | 160 | 5 | a | 3 | 8108097 | 8108117 | UGAAGCUGCCAGCAUGAUCUA SEQ ID NO: 175 |
|  |  |  | b | 3 | 23417152 | 23417172 |  |
| miR167 | 3 | 35 | a | 3 | 8108097 | 8108116 | UGAAGCUGCCAGCAUGAUCU SEQ ID NO: 231 |
|  |  |  | b | 3 | 23417152 | 23417171 |  |
|  |  |  | c | 1 | 11137537 | 11137556 |  |
| miR167 | 2 | 447 | a | 3 | 8108098 | 8108117 | GAAGCUGCCAGCAUGAUCUA SEQ ID NO: 232 |
|  |  |  | b | 3 | 23417153 | 23417172 |  |
| miR167 | 2 | 697 | a | 3 | 8108096 | 8108117 | AUGAAGCUGCCAGCAUGAUCUA SEQ ID NO: 233 |
| miR167 | 5 | 557 | b | 3 | 23417152 | 23417173 | UGAAGCUGCCAGCAUGAUCUAU SEQ ID NO: 234 |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR167 | 1 | 790 | b | 3 | 23417151 | 23417172 | GUGAAGCUGCCAGCAUGAUCUA SEQ ID NO: 235 |
| miR167 | 1 | 281 | c | 1 | 11137537 | 11137557 | UGAAGCUGCCAGCAUGAUCUG SEQ ID NO: 236 |
| miR167 | 6 | 535 | c | 1 | 11137537 | 11137558 | UGAAGCUGCCAGCAUGAUCUGG SEQ ID NO: 177 |
| miR168 | 22 | 1429 | a | 4 | 10578663 | 10578683 | UCGCUUGGUGCAGGUCGGGAA SEQ ID NO: 178 |
|  |  |  | b | 5 | 18376120 | 18376100 |  |
| miR168* | 5 | 489 | a | 4 | 10578748 | 10578768 | CCCGCCUUGCAUCAACUGAAU SEQ ID NO: 237 |
| miR168* | 1 | 1970 | a | 4 | 10578748 | 10578767 | CCCGCCUUGCAUCAACUGAA SEQ ID NO: 238 |
| miR168* | 1 | 2076 | a | 4 | 10578747 | 10578767 | UCCCGCCUUGCAUCAACUGAA SEQ ID NO: 239 |
| miR169 | 614 | 1430 | a | 3 | 4359209 | 4359189 | CAGCCAAGGAUGACUUGCCGA SEQ ID NO: 179 |
| miR169 | 26 | 1749 | a | 3 | 4359209 | 4359190 | CAGCCAAGGAUGACUUGCCG SEQ ID NO: 240 |
|  |  |  | b | 5 | 8527514 | 8527533 |  |
|  |  |  | c | 5 | 15888116 | 15888097 |  |
| miR169 | 119 | 1751 | b | 5 | 8527514 | 8527534 | CAGCCAAGGAUGACUUGCCGG SEQ ID NO: 180 |
|  |  |  | c | 5 | 15888116 | 15888096 |  |
| miR169 | 12 | 1757 | a | 3 | 4359211 | 4359191 | UGCAGCCAAGGAUGACUUGCC SEQ ID NO: 241 |
|  |  |  | b | 5 | 8527512 | 8527532 |  |
| miR169 | 4 | 1762 |  | 3 | 4805824 | 4805805 | AGCCAAGGAUGACUUGCCGG SEQ ID NO: 242 |
|  |  |  |  | 4 | 11483124 | 11483105 |  |
|  |  |  | b | 5 | 8527515 | 8527534 |  |
|  |  |  | c | 5 | 15888115 | 15888096 |  |
| miR169 | 5 | 1766 | a | 3 | 4359209 | 4359188 | CAGCCAAGGAUGACUUGCCGAU SEQ ID NO: 243 |
| miR169 | 1 | 1768 | a | 3 | 4359210 | 4359190 | GCAGCCAAGGAUGACUUGCCG SEQ ID NO: 244 |
|  |  |  | b | 5 | 8527513 | 8527533 |  |
| miR169 | 13 | 1775 |  | 1 | 20043242 | 20043223 | AGCCAAGGAUGACUUGCCGA SEQ ID NO: 245 |
|  |  |  |  | 1 | 20045256 | 20045275 |  |
|  |  |  | a | 3 | 4359208 | 4359189 |  |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR169 | 1 | 1787 | | 1 | 20043242 | 20043222 | AGCCAAGGAUGACUUGCCGAU SEQ ID NO: 246 |
| | | | | 1 | 20045256 | 20045276 | |
| | | | a | 3 | 4359208 | 4359188 | |
| miR169 | 5 | 1802 | c | 5 | 15888116 | 15888095 | CAGCCAAGGAUGACUUGCCGGU SEQ ID NO: 247 |
| miR169 | 3 | 1813 | b | 5 | 8527515 | 8527535 | AGCCAAGGAUGACUUGCCGGA SEQ ID NO: 248 |
| miR169 | 1 | 1817 | | 3 | 4805804 | 4805824 | AGCCAAGGAUGACUUGCCGGU SEQ ID NO: 249 |
| | | | c | 5 | 15888115 | 15888095 | |
| miR169 | 2 | 1820 | | 3 | 4805803 | 4805824 | AGCCAAGGAUGACUUGCCGGUU SEQ ID NO: 250 |
| miR169 | 1 | 1824 | b | 5 | 8527514 | 8527535 | CAGCCAAGGAUGACUUGCCGGA SEQ ID NO: 251 |
| miR169* | 1 | 1772 | a | 3 | 4359018 | 4359037 | GGCAAGUUGUCCUUGGCUAC SEQ ID NO: 252 |
| miR169* | 1 | 1773 | b | 5 | 8527595 | 8527616 | GGCAAGUUGUCCUUCGGCUACA SEQ ID NO: 253 |
| miR169 | 22 | 276 | d | 1 | 20043244 | 20043224 | UGAGCCAAGGAUGACUUGCCG SEQ ID NO: 181 |
| | | | e | 1 | 20045254 | 20045274 | |
| | | | f | 3 | 4805826 | 4805806 | |
| | | | g | 4 | 11483126 | 11483106 | |
| miR169 | 402 | 1514 | h | 1 | 6695555 | 6695535 | UAGCCAAGGAUGACUUGCCUG SEQ ID NO: 182 |
| | | | i | 3 | 9873362 | 9873343 | |
| | | | j | 3 | 9873739 | 9873720 | |
| | | | k | 3 | 9876931 | 9876912 | |
| | | | l | 3 | 9877296 | 9877277 | |
| | | | m | 3 | 9879575 | 9879555 | |
| | | | n | 3 | 9879947 | 9879927 | |
| miR169 | 1 | 1760 | h | 1 | 6695554 | 6695535 | AGCCAAGGAUGACUUGCCUG SEQ ID NO: 254 |
| | | | i | 3 | 9873362 | 9873343 | |
| | | | j | 3 | 9873739 | 9873720 | |
| | | | k | 3 | 9876931 | 9876912 | |
| | | | l | 3 | 9877296 | 9877277 | |
| | | | m | 3 | 9879574 | 9879555 | |
| | | | n | 3 | 9879946 | 9879927 | |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR169 | 48 | 1761 | i | 3 | 9873363 | 9873342 | UAGCCAAGGAUGACUUGCCUGA SEQ ID NO: 255 |
| | | | j | 3 | 9873740 | 9873719 | |
| | | | l | 3 | 9877297 | 9877276 | |
| | | | n | 3 | 9879947 | 9879926 | |
| miR169 | 1 | 1765 | i | 3 | 9873362 | 9873342 | AGCCAAGGAUGACUUGCCUGA SEQ ID NO: 256 |
| | | | j | 3 | 9873739 | 9873719 | |
| | | | l | 3 | 9877296 | 9877276 | |
| | | | n | 3 | 9879946 | 9879926 | |
| miR169 | 3 | 1771 | m | 3 | 9879575 | 9879554 | UAGCCAAGGAUGACUUGCCUGU SEQ ID NO: 257 |
| miR169 | 1 | 1774 | h | 1 | 6695556 | 6695535 | GUAGCCAAGGAUGACUUGCCUG SEQ ID NO: 258 |
| | | | i | 3 | 9873364 | 9873343 | |
| | | | j | 3 | 9873741 | 9873720 | |
| | | | k | 3 | 9876933 | 9876912 | |
| | | | m | 3 | 9879576 | 9879555 | |
| | | | n | 3 | 9879948 | 9879927 | |
| miR169 | 1 | 1776 | i | 3 | 9873363 | 9873341 | UAGCCAAGGAUGACUUGCCUGAC SEQ ID NO: 259 |
| miR169 | 1 | 1815 | | 3 | 4644341 | 4644361 | UAGCCAAGGAUGACUUCCCUU SEQ ID NO: 260 |
| miR169 | 1 | 1990 | h | 1 | 6695555 | 6695536 | UAGCCAAGGAUGACUUGCCU SEQ ID NO: 261 |
| | | | i | 3 | 9873363 | 9873344 | |
| | | | j | 3 | 9873740 | 9873721 | |
| | | | k | 3 | 9876932 | 9876913 | |
| | | | l | 3 | 9877297 | 9877278 | |
| | | | m | 3 | 9879575 | 9879556 | |
| | | | n | 3 | 9879947 | 9879928 | |
| miR170 | 1 | 1431 | a | 5 | 26428840 | 26428820 | UGAUUGAGCCGUGUCAAUAUC SEQ ID NO: 183 |
| miR171 | 34 | 39 | a | 3 | 19084500 | 19084520 | UGAUUGAGCCGCGCCAAUAUC SEQ ID NO: 184 |
| miR171 | 1 | 638 | a | 3 | 19084500 | 19084519 | UGAUUGAGCCGCGCCAAUAU SEQ ID NO: 262 |
| miR171.2 | 1 | 444 | b | 1 | 3961387 | 3961367 | UUGAGCCGUGCCAAUAUCACG SEQ ID NO: 185 |
| | | | c | 1 | 22933780 | 22933760 | |
| miR171.1 | 1 | 1876 | c | 1 | 22933783 | 22933763 | UGAUUGAGCCGUGCCAAUAUC SEQ ID NO: 186 |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| miR172 | 1 | 811 | c | 3 | 3599817 | 3599797 | AGAAUCUUGAUGAUGCUGCAG SEQ ID NO: 188 |
|  |  |  | d | 3 | 20598970 | 20598990 |  |
| miR172* | 1 | 1854 | e | 5 | 24005710 | 24005729 | GCAGCACCAUUAAGAUUCAC SEQ ID NO: 263 |
|  |  |  | a | 5 | 1188298 | 1188279 |  |
| miR172* | 1 | 2019 | a | 5 | 1188298 | 1188278 | GCAGCACCAUUAAGAUUCACA SEQ ID NO: 264 |
|  |  |  | e | 5 | 24005710 | 24005730 |  |
| miR173 | 1 | 886 | a | 3 | 8236168 | 8236189 | UUCGCUUGCAGAGAGAAAUCAC SEQ ID NO: 190 |
| miR173* | 1 | 2033 | a | 3 | 8236234 | 8236254 | UGAUUCUCUGUGUAAGCGAAA SEQ ID NO: 265 |
| miR390 | 89 | 754 | a | 2 | 16069049 | 16069069 | AAGCUCAGGAGGGAUAGCGCC SEQ ID NO: 143 |
|  |  |  | b | 5 | 23654187 | 23654207 |  |
| miR390 | 25 | 1703 | a | 2 | 16069050 | 16069069 | AGCUCAGGAGGGAUAGCGCC SEQ ID NO: 266 |
|  |  |  | b | 5 | 23654188 | 23654207 |  |
| miR390 | 3 | 1784 | a | 2 | 16069049 | 16069068 | AAGCUCAGGAGGGAUAGCGC SEQ ID NO: 267 |
|  |  |  | b | 5 | 23654187 | 23654206 |  |
| miR390 | 3 | 1758 | a | 2 | 16069051 | 16069069 | GCUCAGGAGGGAUAGCGCC SEQ ID NO: 268 |
|  |  |  | b | 5 | 23654189 | 23654207 |  |
| miR390 | 2 | 1972 | a | 2 | 16069050 | 16069070 | AGCUCAGGAGGGAUAGCGCCA SEQ ID NO: 269 |
|  |  |  | b | 5 | 23654188 | 23654208 |  |
| miR390* | 1 | 206 | b | 5 | 23654260 | 23654279 | CGCUAUCCAUCCUGAGUUCC SEQ ID NO: 270 |
| miR390* | 1 | 2051 | b | 5 | 23654260 | 23654280 | CGCUAUCCAUCCUGAGUUCCA SEQ ID NO: 271 |
| miR391 | 7 | 1728 | a | 5 | 24310386 | 24310406 | UUCGCAGGAGAGAUAGCGCCA SEQ ID NO: 144 |
| miR391* | 1 | 1991 | a | 5 | 24310737 | 24310457 | ACGGUAUCUCUCCUACGUAGC SEQ ID NO: 272 |
| miR396* | 1 | 1724 | a | 2 | 4149413 | 4149434 | GGUUCAAUAAAGCUGUGGGAAG SEQ ID NO: 273 |
| miR397 | 1 | 1794 | a | 4 | 2625958 | 2625979 | UCAUUGAGUGCAGCGUUGAUGU SEQ ID NO: 274 |
| miR398 | 4 | 1994 | b | 5 | 4691110 | 4391130 | UGUGUUCUCAGGUCACCCCUG SEQ ID NO: 200 |
|  |  |  | c | 5 | 4394781 | 4694801 |  |
| miR399 | 1 | 1867 | b | 1 | 23349074 | 23349054 | CCUGCCAAAGGAGAGUUGCCC SEQ ID NO: 275 |

TABLE 8A-continued

Validated miRNA sequences cloned from Arabidopsis small RNA libraries

| miRNA | Times isolated | ASRP database No | Locus | Chrom. | Position Start | End | Sequence |
|---|---|---|---|---|---|---|---|
| ASRP1839 | 3 | 1839 | a | 1 | 29427439 | 29427458 | UUCGAUGUCUAGCAGUGCCA SEQ ID NO: 276 |
| miR447 | 1 | 1890 | a | 4 | 1528188 | 1528209 | UUGGGGACGAGAUGUUUUGUUG SEQ ID NO: 146 |
|  |  |  | b | 4 | 1535480 | 1535501 |  |
|  | 0 |  | c | 4 | 1523381 | 1523360 | UUGGGGACGACAUCUUUUGUUG SEQ ID NO: 206 |
| miR403 | 1 | 359 | a | 2 | 19422223 | 19422244 | AUUAGAUUCACGCACAAACUCG SEQ ID NO: 145 |

Table 8B provides another summary of locus-specific expression of 99 predicted miRNA genes coding for validated *Arabidopsis* microRNAs. Expression of a specific locus was considered definitive (dark shading) if a primary transcript was detected by 5' or 3'RACE, or a unique miRNA sequence was cloned or amplified from the ASRP library described here (gray shading with total clones sequenced) or from another published library (Other Refs.). The number of clones corresponding to a specific miRNA or miRNA* (in parentheses) sequence in the ASRP database is shown. Loci for which data support expression from more than one possible gene are indicated by light shading.

Figure 10A:
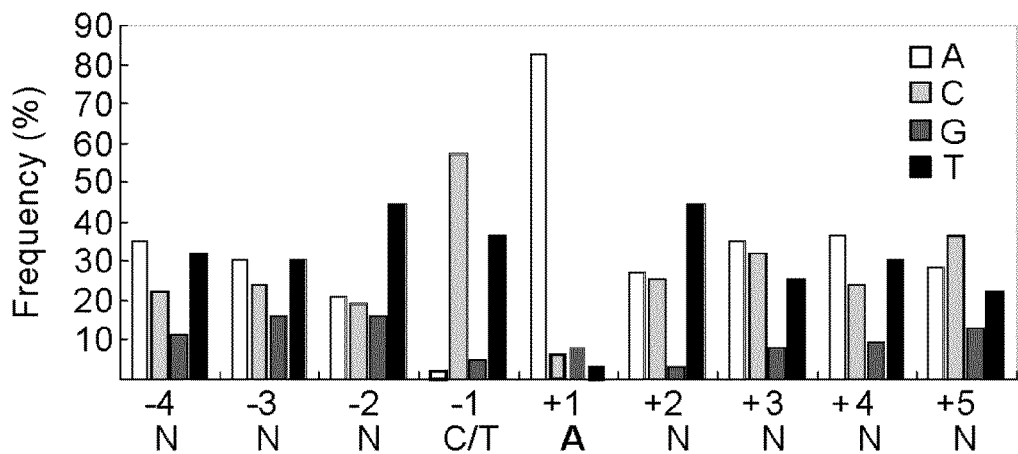

For each 5'RACE product detected, the transcription start site was assigned to the most highly represented sequence among six randomly selected clones. In cases where two clustered sequences were equally represented, the extreme 5' sequence was assigned as the start site. Following this procedure, the 5' ends representing 63 transcripts from the 52 MIRNA loci were identified (FIG. 10 and Table 8). The vast majority of transcripts initiated with an adenosine (83%) that was preceded by a pyrimidine residue (FIG. 10A). Twelve loci yielded multiple transcripts that were consistent with alternative start sites. Three transcripts (one from MIR156a and two from MIR172b) contained introns between the 5' end and foldback sequence. Each of these characteristics is consistent with transcription by RNA pol II.

Figure 10C:
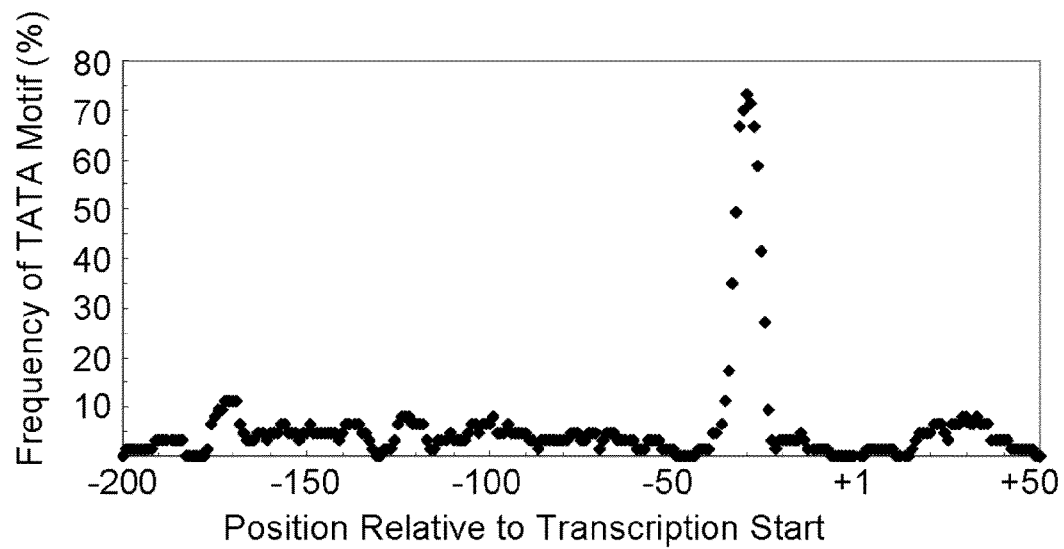

To identify conserved motifs flanking the initiation sites at each mapped locus, a 60-bp genomic segment (−50 to +10 relative to the start site) was computationally analyzed using BioProspector. An 8-nucleotide TATA box-like sequence was detected upstream from 83% of transcription start sites (FIG. 10B). Using MotifMatcher to scan a broader segment (−200 to +50), the TATA-like sequence was shown to be centered at a position removed from the start site (FIG. 10C). The TATA motif at position −30 is entirely consistent with TATA motifs for protein-coding genes (Patikoglou et al., *Genes Dev* 13:3217-3230, 1999; Shahmuradov et al., *Nucleic Acids Res* 31:114-117, 2003). We conclude, therefore, that these are authentic TATA box sequences within core promoter elements of MIRNA genes.

Expression of *Arabidopsis* MIRNA Genes

Despite repeated attempts with multiple primer sets, 5' start sites were mapped for only about one-half of predicted MIRNA genes (Table 8B). This may have been due to either less-than-optimal 5'RACE procedures and low expression levels (false negative results) or lack of expression of some loci predicted to be MIRNA genes. It is also possible that some primer sets were designed within intron sequences. To develop a more comprehensive account of *Arabidopsis* MIRNA genes with validated expression data, informatic and experimental approaches were taken. In the informatic strategy, the ASRP database was scanned for locus-specific miRNA or miRNA* (miRNA-complementary species within miRNA duplexes) sequences (Gustafson et al., *Nucleic Acid Research* 33:D637-D640, 2005). Unique miRNA or miRNA* sequences specific to MIR158a, MIR167d, MIR173, MIR391, MIR397a and MIR164c loci were each represented in the database (FIG. 10). In addition, unique miRNA sequences specific to MIR319c, MIR398a, and MIR399f were represented in an independent *Arabidopsis* small RNA library (Table 8B) (Sunkar & Zhu, *Plant Cell* 16:2001-2019, 2004). For each of three families (MIR390/391, MIR393, and MIR168) in which negative 5'RACE data were obtained, multiple predicted loci encode an identical miRNA that was detected in at least one small RNA library (Reinhart et al., *Genes Dev* 16:1616-1626, 2002; Jones-Rhoades & Bartel, *Mol Cell* 14:787-799, 2004; Sunkar & Zhu, *Plant Cell* 16:2001-2019, 2004; Gustafson et al., *Nucleic Acid Research* 33:D637-D640, 2005). For MIR168a, a locus-specific EST clone (GenBank accession H77158) exists to confirm expression. For two miRNAs that are represented by a single locus (miR173 and miR391), expression was inferred by cloning or detection of the miRNA sequence. Thus, 5'RACE and unambiguous miRNA cloning/detection support expression of 68 of 99 predicted *Arabidopsis* MIRNA loci.

For the remaining 31 predicted MIRNA genes, locus-specific primers were designed to amplify sequences immediately downstream of the precursor foldback sequence through a 3' RACE procedure. Positive results were obtained for five loci.

EXAMPLE 6

Small RNA Formation in Plants

This example provides a demonstration of the ability to produce novel siRNAs using engineered ta-siRNA-generating loci. This demonstration includes miRNA-dependent formation of novel siRNAs for RNAi against exogenous and endogenous RNA sequences, and phenotypes associated with silencing of an endogenous gene (phytoene desaturase, or PDS) using the artificial, engineered cassettes.

Development of Constructs for Wild-Type and Artificial Ta-siRNA Biogenesis Assays in *N. benthamiana*

Figure 11:
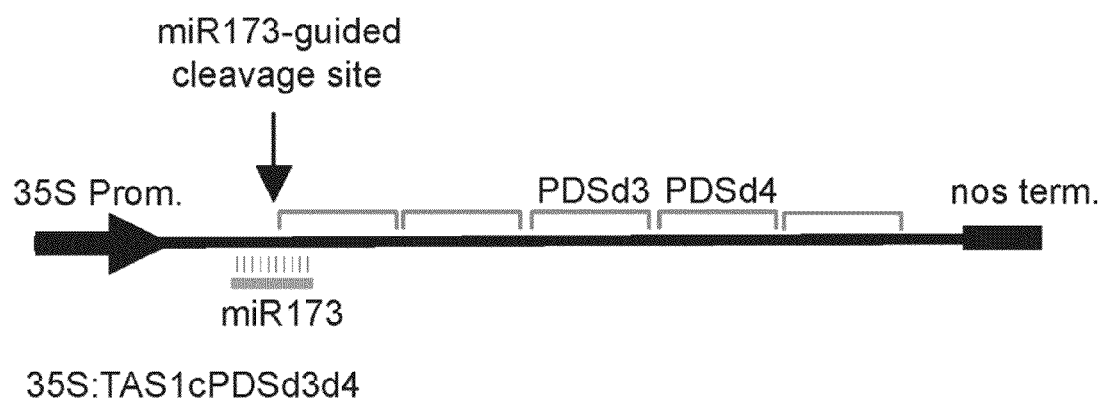
FIG. 11. Graphic representation of an artificial ta-siRNA construct made in the TAS1c context. The construct contains two 21-nt siRNA modules. The represented construct contains siRNAs designed to target mRNAs for *Arabidopsis* phytoene desaturase (PDS).
Figure 12A:
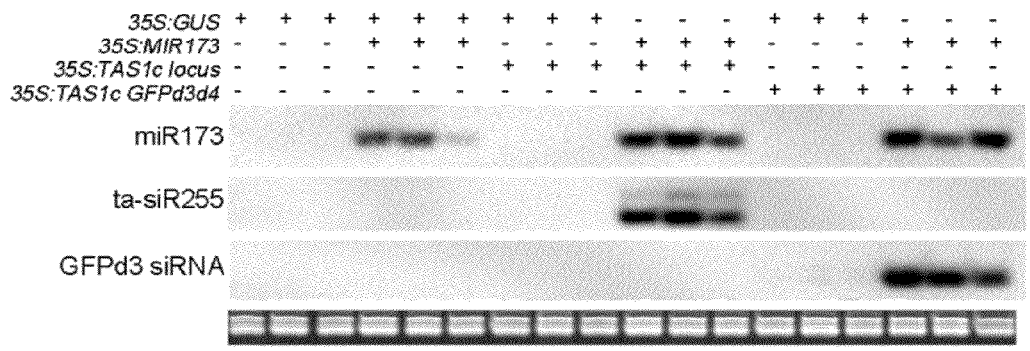
FIG. 12A-D. Demonstration of artificial ta-siRNA biogenesis and activity in *Nicotiana benthamiana*. Introduction of each construct into *N. benthamiana* in a transient assay resulted in miR173-dependent formation of ta-siRNAs. In the case of 35S:TAS1cGFPd3d4 (FIG. 12A,B), the artificial ta-siRNA construct was co-expressed with a functional GFP gene. Expression of at least one artificial ta-siRNA was detected in a miR173-dependent manner, by blot assay using each construct (GFP.
Figure 12B:
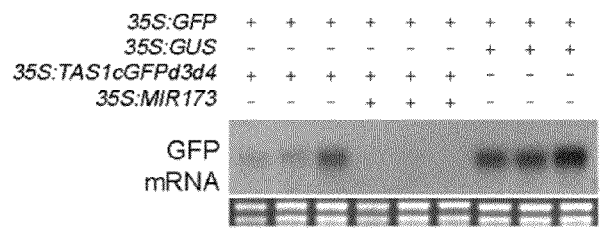
Figure 12C:
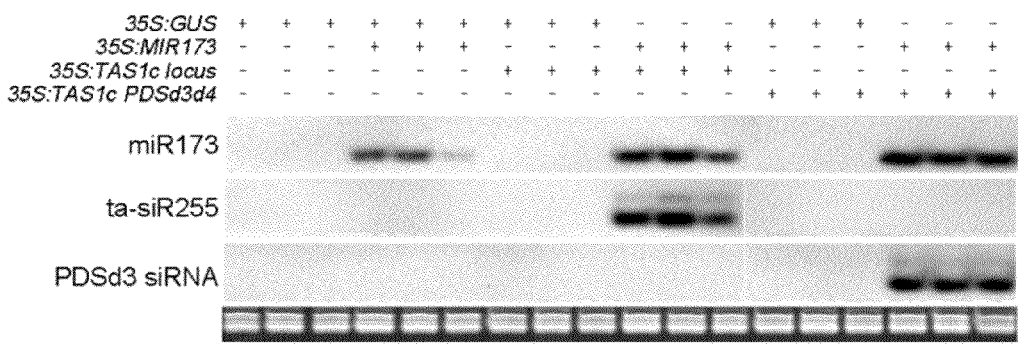
Figure 12D:
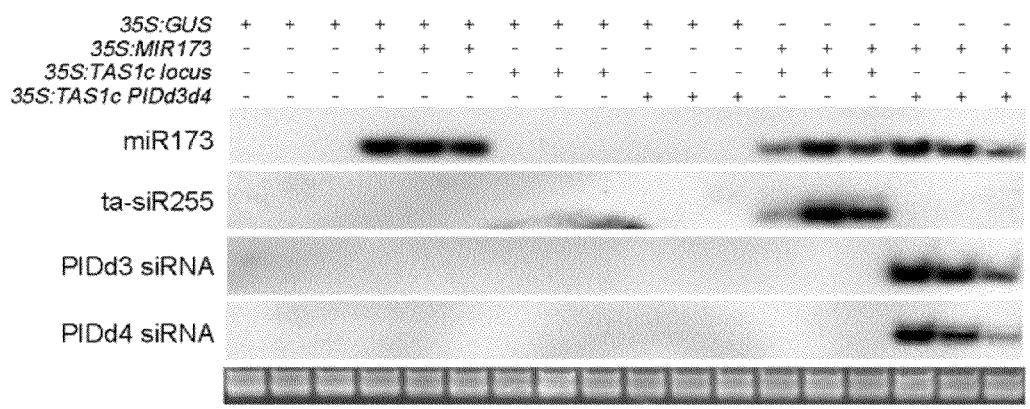

The following artificial ta-siRNAs targeting *Arabidopsis* genes encoding phytoene desaturase (PDS) and PINOID (PID), as well as GFP, were designed and expressed using an *Arabidopsis thaliana* TAS/c-based construct: 35S:TAS1c; 35S:TAS1cGFPd3d4 (SEQ ID NO: 277); 35S:TAS1cPDSd3d4 (SEQ ID NO: 278); and 35S:TAS1cPIDd3d4 (SEQ ID NO: 279). The ta-siRNA constructs were made in the TAS1c context, as shown in FIG. 11.

The artificial ta-siRNAs were expressed in place of the normal 3'D3(+) and 3'D4(+) positions of TAS1c (positional nomenclature as in Allen et al., *Cell* 121:207-221, 2005). Artificial ta-siRNA sequences were chosen based on the principles of the asymmetry rules and presented by Schwarz et al. (*Cell* 115:199-208, 2003) and Khvorova et al. (*Cell* 115:209-216, 2003). The artificial siRNAs chosen were designed as perfect complementary matches to their corresponding target genes, although it is assumed that artificial siRNAs may contain mismatches similar to those in known miRNA:target duplexes (see Allen et al., *Cell* 121:207-221, 2005, for examples). Each of these constructs contained two 21-nt siRNA modules, with the siRNAs designed to target mRNAs for GFP, PDS and PID.

Engineered TAS1c loci were expressed using the CaMV 35S promoter and the nos terminator as regulatory elements. The expressed sequence was inserted between att sites (positions 55 to 79 and 1106 to 1130 in each) for recombination into a "Gateway" vector. The two consecutive, 21-nucleotide engineered ta-siRNAs correspond to nucleotide positions 520 to 561 in each of SEQ ID NOs: 277, 278, and 279. Vector sequence is shown in positions 1 to 99 and 1090 to 1185 of each of these sequences; primers used to amplify the cassettes hybridize at positions 96 to 123 and 1069 to 1089.

Demonstration of Artificial Ta-siRNA Biogenesis and Activity in *N. Benthamiana*

Transient ta-siRNA expression assays in *Nicotiana benthamiana* were done as in Allen et al. (*Cell* 121:207-221, 2005). Stable *Arabidopsis thaliana* transgenic lines were created using the *Agrobacterium* mediated floral dip method. Transgenic seed from transformed plants was plated on Murashige-Skoog media containing kanamycin (50 µg/ml), and blot assays were done as described in Allen et al. (*Cell* 121:207-221, 2005).

Introduction of each construct (35S:TAS1c [which forms wild-type TAS1c ta-siRNAs], $^{35}$S:TAS1cGFPd3d4, 35S:TAS1cPDSd3d4, and 35S:TAS1cPIDd3d4) into *N. benthamiana* in a transient assay resulted in miR173-dependent formation of ta-siRNAs (FIG. 12). In the case of 35S:TAS1cGFPd3d4, the artificial ta-siRNA construct was co-expressed with a functional GFP gene. Expression of at least one artificial ta-siRNA was detected in a miR173-dependent manner, by blot assay using each construct (FIG. 12). The GFP gene was silenced by the artificial GFP ta-siRNAs in a miR173-dependent manner (FIG. 12).

Figure 13:
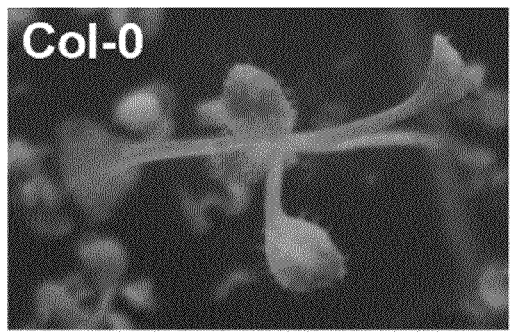
FIG. 13. Artificial ta-siRNA biogenesis and activity in transgenic *Arabidopsis*. The PDS artificial ta-siRNA-generating construct was introduced into wild-type (Col-0) *Arabidopsis* and rdr6-15 mutant plants. Both strong and weak loss-of-function PDS phenotypes were detected, but only in wt plants. The rdr6-15 mutant plants lack a critical factor for ta-siRNA biogenesis.
Figure 13:
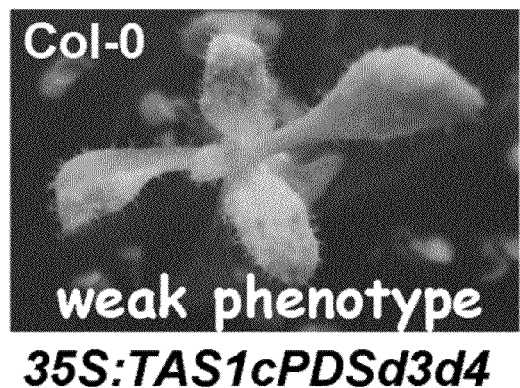
Figure 13:
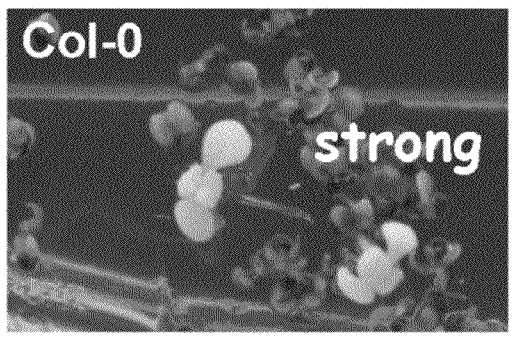
Figure 13:
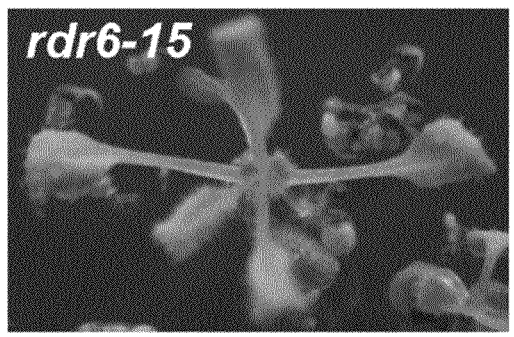

A PDS artificial ta-siRNA-generating construct was introduced into wild-type *Arabidopsis* and rdr6-15 and dcl4-2 (Xie et al., *Proc Natl Acad Sci USA*. 102(36):12984-12989, 2005; Epub 2005 Aug. 29) mutant plants. Both strong and weak loss-of-function PDS phenotypes were detected, but only in wildtype plants and not in rdr6-15 or dcl4-2 plants (Table 9 and FIG. 13). This indicates that functional artificial ta-siRNAs were formed through the activity of the normal ta-siRNA pathway.

TABLE 9

Observed phenotype classes of *Arabidopsis* stable transgenic lines expressing engineered TAS1cPDSd3d4

| | No Phenotype | Weak Phenotype | Strong Phenotype |
| --- | --- | --- | --- |
| Col-0 (n = 102) | 8/102 | 36/102 | 58/102 |
| rdr6-15 (n = 291) | 291/291 | — | — |
| dcl4-2 (n = 15) | 15/15 | — | — |

This disclosure describes the discovery of a new system for RNAi in vivo, and provides methods, constructs, and compositions useful for exploiting this discovery. The disclosure further provides myriad initiator sequences and methods for identifying additional initiator sequences that are useful in directing in vivo generation of predictable 21-mer siRNAs, as well as methods of using constructs containing such an initiator sequence to mediate RNAi. It will be apparent that the precise details of the methods described may be varied or modified without departing from the spirit of the described invention. We claim all such modifications and variations that fall within the scope and spirit of the disclosure and the claims below.

We claim:

1. A method for generating a phased small RNA (phasiRNA) in a plant cell, comprising introducing into the plant cell an effective amount of a microRNA (miRNA) and an engineered nucleic acid molecule comprising an initiator sequence of about 20 to 25 nucleotides with an initiation cleavage site linked to a 21-nucleotide gene suppressing segment engineered to be in about 21-nucleotide register counted either upstream or downstream from the initiation cleavage site.

2. The method of claim 1, wherein the miRNA is 22-nt in length.

3. The method of claim 1, wherein the plant cell is in a legume.

4. The method of claim 3, wherein the legume is selected from the group consisting of *M. truncatula*, soybeans, peanuts, and common.

5. The method of claim 1, wherein the plant cell is in a non-legume.

6. The method of claim 5, wherein the non-legume is selected from the group consisting of corns, rice, wheat, barley, oats, rye, sorghum, sugar cane, grapevine, almonds, apple, peach, sugar beet, tomato, potato, tobacco, cotton, lettuce, sunflower, melons, strawberries, and canola.

7. The method of claim 1, wherein resistance of the plant to a microbe is reduced.

8. The method of claim 1, wherein the plant enters a symbiotic interaction with a microbe.

9. The method of claim 7, wherein the microbe is a rhizobial strain.

10. The method of claim 8, wherein the microbe is a rhizobial strain.

11. The method of claim 3, wherein nodulation in the plant is improved.

12. The method of claim 5, wherein nodulation in the plant is improved.

* * * * *